US009243062B2

(12) United States Patent
Matossian-Rogers

(10) Patent No.: US 9,243,062 B2
(45) Date of Patent: Jan. 26, 2016

(54) PEPTIDES FOR TREATMENT AND DIAGNOSIS OF AUTOIMMUNE DISEASE

(76) Inventor: Arpi Matossian-Rogers, London (GB)

( * ) Notice: Subject to any disclaimer, the term of this patent is extended or adjusted under 35 U.S.C. 154(b) by 1041 days.

(21) Appl. No.: 11/990,281

(22) PCT Filed: Aug. 9, 2006

(86) PCT No.: PCT/GB2006/002977
§ 371 (c)(1),
(2), (4) Date: May 6, 2008

(87) PCT Pub. No.: WO2007/017686
PCT Pub. Date: Feb. 15, 2007

(65) Prior Publication Data
US 2009/0304577 A1  Dec. 10, 2009

(30) Foreign Application Priority Data

Aug. 11, 2005 (GB) .................................. 0516527.9
May 18, 2006 (GB) .................................. 0609920.4
May 18, 2006 (GB) .................................. 0609921.2

(51) Int. Cl.
*A61K 39/00* (2006.01)
*C07K 16/28* (2006.01)
*C07K 16/30* (2006.01)

(52) U.S. Cl.
CPC ............ *C07K 16/2809* (2013.01); *C07K 16/30* (2013.01); *A61K 2039/505* (2013.01); *C07K 2317/54* (2013.01); *C07K 2317/55* (2013.01); *C07K 2317/565* (2013.01); *C07K 2317/73* (2013.01)

(58) Field of Classification Search
None
See application file for complete search history.

(56) References Cited

U.S. PATENT DOCUMENTS

| 5,552,293 | A | * | 9/1996 | Lindholm et al. ............ 435/7.23 |
| 5,665,355 | A | | 9/1997 | Primi |
| 5,795,965 | A | | 8/1998 | Tsuchiya et al. |
| 5,885,966 | A | * | 3/1999 | Meloen et al. ............ 424/185.1 |
| 6,001,809 | A | | 12/1999 | Thorsett et al. |
| 6,689,359 | B1 | * | 2/2004 | Matossian-Rogers ..... 424/131.1 |
| 6,703,491 | B1 | | 3/2004 | Homburger et al. |
| 8,298,547 | B2 | * | 10/2012 | Brown et al. ............ 424/185.1 |
| 2004/0001825 | A1 | | 1/2004 | Govindan et al. |
| 2004/0115196 | A1 | * | 6/2004 | Fukuda et al. ............ 424/145.1 |
| 2004/0136998 | A1 | | 7/2004 | Bander |

FOREIGN PATENT DOCUMENTS

| EP | 1 130 032 | 9/2001 |
| KR | 10-2004-0083918 | 10/2004 |
| WO | 95/06067 | 3/1995 |
| WO | 98/20025 | 5/1998 |
| WO | 98/56416 | 12/1998 |
| WO | 99/05175 | 2/1999 |
| WO | 99/12971 | 6/1999 |
| WO | 01/14424 | 3/2001 |
| WO | 01/27612 | 4/2001 |
| WO | 01/68860 | 9/2001 |
| WO | WO 0179298 A1 * | 10/2001 |
| WO | 02/081496 | 10/2002 |
| WO | 03/024388 | 3/2003 |
| WO | 2004/011026 | 2/2004 |
| WO | 2004/029093 | 4/2004 |
| WO | 2004/094473 | 11/2004 |
| WO | 2005/005638 | 1/2005 |
| WO | 2005/011735 | 2/2005 |
| WO | WO 2005011735 A1 * | 2/2005 |
| WO | 2005/033275 | 4/2005 |
| WO | 2005/053604 | 6/2005 |

OTHER PUBLICATIONS

Database Geneseq [Online], Apr. 21, 2005, "Humanized Monoclonal Antibody Hu4785-2 Heavy Chain", XP002430284.
Database Geneseq [Online], Apr. 21, 2005, "Mouse Monoclonal Antibody 4785 Heavy Chain SEQ ID 38", XP002430283.
Database Geneseq [Online], Apr. 21, 2005, "Humanized Monoclonal Antibody Hu4785-2 VH Region", XP002430282.
Database Geneseq [Online], Apr. 21, 2005, "Mouse Monoclonal Antibody 4785 Heavy Chain SEQ ID 1", XP002430281.
Database Geneseq [Online], Apr. 21, 2005, "Humanized Monoclonal Antibody Hu4785-2 Partial Protein", XP002430280.
U. H. Lee et al., "Molecular Cloning of Agonistic and Antagonistic Monoclonal Antibodies Against Human 4-1BB", European Journal of Immunogenetics, vol. 29, No. 5, pp. 449-452, Oct. 5, 2002.
L. De Giorgi et al., "Induction of Foetal Lethality in AKR Offspring after Repeated Inoculations into AKR Females of Anti-TCR/Vβ6 Monoclonal Antibody", Res. Immunol., vol. 144, No. 4, pp. 245-255, May 1993.
A. Matossian-Rogers et al., "Anti-T-Cell Receptor Vβ6 Breaks Tolerance in Mls$^a$ Mice and Induces Production of Anti-Mls$^a$ Antibodies", Immunology, vol. 78, No. 1, pp. 122-126, Jan. 1993.
L. De Giorgi et al., "Murine Hybridomas Secreting Monoclonal Antibodies Reacting with Mls$^a$ Antigens", Experimental and Clinical Immunogenetics, vol. 10, No. 4, pp. 219-223, 1993.
C. M. Celli et al., "Origin and Pathogenesis of Antiphospholipid Antibodies", Brazilian Journal of Medical and Biological Research, vol. 31, No. 6, pp. 723-732, 1998.
H. Acha-Orbea et al., "Anti-T-Cell Receptor $V_\beta$ Antibodies in Autoimmunity", Immunology Series, Marcel Dekker, New York, NY, US, vol. 59, pp. 193-202, 1993.
C. S. David et al., "A Significant Reduction in the Incidence of Collagen Induced Arthritis in Mice Treated with Anti-TCR $V_\beta$ Antibodies", Journal of Cellular Biochemistry, p. 179, Mar. 15, 1991.

(Continued)

*Primary Examiner* — Michael Szperka
(74) *Attorney, Agent, or Firm* — Wenderoth, Lind & Ponack, L.L.P.

(57) ABSTRACT

There are provided peptides derived from antibodies with reactivity against a GPI linkage epitope and functionally-equivalent ligands. These peptides can be used in the therapy and diagnosis of a variety of diseases, all of which are considered to be caused by the inappropriate presence in the body of autoantibodies which are reactive with GPI linkage epitopes. There is also described a mechanism of action of these autoantibodies which compromises the organism, so causing disease, and a method of prevention of disease and detection of the autoantibody.

29 Claims, 19 Drawing Sheets

(56) References Cited

OTHER PUBLICATIONS

Database NCBI Protein [Online], Aug. 30, 1993, XP002410230.
Database NCBI Protein [Online], Mar. 23, 2002, XP002410289.
Database NCBI Protein [Online], Apr. 11, 1996, XP002410290.
Database NCBI Protein [Online], Mar. 23, 2002, XP002410231.
H. Zhang et al., "Construction, Sequence and Binding Properties of an Anti-CD5 Single Chain Fv Antibody", Tumor Targeting, vol. 2, pp. 314-321, 1996.
L. Diaw et al., "Restricted Immunoglobulin Variable Region (Ig V) Gene Expression Accompanies Secondary Rearrangements of Light Chain Ig V Genes in Mouse Plasmacytomas", The Journal of Experimental Medicine, vol. 190, No. 10, pp. 1405-1415, Nov. 15, 1999.
NCBI Database Search, Accession No.'s: AAG30627, Accessed Feb. 2, 2009.
NCBI Database Search, Accession No.'s: Q54265, Accessed Feb. 2, 2009.
NCBI Database Search, Accession No.'s: CAA65007, Accessed Feb. 2, 2009.
NCBI Database Search, Accession No.'s: AAO60116, Accessed Feb. 2, 2009.
NCBI Database Search, Accession No.'s: AAB38291, Accessed Feb. 2, 2009.
ACS on STN, Registry No. 483478-39-3, Protein Sequence, Accessed STN on Jan. 30, 2003.
Juris Steinbergs et al.; "Short Synthetic CDR-Peptides Forming the Antibody Combining Site of the Monoclonal Antibody Against RNA Bacteriophage fr Neutralize the Phage Activity"; Human Antibody Hybridomas; c. 1996; vol. 7, No. 3; pp. 106-112.
Rudikoff et al. "Single amino acid substitution altering antigen-binding specificity"; PNAS; Mar. 1982; vol. 79; pp. 1979-1983.
GenBank: CAA07389.1, StrM [*Streptomyces glaucescens*], Apr. 15, 2005.
GenBank: CAA55578.1, dTDP-4-keto-6-deoxyglucose 3,5-epimerase [*Streptomyces glaucescens*], Apr. 18, 2005.

* cited by examiner

FIGURE 1A

Heavy Chain

```
         MuIgV_H5'-B         L   V   A   T   A   T   G   V   H
AATGGAGCTG GGTTATTCTC TTCTTGGTAG CAACAGCTAC AGGTGTCCAC

S   Q   V   Q   L   Q   Q   P   G   A   E   L   V   R   P   G   A
TCCCAGGTCC AACTGCAGCA GCCTGGGGCT GAGCTGGTGA GGCCTGGGGC

S   V   K   L   S   C   K   A   S   G   Y   T   F   T   R   N
TTCAGTGAAG CTGTCCTGCA AGGCTTCTGG CTACACCTTC ACCAGGAACT

W   I   N   W   V   K   Q   R   P   G   Q   G   L   E   W   I   G
GGATAAACTG GGTGAAGCAG AGGCCTGGAC AAGGCCTTGA GTGGATCGGA

N   I   Y   P   S   D   S   Y   T   N   Y   N   Q   K   F   K   D
AATATTTATC CTTCTGATAG TTATACTAAC TACAATCAAA AGTTCAAGGA

K   A   T   V   T   V   D   K   S   S   S   T   A   Y   M   Q
CAAGGCCACA GTGACTGTAG ACAAATCCTC CAGCACAGCC TACATGCAGC

L   S   S   P   T   S   E   D   S   A   V   Y   Y   C   T   R   L
TCAGCAGCCC GACATCTGAG GACTCTGCGG TCTATTATTG TACAAGATTG

R   G   L   L   P   D   Y   W   G   Q   G   T   I   L   T   V   S
AGGGGTTTAT TACCTGACTA CTGGGGCCAA GGCACCATTC TCACAGTCTC

S   E   S   Q   S              MuIgMV_H3'-1
CTCAGAGAGT CAGTCCTTCC CAAATGTCTT CCCCCTCGTA AGCTTGGG
```

FIGURE 1B

Light chain

```
            MuIgκV_L5'-A                        V    Y    M    L    W
GGGAATTCAT  GGAGTCACAG  ACCCAGGTCT  TTGTATACAT  GTTGCTGTGG
 L    S    G    V    D    G    D    I    V    M    T    Q    S    Q    K    F    M
TTGTCTGGTG  TTGATGGAGA  CATTGTGATG  ACCCAGTCTC  AAAAATTCAT
 S    T    S    V    G    D    R    V    S    V    T    C    K    A    S    Q
GTCCACATCA  GTAGGAGACA  GGGTCAGCGT  CACCTGCAAG  GCCAGTCAGA
 N    V    D    T    N    V    A    W    Y    Q    Q    K    P    G    Q    S    P
ATGTGGATAC  TAATGTAGCC  TGGTATCAAC  AGAAACCAGG  GCAATCTCCT
 K    A    L    I    Y    S    A    S    Y    R    Y    S    G    V    P    D    R
AAAGCACTGA  TTTACTCGGC  ATCCTACCGG  TACAGTGGAG  TCCCTGATCG
 F    T    G    S    G    S    G    T    D    F    T    L    T    I    S    N
CTTCACAGGC  AGTGGATCTG  GGACAGATTT  CACTCTCACC  ATCAGCAATG
 V    Q    S    E    D    L    A    E    Y    F    C    Q    Q    Y    N    S    Y
TGCAGTCTGA  AGACTTGGCA  GAGTATTTCT  GTCAGCAATA  TAACAGCTAT
 P    L    T    F    G    A    G    T    K    L    E    L    K    R    A    D    A
CCTCTCACGT  TCGGTGCTGG  GACCAAGCTG  GAGCTGAAAC  GGGCTGATGC
 A    P    T    V          MuIgκV_L3'-1
TGCACCAACT  GTA  TCCATCT  TCCCACCATC  CAGTAAGCTT
```

FIGURE 4A

Cell line 13.42a VH-1 DNA Sequence (SEQ ID NO:17)
AGGTCAAGCTGCAGGAGTCAGGACCTGAGCTGGTGAAGCCTGGGGCTTCAGTGAAGGTATC
CTGCAAGGCTTCTGGTTATGCATTCACTAGCTACAACATGTTCTGGGTGAAGCAGAGCCAT
GGAAAGAGCCTTGAGTGGATTGGATATATTGATCCTTACAATGGTGATACTAGATACAGCC
AGAAGTTCAAGGGCAAGGCCACATTGACTGTTGACAAGTCCTCCAGCACAGCCTACATGCA
TCTCAACAGCCTGACATCTGAAGACTCTGCAGTCTATTACTGTGCAAGAAAGGGGATGACG
ACGGGCTATGCTATGGACTACTGGGGCCAAGGGACCACGGTCACCGTCTCCTCA Cell line 13.42a VH-1 Amino Acid Sequence (SEQ ID NO:18)
VKLQESGPELVKPGASVKVSCKASGYAFTSYNMFWVKQSHGKSLEWIGYIDPYNGDTRYSQ
KFKGKATLTVDKSSSTAYMHLNSLTSEDSAVYYCARKGMTTGYAMDYWGQGTTVTVSS Cell line 13.42a VL DNA sequence (SEQ ID NO:19)
GACATCCAGATGACTCAGTCTCCATCCTCCCTGTCTGCCTCTCTGGGAGACAGAGTCACCA
TCAGTTGTAGGGCAAGTCAGGACATTAGTAATTATTTAAACTGGTATCAGCAGAAACCAGA
TGGAACTGTTAAACTCCTGCTCTACTACACATCAAGATTACACTCAGGAGTCCCATCAAGG
TTCAGTGGCAGTGGGTCTGGAACAGATTATTCTCTCACCATTAGCAACCTGGAACAAGAAG
ATGTTGCCACTTACTTTTGCCAACAGGGTAATACGTTTCCGACGTTCGGTGGAGGCACCAA
GCTGGAAATCAAACGG Cell line 13.42a VL Amino acid sequence (SEQ ID NO:20)
DIQMTQSPSSLSASLGDRVTISCRASQDISNYLNWYQQKPDGTVKLLLYYTSRLHSGVPSR
FSGSGSGTDYSLTISNLEQEDVATYFCQQGNTFPTFGGGTKLEIKR

FIGURE 4B

Cell line 32.15 VH DNA sequence (SEQ ID NO:33)
AGGTGCAACTGCAGGAGTCTGGACCTGAGCTGAAGAAGCCTGGAGAGACAGTCAAGATCTC
CTGCAAGGCTTCTGGGTATACCTTCACAAACTATGGAATGAACTGGGTGAAGCAGGCTCCA
GGAAAGGGTTTAAAGTGGATGGGCTGGATAAACACCTACACTGGAGAGCCAACATATGCTG
ATGACTTCAAGGGACGGTTTGCCTTCTCTTTGGAAACCTCTGCCAGCACTGCCTATTTGCA
GATCAACAACCTCAAAAATGAGGACACGGCTACATATTTCTGTGCAAGGGAAGGGTTGTAT
GGTAACTACTTTGACTACTGGGGCCAAGGGACCACGGTCACCGTCTCCTCA

Cell line 32.15 VH Amino acid sequence (SEQ ID NO:34)
VQLQESGPELKKPGETVKISCKASGYTFTNYGMNWVKQAPGKGLKWMG**WINTYTGEPTYAD
DFKGRFAFSLETSASTAYLQINNLKNEDTATYFCAREGLYGNYF**DYWGQGTTVTVSS

Cell line 32.15 VL DNA sequence (SEQ ID NO:35)
GACATCCAGATGACACAGTCTCCAAAATTCATGTCCACATCAGTAGGAGACAGGGTCAGCG
TCACCTGCAAGGCCAGTCAGAATGTGGGTACTAATGTAGCCTGGTATCAACAGAAACCAGG
GCAATCTCCTAAAGCACTGATTTACTCGGCATCCTACCGGTACAGTGGAGTCCCTGATCGC
TTCACAGGCAGTGGATCTGGGACAGATTTCACTCTCACCATCAGCAATGTGCAGTCTGAAG
ACTTGGCAGAGTATTTCTGTCAGCAATATAACAGCTATCCTCTCACGTTCGGTGCTGGGAC
CAAGCTGGAGCTGAAACGG

Cell line 32.15 VL Amino acid sequence (SEQ ID NO:36)
DIQMTQSPKFMSTSVGDRVSVTCKASQNVGTNVAWYQQKPGQSPKALIYSASYRYSGVPDR
FTGSGSGTDFTLTISNVQSEDLAEYFCQQYNSYPLTFGAGTKLELKR

FIGURE 4C

Cell line 32.17 VH DNA sequence (SEQ ID NO:49)
AGGTCAAACTGCAGGAGTCAGGGGCTGAGCTGGTGAGGCCTGGGGCTTCAGTGAAGCTGTC
CTGCAAGGCTTCTGGCTACACCTTCACCAGGAACTGGATAAACTGGGTGAAGCAGAGGCCT
GGACAAGGCCTTGAGTGGATCGGAAATATTTATCCTTCTGATAGTTATACTAACTACAATC
AAAAGTTCAAGGACAAGGCCACAGTGACTGTAGACAAATCCTCCAGCACAGCCTACATGCA
GCTCAGCAGCCCGACATCTGAGGACTCTGCGGTCTATTATTGTACAAGATTGAGGGGTTTA
TTACCTGACTACTGGGGCCAAGGGACCACGGTCACCGTCTCCTCA

Cell line 32.17 VH Amino acid sequence (SEQ ID NO:50)
VKLQESGAELVRPGASVKLSCKAS<u>GYTFTRNWINW</u>VKQRPGQGLEWIG<u>NIYPSDSYTNYNQ
KFKD</u>KATVTVDKSSSTAYMQLSSPTSEDSAVYYCTR<u>LRGLLPDY</u>WGQGTTVTVSS

Cell line 32.17 VL DNA sequence (SEQ ID NO:51)
GACATTGTGCTAACCCAATCTCCAGTATCCATAACTGCATCTCGAGGGGAGAAGGTCACCA
TCACCTGCCGTGCCAGCTCAAGTATAAGTTCCAATTACTTACACTGTTACCAGCAGAAGCC
AGGATCCTCCCCTAAACTTTTGATTTATAGGACATCCATCCTGGCATCTGGAGTCCTAGAC
AGCTTCAGTGGCAGTGGGTCTGAGAGCTCTTACACTCTGACAATCAGCTGCATGCAGGACG
AAGTTGCTGCCACTTACTATTGTCAGCAGGGGAGTAGTAGCCCCCTCACGTTCGGTGCTGG
GACCAAGCTGGAGCTGAAACGG

Cell line 32.17 VL Amino acid sequence (SEQ ID NO:52)
DIVLTQSPVSITASRGEKVTITC<u>RASSSISSNYL</u>HCYQQKPGSSPKLLIY<u>RTSILAS</u>GVLD
SFSGSGSESSYTLTISCMQDEVAATYYC<u>QQGSSSPLT</u>FGAGTKLELKR

FIGURE 4D

Cell line 32.75 VH DNA sequence (SEQ ID NO:65)
AGGTCAAACTGCAGGAGTCAGGGGCTGAGCTGGTGAGGCCTGGGGCTTCAGTGAAGCTGTC
CTGCAAGGCTTCTGGCTACACCTTCACCAGGAACTGGATAAACTGGGTGAAGCAGAGGCCT
GGACAAGGCCTTGAGTGGATCGGAAATATTTATCCTTCTGATAGTTATACTAACTACAATC
AAAAGTTCAAGGACAAGGCCACAGTGACTGTAGACAAATCCTCCAGCACAGCCTACATGCA
GCTCAGCAGCCCGACATCTGAGGACTCTGCGGTCTATTATTGTACAAGATTGAGGGGTTTA
TTACCTGACTACTGGGGCCAAGGGACCACGGTCACCGTCTCCTCA

Cell line 32.75 VH Amino acid sequence (SEQ ID NO:66)
VKLQESGAELVRPGASVKLSCKASGYTFTRNWINWVKQRPGQGLEWIG**NIYPSDSYTNYNQ
KFKDKATVTVDKSSSTAYMQLSSPTSEDSAVYYCTRLRGLLPDY**WGQGTTVTVSS

Cell line 32.75 VL DNA sequence (SEQ ID NO:67)
GACATCCAGATGACACAGTCTCCAAAATTCATGTCCACATCAGTAGGAGACAGGGTCAGCG
TCACCTGCAAGGCCAGTCAGAATGTGGATACTAATGTAGCCTGGTATCAACAGAAACCAGG
GCAATCTCCTAAAGCACTGATTTACTCGGCATCCTACCGGTACAGTGGAGTCCCTGATCGC
TTCACAGGCAGTGGATCTGGGACAGATTTCACTCTCACCATCAGCAATGTGCAGTCTGAAG
ACTTGGCAGAGTATTTCTGTCAGCAATATAACAGCTATCCTCCTACGTTCGGTGCTGGGAC
CAAGCTGGAGCTGAAACGG

Cell line 32.75 VL Amino acid sequence (SEQ ID NO:68)
DIQMTQSPKFMSTSVGDRVSVTCKASQNVDTNVAWYQQKPGQSPKALIYSASYRYSGVPDR
FTGSGSGTDFTLTISNVQSEDLAEYFCQQYNSYPPTFGAGTKLELKR

FIGURE 4E

Cell line 32.2 VH-1 DNA sequence (SEQ ID NO:81)
AGGTGAAGCTGCAGGAGTCAGGACCTGAGCTGAAGAAGCCTGGAGAGACAGTCAAGATCTC
CTGCAAGGCTTCTGGGTATACCTTCACAAACTATGGAATGAACTGGGTGAAGCAGGCTCCA
GGAAAGGGTTTAAAGTGGATGGGCTGGATAAACACCTACACTGGAGAGCCAACATATGCTG
ATGACTTCAAGGGACGGTTTGCCTTCTCTTTGGAAACCTCTGCCAGCACTGCCTATTTGCA
GATCAACAACCTCAAAAATGAGGACACGGCTACATATTTCTGTGCAAGGGAAGGGTTGTAT
GGTAACTACTTTGACTACTGGGGCCAAGGGACCACGGTCACCGTCTCCTCA Cell line 32.2 VH-1 Amino acid sequence (SEQ ID NO:82)
VKLQESGPELKKPGETVKISCKASGYTFTNYGMNWVKQAPGKGLKWMGWINTYTGEPTYAD
DFKGRFAFSLETSASTAYLQINNLKNEDTATYFCAREGLYGNYFDYWGQGTTVTVSS Cell line 32.2 VL DNA sequence (SEQ ID NO:83)
GACATCCAGATGACCCAGTCTCCAAAATTCATGTCCACATCAGTAGGAGACAGGGTCAGCG
TCACCTGCAAGGCCAGTCAGAATGTGGGTACTAATGTAGCCTGGTATCAACAGAAACCAGG
GCAATCTCCTAAAGCACTGATTTACTCGGCATCCTACCGGTACAGTGGAGTCCCTGATCGC
TTCACAGGCAGTGGATCTGGGACAGATTTCACTCTCACCATCAGCAATGTGCAGTCTGAAG
ACTTGGCAGAGTATTTCTGTCAGCAATATAACAGCTATCCTCTCACGTTCGGTGCTGGGAC
CAAGCTGGAAATAAAACGG Cell line 32.2 VL Amino acid sequence (SEQ ID NO:84)
DIQMTQSPKFMSTSVGDRVSVTCKASQNVGTNVAWYQQKPGQSPKALIYSASYRYSGVPDR
FTGSGSGTDFTLTISNVQSEDLAEYFCQQYNSYPLTFGAGTKLEIKR Males - Fasting capillary glucose [mmo/L]

Males - Fructosamine corrected [umol/g]

FIGURE 12A

|  | IgM CDR-H1 | Reactivity |
|---|---|---|
| SEQ ID NO:6 (Example 1) | GYTFTRNWINW | - |
| SEQ ID NO:31 (Example 5) | GYTFTNYGMNW | - |
| SEQ ID NO:41 (Example 5) | GYTFTRNWINW | - |
| SEQ ID NO:51 (Example 5) | GYTFTRNWINW | - |
| SEQ ID NO:61 (Example 5) | GYTFTNYGMNW | - |
| SEQ ID NO:97 (A39276) | GYTFTNFWIGW | Anti-RF |
| SEQ ID NO:98 (AAL59371.1) | GYTFTYNAIQW | Anti-CL |
| SEQ ID NO:99 (AAB32203.1) | GYTFTSYWMQW | Anti-RNA |
| SEQ ID NO:100 (AAT76246.1) | GYTFTTYWMHW | Anti-sDNA |
| SEQ ID NO:101 (AAR90999.1) | GYTFTDYYMNW | Anti-NA |
| SEQ ID NO:102 (AAB46762.1) | GYTFTEYYVNW | Anti-VA |
| SEQ ID NO:103 (AAG33839.1) | GYTFTDYYIHW | Anti-RF |
| SEQ ID NO:104 (AAT76245.1) | GYTFTSYWMHW | Anti-sDNA |
| SEQ ID NO:105 (CAA84376.1) | GYTFTGYYIHW | Anti-RF |
| SEQ ID NO:106 (AAB46761.1) | GYTFTSYWMHW | Anti-VA |
| CONSERVED RESIDUES SEQ ID NO:162 | GYTFT-----W | - |

Consensus sequence

IgM CDR-H1    G-Y-T-F-T-x-x-x-x-x-W

General formula

IgM CDR-H1    G-Y-T-F-T-[RNYSTDEG]-[NYF]-[WGAY]-[IMV]-[NGQH]-W

Conserved and predominant residues

IgM CDR-H1    G-Y-T-F-T-[RNS]-Y-W-[IM]-N-W

|  | IgG CDR-H1 | Reactivity |
|---|---|---|
| SEQ ID NO:21 (Example 5) | GYAFTSYNMFW | - |
| SEQ ID NO:99 (AAB32203.1) | GYTFTSYWMQW | Anti-RNA |
| SEQ ID NO:107 (AAB58061.1) | GYTFTDYNMHW | Anti-CD8 |
| SEQ ID NO:108 (F30502) | GYSFTGYNMNW | Anti-RNA |
| SEQ ID NO:109 (AAR91003.1) | GYAFSSYWMNW | Anti-NA |
| SEQ ID NO:110 (AAT76236.1) | GYTFTSYVMHW | Anti-sDNA |
| SEQ ID NO:104 (AAT76245.1) | GYTFTSYWMHW | Anti-sDNA |
| SEQ ID NO:106 (AAB46761.1) | GYTFTSYWMHW | Anti-VA |
| CONSERVED RESIDUES SEQ ID NO:163 | GY-F--Y-M-W | - |

Consensus sequence

IgG CDR-H1    G-Y-x-F-x-x-Y-x-M-x-W

General formula

IgG CDR-H1    G-Y-[ATS]-F-[T/S]-[SDG]-Y-[NWV]-M-[FQHN]-W

Conserved and predominant residues

IgG CDR-H1    G-Y-T-F-T-S-Y-W-M-H-W

FIGURE 12B

|            |            | IgM CDR-H2 | Reactivity |
|---|---|---|---|
| SEQ ID NO:8 | (Example 1) | NIYPSDSYTNYNQKFKD | - |
| SEQ ID NO:32 | (Example 5) | WINTYTGEPTYADDFKG | - |
| SEQ ID NO:42 | (Example 5) | NIYPSDSYTNYNQKFKD | - |
| SEQ ID NO:52 | (Example 5) | NIYPSDSYTNYNQKFKD | - |
| SEQ ID NO:62 | (Example 5) | WINTYTGEPTYADDFKG | - |
| SEQ ID NO:111 | (AAB32203.1) | EIDPSDSYTNYNQKFKG | Anti-RNA |
| SEQ ID NO:112 | (AAT68292.1) | AIDTSDSYTYYNQKFKG | Anti-TG |
| SEQ ID NO:113 | (A39276) | NIYPGGDYTNYIEKFKG | Anti-RF |
| SEQ ID NO:114 | (AAB58061.1) | YIYPYTGGTGYNQKFKN | Anti-CD8 |
| SEQ ID NO:115 | (1921302A) | NINPYYGSTSYNQKFKG | Anti-CL |
| Conserved Residues SEQ ID NO:164 | | -I--------Y---FK- | - |

Consensus sequence

IgM CDR-H2   x-I-x-x-x-x-x-x-x-x-Y-x-x-x-F-K-x

General formula

IgM CDR-H2   [NWEAY]-I-[YND]-[PT]-[SYG]-[DTGY]-[SGD]-[YEGS]-[TP]-[NTYGS]-
             Y-[NAI]-[QDE]-[KD]-F-K-[DGN]

Conserved and predominant residues

IgM CDR-H2   N-I-Y-P-S-D-S-Y-T-N-Y-N-Q-K-F-K-G

|            |            | IgG CDR-H2 | Reactivity |
|---|---|---|---|
| SEQ ID NO:22 | (Example 5) | YIDPYNGDTRYSQKFKG | - |
| SEQ ID NO:116 | (AAR91004.1) | WIDPANGDTEYASKFQG | Anti-NA |
| SEQ ID NO:117 | (F30502) | KINPYYGSTSYNQKFKG | Anti-RNA |
| SEQ ID NO:118 | (AAT76236.1) | YINPYNDGTKYNEKFKG | Anti-sDNA |
| SEQ ID NO:119 | (AAB46758.1) | WIDPENGDTEYAPKFQG | Anti-VA |
| SEQ ID NO:115 | (1921302A) | NINPYYGSTSYNQKFKG | Anti-CL |
| SEQ ID NO:120 | (AAE72083.1) | LINPFSGDTNYSQKFTG | Anti-3H1 |
| SEQ ID NO:121 | (B30502) | YINPYNDGTKYNEKFKG | Anti-RNA |
| SEQ ID NO:123 | (AAR91007.1) | WIDPENGDTEYASKFQG | Anti-NA |
| Conserved Residues SEQ ID NO:165 | | -I-P----T-Y--KF-G | - |

Consensus sequence

IgG CDR-H2   x-I-x-P-x-x-x-x-T-x-Y-x-x-K-F-x-G

General formula

IgG CDR-H2   [YWKNLR]-I-[DN]-P-[YAEFS]-[NYS]-[GD]-[DSG]-T-[RESKN]-Y-[SAN]-
             [QSEP]-K-F-[KQT]-G

Conserved and predominant residues

IgG CDR-H2   [YW]-I-N-P-Y-N-G-D-T-[ES]-Y-N-Q-K-F-K-G

FIGURE 12C

| | IgM CDR-L1 | Reactivity |
|---|---|---|
| SEQ ID NO:12 (Example 1) | KASQNVDTNVA | – |
| SEQ ID NO:34 (Example 5) | KASQNVGTNVA | – |
| SEQ ID NO:44 (Example 5) | RASSSISSNYL | – |
| SEQ ID NO:54 (Example 5) | KASQNVDTNVA | – |
| SEQ ID NO:64 (Example 5) | KASQNVGTNVA | – |
| SEQ ID NO:124 (AAS01840.1) | KASQNVGTNVA | Anti-NA |
| SEQ ID NO:125 (AAS01841.1) | KASQNVRTAVA | Anti-NA |
| SEQ ID NO:126 (AAT76271.1) | KASQDVSTAVA | Anti-sDNA |
| SEQ ID NO:127 (AAB46763.1) | KASQSVDYDGDSYMN | Anti-VA |
| SEQ ID NO:128 (AAA20447.1) | RASQSVSSYLA | Anti-RF |
| SEQ ID NO:129 (PC4282) | RASQSVSNYLA | Anti-RO |
| SEQ ID NO:130 (CAA56180.1) | RASQTVRKNYLA | Anti-TG |
| CONSERVED RESIDUES SEQ ID NO:166 | -AS-------- | – |

Consensus sequence

IgM CDR-L1    x-A-S-x-x-x-x-x-x-x-x

General formula

IgM CDR-L1    [KR]-A-S-[QS]-[NSDT]-[VI]-[DGSR]-[TSYNK]-[NADY]-[VYGL]-[ALD]

Conserved and predominant residues

IgM CDR-L1    K-A-S-Q-N-V-S-T-N-V-A

| | IgG CDR-L1 | Reactivity |
|---|---|---|
| SEQ ID NO:24 (Example 5) | RASQDISNYLN | – |
| SEQ ID NO:131 (1921302B) | RASQSISNYLH | Anti-CL |
| SEQ ID NO:132 (AAL59380.1) | RASQSISSYLN | Anti-CL |
| SEQ ID NO:133 (AAL59377.1) | RASQSISSYLN | Anti-CL |
| SEQ ID NO:134 (CAA63587.1) | RASQGISNWLA | Anti-TG |
| SEQ ID NO:135 (AAG30434.1) | RASQGISSYLA | Anti-CL |
| SEQ ID NO:129 (PC4282) | RASQSVSNYLA | Anti-RO |
| SEQ ID NO:136 (CAA56181.1) | RASRGISNYLA | Anti-TG |
| SEQ ID NO:137 (AAE72082.1) | KASQDINGYLN | Anti-3H1 |
| CONSERVED RESIDUES SEQ ID NO:167 | -AS------L- | – |

Consensus sequence

IgG CDR-L1    x-A-S-x-x-x-x-x-x-L-x

General formula

IgG CDR-L1    [RK]-A-S-[QR]-[DSG]-[IV]-[SN]-[NSG]-[YW]-L-[NHA]

Conserved and predominant residues

IgG CDR-L1    R-A-S-Q-S-I-S-N-Y-L-[NA]

FIGURE 12D

|  | IgM CDR-L2 | Reactivity |
|---|---|---|
| SEQ ID NO:14 (Example 1) | SASYRYS | - |
| SEQ ID NO:35 (Example 5) | SASYRYS | - |
| SEQ ID NO:45 (Example 5) | RTSILAS | - |
| SEQ ID NO:55 (Example 5) | SASYRYS | - |
| SEQ ID NO:65 (Example 5) | SASYRYS | - |
| SEQ ID NO:138 (AAS01840.1) | SASYRYS | Anti-NA |
| SEQ ID NO:139 (G30502) | WASTRES | Anti-RNA |
| SEQ ID NO:140 (AAL59376.1) | WASTRES | Anti-CL |
| SEQ ID NO:141 (AAL59379.1) | WASTRES | Anti-CL |
| CONSERVED RESIDUES SEQ ID NO:168 | --S---S | - |

Consensus sequence

IgM CDR-L2   x-x-S-x-x-x-S

General formula

IgM CDR-L2   [SRW]-[AT]-S-[YIT]-[RL]-[YAE]-S

Conserved and predominant residues

IgM CDR-L2   S-A-S-Y-R-Y-S

|  | IgG CDR-L2 | Reactivity |
|---|---|---|
| SEQ ID NO:25 (Example 5) | YTSRLHS | - |
| SEQ ID NO:142 (AAT76280.1) | LTSNLAS | Anti-sDNA |
| SEQ ID NO:143 (AAB46767.1) | DTSKLAS | Anti-VA |
| SEQ ID NO:144 (AAB46765.1) | DTSNLAS | Anti-VA |
| SEQ ID NO:145 (AAB46766.1) | YTSNLAP | Anti-VA |
| SEQ ID NO:146 (AAB46764.1) | YTSNLAP | Anti-VA |
| SEQ ID NO:147 (AAS01843.1) | TTSNLAS | Anti-NA |
| SEQ ID NO:148 (AAG30433.1) | KTSVLGS | Anti-CL |
| SEQ ID NO:149 (CAC22102.1) | TTSNLAS | Anti-TRKA |
| CONSERVED RESIDUES SEQ ID NO:169 | -TS-L-- | - |

Consensus sequence

IgG CDR-L2   x-T-S-x-L-x-x

General formula

IgG CDR-L2   [YLDTK]-T-S-[RNKV]-L-[HAG]-[SP]

Conserved and predominant residues

IgG CDR-L2   Y-T-S-N-L-A-S

FIGURE 12E

|  | IgM CDR-L3 | Reactivity |
|---|---|---|
| SEQ ID NO:16 (EXAMPLE 1) | QQYNSYPLT | - |
| SEQ ID NO:36 (EXAMPLE 5) | QQYNSYPLT | - |
| SEQ ID NO:46 (EXAMPLE 5) | QQGSSSPLT | - |
| SEQ ID NO:56 (EXAMPLE 5) | QQYNSYPPT | - |
| SEQ ID NO:66 (EXAMPLE 5) | QQYNSYPLT | - |
| SEQ ID NO:150 (AAS01840.1) | QQYNSYPYT | Anti-NA |
| SEQ ID NO:151 (AAB46766.1) | QQWSSDPLT | Anti-VA |
| SEQ ID NO:152 (PC4282) | QQRASWPLT | Anti-RO |
| SEQ ID NO:153 (S67940) | QQYGSSPYT | Anti-TG |
| SEQ ID NO:154 (CAA56180.1) | QQYGSSPIT | Anti-TG |
| CONSERVED RESIDUES SEQ ID NO:170 | QQ--S-P-T | - |

Consensus sequence

IgM CDR-L3   Q-Q-x-x-S-x-P-x-T

General formula

IgM CDR-L3   Q-Q-[YGWR]-[NSAG]-S-[YSDW]-P-[LPYI]-T

Conserved and predominant residues

IgM CDR-L3   Q-Q-Y-N-S-Y-P-L-T

|  | IgG CDR-L3 | Reactivity |
|---|---|---|
| SEQ ID NO:26 (EXAMPLE 5) | QQGNTFPTF | - |
| SEQ ID NO:155 (AAB58062.1) | QQNNEDPYT | Anti-CD8 |
| SEQ ID NO:156 (AAS01844.1) | QQSNEDPRT | Anti-NA |
| SEQ ID NO:157 (C30502) | QQTNSWPRT | Anti-RNA |
| SEQ ID NO:158 (AAB46763.1) | QQNNEDPFT | Anti-VA |
| SEQ ID NO:150 (AAS01840.1) | QQYNSYPYT | Anti-NA |
| CONSERVED RESIDUES SEQ ID NO:171 | QQ-N--P-- | - |

Consensus sequence

IgG CDR-L3   Q-Q-x-N-x-x-P-x-x

General formula

IgG CDR-L3   Q-Q-[GNSTY]-N-[TES]-[FDWY]-P-[TYRF]-[FT]

Conserved and predominant residues

IgG CDR-L3   Q-Q-N-N-E-D-P-[YR]-T

SEQUENCE LISTING

<160> NUMBER OF SEQ ID NOS: 202

<210> SEQ ID NO 1
<211> LENGTH: 448
<212> TYPE: DNA
<213> ORGANISM: Mus musculus
<220> FEATURE:
<223> OTHER INFORMATION: DNA encoding heavy chain variable

<400> SEQUENCE: 1

```
aatggagctg ggttattctc ttcttggtag caacagctac aggtgtccac tcccaggtcc    60
aactgcagca gcctggggct gagctggtga ggcctggggc ttcagtgaag ctgtcctgca   120
aggcttctgg ctacaccttc accaggaact ggataaactg ggtgaagcag aggcctggac   180
aaggccttga gtggatcgga aatatttatc cttctgatag ttatactaac tacaatcaaa   240
agttcaagga caaggccaca gtgactgtag acaaatcctc cagcacagcc tacatgcagc   300
tcagcagccc gacatctgag gactctgcgg tctattattg tacaagattg aggggttat    360 tacctgacta ctggggccaa ggcaccattc tcacagtctc ctcagagagt cagtccttcc   420
caaatgtctt cccctcgta agcttggg                                        448
```

<210> SEQ ID NO 2
<211> LENGTH: 131
<212> TYPE: PRT
<213> ORGANISM: Mus musculus
<220> FEATURE:
<223> OTHER INFORMATION: Protein heavy chain variable

<400> SEQUENCE: 2

```
Leu Val Ala Thr Ala Thr Gly Val His Ser Gln Val Gln Leu Gln Gln
1               5                   10                  15

Pro Gly Ala Glu Leu Val Arg Pro Gly Ala Ser Val Lys Leu Ser Cys
            20                  25                  30

Lys Ala Ser Gly Tyr Thr Phe Thr Arg Asn Trp Ile Asn Trp Val Lys
        35                  40                  45

Gln Arg Pro Gly Gln Gly Leu Glu Trp Ile Gly Asn Ile Tyr Pro Ser
    50                  55                  60

Asp Ser Tyr Thr Asn Tyr Asn Gln Lys Phe Lys Asp Lys Ala Thr Val
65                  70                  75                  80

Thr Val Asp Lys Ser Ser Ser Thr Ala Tyr Met Gln Leu Ser Ser Pro
                85                  90                  95

Thr Ser Glu Asp Ser Ala Val Tyr Tyr Cys Thr Arg Leu Arg Gly Leu
            100                 105                 110

Leu Pro Asp Tyr Trp Gly Gln Gly Thr Ile Leu Thr Val Ser Ser Glu
        115                 120                 125

Ser Gln Ser
    130
```

<210> SEQ ID NO 3
<211> LENGTH: 440
<212> TYPE: DNA
<213> ORGANISM: Mus musculus
<220> FEATURE:
<223> OTHER INFORMATION: DNA encoding light chain variable

<400> SEQUENCE: 3

```
gggaattcat ggagtcacag acccaggtct tgtatacat gttgctgtgg ttgtctggtg     60
ttgatggaga cattgtgatg acccagtctc aaaaattcat gtccacatca gtaggagaca   120
```

```
gggtcagcgt cacctgcaag gccagtcaga atgtggatac taatgtagcc tggtatcaac    180
agaaaccagg gcaatctcct aaagcactga tttactcggc atcctaccgg tacagtggag    240
tccctgatcg cttcacaggc agtggatctg gacagattt cactctcacc atcagcaatg     300
tgcagtctga agacttggca gagtatttct gtcagcaata taacagctat cctctcacgt    360
tcggtgctgg gaccaagctg gagctgaaac gggctgatgc tgcaccaact gtatccatct    420
tcccaccatc cagtaagctt                                                440

<210> SEQ ID NO 4
<211> LENGTH: 127
<212> TYPE: PRT
<213> ORGANISM: Mus musculus
<220> FEATURE:
<223> OTHER INFORMATION: Protein light chain variable

<400> SEQUENCE: 4

Val Tyr Met Leu Leu Trp Leu Ser Gly Val Asp Gly Asp Ile Val Met
1               5                   10                  15

Thr Gln Ser Gln Lys Phe Met Ser Thr Ser Val Gly Asp Arg Val Ser
            20                  25                  30

Val Thr Cys Lys Ala Ser Gln Asn Val Asp Thr Asn Val Ala Trp Tyr
        35                  40                  45

Gln Gln Lys Pro Gly Gln Ser Pro Lys Ala Leu Ile Tyr Ser Ala Ser
    50                  55                  60

Tyr Arg Tyr Ser Gly Val Pro Asp Arg Phe Thr Gly Ser Gly Ser Gly
65                  70                  75                  80

Thr Asp Phe Thr Leu Thr Ile Ser Asn Val Gln Ser Glu Asp Leu Ala
                85                  90                  95

Glu Tyr Phe Cys Gln Gln Tyr Asn Ser Tyr Pro Leu Thr Phe Gly Ala
            100                 105                 110

Gly Thr Lys Leu Glu Leu Lys Arg Ala Asp Ala Ala Pro Thr Val
        115                 120                 125

<210> SEQ ID NO 5
<211> LENGTH: 33
<212> TYPE: DNA
<213> ORGANISM: Mus musculus
<220> FEATURE:
<223> OTHER INFORMATION: DNA Heavy chain HV1

<400> SEQUENCE: 5
ggctacacct tcaccaggaa ctggataaac tgg                                 33

<210> SEQ ID NO 6
<211> LENGTH: 11
<212> TYPE: PRT
<213> ORGANISM: Mus musculus
<220> FEATURE:
<223> OTHER INFORMATION: Protein Heavy chain HV1

<400> SEQUENCE: 6

Gly Tyr Thr Phe Thr Arg Asn Trp Ile Asn Trp
1               5                   10

<210> SEQ ID NO 7
<211> LENGTH: 51
<212> TYPE: DNA
<213> ORGANISM: Mus musculus
<220> FEATURE:
<223> OTHER INFORMATION: DNA Heavy chain HV2
```

-continued

<400> SEQUENCE: 7
aatatttatc cttctgatag ttatactaac tacaatcaaa agttcaagga c    51

<210> SEQ ID NO 8
<211> LENGTH: 17
<212> TYPE: PRT
<213> ORGANISM: Mus musculus
<220> FEATURE:
<223> OTHER INFORMATION: Protein Heavy chain HV2

<400> SEQUENCE: 8

Asn Ile Tyr Pro Ser Asp Ser Tyr Thr Asn Tyr Asn Gln Lys Phe Lys
1               5                   10                  15
Asp

<210> SEQ ID NO 9
<211> LENGTH: 24
<212> TYPE: DNA
<213> ORGANISM: Mus musculus
<220> FEATURE:
<223> OTHER INFORMATION: DNA Heavy Chain HV3

<400> SEQUENCE: 9
ttgaggggtt tattacctga ctac    24

<210> SEQ ID NO 10
<211> LENGTH: 8
<212> TYPE: PRT
<213> ORGANISM: Mus musculus
<220> FEATURE:
<223> OTHER INFORMATION: Protein Heavy Chain HV3

<400> SEQUENCE: 10

Leu Arg Gly Leu Leu Pro Asp Tyr
1               5

<210> SEQ ID NO 11
<211> LENGTH: 33
<212> TYPE: DNA
<213> ORGANISM: Mus musculus
<220> FEATURE:
<223> OTHER INFORMATION: DNA Light Chain HV1

<400> SEQUENCE: 11
aaggccagtc agaatgtgga tactaatgta gcc    33

<210> SEQ ID NO 12
<211> LENGTH: 11
<212> TYPE: PRT
<213> ORGANISM: Mus musculus
<220> FEATURE:
<223> OTHER INFORMATION: Protein Light Chain HV1

<400> SEQUENCE: 12

Lys Ala Ser Gln Asn Val Asp Thr Asn Val Ala
1               5                   10

<210> SEQ ID NO 13
<211> LENGTH: 21
<212> TYPE: DNA
<213> ORGANISM: Mus musculus
<220> FEATURE:
<223> OTHER INFORMATION: DNA Light chain HV2

<400> SEQUENCE: 13

```
tcggcatcct accggtacag t                                              21
```

<210> SEQ ID NO 14
<211> LENGTH: 7
<212> TYPE: PRT
<213> ORGANISM: Mus musculus
<220> FEATURE:
<223> OTHER INFORMATION: Protein Light chain HV2

<400> SEQUENCE: 14

Ser Ala Ser Tyr Arg Tyr Ser
1               5

<210> SEQ ID NO 15
<211> LENGTH: 27
<212> TYPE: DNA
<213> ORGANISM: Mus musculus
<220> FEATURE:
<223> OTHER INFORMATION: DNA Light chain HV3

<400> SEQUENCE: 15

```
cagcaatata acagctatcc tctcacg                                        27
```

<210> SEQ ID NO 16
<211> LENGTH: 9
<212> TYPE: PRT
<213> ORGANISM: Mus musculus
<220> FEATURE:
<223> OTHER INFORMATION: Protein Light chain HV3

<400> SEQUENCE: 16

Gln Gln Tyr Asn Ser Tyr Pro Leu Thr
1               5

<210> SEQ ID NO 17
<211> LENGTH: 359
<212> TYPE: DNA
<213> ORGANISM: Mus musculus
<220> FEATURE:
<223> OTHER INFORMATION: Cell line 13.42a VH-1 DNA Sequence

<400> SEQUENCE: 17

```
aggtcaagct gcaggagtca ggacctgagc tggtgaagcc tggggcttca gtgaaggtat    60
cctgcaaggc ttctggttat gcattcacta gctacaacat gttctgggtg aagcagagcc   120
atggaaagag ccttgagtgg attggatata ttgatcctta caatggtgat actagataca   180
gccagaagtt caagggcaag gccacattga ctgttgacaa gtcctccagc acagcctaca   240
tgcatctcaa cagcctgaca tctgaagact ctgcagtcta ttactgtgca agaaagggga   300
tgacgacggg ctatgctatg gactactggg gccaaggac cacggtcacc gtctcctca    359
```

<210> SEQ ID NO 18
<211> LENGTH: 119
<212> TYPE: PRT
<213> ORGANISM: Mus musculus
<220> FEATURE:
<223> OTHER INFORMATION: Cell line 13.42a VH-1 Amino Acid Sequence

<400> SEQUENCE: 18

Val Lys Leu Gln Glu Ser Gly Pro Glu Leu Val Lys Pro Gly Ala Ser
1               5                   10                  15

Val Lys Val Ser Cys Lys Ala Ser Gly Tyr Ala Phe Thr Ser Tyr Asn
            20                  25                  30

Met Phe Trp Val Lys Gln Ser His Gly Lys Ser Leu Glu Trp Ile Gly

```
                35                  40                  45
Tyr Ile Asp Pro Tyr Asn Gly Asp Thr Arg Tyr Ser Gln Lys Phe Lys
            50                  55                  60

Gly Lys Ala Thr Leu Thr Val Asp Lys Ser Ser Ser Thr Ala Tyr Met
 65                  70                  75                  80

His Leu Asn Ser Leu Thr Ser Glu Asp Ser Ala Val Tyr Tyr Cys Ala
                 85                  90                  95

Arg Lys Gly Met Thr Thr Gly Tyr Ala Met Asp Tyr Trp Gly Gln Gly
            100                 105                 110

Thr Thr Val Thr Val Ser Ser
        115

<210> SEQ ID NO 19
<211> LENGTH: 321
<212> TYPE: DNA
<213> ORGANISM: Mus musculus
<220> FEATURE:
<223> OTHER INFORMATION: Cell line 13.42a VL DNA sequence

<400> SEQUENCE: 19
gacatccaga tgactcagtc tccatcctcc ctgtctgcct ctctgggaga cagagtcacc     60
atcagttgta gggcaagtca ggacattagt aattatttaa actggtatca gcagaaacca    120
gatggaactg ttaaactcct gctctactac acatcaagat tacactcagg agtcccatca    180
aggttcagtg gcagtgggtc tggaacagat tattctctca ccattagcaa cctggaacaa    240
gaagatgttg ccacttactt ttgccaacag ggtaatacgt ttccgacgtt cggtggaggc    300
accaagctgg aaatcaaacg g                                              321

<210> SEQ ID NO 20
<211> LENGTH: 107
<212> TYPE: PRT
<213> ORGANISM: Mus musculus
<220> FEATURE:
<223> OTHER INFORMATION: Cell line 13.42a VL Amino acid sequence

<400> SEQUENCE: 20

Asp Ile Gln Met Thr Gln Ser Pro Ser Ser Leu Ser Ala Ser Leu Gly
  1               5                  10                  15

Asp Arg Val Thr Ile Ser Cys Arg Ala Ser Gln Asp Ile Ser Asn Tyr
             20                  25                  30

Leu Asn Trp Tyr Gln Gln Lys Pro Asp Gly Thr Val Lys Leu Leu Leu
         35                  40                  45

Tyr Tyr Thr Ser Arg Leu His Ser Gly Val Pro Ser Arg Phe Ser Gly
     50                  55                  60

Ser Gly Ser Gly Thr Asp Tyr Ser Leu Thr Ile Ser Asn Leu Glu Gln
 65                  70                  75                  80

Glu Asp Val Ala Thr Tyr Phe Cys Gln Gln Gly Asn Thr Phe Pro Thr
                 85                  90                  95

Phe Gly Gly Gly Thr Lys Leu Glu Ile Lys Arg
            100                 105

<210> SEQ ID NO 21
<211> LENGTH: 33
<212> TYPE: DNA
<213> ORGANISM: Mus musculus
<220> FEATURE:
<223> OTHER INFORMATION: Cell line 13.42a DNA Heavy chain HV1

<400> SEQUENCE: 21
```
ggttatgcat tcactagcta caacatgttc tgg                        33

<210> SEQ ID NO 22
<211> LENGTH: 11
<212> TYPE: PRT
<213> ORGANISM: Mus musculus
<220> FEATURE:
<223> OTHER INFORMATION: Cell line 13.42a Protein Heavy chain HV1

<400> SEQUENCE: 22

Gly Tyr Ala Phe Thr Ser Tyr Asn Met Phe Trp
1               5                   10

<210> SEQ ID NO 23
<211> LENGTH: 51
<212> TYPE: DNA
<213> ORGANISM: Mus musculus
<220> FEATURE:
<223> OTHER INFORMATION: Cell line 13.42a DNA Heavy chain HV2

<400> SEQUENCE: 23
tatattgatc cttacaatgg tgatactaga tacagccaga agttcaaggg c     51

<210> SEQ ID NO 24
<211> LENGTH: 17
<212> TYPE: PRT
<213> ORGANISM: Mus musculus
<220> FEATURE:
<223> OTHER INFORMATION: Cell line 13.42a Protein Heavy chain HV2

<400> SEQUENCE: 24

Tyr Ile Asp Pro Tyr Asn Gly Asp Thr Arg Tyr Ser Gln Lys Phe Lys
1               5                   10                  15

Gly

<210> SEQ ID NO 25
<211> LENGTH: 24
<212> TYPE: DNA
<213> ORGANISM: Mus musculus
<220> FEATURE:
<223> OTHER INFORMATION: Cell line 13.42a DNA Heavy chain HV3

<400> SEQUENCE: 25
aaggggatga cgacgggcta tgct                                  24

<210> SEQ ID NO 26
<211> LENGTH: 8
<212> TYPE: PRT
<213> ORGANISM: Mus musculus
<220> FEATURE:
<223> OTHER INFORMATION: Cell line 13.42a Protein Heavy Chain HV3

<400> SEQUENCE: 26

Lys Gly Met Thr Thr Gly Tyr Ala
1               5

<210> SEQ ID NO 27
<211> LENGTH: 33
<212> TYPE: DNA
<213> ORGANISM: Mus musculus
<220> FEATURE:
<223> OTHER INFORMATION: Cell line 13.42a DNA Light Chain HV1

<400> SEQUENCE: 27
agggcaagtc aggacattag taattattta aac                        33

<210> SEQ ID NO 28
<211> LENGTH: 11
<212> TYPE: PRT
<213> ORGANISM: Mus musculus
<220> FEATURE:
<223> OTHER INFORMATION: Cell line 13.42a Protein Light Chain HV1

<400> SEQUENCE: 28

Arg Ala Ser Gln Asp Ile Ser Asn Tyr Leu Asn
1               5                   10

<210> SEQ ID NO 29
<211> LENGTH: 21
<212> TYPE: DNA
<213> ORGANISM: Mus musculus
<220> FEATURE:
<223> OTHER INFORMATION: Cell line 13.42a DNA Light chain HV2

<400> SEQUENCE: 29
tacacatcaa gattacactc a                                              21

<210> SEQ ID NO 30
<211> LENGTH: 7
<212> TYPE: PRT
<213> ORGANISM: Mus musculus
<220> FEATURE:
<223> OTHER INFORMATION: Cell line 13.42a Protein Light chain HV2

<400> SEQUENCE: 30

Tyr Thr Ser Arg Leu His Ser
1               5

<210> SEQ ID NO 31
<211> LENGTH: 27
<212> TYPE: DNA
<213> ORGANISM: Mus musculus
<220> FEATURE:
<223> OTHER INFORMATION: Cell line 13.42a DNA Light chain HV3

<400> SEQUENCE: 31
caacagggta atacgtttcc gacgttc                                        27

<210> SEQ ID NO 32
<211> LENGTH: 9
<212> TYPE: PRT
<213> ORGANISM: Mus musculus
<220> FEATURE:
<223> OTHER INFORMATION: Cell line 13.42a Protein Light chain HV3

<400> SEQUENCE: 32

Gln Gln Gly Asn Thr Phe Pro Thr Phe
1               5

<210> SEQ ID NO 33
<211> LENGTH: 356
<212> TYPE: DNA
<213> ORGANISM: Mus musculus
<220> FEATURE:
<223> OTHER INFORMATION: Cell line 32.15 VH DNA sequence

<400> SEQUENCE: 33
aggtgcaact gcaggagtct ggacctgagc tgaagaagcc tggagagaca gtcaagatct    60
cctgcaaggc ttctgggtat accttcacaa actatggaat gaactgggtg aagcaggctc   120
caggaaaggg tttaaagtgg atgggctgga taaacaccta cactggagag ccaacatatg   180

```
ctgatgactt caagggacgg tttgccttct ctttggaaac ctctgccagc actgcctatt    240
tgcagatcaa caacctcaaa aatgaggaca cggctacata tttctgtgca agggaagggt    300
tgtatggtaa ctactttgac tactggggcc aagggaccac ggtcaccgtc tcctca        356
```

```
<210> SEQ ID NO 34
<211> LENGTH: 118
<212> TYPE: PRT
<213> ORGANISM: Mus musculus
<220> FEATURE:
<223> OTHER INFORMATION: Cell line 32.15 VH Amino acid sequence

<400> SEQUENCE: 34

Val Gln Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Ala Asp Asp Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Glu Gly Leu Tyr Gly Asn Tyr Phe Asp Tyr Trp Gly Gln Gly Thr
            100                 105                 110

Thr Val Thr Val Ser Ser
        115
```

```
<210> SEQ ID NO 35
<211> LENGTH: 324
<212> TYPE: DNA
<213> ORGANISM: Mus musculus
<220> FEATURE:
<223> OTHER INFORMATION: Cell line 32.15 VL DNA sequence

<400> SEQUENCE: 35
gacatccaga tgacacagtc tccaaaattc atgtccacat cagtaggaga cagggtcagc    60
gtcacctgca aggccagtca gaatgtgggt actaatgtag cctggtatca acagaaacca    120
gggcaatctc ctaaagcact gatttactcg gcatcctacc ggtacagtgg agtccctgat    180
cgcttcacag gcagtggatc tgggacagat ttcactctca ccatcagcaa tgtgcagtct    240
gaagacttgg cagagtattt ctgtcagcaa tataacagct atcctctcac gttcggtgct    300
gggaccaagc tggagctgaa acgg                                          324
```

```
<210> SEQ ID NO 36
<211> LENGTH: 108
<212> TYPE: PRT
<213> ORGANISM: Mus musculus
<220> FEATURE:
<223> OTHER INFORMATION: Cell line 32.15 VL Amino acid sequence

<400> SEQUENCE: 36

Asp Ile Gln Met Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30
```

```
Val Ala Trp Tyr Gln Gln Lys Pro Gly Gln Ser Pro Lys Ala Leu Ile
            35                  40                  45

Tyr Ser Ala Ser Tyr Arg Tyr Ser Gly Val Pro Asp Arg Phe Thr Gly
 50                  55                  60

Ser Gly Ser Gly Thr Asp Phe Thr Leu Thr Ile Ser Asn Val Gln Ser
 65                  70                  75                  80

Glu Asp Leu Ala Glu Tyr Phe Cys Gln Gln Tyr Asn Ser Tyr Pro Leu
                85                  90                  95

Thr Phe Gly Ala Gly Thr Lys Leu Glu Leu Lys Arg
            100                 105
```

```
<210> SEQ ID NO 37
<211> LENGTH: 33
<212> TYPE: DNA
<213> ORGANISM: Mus musculus
<220> FEATURE:
<223> OTHER INFORMATION: Cell line 32.15 DNA Heavy chain HV1

<400> SEQUENCE: 37
gggtatacct tcacaaacta tggaatgaac tgg                              33

<210> SEQ ID NO 38
<211> LENGTH: 11
<212> TYPE: PRT
<213> ORGANISM: Mus musculus
<220> FEATURE:
<223> OTHER INFORMATION: Cell line 32.15 Protein Heavy chain HV1

<400> SEQUENCE: 38

Gly Tyr Thr Phe Thr Asn Tyr Gly Met Asn Trp
 1               5                   10

<210> SEQ ID NO 39
<211> LENGTH: 51
<212> TYPE: DNA
<213> ORGANISM: Mus musculus
<220> FEATURE:
<223> OTHER INFORMATION: Cell line 32.15 DNA Heavy chain HV2

<400> SEQUENCE: 39
tggataaaca cctacactgg agagccaaca tatgctgatg acttcaaggg a           51

<210> SEQ ID NO 40
<211> LENGTH: 17
<212> TYPE: PRT
<213> ORGANISM: Mus musculus
<220> FEATURE:
<223> OTHER INFORMATION: Cell line 32.15 Protein Heavy chain HV2

<400> SEQUENCE: 40

Trp Ile Asn Thr Tyr Thr Gly Glu Pro Thr Tyr Ala Asp Asp Phe Lys
 1               5                   10                  15

Gly

<210> SEQ ID NO 41
<211> LENGTH: 24
<212> TYPE: DNA
<213> ORGANISM: Mus musculus
<220> FEATURE:
<223> OTHER INFORMATION: Cell line 32.15 DNA Heavy Chain HV3

<400> SEQUENCE: 41
gaagggttgt atggtaacta cttt                                        24
```

```
<210> SEQ ID NO 42
<211> LENGTH: 8
<212> TYPE: PRT
<213> ORGANISM: Mus musculus
<220> FEATURE:
<223> OTHER INFORMATION: Cell line 32.15 Protein Heavy Chain HV3

<400> SEQUENCE: 42

Glu Gly Leu Tyr Gly Asn Tyr Phe
1               5

<210> SEQ ID NO 43
<211> LENGTH: 33
<212> TYPE: DNA
<213> ORGANISM: Mus musculus
<220> FEATURE:
<223> OTHER INFORMATION: Cell line 32.15 DNA Light Chain HV1

<400> SEQUENCE: 43
aaggccagtc agaatgtggg tactaatgta gcc                                33

<210> SEQ ID NO 44
<211> LENGTH: 11
<212> TYPE: PRT
<213> ORGANISM: Mus musculus
<220> FEATURE:
<223> OTHER INFORMATION: Cell line 32.15 Protein Light Chain HV1

<400> SEQUENCE: 44

Lys Ala Ser Gln Asn Val Gly Thr Asn Val Ala
1               5                   10

<210> SEQ ID NO 45
<211> LENGTH: 21
<212> TYPE: DNA
<213> ORGANISM: Mus musculus
<220> FEATURE:
<223> OTHER INFORMATION: Cell line 32.15 DNA Light chain HV2

<400> SEQUENCE: 45
tcggcatcct accggtacag t                                             21

<210> SEQ ID NO 46
<211> LENGTH: 7
<212> TYPE: PRT
<213> ORGANISM: Mus musculus
<220> FEATURE:
<223> OTHER INFORMATION: Cell line 32.15 Protein Light chain HV2

<400> SEQUENCE: 46

Ser Ala Ser Tyr Arg Tyr Ser
1               5

<210> SEQ ID NO 47
<211> LENGTH: 27
<212> TYPE: DNA
<213> ORGANISM: Mus musculus
<220> FEATURE:
<223> OTHER INFORMATION: Cell line 32.15 DNA Light chain HV3

<400> SEQUENCE: 47
cagcaatata acagctatcc tctcacg                                       27

<210> SEQ ID NO 48
<211> LENGTH: 9
<212> TYPE: PRT
```

<213> ORGANISM: Mus musculus
<220> FEATURE:
<223> OTHER INFORMATION: Cell line 32.15 Protein Light chain HV3

<400> SEQUENCE: 48

Gln Gln Tyr Asn Ser Tyr Pro Leu Thr
1               5

<210> SEQ ID NO 49
<211> LENGTH: 350
<212> TYPE: DNA
<213> ORGANISM: Mus musculus
<220> FEATURE:
<223> OTHER INFORMATION: Cell line 32.17 VH DNA sequence

<400> SEQUENCE: 49
aggtcaaact gcaggagtca ggggctgagc tggtgaggcc tggggcttca gtgaagctgt      60
cctgcaaggc ttctggctac accttcacca ggaactggat aaactgggtg aagcagaggc     120
ctggacaagg ccttgagtgg atcggaaata tttatccttc tgatagttat actaactaca     180
atcaaaagtt caaggacaag gccacagtga ctgtagacaa atcctccagc acagcctaca     240
tgcagctcag cagcccgaca tctgaggact ctgcggtcta ttattgtaca agattgaggg     300
gtttattacc tgactactgg ggccaaggga ccacggtcac cgtctcctca                350

<210> SEQ ID NO 50
<211> LENGTH: 116
<212> TYPE: PRT
<213> ORGANISM: Mus musculus
<220> FEATURE:
<223> OTHER INFORMATION: Cell line 32.17 VH Amino acid sequence

<400> SEQUENCE: 50

Val Lys Leu Gln Glu Ser Gly Ala Glu Leu Val Arg Pro Gly Ala Ser
1               5                   10                  15

Val Lys Leu Ser Cys Lys Ala Ser Gly Tyr Thr Phe Thr Arg Asn Trp
            20                  25                  30

Ile Asn Trp Val Lys Gln Arg Pro Gly Gln Gly Leu Glu Trp Ile Gly
        35                  40                  45

Asn Ile Tyr Pro Ser Asp Ser Tyr Thr Asn Tyr Asn Gln Lys Phe Lys
    50                  55                  60

Asp Lys Ala Thr Val Thr Val Asp Lys Ser Ser Ser Thr Ala Tyr Met
65                  70                  75                  80

Gln Leu Ser Ser Pro Thr Ser Glu Asp Ser Ala Val Tyr Tyr Cys Thr
                85                  90                  95

Arg Leu Arg Gly Leu Leu Pro Asp Tyr Trp Gly Gln Gly Thr Thr Val
            100                 105                 110

Thr Val Ser Ser
        115

<210> SEQ ID NO 51
<211> LENGTH: 327
<212> TYPE: DNA
<213> ORGANISM: Mus musculus
<220> FEATURE:
<223> OTHER INFORMATION: Cell line 32.17 VL DNA sequence

<400> SEQUENCE: 51
gacattgtgc taacccaatc tccagtatcc ataactgcat ctcgagggga gaaggtcacc      60
atcacctgcc gtgccagctc aagtataagt tccaattact acactgttta ccagcagaag     120

```
ccaggatcct ccccctaaact tttgatttat aggacatcca tcctggcatc tggagtccta    180
gacagcttca gtggcagtgg gtctgagagc tcttacactc tgacaatcag ctgcatgcag    240
gacgaagttg ctgccactta ctattgtcag caggggagta gtagcccct cacgttcggt    300 gctgggacca agctggagct gaaacgg                                         327
```

<210> SEQ ID NO 52
<211> LENGTH: 109
<212> TYPE: PRT
<213> ORGANISM: Mus musculus
<220> FEATURE:
<223> OTHER INFORMATION: Cell line 32.17 VL Amino acid sequence

<400> SEQUENCE: 52

```
Asp Ile Val Leu Thr Gln Ser Pro Val Ser Ile Thr Ala Ser Arg Gly
1               5                   10                  15

Glu Lys Val Thr Ile Thr Cys Arg Ala Ser Ser Ser Ile Ser Ser Asn
            20                  25                  30

Tyr Leu His Cys Tyr Gln Gln Lys Pro Gly Ser Ser Pro Lys Leu Leu
        35                  40                  45

Ile Tyr Arg Thr Ser Ile Leu Ala Ser Gly Val Leu Asp Ser Phe Ser
    50                  55                  60

Gly Ser Gly Ser Glu Ser Ser Tyr Thr Leu Thr Ile Ser Cys Met Gln
65                  70                  75                  80

Asp Glu Val Ala Ala Thr Tyr Tyr Cys Gln Gln Gly Ser Ser Ser Pro
                85                  90                  95

Leu Thr Phe Gly Ala Gly Thr Lys Leu Glu Leu Lys Arg
            100                 105
```

<210> SEQ ID NO 53
<211> LENGTH: 30
<212> TYPE: DNA
<213> ORGANISM: Mus musculus
<220> FEATURE:
<223> OTHER INFORMATION: Cell line 32.17 DNA Heavy chain HV1

<400> SEQUENCE: 53

```
ggctacacct tcaccaggaa ctggataaac                                       30
```

<210> SEQ ID NO 54
<211> LENGTH: 11
<212> TYPE: PRT
<213> ORGANISM: Mus musculus
<220> FEATURE:
<223> OTHER INFORMATION: Cell line 32.17 Protein Heavy chain HV1

<400> SEQUENCE: 54

```
Gly Tyr Thr Phe Thr Arg Asn Trp Ile Asn Trp
1               5                   10
```

<210> SEQ ID NO 55
<211> LENGTH: 51
<212> TYPE: DNA
<213> ORGANISM: Mus musculus
<220> FEATURE:
<223> OTHER INFORMATION: Cell line 32.17 DNA Heavy chain HV2

<400> SEQUENCE: 55

```
aatatttatc cttctgatag ttatactaac tacaatcaaa agttcaagga c              51
```

<210> SEQ ID NO 56
<211> LENGTH: 17

```
<212> TYPE: PRT
<213> ORGANISM: Mus musculus
<220> FEATURE:
<223> OTHER INFORMATION: Cell line 32.17 Protein Heavy chain HV2

<400> SEQUENCE: 56

Asn Ile Tyr Pro Ser Asp Ser Tyr Thr Asn Tyr Asn Gln Lys Phe Lys
1               5                   10                  15

Asp

<210> SEQ ID NO 57
<211> LENGTH: 24
<212> TYPE: DNA
<213> ORGANISM: Mus musculus
<220> FEATURE:
<223> OTHER INFORMATION: Cell line 32.17 DNA Heavy Chain HV3

<400> SEQUENCE: 57
ttgaggggtt tattacctga ctac                                          24

<210> SEQ ID NO 58
<211> LENGTH: 8
<212> TYPE: PRT
<213> ORGANISM: Mus musculus
<220> FEATURE:
<223> OTHER INFORMATION: Cell line 32.17 Protein Heavy Chain HV3

<400> SEQUENCE: 58

Leu Arg Gly Leu Leu Pro Asp Tyr
1               5

<210> SEQ ID NO 59
<211> LENGTH: 42
<212> TYPE: DNA
<213> ORGANISM: Mus musculus
<220> FEATURE:
<223> OTHER INFORMATION: Cell line 32.17 DNA Light Chain HV1

<400> SEQUENCE: 59
atcacctgcc gtgccagctc aagtataagt tccaattact ta                      42

<210> SEQ ID NO 60
<211> LENGTH: 11
<212> TYPE: PRT
<213> ORGANISM: Mus musculus
<220> FEATURE:
<223> OTHER INFORMATION: Cell line 32.17 Protein Light Chain HV1

<400> SEQUENCE: 60

Arg Ala Ser Ser Ser Ile Ser Ser Asn Tyr Leu
1               5                   10

<210> SEQ ID NO 61
<211> LENGTH: 21
<212> TYPE: DNA
<213> ORGANISM: Mus musculus
<220> FEATURE:
<223> OTHER INFORMATION: Cell line 32.17 DNA Light chain HV2

<400> SEQUENCE: 61
aggacatcca tcctggcatc t                                             21

<210> SEQ ID NO 62
<211> LENGTH: 7
<212> TYPE: PRT
<213> ORGANISM: Mus musculus
```

<220> FEATURE:
<223> OTHER INFORMATION: Cell line 32.17 Protein Light chain HV2

<400> SEQUENCE: 62

Arg Thr Ser Ile Leu Ala Ser
1               5

<210> SEQ ID NO 63
<211> LENGTH: 27
<212> TYPE: DNA
<213> ORGANISM: Mus musculus
<220> FEATURE:
<223> OTHER INFORMATION: Cell line 32.17 DNA Light chain HV3

<400> SEQUENCE: 63
cagcagggga gtagtagccc cctcacg                                          27

<210> SEQ ID NO 64
<211> LENGTH: 9
<212> TYPE: PRT
<213> ORGANISM: Mus musculus
<220> FEATURE:
<223> OTHER INFORMATION: Cell line 32.17 Protein Light chain HV3

<400> SEQUENCE: 64

Gln Gln Gly Ser Ser Ser Pro Leu Thr
1               5

<210> SEQ ID NO 65
<211> LENGTH: 350
<212> TYPE: DNA
<213> ORGANISM: Mus musculus
<220> FEATURE:
<223> OTHER INFORMATION: Cell line 32.75 VH DNA sequence

<400> SEQUENCE: 65
aggtcaaact gcaggagtca ggggctgagc tggtgaggcc tggggcttca gtgaagctgt      60
cctgcaaggc ttctggctac accttcacca ggaactggat aaactgggtg aagcagaggc    120
ctggacaagg ccttgagtgg atcggaaata tttatccttc tgatagttat actaactaca    180
atcaaaagtt caaggacaag gccacagtga ctgtagacaa atcctccagc acagcctaca    240
tgcagctcag cagcccgaca tctgaggact ctgcggtcta ttattgtaca agattgaggg    300
gtttattacc tgactactgg ggccaaggga ccacggtcac cgtctcctca                350

<210> SEQ ID NO 66
<211> LENGTH: 116
<212> TYPE: PRT
<213> ORGANISM: Mus musculus
<220> FEATURE:
<223> OTHER INFORMATION: Cell line 32.75 VH Amino acid sequence

<400> SEQUENCE: 66

Val Lys Leu Gln Glu Ser Gly Ala Glu Leu Val Arg Pro Gly Ala Ser
1               5                   10                  15

Val Lys Leu Ser Cys Lys Ala Ser Gly Tyr Thr Phe Thr Arg Asn Trp
                20                  25                  30

Ile Asn Trp Val Lys Gln Arg Pro Gly Gln Gly Leu Glu Trp Ile Gly
            35                  40                  45

Asn Ile Tyr Pro Ser Asp Ser Tyr Thr Asn Tyr Asn Gln Lys Phe Lys
        50                  55                  60

Asp Lys Ala Thr Val Thr Val Asp Lys Ser Ser Ser Thr Ala Tyr Met
65                  70                  75                  80

```
Gln Leu Ser Ser Pro Thr Ser Glu Asp Ser Ala Val Tyr Tyr Cys Thr
                85                  90                  95

Arg Leu Arg Gly Leu Leu Pro Asp Tyr Trp Gly Gln Gly Thr Thr Val
            100                 105                 110

Thr Val Ser Ser
        115

<210> SEQ ID NO 67
<211> LENGTH: 324
<212> TYPE: DNA
<213> ORGANISM: Mus musculus
<220> FEATURE:
<223> OTHER INFORMATION: Cell line 32.75 VL DNA sequence

<400> SEQUENCE: 67
gacatccaga tgacacagtc tccaaaattc atgtccacat cagtaggaga cagggtcagc    60
gtcacctgca aggccagtca gaatgtggat actaatgtag cctggtatca acagaaacca   120
gggcaatctc ctaaagcact gatttactcg gcatcctacc ggtacagtgg agtccctgat   180
cgcttcacag gcagtggatc tgggacagat ttcactctca ccatcagcaa tgtgcagtct   240
gaagacttgg cagagtattt ctgtcagcaa tataacagct atcctcctac gttcggtgct   300
gggaccaagc tggagctgaa acgg                                          324

<210> SEQ ID NO 68
<211> LENGTH: 108
<212> TYPE: PRT
<213> ORGANISM: Mus musculus
<220> FEATURE:
<223> OTHER INFORMATION: Cell line 32.75 VL Amino acid sequence

<400> SEQUENCE: 68

Asp Ile Gln Met Thr Gln Ser Pro Lys Phe Met Ser Thr Ser Val Gly
1               5                   10                  15

Asp Arg Val Ser Val Thr Cys Lys Ala Ser Gln Asn Val Asp Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro Pro
                85                  90                  95

Thr Phe Gly Ala Gly Thr Lys Leu Glu Leu Lys Arg
            100                 105

<210> SEQ ID NO 69
<211> LENGTH: 33
<212> TYPE: DNA
<213> ORGANISM: Mus musculus
<220> FEATURE:
<223> OTHER INFORMATION: Cell line 32.75 DNA Heavy chain HV1

<400> SEQUENCE: 69
ggctacacct tcaccaggaa ctggataaac tgg                                 33

<210> SEQ ID NO 70
<211> LENGTH: 11
<212> TYPE: PRT
```

```
<213> ORGANISM: Mus musculus
<220> FEATURE:
<223> OTHER INFORMATION: Cell line 32.75 Protein Heavy chain HV1

<400> SEQUENCE: 70

Gly Tyr Thr Phe Thr Arg Asn Trp Ile Asn Trp
1               5                   10

<210> SEQ ID NO 71
<211> LENGTH: 51
<212> TYPE: DNA
<213> ORGANISM: Mus musculus
<220> FEATURE:
<223> OTHER INFORMATION: Cell line 32.75 DNA Heavy chain HV2

<400> SEQUENCE: 71
aatatttatc cttctgatag ttatactaac tacaatcaaa agttcaagga c          51

<210> SEQ ID NO 72
<211> LENGTH: 17
<212> TYPE: PRT
<213> ORGANISM: Mus musculus
<220> FEATURE:
<223> OTHER INFORMATION: Cell line 32.75 Protein Heavy chain HV2

<400> SEQUENCE: 72

Asn Ile Tyr Pro Ser Asp Ser Tyr Thr Asn Tyr Asn Gln Lys Phe Lys
1               5                   10                  15

Asp

<210> SEQ ID NO 73
<211> LENGTH: 24
<212> TYPE: DNA
<213> ORGANISM: Mus musculus
<220> FEATURE:
<223> OTHER INFORMATION: Cell line 32.75 DNA Heavy Chain HV3

<400> SEQUENCE: 73
ttgaggggtt tattacctga ctac                                        24

<210> SEQ ID NO 74
<211> LENGTH: 8
<212> TYPE: PRT
<213> ORGANISM: Mus musculus
<220> FEATURE:
<223> OTHER INFORMATION: Cell line 32.75 Protein Heavy Chain HV3

<400> SEQUENCE: 74

Leu Arg Gly Leu Leu Pro Asp Tyr
1               5

<210> SEQ ID NO 75
<211> LENGTH: 33
<212> TYPE: DNA
<213> ORGANISM: Mus musculus
<220> FEATURE:
<223> OTHER INFORMATION: Cell line 32.75 DNA Light Chain HV1

<400> SEQUENCE: 75
aaggccagtc agaatgtgga tactaatgta gcc                              33

<210> SEQ ID NO 76
<211> LENGTH: 11
<212> TYPE: PRT
<213> ORGANISM: Mus musculus
<220> FEATURE:
```

<223> OTHER INFORMATION: Cell line 32.75 Protein Light Chain HV1

<400> SEQUENCE: 76

Lys Ala Ser Gln Asn Val Asp Thr Asn Val Ala
1               5                   10

<210> SEQ ID NO 77
<211> LENGTH: 21
<212> TYPE: DNA
<213> ORGANISM: Mus musculus
<220> FEATURE:
<223> OTHER INFORMATION: Cell line 32.75 DNA Light chain HV2

<400> SEQUENCE: 77
tcggcatcct accggtacag t                                                    21

<210> SEQ ID NO 78
<211> LENGTH: 7
<212> TYPE: PRT
<213> ORGANISM: Mus musculus
<220> FEATURE:
<223> OTHER INFORMATION: Cell line 32.75 Protein Light chain HV2

<400> SEQUENCE: 78

Ser Ala Ser Tyr Arg Tyr Ser
1               5

<210> SEQ ID NO 79
<211> LENGTH: 27
<212> TYPE: DNA
<213> ORGANISM: Mus musculus
<220> FEATURE:
<223> OTHER INFORMATION: Cell line 32.75 DNA Light chain HV3

<400> SEQUENCE: 79
cagcaatata acagctatcc tcctacg                                              27

<210> SEQ ID NO 80
<211> LENGTH: 9
<212> TYPE: PRT
<213> ORGANISM: Mus musculus
<220> FEATURE:
<223> OTHER INFORMATION: Cell line 32.75 Protein Light chain HV3

<400> SEQUENCE: 80

Gln Gln Tyr Asn Ser Tyr Pro Pro Thr
1               5

<210> SEQ ID NO 81
<211> LENGTH: 356
<212> TYPE: DNA
<213> ORGANISM: Mus musculus
<220> FEATURE:
<223> OTHER INFORMATION: Cell line 32.2 VH-1 DNA sequence

<400> SEQUENCE: 81
aggtgaagct gcaggagtca ggacctgagc tgaagaagcc tggagagaca gtcaagatct          60
cctgcaaggc ttctgggtat accttcacaa actatggaat gaactgggtg aagcaggctc         120
caggaaaggg tttaaagtgg atgggctgga taaacaccta cactggagag ccaacatatg         180
ctgatgactt caagggacgg tttgccttct ctttggaaac ctctgccagc actgcctatt         240
tgcagatcaa caacctcaaa aatgaggaca cggctacata tttctgtgca agggaagggt         300
tgtatggtaa ctactttgac tactggggcc aagggaccac ggtcaccgtc tcctca            356

<210> SEQ ID NO 82
<211> LENGTH: 118
<212> TYPE: PRT
<213> ORGANISM: Mus musculus
<220> FEATURE:
<223> OTHER INFORMATION: Cell line 32.2 VH-1 Amino acid sequence

<400> SEQUENCE: 82

Val Lys Leu Gln Glu Ser Gly Pro Glu Leu Lys Lys Pro Gly Glu Thr
1               5                   10                  15

Val Lys Ile Ser Cys Lys Ala Ser Gly Tyr Thr Phe Thr Asn Tyr Gly
            20                  25                  30

Met Asn Trp Val Lys Gln Ala Pro Gly Lys Gly Leu Lys Trp Met Gly
        35                  40                  45

Trp Ile Asn Thr Tyr Thr Gly Glu Pro Thr Tyr Ala Asp Asp Phe Lys
    50                  55                  60

Gly Arg Phe Ala Phe Ser Leu Glu Thr Ser Ala Ser Thr Ala Tyr Leu
65                  70                  75                  80

Gln Ile Asn Asn Leu Lys Asn Glu Asp Thr Ala Thr Tyr Phe Cys Ala
                85                  90                  95

Arg Glu Gly Leu Tyr Gly Asn Tyr Phe Asp Tyr Trp Gly Gln Gly Thr
            100                 105                 110

Thr Val Thr Val Ser Ser
        115

<210> SEQ ID NO 83
<211> LENGTH: 324
<212> TYPE: DNA
<213> ORGANISM: Mus musculus
<220> FEATURE:
<223> OTHER INFORMATION: Cell line 32.2 VL DNA sequence

<400> SEQUENCE: 83
gacatccaga tgacccagtc tccaaaattc atgtccacat cagtaggaga cagggtcagc        60
gtcacctgca aggccagtca gaatgtgggt actaatgtag cctggtatca acagaaacca       120
gggcaatctc ctaaagcact gatttactcg gcatcctacc ggtacagtgg agtccctgat       180
cgcttcacag gcagtggatc tgggacagat ttcactctca ccatcagcaa tgtgcagtct       240
gaagacttgg cagagtattt ctgtcagcaa tataacagct atcctctcac gttcggtgct       300
gggaccaagc tggaaataaa acgg                                              324

<210> SEQ ID NO 84
<211> LENGTH: 108
<212> TYPE: PRT
<213> ORGANISM: Mus musculus
<220> FEATURE:
<223> OTHER INFORMATION: Cell line 32.2 VL Amino acid sequence

<400> SEQUENCE: 84

Asp Ile Gln Met Thr Gln Ser Pro Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser

```
                65                  70                  75                  80
Glu Asp Leu Ala Glu Tyr Phe Cys Gln Gln Tyr Asn Ser Tyr Pro Leu
                    85                  90                  95

Thr Phe Gly Ala Gly Thr Lys Leu Glu Ile Lys Arg
            100                 105
```

```
<210> SEQ ID NO 85
<211> LENGTH: 33
<212> TYPE: DNA
<213> ORGANISM: Mus musculus
<220> FEATURE:
<223> OTHER INFORMATION: Cell line 32.2 DNA Heavy chain HV1

<400> SEQUENCE: 85
gggtatacct tcacaaacta tggaatgaac tgg                            33

<210> SEQ ID NO 86
<211> LENGTH: 11
<212> TYPE: PRT
<213> ORGANISM: Mus musculus
<220> FEATURE:
<223> OTHER INFORMATION: Cell line 32.2 Protein Heavy chain HV1

<400> SEQUENCE: 86

Gly Tyr Thr Phe Thr Asn Tyr Gly Met Asn Trp
1               5                   10

<210> SEQ ID NO 87
<211> LENGTH: 51
<212> TYPE: DNA
<213> ORGANISM: Mus musculus
<220> FEATURE:
<223> OTHER INFORMATION: Cell line 32.2 DNA Heavy chain HV2

<400> SEQUENCE: 87
tggataaaca cctacactgg agagccaaca tatgctgatg acttcaaggg a         51

<210> SEQ ID NO 88
<211> LENGTH: 17
<212> TYPE: PRT
<213> ORGANISM: Mus musculus
<220> FEATURE:
<223> OTHER INFORMATION: Cell line 32.2 Protein Heavy chain HV2

<400> SEQUENCE: 88

Trp Ile Asn Thr Tyr Thr Gly Glu Pro Thr Tyr Ala Asp Asp Phe Lys
1               5                   10                  15
Gly

<210> SEQ ID NO 89
<211> LENGTH: 24
<212> TYPE: DNA
<213> ORGANISM: Mus musculus
<220> FEATURE:
<223> OTHER INFORMATION: Cell line 32.2 DNA Heavy Chain HV3

<400> SEQUENCE: 89
gaagggttgt atggtaacta cttt                                      24

<210> SEQ ID NO 90
<211> LENGTH: 8
<212> TYPE: PRT
<213> ORGANISM: Mus musculus
<220> FEATURE:
<223> OTHER INFORMATION: Cell line 32.2 Protein Heavy Chain HV3
```

<400> SEQUENCE: 90

Glu Gly Leu Tyr Gly Asn Tyr Phe
1               5

<210> SEQ ID NO 91
<211> LENGTH: 33
<212> TYPE: DNA
<213> ORGANISM: Mus musculus
<220> FEATURE:
<223> OTHER INFORMATION: Cell line 32.2 DNA Light Chain HV1

<400> SEQUENCE: 91
aaggccagtc agaatgtggg tactaatgta gcc                33

<210> SEQ ID NO 92
<211> LENGTH: 11
<212> TYPE: PRT
<213> ORGANISM: Mus musculus
<220> FEATURE:
<223> OTHER INFORMATION: Cell line 32.2 Protein Light Chain HV1

<400> SEQUENCE: 92

Lys Ala Ser Gln Asn Val Gly Thr Asn Val Ala
1               5                   10

<210> SEQ ID NO 93
<211> LENGTH: 21
<212> TYPE: DNA
<213> ORGANISM: Mus musculus
<220> FEATURE:
<223> OTHER INFORMATION: Cell line 32.2 DNA Light chain HV2

<400> SEQUENCE: 93
tcggcatcct accggtacag t                21

<210> SEQ ID NO 94
<211> LENGTH: 7
<212> TYPE: PRT
<213> ORGANISM: Mus musculus
<220> FEATURE:
<223> OTHER INFORMATION: Cell line 32.2 Protein Light chain HV2

<400> SEQUENCE: 94

Ser Ala Ser Tyr Arg Tyr Ser
1               5

<210> SEQ ID NO 95
<211> LENGTH: 27
<212> TYPE: DNA
<213> ORGANISM: Mus musculus
<220> FEATURE:
<223> OTHER INFORMATION: Cell line 32.2 DNA Light chain HV3

<400> SEQUENCE: 95
cagcaatata acagctatcc tctcacg                27

<210> SEQ ID NO 96
<211> LENGTH: 9
<212> TYPE: PRT
<213> ORGANISM: Mus musculus
<220> FEATURE:
<223> OTHER INFORMATION: Cell line 32.2 Protein Light chain HV3

<400> SEQUENCE: 96

Gln Gln Tyr Asn Ser Tyr Pro Leu Thr

```
<210> SEQ ID NO 97
<211> LENGTH: 11
<212> TYPE: PRT
<213> ORGANISM: Mus musculus
<220> FEATURE:
<223> OTHER INFORMATION: A39276 CDR-H1

<400> SEQUENCE: 97

Gly Tyr Thr Phe Thr Asn Phe Trp Ile Gly Trp
1               5                   10

<210> SEQ ID NO 98
<211> LENGTH: 11
<212> TYPE: PRT
<213> ORGANISM: Homo sapiens
<220> FEATURE:
<223> OTHER INFORMATION: AAL59371.1 CDR-H1

<400> SEQUENCE: 98

Gly Tyr Thr Phe Thr Tyr Asn Ala Ile Gln Trp
1               5                   10

<210> SEQ ID NO 99
<211> LENGTH: 11
<212> TYPE: PRT
<213> ORGANISM: Mus musculus
<220> FEATURE:
<223> OTHER INFORMATION: AAB32203.1 CDR-H1

<400> SEQUENCE: 99

Gly Tyr Thr Phe Thr Ser Tyr Trp Met Gln Trp
1               5                   10

<210> SEQ ID NO 100
<211> LENGTH: 11
<212> TYPE: PRT
<213> ORGANISM: Mus musculus
<220> FEATURE:
<223> OTHER INFORMATION: AAT76246.1 CDR-H1

<400> SEQUENCE: 100

Gly Tyr Thr Phe Thr Thr Tyr Trp Met His Trp
1               5                   10

<210> SEQ ID NO 101
<211> LENGTH: 11
<212> TYPE: PRT
<213> ORGANISM: Mus musculus
<220> FEATURE:
<223> OTHER INFORMATION: AAR90999.1 CDR-H1

<400> SEQUENCE: 101

Gly Tyr Thr Phe Thr Asp Tyr Tyr Met Asn Trp
1               5                   10

<210> SEQ ID NO 102
<211> LENGTH: 11
<212> TYPE: PRT
<213> ORGANISM: Mus musculus
<220> FEATURE:
<223> OTHER INFORMATION: AAB46762.1 CDR-H1

<400> SEQUENCE: 102

Gly Tyr Thr Phe Thr Glu Tyr Tyr Val Asn Trp
1               5                   10
```

<210> SEQ ID NO 103
<211> LENGTH: 11
<212> TYPE: PRT
<213> ORGANISM: Homo sapiens
<220> FEATURE:
<223> OTHER INFORMATION: AAG33839.1 CDR-H1

<400> SEQUENCE: 103

Gly Tyr Thr Phe Thr Asp Tyr Tyr Ile His Trp
1               5                   10

<210> SEQ ID NO 104
<211> LENGTH: 11
<212> TYPE: PRT
<213> ORGANISM: Mus musculus
<220> FEATURE:
<223> OTHER INFORMATION: AAT76245.1 CDR-H1

<400> SEQUENCE: 104

Gly Tyr Thr Phe Thr Ser Tyr Trp Met His Trp
1               5                   10

<210> SEQ ID NO 105
<211> LENGTH: 11
<212> TYPE: PRT
<213> ORGANISM: Homo sapiens
<220> FEATURE:
<223> OTHER INFORMATION: CAA84376.1 CDR-H1

<400> SEQUENCE: 105

Gly Tyr Thr Phe Thr Gly Tyr Tyr Ile His Trp
1               5                   10

<210> SEQ ID NO 106
<211> LENGTH: 11
<212> TYPE: PRT
<213> ORGANISM: Mus musculus
<220> FEATURE:
<223> OTHER INFORMATION: AAB46761.1 CDR-H1

<400> SEQUENCE: 106

Gly Tyr Thr Phe Thr Ser Tyr Trp Met His Trp
1               5                   10

<210> SEQ ID NO 107
<211> LENGTH: 11
<212> TYPE: PRT
<213> ORGANISM: Mus musculus
<220> FEATURE:
<223> OTHER INFORMATION: AAB58061.1 CDR-H1

<400> SEQUENCE: 107

Gly Tyr Thr Phe Thr Asp Tyr Asn Met His Trp
1               5                   10

<210> SEQ ID NO 108
<211> LENGTH: 11
<212> TYPE: PRT
<213> ORGANISM: Mus musculus
<220> FEATURE:
<223> OTHER INFORMATION: F30502 CDR-H1

<400> SEQUENCE: 108

Gly Tyr Ser Phe Thr Gly Tyr Asn Met Asn Trp
1               5                   10

<210> SEQ ID NO 109
<211> LENGTH: 11
<212> TYPE: PRT
<213> ORGANISM: Mus musculus
<220> FEATURE:
<223> OTHER INFORMATION: AAR91003.1 CDR-H1

<400> SEQUENCE: 109

Gly Tyr Ala Phe Ser Ser Tyr Trp Met Asn Trp
1               5                   10

<210> SEQ ID NO 110
<211> LENGTH: 11
<212> TYPE: PRT
<213> ORGANISM: Mus musculus
<220> FEATURE:
<223> OTHER INFORMATION: AAT76236.1 CDR-H1

<400> SEQUENCE: 110

Gly Tyr Thr Phe Thr Ser Tyr Val Met His Trp
1               5                   10

<210> SEQ ID NO 111
<211> LENGTH: 17
<212> TYPE: PRT
<213> ORGANISM: Mus musculus
<220> FEATURE:
<223> OTHER INFORMATION: AAB32203.1 CDR-H2

<400> SEQUENCE: 111

Glu Ile Asp Pro Ser Asp Ser Tyr Thr Asn Tyr Asn Gln Lys Phe Lys
1               5                   10                  15

Gly

<210> SEQ ID NO 112
<211> LENGTH: 17
<212> TYPE: PRT
<213> ORGANISM: Mus musculus
<220> FEATURE:
<223> OTHER INFORMATION: AAT68292.1 CDR-H2

<400> SEQUENCE: 112

Ala Ile Asp Thr Ser Asp Ser Tyr Thr Tyr Tyr Asn Gln Lys Phe Lys
1               5                   10                  15

Gly

<210> SEQ ID NO 113
<211> LENGTH: 17
<212> TYPE: PRT
<213> ORGANISM: Mus musculus
<220> FEATURE:
<223> OTHER INFORMATION: A39276 CDR-H2

<400> SEQUENCE: 113

Asn Ile Tyr Pro Gly Gly Asp Tyr Thr Asn Tyr Ile Glu Lys Phe Lys
1               5                   10                  15

Gly

<210> SEQ ID NO 114
<211> LENGTH: 17
<212> TYPE: PRT
<213> ORGANISM: Mus musculus
<220> FEATURE:
<223> OTHER INFORMATION: AAB58061 CDR-H2

```
<400> SEQUENCE: 114

Tyr Ile Tyr Pro Tyr Thr Gly Gly Thr Gly Tyr Asn Gln Lys Phe Lys
1               5                   10                  15

Asn

<210> SEQ ID NO 115
<211> LENGTH: 17
<212> TYPE: PRT
<213> ORGANISM: Mus musculus
<220> FEATURE:
<223> OTHER INFORMATION: 1921302A CDR-H2

<400> SEQUENCE: 115

Asn Ile Asn Pro Tyr Tyr Gly Ser Thr Ser Tyr Asn Gln Lys Phe Lys
1               5                   10                  15

Gly

<210> SEQ ID NO 116
<211> LENGTH: 17
<212> TYPE: PRT
<213> ORGANISM: Mus musculus
<220> FEATURE:
<223> OTHER INFORMATION: AAR91004.1 CDR-H2

<400> SEQUENCE: 116

Trp Ile Asp Pro Ala Asn Gly Asp Thr Glu Tyr Ala Ser Lys Phe Gln
1               5                   10                  15

Gly

<210> SEQ ID NO 117
<211> LENGTH: 17
<212> TYPE: PRT
<213> ORGANISM: Mus musculus
<220> FEATURE:
<223> OTHER INFORMATION: F30502 CDR-H2

<400> SEQUENCE: 117

Lys Ile Asn Pro Tyr Tyr Gly Ser Thr Ser Tyr Asn Gln Lys Phe Lys
1               5                   10                  15

Gly

<210> SEQ ID NO 118
<211> LENGTH: 17
<212> TYPE: PRT
<213> ORGANISM: Mus musculus
<220> FEATURE:
<223> OTHER INFORMATION: AAT76236.1 CDR-H2

<400> SEQUENCE: 118

Tyr Ile Asn Pro Tyr Asn Asp Gly Thr Lys Tyr Asn Glu Lys Phe Lys
1               5                   10                  15

Gly

<210> SEQ ID NO 119
<211> LENGTH: 17
<212> TYPE: PRT
<213> ORGANISM: Mus musculus
<220> FEATURE:
<223> OTHER INFORMATION: AAB46758 CDR-H2

<400> SEQUENCE: 119

Trp Ile Asp Pro Glu Asn Gly Asp Thr Glu Tyr Ala Pro Lys Phe Gln
1               5                   10                  15
```

Gly

<210> SEQ ID NO 120
<211> LENGTH: 17
<212> TYPE: PRT
<213> ORGANISM: Mus musculus
<220> FEATURE:
<223> OTHER INFORMATION: AAE72083 CDR-H2

<400> SEQUENCE: 120

Leu Ile Asn Pro Phe Ser Gly Asp Thr Asn Tyr Ser Gln Lys Phe Thr
1               5                   10                  15

Gly

<210> SEQ ID NO 121
<211> LENGTH: 17
<212> TYPE: PRT
<213> ORGANISM: Mus musculus
<220> FEATURE:
<223> OTHER INFORMATION: B30502 CDR-H2

<400> SEQUENCE: 121

Tyr Ile Asn Pro Tyr Asn Asp Gly Thr Lys Tyr Asn Glu Lys Phe Lys
1               5                   10                  15

Gly

<210> SEQ ID NO 122

<400> SEQUENCE: 122

000

<210> SEQ ID NO 123
<211> LENGTH: 17
<212> TYPE: PRT
<213> ORGANISM: Mus musculus
<220> FEATURE:
<223> OTHER INFORMATION: AAR91007.1 CDR-H2

<400> SEQUENCE: 123

Trp Ile Asp Pro Glu Asn Gly Asp Thr Glu Tyr Ala Ser Lys Phe Gln
1               5                   10                  15

Gly

<210> SEQ ID NO 124
<211> LENGTH: 11
<212> TYPE: PRT
<213> ORGANISM: Mus musculus
<220> FEATURE:
<223> OTHER INFORMATION: AAS01840.1 CDR-L1

<400> SEQUENCE: 124

Lys Ala Ser Gln Asn Val Gly Thr Asn Val Ala
1               5                   10

<210> SEQ ID NO 125
<211> LENGTH: 11
<212> TYPE: PRT
<213> ORGANISM: Mus musculus
<220> FEATURE:
<223> OTHER INFORMATION: AAS01841.1 CDR-L1

<400> SEQUENCE: 125

Lys Ala Ser Gln Asn Val Arg Thr Ala Val Ala

```
<210> SEQ ID NO 126
<211> LENGTH: 11
<212> TYPE: PRT
<213> ORGANISM: Mus musculus
<220> FEATURE:
<223> OTHER INFORMATION: AAT76271.1 CDR-L1

<400> SEQUENCE: 126

Lys Ala Ser Gln Asp Val Ser Thr Ala Val Ala
1               5                   10

<210> SEQ ID NO 127
<211> LENGTH: 15
<212> TYPE: PRT
<213> ORGANISM: Mus musculus
<220> FEATURE:
<223> OTHER INFORMATION: AAB46763.1 CDR-L1

<400> SEQUENCE: 127

Lys Ala Ser Gln Ser Val Asp Tyr Asp Gly Asp Ser Tyr Met Asn
1               5                   10                  15

<210> SEQ ID NO 128
<211> LENGTH: 11
<212> TYPE: PRT
<213> ORGANISM: Homo sapiens
<220> FEATURE:
<223> OTHER INFORMATION: AAA20447.1 CDR-L1

<400> SEQUENCE: 128

Arg Ala Ser Gln Ser Val Ser Ser Tyr Leu Ala
1               5                   10

<210> SEQ ID NO 129
<211> LENGTH: 11
<212> TYPE: PRT
<213> ORGANISM: Homo sapiens
<220> FEATURE:
<223> OTHER INFORMATION: PC4282 CDR-L1

<400> SEQUENCE: 129

Arg Ala Ser Gln Ser Val Ser Asn Tyr Leu Ala
1               5                   10

<210> SEQ ID NO 130
<211> LENGTH: 12
<212> TYPE: PRT
<213> ORGANISM: Homo sapiens
<220> FEATURE:
<223> OTHER INFORMATION: CAA56180.1 CDR-L1

<400> SEQUENCE: 130

Arg Ala Ser Gln Thr Val Arg Lys Asn Tyr Leu Ala
1               5                   10

<210> SEQ ID NO 131
<211> LENGTH: 11
<212> TYPE: PRT
<213> ORGANISM: Mus musculus
<220> FEATURE:
<223> OTHER INFORMATION: 1921302B CDR-L1

<400> SEQUENCE: 131

Arg Ala Ser Gln Ser Ile Ser Asn Tyr Leu His
1               5                   10
```

```
<210> SEQ ID NO 132
<211> LENGTH: 11
<212> TYPE: PRT
<213> ORGANISM: Homo sapiens
<220> FEATURE:
<223> OTHER INFORMATION: AAL59380.1 CDR-L1

<400> SEQUENCE: 132

Arg Ala Ser Gln Ser Ile Ser Ser Tyr Leu Asn
1               5                   10

<210> SEQ ID NO 133
<211> LENGTH: 11
<212> TYPE: PRT
<213> ORGANISM: Homo sapiens
<220> FEATURE:
<223> OTHER INFORMATION: AAL59377.1 CDR-L1

<400> SEQUENCE: 133

Arg Ala Ser Gln Ser Ile Ser Ser Tyr Leu Asn
1               5                   10

<210> SEQ ID NO 134
<211> LENGTH: 11
<212> TYPE: PRT
<213> ORGANISM: Homo sapiens
<220> FEATURE:
<223> OTHER INFORMATION: CAA63587.1 CDR-L1

<400> SEQUENCE: 134

Arg Ala Ser Gln Gly Ile Ser Asn Trp Leu Ala
1               5                   10

<210> SEQ ID NO 135
<211> LENGTH: 11
<212> TYPE: PRT
<213> ORGANISM: Homo sapiens
<220> FEATURE:
<223> OTHER INFORMATION: AAG30434.1 CDR-L1

<400> SEQUENCE: 135

Arg Ala Ser Gln Gly Ile Ser Ser Tyr Leu Ala
1               5                   10

<210> SEQ ID NO 136
<211> LENGTH: 11
<212> TYPE: PRT
<213> ORGANISM: Homo sapiens
<220> FEATURE:
<223> OTHER INFORMATION: CAA56181.1 CDR-L1

<400> SEQUENCE: 136

Arg Ala Ser Arg Gly Ile Ser Asn Tyr Leu Ala
1               5                   10

<210> SEQ ID NO 137
<211> LENGTH: 11
<212> TYPE: PRT
<213> ORGANISM: Mus musculus
<220> FEATURE:
<223> OTHER INFORMATION: AAE72082.1 CDR-L1

<400> SEQUENCE: 137

Lys Ala Ser Gln Asp Ile Asn Gly Tyr Leu Asn
1               5                   10
```

```
<210> SEQ ID NO 138
<211> LENGTH: 7
<212> TYPE: PRT
<213> ORGANISM: Mus musculus
<220> FEATURE:
<223> OTHER INFORMATION: AAS01840.1 CDR-L2

<400> SEQUENCE: 138

Ser Ala Ser Tyr Arg Tyr Ser
1               5

<210> SEQ ID NO 139
<211> LENGTH: 7
<212> TYPE: PRT
<213> ORGANISM: Mus musculus
<220> FEATURE:
<223> OTHER INFORMATION: G30502 CDR-L2

<400> SEQUENCE: 139

Trp Ala Ser Thr Arg Glu Ser
1               5

<210> SEQ ID NO 140
<211> LENGTH: 7
<212> TYPE: PRT
<213> ORGANISM: Homo sapiens
<220> FEATURE:
<223> OTHER INFORMATION: AAL59376.1 CDR-L2

<400> SEQUENCE: 140

Trp Ala Ser Thr Arg Glu Ser
1               5

<210> SEQ ID NO 141
<211> LENGTH: 7
<212> TYPE: PRT
<213> ORGANISM: Mus musculus
<220> FEATURE:
<223> OTHER INFORMATION: AAL59379.1 CDR-L2

<400> SEQUENCE: 141

Trp Ala Ser Thr Arg Glu Ser
1               5

<210> SEQ ID NO 142
<211> LENGTH: 7
<212> TYPE: PRT
<213> ORGANISM: Mus musculus
<220> FEATURE:
<223> OTHER INFORMATION: AAT76280.1 CDR-L2

<400> SEQUENCE: 142

Leu Thr Ser Asn Leu Ala Ser
1               5

<210> SEQ ID NO 143
<211> LENGTH: 7
<212> TYPE: PRT
<213> ORGANISM: Mus musculus
<220> FEATURE:
<223> OTHER INFORMATION: AAB46767.1 CDR-L2

<400> SEQUENCE: 143

Asp Thr Ser Lys Leu Ala Ser
1               5
```

```
<210> SEQ ID NO 144
<211> LENGTH: 7
<212> TYPE: PRT
<213> ORGANISM: Mus musculus
<220> FEATURE:
<223> OTHER INFORMATION: AAB46765.1 CDR-L2

<400> SEQUENCE: 144

Asp Thr Ser Asn Leu Ala Ser
1               5

<210> SEQ ID NO 145
<211> LENGTH: 7
<212> TYPE: PRT
<213> ORGANISM: Mus musculus
<220> FEATURE:
<223> OTHER INFORMATION: AAB46766.1 CDR-L2

<400> SEQUENCE: 145

Tyr Thr Ser Asn Leu Ala Pro
1               5

<210> SEQ ID NO 146
<211> LENGTH: 7
<212> TYPE: PRT
<213> ORGANISM: Mus musculus
<220> FEATURE:
<223> OTHER INFORMATION: AAB46764.1 CDR-L2

<400> SEQUENCE: 146

Tyr Thr Ser Asn Leu Ala Pro
1               5

<210> SEQ ID NO 147
<211> LENGTH: 7
<212> TYPE: PRT
<213> ORGANISM: Mus musculus
<220> FEATURE:
<223> OTHER INFORMATION: AAS01843.1 CDR-L2

<400> SEQUENCE: 147

Thr Thr Ser Asn Leu Ala Ser
1               5

<210> SEQ ID NO 148
<211> LENGTH: 7
<212> TYPE: PRT
<213> ORGANISM: Homo sapiens
<220> FEATURE:
<223> OTHER INFORMATION: AAG30433.1 CDR-L2

<400> SEQUENCE: 148

Lys Thr Ser Val Leu Gly Ser
1               5

<210> SEQ ID NO 149
<211> LENGTH: 7
<212> TYPE: PRT
<213> ORGANISM: Mus musculus
<220> FEATURE:
<223> OTHER INFORMATION: CAC22102.1 CDR-L2

<400> SEQUENCE: 149

Thr Thr Ser Asn Leu Ala Ser
1               5

<210> SEQ ID NO 150
```

```
<211> LENGTH: 9
<212> TYPE: PRT
<213> ORGANISM: Mus musculus
<220> FEATURE:
<223> OTHER INFORMATION: AAS01840.1 CDR-L3

<400> SEQUENCE: 150

Gln Gln Tyr Asn Ser Tyr Pro Tyr Thr
1               5

<210> SEQ ID NO 151
<211> LENGTH: 9
<212> TYPE: PRT
<213> ORGANISM: Mus musculus
<220> FEATURE:
<223> OTHER INFORMATION: AAB46766.1 CDR-L3

<400> SEQUENCE: 151

Gln Gln Trp Ser Ser Asp Pro Leu Thr
1               5

<210> SEQ ID NO 152
<211> LENGTH: 9
<212> TYPE: PRT
<213> ORGANISM: Homo sapiens
<220> FEATURE:
<223> OTHER INFORMATION: PC4282 CDR-L3

<400> SEQUENCE: 152

Gln Gln Arg Ala Ser Trp Pro Leu Thr
1               5

<210> SEQ ID NO 153
<211> LENGTH: 9
<212> TYPE: PRT
<213> ORGANISM: Mus musculus
<220> FEATURE:
<223> OTHER INFORMATION: S67940 CDR-L3

<400> SEQUENCE: 153

Gln Gln Tyr Gly Ser Ser Pro Tyr Thr
1               5

<210> SEQ ID NO 154
<211> LENGTH: 9
<212> TYPE: PRT
<213> ORGANISM: Mus musculus
<220> FEATURE:
<223> OTHER INFORMATION: CAA56180.1 CDR-L3

<400> SEQUENCE: 154

Gln Gln Tyr Gly Ser Ser Pro Ile Thr
1               5

<210> SEQ ID NO 155
<211> LENGTH: 9
<212> TYPE: PRT
<213> ORGANISM: Mus musculus
<220> FEATURE:
<223> OTHER INFORMATION: AAB58062.1 CDR-L3

<400> SEQUENCE: 155

Gln Gln Asn Asn Glu Asp Pro Tyr Thr
1               5

<210> SEQ ID NO 156
<211> LENGTH: 9
```

```
<212> TYPE: PRT
<213> ORGANISM: Mus musculus
<220> FEATURE:
<223> OTHER INFORMATION: AAS01844.1 CDR-L3

<400> SEQUENCE: 156

Gln Gln Ser Asn Glu Asp Pro Arg Thr
1               5

<210> SEQ ID NO 157
<211> LENGTH: 9
<212> TYPE: PRT
<213> ORGANISM: Mus musculus
<220> FEATURE:
<223> OTHER INFORMATION: C30502 CDR-L3

<400> SEQUENCE: 157

Gln Gln Thr Asn Ser Trp Pro Arg Thr
1               5

<210> SEQ ID NO 158
<211> LENGTH: 9
<212> TYPE: PRT
<213> ORGANISM: Mus musculus
<220> FEATURE:
<223> OTHER INFORMATION: AAB46763.1 CDR-L3

<400> SEQUENCE: 158

Gln Gln Asn Asn Glu Asp Pro Phe Thr
1               5

<210> SEQ ID NO 159
<211> LENGTH: 18
<212> TYPE: PRT
<213> ORGANISM: Artificial Sequence
<220> FEATURE:
<223> OTHER INFORMATION: Synthetic Construct; Synthetic monomer peptide
<220> FEATURE:
<223> OTHER INFORMATION: B71 monomer peptide

<400> SEQUENCE: 159

Cys Asn Ile Tyr Pro Ser Asp Ser Tyr Thr Asn Tyr Asn Gln Lys Phe
1               5                   10                  15

Lys Asp

<210> SEQ ID NO 160
<211> LENGTH: 9
<212> TYPE: PRT
<213> ORGANISM: Artificial Sequence
<220> FEATURE:
<223> OTHER INFORMATION: Synthetic Construct; Synthetic monomer peptide
<220> FEATURE:
<223> OTHER INFORMATION: C80 monomer peptide

<400> SEQUENCE: 160

Cys Leu Arg Gly Leu Leu Pro Asp Tyr
1               5

<210> SEQ ID NO 161
<211> LENGTH: 10
<212> TYPE: PRT
<213> ORGANISM: Artificial Sequence
<220> FEATURE:
<223> OTHER INFORMATION: Synthetic Construct; Synthetic monomer peptide
<220> FEATURE:
<223> OTHER INFORMATION: F90 monomer peptide

<400> SEQUENCE: 161
```

```
Cys Gln Gln Tyr Asn Ser Tyr Pro Leu Thr
1               5                   10

<210> SEQ ID NO 162
<211> LENGTH: 11
<212> TYPE: PRT
<213> ORGANISM: Artificial Sequence
<220> FEATURE:
<223> OTHER INFORMATION: Synthetic Construct; Consensus Sequence 1
<220> FEATURE:
<221> NAME/KEY: misc_feature
<222> LOCATION: (1)...(11)
<223> OTHER INFORMATION: Xaa is any amino acid

<400> SEQUENCE: 162

Gly Tyr Xaa Phe Thr Xaa Xaa Xaa Xaa Xaa Trp
1               5                   10

<210> SEQ ID NO 163
<211> LENGTH: 17
<212> TYPE: PRT
<213> ORGANISM: Artificial Sequence
<220> FEATURE:
<223> OTHER INFORMATION: Synthetic Construct; Consensus Sequence 2
<220> FEATURE:
<221> NAME/KEY: misc_feature
<222> LOCATION: (1)...(17)
<223> OTHER INFORMATION: Xaa is any amino acid

<400> SEQUENCE: 163

Xaa Ile Xaa Xaa Xaa Xaa Xaa Xaa Xaa Xaa Tyr Xaa Xaa Xaa Phe Lys
1               5                   10                  15

Xaa

<210> SEQ ID NO 164
<211> LENGTH: 11
<212> TYPE: PRT
<213> ORGANISM: Artificial Sequence
<220> FEATURE:
<223> OTHER INFORMATION: Synthetic Construct; Consensus Sequence 3
<220> FEATURE:
<221> NAME/KEY: misc_feature
<222> LOCATION: (1)...(11)
<223> OTHER INFORMATION: Xaa is any amino acid

<400> SEQUENCE: 164

Xaa Ala Ser Xaa Xaa Xaa Xaa Xaa Xaa Xaa Xaa
1               5                   10

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct; Consensus Sequence 4
<220> FEATURE:
<221> NAME/KEY: misc_feature
<222> LOCATION: (1)...(7)
<223> OTHER INFORMATION: Xaa is any amino acid

<400> SEQUENCE: 165

Xaa Xaa Ser Xaa Xaa Xaa Ser
1               5

<210> SEQ ID NO 166
<211> LENGTH: 9
<212> TYPE: PRT
<213> ORGANISM: Artificial Sequence
```

```
<220> FEATURE:
<223> OTHER INFORMATION: Synthetic Construct; Consensus Sequence 5
<220> FEATURE:
<221> NAME/KEY: misc_feature
<222> LOCATION: (1)...(9)
<223> OTHER INFORMATION: Xaa is any amino acid

<400> SEQUENCE: 166

Gln Gln Xaa Xaa Xaa Xaa Pro Xaa Xaa
1               5

<210> SEQ ID NO 167
<211> LENGTH: 11
<212> TYPE: PRT
<213> ORGANISM: Artificial Sequence
<220> FEATURE:
<223> OTHER INFORMATION: Synthetic Construct; Consensus Sequence 6
<220> FEATURE:
<221> NAME/KEY: misc_feature
<222> LOCATION: (1)...(11)
<223> OTHER INFORMATION: Xaa is any amino acid

<400> SEQUENCE: 167

Gly Tyr Thr Phe Thr Xaa Xaa Xaa Xaa Xaa Trp
1               5                   10

<210> SEQ ID NO 168
<211> LENGTH: 11
<212> TYPE: PRT
<213> ORGANISM: Artificial Sequence
<220> FEATURE:
<223> OTHER INFORMATION: Synthetic Construct; Consensus Sequence 7
<220> FEATURE:
<221> NAME/KEY: misc_feature
<222> LOCATION: (1)...(11)
<223> OTHER INFORMATION: Xaa is any amino acid

<400> SEQUENCE: 168

Gly Tyr Xaa Phe Xaa Xaa Tyr Xaa Met Xaa Trp
1               5                   10

<210> SEQ ID NO 169
<211> LENGTH: 17
<212> TYPE: PRT
<213> ORGANISM: Artificial Sequence
<220> FEATURE:
<223> OTHER INFORMATION: Synthetic Construct; Consensus Sequence 8
<220> FEATURE:
<221> NAME/KEY: misc_feature
<222> LOCATION: (1)...(17)
<223> OTHER INFORMATION: Xaa is any amino acid

<400> SEQUENCE: 169

Xaa Ile Xaa Xaa Xaa Xaa Xaa Xaa Xaa Xaa Tyr Xaa Xaa Xaa Phe Lys
1               5                   10                  15

Xaa

<210> SEQ ID NO 170
<211> LENGTH: 17
<212> TYPE: PRT
<213> ORGANISM: Artificial Sequence
<220> FEATURE:
<223> OTHER INFORMATION: Synthetic Construct; Consensus Sequence 9
<220> FEATURE:
<221> NAME/KEY: misc_feature
<222> LOCATION: (1)...(17)
<223> OTHER INFORMATION: Xaa is any amino acid

<400> SEQUENCE: 170
```

```
Xaa Ile Xaa Pro Xaa Xaa Xaa Xaa Thr Xaa Tyr Xaa Xaa Lys Phe Xaa
1               5                   10                  15

Gly
```

<210> SEQ ID NO 171
<211> LENGTH: 11
<212> TYPE: PRT
<213> ORGANISM: Artificial Sequence
<220> FEATURE:
<223> OTHER INFORMATION: Synthetic Construct; Consensus Sequence 10
<220> FEATURE:
<221> NAME/KEY: misc_feature
<222> LOCATION: (1)...(11)
<223> OTHER INFORMATION: Xaa is any amino acid

<400> SEQUENCE: 171

```
Xaa Ala Ser Xaa Xaa Xaa Xaa Xaa Xaa Xaa Xaa
1               5                   10
```

<210> SEQ ID NO 172
<211> LENGTH: 11
<212> TYPE: PRT
<213> ORGANISM: Artificial Sequence
<220> FEATURE:
<223> OTHER INFORMATION: Synthetic Construct; Consensus Sequence 11
<220> FEATURE:
<221> NAME/KEY: misc_feature
<222> LOCATION: (1)...(11)
<223> OTHER INFORMATION: Xaa is any amino acid

<400> SEQUENCE: 172

```
Xaa Ala Ser Xaa Xaa Xaa Xaa Xaa Xaa Leu Xaa
1               5                   10
```

<210> SEQ ID NO 173
<211> LENGTH: 7
<212> TYPE: PRT
<213> ORGANISM: Artificial Sequence
<220> FEATURE:
<223> OTHER INFORMATION: Synthetic Construct; Consensus Sequence 12
<220> FEATURE:
<221> NAME/KEY: misc_feature
<222> LOCATION: (1)...(7)
<223> OTHER INFORMATION: Xaa is any amino acid

<400> SEQUENCE: 173

```
Xaa Xaa Ser Xaa Xaa Xaa Ser
1               5
```

<210> SEQ ID NO 174
<211> LENGTH: 7
<212> TYPE: PRT
<213> ORGANISM: Artificial Sequence
<220> FEATURE:
<223> OTHER INFORMATION: Synthetic Construct; Consensus Sequence 13
<220> FEATURE:
<221> NAME/KEY: misc_feature
<222> LOCATION: (1)...(7)
<223> OTHER INFORMATION: Xaa is any amino acid

<400> SEQUENCE: 174

```
Xaa Thr Ser Xaa Leu Xaa Xaa
1               5
```

<210> SEQ ID NO 175
<211> LENGTH: 9
<212> TYPE: PRT
<213> ORGANISM: Artificial Sequence
<220> FEATURE:

<223> OTHER INFORMATION: Synthetic Construct; Consensus Sequence 14
<220> FEATURE:
<221> NAME/KEY: misc_feature
<222> LOCATION: (1)...(9)
<223> OTHER INFORMATION: Xaa is any amino acid

<400> SEQUENCE: 175

Gln Gln Xaa Xaa Ser Xaa Pro Xaa Thr
1               5

<210> SEQ ID NO 176
<211> LENGTH: 9
<212> TYPE: PRT
<213> ORGANISM: Artificial Sequence
<220> FEATURE:
<223> OTHER INFORMATION: Synthetic Construct; Consensus Sequence 15
<220> FEATURE:
<221> NAME/KEY: misc_feature
<222> LOCATION: (1)...(9)
<223> OTHER INFORMATION: Xaa is any amino acid

<400> SEQUENCE: 176

Gln Gln Xaa Asn Xaa Xaa Pro Xaa Xaa
1               5

<210> SEQ ID NO 177
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (7)..(7)
<223> OTHER INFORMATION: Xaa can Tyr or Asn
<220> FEATURE:
<221> NAME/KEY: misc_feature
<222> LOCATION: (9)..(9)
<223> OTHER INFORMATION: Xaa can be Ile or Met

<400> SEQUENCE: 177

Gly Tyr Thr Phe Thr Arg Xaa Trp Xaa Asn Trp
1               5                   10

<210> SEQ ID NO 178
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (5)..(5)
<223> OTHER INFORMATION: Xaa can be Ser or Tyr
<220> FEATURE:
<221> NAME/KEY: misc_feature
<222> LOCATION: (7)..(7)
<223> OTHER INFORMATION: Xaa can be Ser or Gly
<220> FEATURE:
<221> NAME/KEY: misc_feature
<222> LOCATION: (17)..(17)
<223> OTHER INFORMATION: Xaa can be Asp or Gly

<400> SEQUENCE: 178

Asn Ile Tyr Pro Xaa Asp Xaa Tyr Thr Asn Tyr Asn Gln Lys Phe Lys
1               5                   10                  15

Xaa

<210> SEQ ID NO 179
<211> LENGTH: 8

```
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (2)..(2)
<223> OTHER INFORMATION: Xaa can be any Arg or Gly
<220> FEATURE:
<221> NAME/KEY: misc_feature
<222> LOCATION: (7)..(7)
<223> OTHER INFORMATION: Xaa can be Asp or Tyr

<400> SEQUENCE: 179

Leu Xaa Gly Leu Leu Pro Xaa Tyr
 1               5

<210> SEQ ID NO 180
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (7)..(7)
<223> OTHER INFORMATION: Xaa can be any Asp, Ser or Gly

<400> SEQUENCE: 180

Lys Ala Ser Gln Asn Val Xaa Thr Asn Val Ala
 1               5                  10

<210> SEQ ID NO 181
<211> LENGTH: 7
<212> TYPE: PRT
<213> ORGANISM: Artificial Sequence
<220> FEATURE:
<223> OTHER INFORMATION: Synthetic construct

<400> SEQUENCE: 181

Ser Ala Ser Tyr Arg Tyr Ser
 1               5

<210> SEQ ID NO 182
<211> LENGTH: 9
<212> TYPE: PRT
<213> ORGANISM: Artificial Sequence
<220> FEATURE:
<223> OTHER INFORMATION: Synthetic construct

<400> SEQUENCE: 182

Gln Gln Tyr Asn Ser Tyr Pro Leu Thr
 1               5

<210> SEQ ID NO 183
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (6)..(6)
<223> OTHER INFORMATION: Xaa can be Arg, Asn or Ser
<220> FEATURE:
<221> NAME/KEY: misc_feature
<222> LOCATION: (9)..(9)
<223> OTHER INFORMATION: Xaa can be Ile or Met

<400> SEQUENCE: 183
```

```
Gly Tyr Thr Phe Thr Xaa Tyr Trp Xaa Asn Trp
1               5                   10
```

<210> SEQ ID NO 184
<211> LENGTH: 11
<212> TYPE: PRT
<213> ORGANISM: Artificial Sequence
<220> FEATURE:
<223> OTHER INFORMATION: Synthetic construct

<400> SEQUENCE: 184

```
Gly Tyr Thr Phe Thr Ser Tyr Trp Met His Trp
1               5                   10
```

<210> SEQ ID NO 185
<211> LENGTH: 17
<212> TYPE: PRT
<213> ORGANISM: Artificial Sequence
<220> FEATURE:
<223> OTHER INFORMATION: Synthetic construct

<400> SEQUENCE: 185

```
Asn Ile Tyr Pro Ser Asp Ser Tyr Thr Asn Tyr Asn Gln Lys Phe Lys
1               5                   10                  15

Gly
```

<210> SEQ ID NO 186
<211> LENGTH: 17
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (1)..(1)
<223> OTHER INFORMATION: Xaa can be Tyr or Trp
<220> FEATURE:
<221> NAME/KEY: misc_feature
<222> LOCATION: (10)..(10)
<223> OTHER INFORMATION: Xaa can be Glu or Ser

<400> SEQUENCE: 186

```
Xaa Ile Asn Pro Tyr Asn Gly Asp Thr Xaa Tyr Asn Gln Lys Phe Lys
1               5                   10                  15

Gly
```

<210> SEQ ID NO 187
<211> LENGTH: 11
<212> TYPE: PRT
<213> ORGANISM: Artificial Sequence
<220> FEATURE:
<223> OTHER INFORMATION: Synthetic construct

<400> SEQUENCE: 187

```
Lys Ala Ser Gln Asn Val Ser Thr Asn Val Ala
1               5                   10
```

<210> SEQ ID NO 188
<211> LENGTH: 11
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (11)..(11)
<223> OTHER INFORMATION: Xaa can be Asn or Ala

<400> SEQUENCE: 188

Arg Ala Ser Gln Ser Ile Ser Asn Tyr Leu Xaa
1               5                   10

<210> SEQ ID NO 189
<211> LENGTH: 7
<212> TYPE: PRT
<213> ORGANISM: Artificial Sequence
<220> FEATURE:
<223> OTHER INFORMATION: Synthetic construct

<400> SEQUENCE: 189

Ser Ala Ser Tyr Arg Tyr Ser
1               5

<210> SEQ ID NO 190
<211> LENGTH: 7
<212> TYPE: PRT
<213> ORGANISM: Artificial Sequence
<220> FEATURE:
<223> OTHER INFORMATION: Synthetic construct

<400> SEQUENCE: 190

Tyr Thr Ser Asn Leu Ala Ser
1               5

<210> SEQ ID NO 191
<211> LENGTH: 9
<212> TYPE: PRT
<213> ORGANISM: Artificial Sequence
<220> FEATURE:
<223> OTHER INFORMATION: Synthetic construct

<400> SEQUENCE: 191

Gln Gln Tyr Asn Ser Tyr Pro Leu Thr
1               5

<210> SEQ ID NO 192
<211> LENGTH: 9
<212> TYPE: PRT
<213> ORGANISM: Artificial Sequence
<220> FEATURE:
<223> OTHER INFORMATION: Synthetic construct
<220> FEATURE:
<221> NAME/KEY: misc_feature
<222> LOCATION: (8)..(8)
<223> OTHER INFORMATION: Xaa can be Tyr or Arg

<400> SEQUENCE: 192

Gln Gln Asn Asn Glu Asp Pro Xaa Thr
1               5

<210> SEQ ID NO 193
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)..(3)
<223> OTHER INFORMATION: Xaa is Thr or Ala
<220> FEATURE:
<221> NAME/KEY: misc_feature
<222> LOCATION: (6)..(6)
<223> OTHER INFORMATION: Xaa is Arg, Asn or Ser
<220> FEATURE:
<221> NAME/KEY: misc_feature
<222> LOCATION: (7)..(7)

```
<223> OTHER INFORMATION: Xaa is Tyr or Asn
<220> FEATURE:
<221> NAME/KEY: misc_feature
<222> LOCATION: (8)...(8)
<223> OTHER INFORMATION: Xaa is Trp, Gly or Asn
<220> FEATURE:
<221> NAME/KEY: misc_feature
<222> LOCATION: (9)...(9)
<223> OTHER INFORMATION: Xaa is Ile or Met
<220> FEATURE:
<221> NAME/KEY: misc_feature
<222> LOCATION: (10)...(10)
<223> OTHER INFORMATION: Xaa is Asn or Phe

<400> SEQUENCE: 193

Gly Tyr Xaa Phe Thr Xaa Xaa Xaa Xaa Xaa Trp
1               5                   10

<210> SEQ ID NO 194
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: Xaa is Asn, Trp or Tyr
<220> FEATURE:
<221> NAME/KEY: misc_feature
<222> LOCATION: (3)...(3)
<223> OTHER INFORMATION: Xaa is Tyr, Asn or Asp
<220> FEATURE:
<221> NAME/KEY: misc_feature
<222> LOCATION: (4)...(4)
<223> OTHER INFORMATION: Xaa is Pro or Thr
<220> FEATURE:
<221> NAME/KEY: misc_feature
<222> LOCATION: (5)...(5)
<223> OTHER INFORMATION: Xaa is Ser or Tyr
<220> FEATURE:
<221> NAME/KEY: misc_feature
<222> LOCATION: (6)...(6)
<223> OTHER INFORMATION: Xaa is Asp, Asn or Thr
<220> FEATURE:
<221> NAME/KEY: misc_feature
<222> LOCATION: (7)...(7)
<223> OTHER INFORMATION: Xaa is Ser or Gly
<220> FEATURE:
<221> NAME/KEY: misc_feature
<222> LOCATION: (8)...(8)
<223> OTHER INFORMATION: Xaa is Try, Asp or Glu
<220> FEATURE:
<221> NAME/KEY: misc_feature
<222> LOCATION: (9)...(9)
<223> OTHER INFORMATION: Xaa is Thr or Pro
<220> FEATURE:
<221> NAME/KEY: misc_feature
<222> LOCATION: (10)...(10)
<223> OTHER INFORMATION: Xaa is Asn, Arg or Thr
<220> FEATURE:
<221> NAME/KEY: misc_feature
<222> LOCATION: (12)...(12)
<223> OTHER INFORMATION: Xaa is Asn, Ser or Ala
<220> FEATURE:
<221> NAME/KEY: misc_feature
<222> LOCATION: (13)...(13)
<223> OTHER INFORMATION: Xaa is Gln or Asp
<220> FEATURE:
<221> NAME/KEY: misc_feature
<222> LOCATION: (14)...(14)
<223> OTHER INFORMATION: Xaa is Lys or Asp
<220> FEATURE:
<221> NAME/KEY: misc_feature
<222> LOCATION: (17)...(17)
<223> OTHER INFORMATION: Xaa is Asp or Gly
```

-continued

```
<400> SEQUENCE: 194

Xaa Ile Xaa Xaa Xaa Xaa Xaa Xaa Xaa Xaa Tyr Xaa Xaa Xaa Phe Lys
1               5                   10                  15

Xaa

<210> SEQ ID NO 195
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (6)...(6)
<223> OTHER INFORMATION: Xaa is Arg, Asn, Tyr, Ser, Thr, Asp, Glu or
      Gly
<220> FEATURE:
<221> NAME/KEY: misc_feature
<222> LOCATION: (7)...(7)
<223> OTHER INFORMATION: Xaa is Asn, Tyr or Phe
<220> FEATURE:
<221> NAME/KEY: misc_feature
<222> LOCATION: (8)...(8)
<223> OTHER INFORMATION: Xaa is Trp, Gly, Ala or Tyr
<220> FEATURE:
<221> NAME/KEY: misc_feature
<222> LOCATION: (9)...(9)
<223> OTHER INFORMATION: Xaa is Ile, Met or Val
<220> FEATURE:
<221> NAME/KEY: misc_feature
<222> LOCATION: (10)...(10)
<223> OTHER INFORMATION: Xaa is Asn, Gly, Gln or His

<400> SEQUENCE: 195

Gly Tyr Thr Phe Thr Xaa Xaa Xaa Xaa Xaa Trp
1               5                   10

<210> SEQ ID NO 196
<211> LENGTH: 11
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)...(3)
<223> OTHER INFORMATION: Xaa is Ala, Thr or Ser
<220> FEATURE:
<221> NAME/KEY: misc_feature
<222> LOCATION: (5)...(5)
<223> OTHER INFORMATION: Xaa is Thr or Ser
<220> FEATURE:
<221> NAME/KEY: misc_feature
<222> LOCATION: (6)...(6)
<223> OTHER INFORMATION: Xaa is Ser, Asp or Gly
<220> FEATURE:
<221> NAME/KEY: misc_feature
<222> LOCATION: (8)...(8)
<223> OTHER INFORMATION: Xaa is Asn, Trp or Val
<220> FEATURE:
<221> NAME/KEY: misc_feature
<222> LOCATION: (10)...(10)
<223> OTHER INFORMATION: Xaa is Phe, Gln, His or Asn

<400> SEQUENCE: 196

Gly Tyr Xaa Phe Xaa Xaa Tyr Xaa Met Xaa Trp
1               5                   10

<210> SEQ ID NO 197
<211> LENGTH: 17
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: Xaa is Asn, Trp, Glu, Ala or Tyr
<220> FEATURE:
<221> NAME/KEY: misc_feature
<222> LOCATION: (3)...(3)
<223> OTHER INFORMATION: Xaa is Tyr, Asn or Asp
<220> FEATURE:
<221> NAME/KEY: misc_feature
<222> LOCATION: (4)...(4)
<223> OTHER INFORMATION: Xaa is Pro or Thr
<220> FEATURE:
<221> NAME/KEY: misc_feature
<222> LOCATION: (5)...(5)
<223> OTHER INFORMATION: Xaa is Ser, Tyr or Gly
<220> FEATURE:
<221> NAME/KEY: misc_feature
<222> LOCATION: (6)...(6)
<223> OTHER INFORMATION: Xaa is Asp, Thr, Gly or Tyr
<220> FEATURE:
<221> NAME/KEY: misc_feature
<222> LOCATION: (7)...(7)
<223> OTHER INFORMATION: Xaa is Ser, Gly or Asp
<220> FEATURE:
<221> NAME/KEY: misc_feature
<222> LOCATION: (8)...(8)
<223> OTHER INFORMATION: Xaa is Tyr, Glu, Gly or Ser
<220> FEATURE:
<221> NAME/KEY: misc_feature
<222> LOCATION: (9)...(9)
<223> OTHER INFORMATION: Xaa is Thr or Pro
<220> FEATURE:
<221> NAME/KEY: misc_feature
<222> LOCATION: (10)...(10)
<223> OTHER INFORMATION: Xaa is Asn, Thr, Tyr, Gly or Ser
<220> FEATURE:
<221> NAME/KEY: misc_feature
<222> LOCATION: (12)...(12)
<223> OTHER INFORMATION: Xaa is Asn, Ala or Ile
<220> FEATURE:
<221> NAME/KEY: misc_feature
<222> LOCATION: (13)...(13)
<223> OTHER INFORMATION: Xaa is Gln, Asp or Glu
<220> FEATURE:
<221> NAME/KEY: misc_feature
<222> LOCATION: (14)...(14)
<223> OTHER INFORMATION: Xaa is Lys or Asp
<220> FEATURE:
<221> NAME/KEY: misc_feature
<222> LOCATION: (17)...(17)
<223> OTHER INFORMATION: Xaa is Asp, Gly or Asn

<400> SEQUENCE: 197

Xaa Ile Xaa Xaa Xaa Xaa Xaa Xaa Xaa Xaa Tyr Xaa Xaa Xaa Phe Lys
1               5                   10                  15

Xaa

<210> SEQ ID NO 198
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: Xaa is Tyr, Trp, Lys, Asn, Leu or Arg
<220> FEATURE:
<221> NAME/KEY: misc_feature
<222> LOCATION: (3)...(3)
<223> OTHER INFORMATION: Xaa is Asp or Asn
<220> FEATURE:
<221> NAME/KEY: misc_feature
```

```
<222> LOCATION: (5)...(5)
<223> OTHER INFORMATION: Xaa is Tyr, Ala, Glu, Phe or Ser
<220> FEATURE:
<221> NAME/KEY: misc_feature
<222> LOCATION: (6)...(6)
<223> OTHER INFORMATION: Xaa is Asn, Tyr or Ser
<220> FEATURE:
<221> NAME/KEY: misc_feature
<222> LOCATION: (7)...(7)
<223> OTHER INFORMATION: Xaa is Gly or Asp
<220> FEATURE:
<221> NAME/KEY: misc_feature
<222> LOCATION: (8)...(8)
<223> OTHER INFORMATION: Xaa is Asp, Ser or Gly
<220> FEATURE:
<221> NAME/KEY: misc_feature
<222> LOCATION: (10)...(10)
<223> OTHER INFORMATION: Xaa is Arg, Glu, Ser, Lys or Asn
<220> FEATURE:
<221> NAME/KEY: misc_feature
<222> LOCATION: (12)...(12)
<223> OTHER INFORMATION: Xaa is Ser, Ala or Asn
<220> FEATURE:
<221> NAME/KEY: misc_feature
<222> LOCATION: (13)...(13)
<223> OTHER INFORMATION: Xaa is Gln, Ser, Glu or Pro
<220> FEATURE:
<221> NAME/KEY: misc_feature
<222> LOCATION: (16)...(16)
<223> OTHER INFORMATION: Xaa is Lys, Gln or Thr

<400> SEQUENCE: 198

Xaa Ile Xaa Pro Xaa Xaa Xaa Xaa Thr Xaa Tyr Xaa Xaa Lys Phe Xaa
1               5                   10                  15

Gly

<210> SEQ ID NO 199
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)...(3)
<223> OTHER INFORMATION: Xaa is Tyr, Gly, Trp or Arg
<220> FEATURE:
<221> NAME/KEY: misc_feature
<222> LOCATION: (4)...(4)
<223> OTHER INFORMATION: Xaa is Asn, Ser, Ala or Gly
<220> FEATURE:
<221> NAME/KEY: misc_feature
<222> LOCATION: (6)...(6)
<223> OTHER INFORMATION: Xaa is Tyr, Ser, Asp or Trp
<220> FEATURE:
<221> NAME/KEY: misc_feature
<222> LOCATION: (8)...(8)
<223> OTHER INFORMATION: Xaa is Leu, Pro, Tyr or Ile

<400> SEQUENCE: 199

Gln Gln Xaa Xaa Ser Xaa Pro Xaa Thr
1               5

<210> SEQ ID NO 200
<211> LENGTH: 9
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)...(3)
<223> OTHER INFORMATION: Xaa is Gly, Asn, Ser, Thr or Tyr
```

```
<220> FEATURE:
<221> NAME/KEY: misc_feature
<222> LOCATION: (5)...(5)
<223> OTHER INFORMATION: Xaa is Thr, Glu or Ser
<220> FEATURE:
<221> NAME/KEY: misc_feature
<222> LOCATION: (6)...(6)
<223> OTHER INFORMATION: Xaa is Phe, Asp, Trp or Tyr
<220> FEATURE:
<221> NAME/KEY: misc_feature
<222> LOCATION: (8)...(8)
<223> OTHER INFORMATION: Xaa is Thr, Tyr, Arg or Phe
<220> FEATURE:
<221> NAME/KEY: misc_feature
<222> LOCATION: (9)...(9)
<223> OTHER INFORMATION: Xaa is Phe or Thr

<400> SEQUENCE: 200

Gln Gln Xaa Asn Xaa Xaa Pro Xaa Xaa
 1               5

<210> SEQ ID NO 201
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (3)...(3)
<223> OTHER INFORMATION: Xaa is Tyr, Ser or Asn
<220> FEATURE:
<221> NAME/KEY: misc_feature
<222> LOCATION: (4)...(4)
<223> OTHER INFORMATION: Xaa is Pro or Ser
<220> FEATURE:
<221> NAME/KEY: misc_feature
<222> LOCATION: (5)...(5)
<223> OTHER INFORMATION: Xaa is Ser, Gly or Asn
<220> FEATURE:
<221> NAME/KEY: misc_feature
<222> LOCATION: (6)...(6)
<223> OTHER INFORMATION: Xaa is Gly or Ser
<220> FEATURE:
<221> NAME/KEY: misc_feature
<222> LOCATION: (7)...(7)
<223> OTHER INFORMATION: Xaa is Ser or Gly
<220> FEATURE:
<221> NAME/KEY: misc_feature
<222> LOCATION: (8)...(8)
<223> OTHER INFORMATION: Xaa is Thr, Gly or Ser
<220> FEATURE:
<221> NAME/KEY: misc_feature
<222> LOCATION: (10)...(10)
<223> OTHER INFORMATION: Xaa is Asn or Tyr
<220> FEATURE:
<221> NAME/KEY: misc_feature
<222> LOCATION: (12)...(12)
<223> OTHER INFORMATION: Xaa is Asn, Ala or Pro
<220> FEATURE:
<221> NAME/KEY: misc_feature
<222> LOCATION: (13)...(13)
<223> OTHER INFORMATION: Xaa is Gln, Asp or Ser
<220> FEATURE:
<221> NAME/KEY: misc_feature
<222> LOCATION: (14)...(14)
<223> OTHER INFORMATION: Xaa is Lys or Ser
<220> FEATURE:
<221> NAME/KEY: misc_feature
<222> LOCATION: (15)...(15)
<223> OTHER INFORMATION: Xaa is Phe, Val or Lys
<220> FEATURE:
<221> NAME/KEY: misc_feature
<222> LOCATION: (16)...(16)
<223> OTHER INFORMATION: Xaa is Lys or Gln
```

```
<220> FEATURE:
<221> NAME/KEY: misc_feature
<222> LOCATION: (17)...(17)
<223> OTHER INFORMATION: Xaa is Gly or Arg

<400> SEQUENCE: 201

Glu Ile Xaa Xaa Xaa Xaa Xaa Xaa Thr Xaa Tyr Xaa Xaa Xaa Xaa Xaa Xaa
1               5                   10                  15

<210> SEQ ID NO 202
<211> LENGTH: 17
<212> TYPE: PRT
<213> ORGANISM: Artificial Sequence
<220> FEATURE:
<223> OTHER INFORMATION: Synthetic Construct
<220> FEATURE:
<221> NAME/KEY: misc_feature
<222> LOCATION: (1)...(1)
<223> OTHER INFORMATION: Xaa is Gly, Asn, Ser, Thr or Tyr
<220> FEATURE:
<221> NAME/KEY: misc_feature
<222> LOCATION: (3)...(3)
<223> OTHER INFORMATION: Xaa is Thr, Glu or Ser
<220> FEATURE:
<221> NAME/KEY: misc_feature
<222> LOCATION: (8)...(8)
<223> OTHER INFORMATION: Xaa is Phe, Asp, Trp or Tyr
<220> FEATURE:
<221> NAME/KEY: misc_feature
<222> LOCATION: (11)...(11)
<223> OTHER INFORMATION: Xaa is Thr, Tyr, Arg or Phe
<220> FEATURE:
<221> NAME/KEY: misc_feature
<222> LOCATION: (14)...(14)
<223> OTHER INFORMATION: Xaa is Phe or Thr
<220> FEATURE:
<221> NAME/KEY: misc_feature
<222> LOCATION: (15)...(15)
<223> OTHER INFORMATION: Xaa is Phe or Thr

<400> SEQUENCE: 202

Xaa Ile Xaa Pro Ser Gly Gly Xaa Thr Tyr Xaa Ala Asp Xaa Xaa Lys Gly
1               5                   10                  15
```

PEPTIDES FOR TREATMENT AND DIAGNOSIS OF AUTOIMMUNE DISEASE

This application is a U.S. national stage of International Application No. PCT/GB2006/002977 filed Aug. 9, 2006.

The invention provides peptides derived from antibodies with reactivity against a GPI linkage epitope and functionally-equivalent ligands. These peptides can be used in the therapy and diagnosis of a variety of diseases, all of which are considered to be caused by the inappropriate presence in the body of autoantibodies which are reactive with GPI linkage epitopes. The invention also describes a mechanism of action of these autoantibodies which compromises the organism, so causing disease, and describes a method of prevention of disease and detection of such autoantibody.

All publications, patents and patent applications cited herein are incorporated in full by reference.

BACKGROUND TO THE INVENTION

The invention relates to a new concept regarding the cause of autoimmune diseases, and other diseases currently not considered autoimmune. This concept was originally described in international patent application WO99/05175, where the incidence of naturally-occurring autoantibodies with a specific reactivity was linked to various autoimmune diseases, such as diabetes. The concept is that most diseases of infectious or non-infectious origin, with or without genetic predisposition or conditions related to the ageing process, become manifest or are aggravated by the emergence of a multispecific autoantibody. A large proportion of the population generate this autoantibody, which compromises all systems and organs which are affected by blood glucose levels, insulin levels, other hormone levels controlled by or affecting insulin and/or GPI-linked molecules, other regulatory molecules recognised by the autoantibody and phospholipids. These autoantibodies have the potential to accelerate ageing and age-related diseases, promote cancers, mediate the manifestation of diseases whether or not based on genetic predisposition and interfere with first line defence against infectious agents. That is, there is an underlying pathogenic problem which is the production of the autoantibody which depending on individual susceptibility, leads to one or more problematic conditions or diseases. An analogy would be that for any given drug, there may be one or more side-effects, none of which would be present in the absence of the drug. So, these antibodies are considered to be causative of a multitude of different disorders manifested through the same mechanism.

The pathogenic autoantibody is represented by a monoclonal antibody which recognises anti-TCR Vβ antibodies, molecules with signalling capacity, phospholipids including phosphatidyl inositol, second messengers of insulin action, single and double-stranded DNA and elements of the GPI-linkage.

Although certain therapies exist for the diseases and conditions which are discussed herein, most of these diseases remain problematic and are a significant cause of morbidity and mortality. There thus remains a great need for novel therapies to be derived that are effective in the prevention, treatment and diagnosis of these conditions. Of course, in view of the wide variety of diseases of the type discussed herein, it would be of great benefit were it to be possible to derive a single therapy that would be effective for all these diseases.

The applicant has now established that certain peptides or antibodies termed peptide-counteracting antibodies may be used in the prevention, therapy and diagnosis of a wide variety of diseases and conditions.

SUMMARY OF THE INVENTION

According to the invention, there is provided a peptide derived from an antibody with reactivity against a GPI linkage epitope, or a functionally-equivalent ligand.

The concept that has emerged from the Applicant's research is that many diseases become manifest or are aggravated by the emergence of a certain autoantibody. This antibody has reactivity against a GPI linkage epitope, but is multispecific in the sense that it also exhibits reactivity against epitopes in anti-TCR Vβ antibodies, molecules with signalling capacity, phospholipids including phosphatidyl inositol, phosphatidyl serine and cardiolipin (diacyl glycerol), and phospholipid glycans, second messengers of insulin action, single and double-stranded DNA and elements of the GPI-linkage. Elements of this discovery were first reported in International patent application WO99/05175 (A. Matossian-Rogers), the entire content of which is incorporated herein by reference.

One of the disorders linked to the presence of these autoantibodies is diabetes. The current thinking regarding causation of diabetes does not make any mechanistic link between infections and the theory of autoimmune T cell destruction of β cells (which subsequently leads to the emergence of many known autoantibodies). The key observations of initial increases in insulin output and dysregulated glucagon secretion in diabetics are also not accommodated by present theories.

Applying the concept on which the present invention is based to the specific case of diabetes, infections result in monoclonal or polyclonal T cell proliferation and increasing T cell numbers which are then homeostatically regulated. This involves the death of T cells releasing T cell receptor (TCR) fragments which generate antibodies (anti-TCR Vβ) by which different T cells are identified[1]. Such antibodies can in turn stimulate the development of anti-anti-TCR Vβ antibodies. These monoclonal anti-anti-TCR Vβ antibodies not only bind to anti-TCR Vβ antibodies but also to human pancreatic α cells in in vitro studies (see WO99/05175). These anti-anti-TCR Vβ antibodies are also reactive against phospholipids such as cardiolipin, phosphatidyl serine and phosphatidyl inositol.

It is conceivable that anti-anti-TCR Vβ antibodies recognise GPI-linked molecules on α cells due to their cross-reactive recognition of phosphatidyl inositol, one of the elements of the GPI linkage. Phosphatidylinositol has been demonstrated to significantly inhibit the binding of an anti-GPI antibody to the GPI-linked target molecule[2]. GPI linkages are sensitive to insulin action via insulin activated phospholipases[3,4]. GPI-linked molecules, which are rapidly hydrolysed by phospholipases, have been shown to generate second messengers in cultured pituitary lactotrophs[5]. Thus it is possible to envisage how antibodies binding to GPI-linked molecules on α cells would disrupt the normal negative feedback by insulin on glucagon secretion by these cells, thereby increasing glucagon output.

Glucagon participates in nutrient-induced insulin secretion by stimulating cAMP production in islet β cells; insulin production from purified β cells is markedly increased after addition of glucagon or α cells[6]. Glucagon has also been shown to enhance the amplitude of pulsatile insulin release in response to glucose[7]. Therefore, the effect of such antibodies on pancreatic islet cells should be the over-production of insulin.

This has in fact been shown to be the case and data presented in WO99/05175 support this contention. When human pancreatic islet cells isolated from cadaveric donors were exposed to monoclonal anti-anti-TCR Vβ antibodies, insulin secretion was found to be dysregulated compared to control cells. Thus binding of the anti-anti-TCR Vβ antibodies to pancreatic α cells in vitro leads to dysregulation of insulin secretion. Furthermore, in newly diagnosed diabetic children, auto-antibodies were found to bind to monoclonal anti-TCR Vβ antibodies (see Table 2). These auto-antibodies are analogous to anti-anti-TCR Vβ antibodies. These auto-antibodies may be responsible for the lack of responsiveness of α cells to normal physiological stimuli in diabetics giving rise to hyperglycaemia and counter-regulatory defects. Certainly a role for these molecules is suggested by the fact that the monoclonal anti-anti-TCR Vβ antibodies do not bind to the islets of established type I diabetics, presumably because the target molecules are either downregulated or already saturated with the auto-antibodies.

Peptides

Peptides have now been devised that are based on the structure of monoclonal antibodies which represent the polyspecific autoantibody described above. Such peptides have been shown to be immunogenic in rabbits and to result in the generation of antibodies which reacted with a broad spectrum of human sera Such peptides have also been shown to provide useful therapeutic effects in human patients. It is therefore proposed that polyclonal or monoclonal antibodies generated against these peptides or equivalent ligands, and the peptides and equivalent ligands themselves, may be used both therapeutically and in analytical techniques to qualitatively or quantitatively detect the presence of the autoantibodies or counteracting antibodies made against them.

As used herein, the term "peptide" includes any moiety comprising amino acids joined to each other by peptide bonds or modified peptide bonds, i.e. peptide isosteres. This term refers both to short chains (5-20 amino acids) and to longer chain oligopeptides (20-500 amino acids). Preferably, the peptide comprises at least 5, at least 10, at least 15, at least 20, at least 25, at least 30, at least 35, at least 40 or at least 45 amino acids joined to each other by peptide bonds or modified peptide bonds.

Preferably, a peptide according to the invention comprises the amino acid sequence of an antibody with reactivity against a GPI linkage epitope and one or more of the following moieties: an anti-TCR Vβ antibody, a molecule with signalling capacity, a phospholipid (including phosphatidyl inositol, phosphatidyl serine, cardiolipin (diacyl glycerol), or phospholipid glycan), a second messenger of insulin action, and single or double-stranded DNA. The antibody may also show reactivity against one or more cell types, including human pancreatic a cells, follicular cells of the thyroid, cells of the adrenal medulla, stomach and intestinal tract, salivary glands, ovary, striated muscle and connective tissue given as examples from a non-exhaustive list. The term "reactivity" means that the antibodies have substantially greater affinity for the recited antigens than their affinity for other antigens to which no specific binding is exhibited. Preferably this substantially greater affinity is at least 1.5-fold, more preferably at least 2-fold, more preferably 5-fold, 10-fold, 100-fold, 1000-fold, 10,000-fold, 100,000-fold, $10^6$-fold or more. It will be understood by those of skill in the art that although antibodies are highly specific, particular antibodies may be highly specific for more than one antigen. Various terms have been used in the art to describe this phenomenon, including the term "cross-reactivity". The antigens to which the antibody cross-reacts may be structurally similar or may be structurally disimilar. These antibodies with reactivity against a GPI linkage epitope and one or more of the moieties or cell types recited above are examples of such "cross-reactivity".

A peptide according to the invention may thus be a fragment of an antibody with the properties recited above. For example, such fragments may be derived from the variable regions of appropriate antibodies—Fab, F(ab')2, Fv and ScFv portions are examples of antibody fragments that have advantageous properties. Methods for constructing such antibody fragments are well documented in the art (Molecular Immunology, Hames, B. D. and Glover D. M. eds., IRL Press, New York, 1996; Practical Immunology, Hay, F. and Westwood, O. Blackwell Science Ltd., 2002). Preferred antibodies from which to derive such fragments are described in International patent application WO99/05175.

In some embodiments, the antibodies, equivalent ligands and uses thereof disclosed in WO99/05175 are specifically excluded from the scope of the present invention.

Particularly preferred variable regions from which peptides according to the invention may be derived are those whose sequences are presented herein as SEQ ID NOs:2 (heavy chain) and 4 (light chain). The genes encoding these variable regions were isolated from murine monoclonal cells which secrete antibody recognising the anti-TCR Vβ antibodies. The corresponding DNA sequences are presented in SEQ ID NOs:1 and 3.

Other preferred variable regions from which peptides according to the invention may be derived are those whose sequences are presented herein as SEQ ID Nos:18, 20, 34, 36, 50, 52, 66, 68, 82 and 84. The genes encoding these variable regions were also isolated from murine monoclonal cells which secrete antibody recognising anti-TCR Vβ antibodies. The corresponding DNA sequences are presented in SEQ ID NOs:17, 19, 33, 35, 49, 51, 65, 67, 81 and 83.

A peptide according to the invention may preferably be a fragment of the hypervariable region of an antibody with the properties recited above. The hypervariable regions of an antibody are the regions that directly contact a portion of the antigen's surface. For this reason, hypervariable regions are also sometimes referred to as complementarity determining regions, or CDRs. Each of the heavy and light chains has three CDRs, designated CDR-H1, CDR-H2, CDR-H3, CDR-L1, CDR-L2 and CDR-L3 herein.

Particularly preferred hypervariable regions from which peptides according to the invention may be derived are those whose sequences are presented herein as SEQ ID NOs:6, 8, 10, 12, 14 and 16.

Certain peptides conforming to the sequences of these hypervariable regions have been constructed and tested for efficacy as antigens capable of binding to anti-TCR Vβ antibodies. These peptides have the amino acid sequences recited in SEQ ID NOs:8, 10 and 16 and are particularly preferred peptides according to the present invention.

Other preferred hypervariable regions from which peptides according to the invention may be derived are those whose sequences are presented herein as SEQ ID NOs:22, 24, 26, 28, 30, 32, 38, 40, 42, 44, 46, 48, 54, 56, 58, 60, 62, 64, 70, 72, 74, 76, 78, 80, 86, 88, 90, 92, 94 and 96.

The invention also provides that such peptides may be linked together to form dimers or multimers. The dimers or multimers may be homodimers or homomultimers, or may be heterodimers or heteromultimers. Such linked molecules may be more efficacious than using single peptides in isolation, since the binding efficacy may increase due to the greater availability of binding sites and/or the range of epitopes displayed. The peptides may be linked directly, or may be linked together by linker molecules such as amino acids (particularly glycine), peptides or chemical linking groups. Preferred multimers include homodimers comprising the amino acid sequences presented in SEQ ID NO:8, SEQ ID NO:10 or SEQ ID NO:16. Homodimers comprising the amino acid sequences presented in SEQ ID NO:8, SEQ ID NO:10 or SEQ ID NO:16 and an additional N terminal cysteine residue have been shown to provide useful therapeutic effects in human patients (see Examples 6 and 7 herein). These peptides may also include combinations of the peptides whose amino acid sequences are recited in SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96. Preferred combinations of peptides include those including the peptides whose amino acid sequences are recited in SEQ ID NOs:8, 10 and 16 (for example, SEQ ID NOs:8 and 10, SEQ ID NOs:8 and 16, SEQ ID NOs:10 and 16 and SEQ ID NOs:8, 10 and 16).

Peptides according to the above-described aspects of the invention may contain amino acids other than the 20 gene-encoded amino acids, modified either by natural processes, such as by post-translational processing or by chemical modification techniques which are well known in the art. Among the known modifications which may commonly be present in polypeptides of the present invention are glycosylation, lipid attachment, sulphation, gamma-carboxylation, for instance of glutamic acid residues, hydroxylation and ADP-ribosylation. Other potential modifications include acetylation, acylation, amidation, covalent attachment of flavin, covalent attachment of a haeme moiety, covalent attachment of a nucleotide or nucleotide derivative, covalent attachment of a lipid derivative, covalent attachment of phosphatidylinositol, cross-linking (for example, between cysteine residues), cyclization, disulphide bond formation, demethylation, formation of covalent cross-links, formation of cysteine, formation of pyroglutamate, formylation, GPI anchor formation, iodination, methylation, myristoylation, oxidation, proteolytic processing, phosphorylation, prenylation, racemization, selenoylation, transfer-RNA mediated addition of amino acids to proteins such as arginylation, and ubiquitination. Modifications can occur anywhere in a peptide, including the peptide backbone, the amino acid side-chains and the amino or carboxyl termini.

Peptides according to the invention may be homologous to the peptides explicitly identified above in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96. Two polypeptides are said to be "homologous", as the term is used herein, if the sequence of one of the polypeptides has a high enough degree of identity or similarity to the sequence of the other polypeptide. "Identity" indicates that at any particular position in the aligned sequences, the amino acid residue is identical between the sequences. "Similarity" indicates that, at any particular position in the aligned sequences, the amino acid residue is of a similar type between the sequences. Degrees of identity and similarity can be readily calculated (Computational Molecular Biology, Lesk, A. M., ed., Oxford University Press, New York, 1988; Biocomputing. Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., M Stockton Press, New York, 1991).

Typically, greater than 25% identity between two peptides (preferably, over a specified region such as a hypervariable region) is considered to be an indication of functional equivalence. Preferably, functionally equivalent polypeptides of the first aspect of the invention have a degree of sequence identity with a peptide as recited in any one of SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96, or with active fragments thereof, of greater than 25%. More preferred polypeptides have degrees of identity of greater than 30%, 40%, 50%, 60%, 70%, 80%, 90%, 95%, 98% or 99%, respectively with these peptides, or with active fragments thereof.

Percentage identity, as referred to herein, is as determined using BLAST version 2.1.3 using the default parameters specified by the NCBI (the National Center for Biotechnology Information; http://www.ncbi.nlm.nih.gov/) [Blosum 62 matrix; gap open penalty=11 and gap extension penalty=1].

Homologous peptides therefore include natural biological variants (for example, allelic variants or geographical variations within the species from which the peptides are derived) and mutants (such as mutants containing amino acid substitutions, insertions, modifications or deletions) of the peptides that are explicitly identified above in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96. Such mutants may include peptides in which one or more of the amino acid residues are substituted with a conserved or non-conserved amino acid residue (preferably a conserved amino acid residue) and such substituted amino acid residue may or may not be one that is encoded by the genetic code. Typical such substitutions are among the group Ala, Val, Leu and Ile; among Ser and Thr; among the acidic residues Asp and Glu; among Asn and Gln; among the basic residues Lys and Arg; or among the aromatic residues Phe and Tyr. Particularly preferred are variants in which several, i.e. between 1 and 5, 1 and 3, 1 and 2 or just 1 amino acids are substituted, deleted or added in any combination. Especially preferred are silent substitutions, additions and deletions, which do not alter the properties and activities of the protein. Such mutants also include peptides in which one or more of the amino acid residues includes a substituent group as described above.

Such variants include extended or truncated versions of the peptides explicitly identified herein in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96. For extended variants, it is considered highly likely that the antigenic region of these peptides will fold correctly and show antigenic activity if additional residues C terminal and/or N terminal of the sequences are included in the peptide fragment. For example, an additional 5, 10, 20, 30, 40, 50, 100 or even as many as 200 amino acid residues from the peptides explicitly identified herein in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96, or from homologous sequences, may be included at either or both the C terminal and/or N terminal of the boundaries of the peptides, without prejudicing the ability of the polypeptide fragments to fold correctly.

For truncated variants of these peptides, one or more amino acid residues may generally be deleted at either or both the C terminus or the N terminus of the peptides, without compromising the ability of these peptides to fold correctly.

The reason for using modified, mutated or substituted peptides may be, for example, to generate peptides having similar or improved therapeutic and/or pharmacokinetic properties to those of the wild type peptide. Such peptides should retain the efficacy of the wild type peptide, for example, in binding to its biological target. For example, when the susceptibility of the peptide to cleavage by peptidases following injection into the subject is a problem, replacement of a particularly sensitive peptide bond with a non-cleavable peptide mimetic can provide a peptide more stable and thus more useful as a therapeutic. Similarly, the replacement of an L-amino acid residue is a standard way of rendering the peptide less sensitive to proteolysis, and finally more similar to organic compounds other than peptides. Also useful are amino-terminal blocking groups such as t-butyloxycarbonyl, acetyl, theyl, succinyl, methoxysuccinyl, suberyl, adipyl, azelayl, dansyl, benzyloxycarbonyl, fluorenylmethoxycarbonyl, methoxyazelayl, methoxyadipyl, methoxysuberyl, and 2,4,-dinitrophenyl. Blocking the charged N- and C-termini of the peptides would have the additional benefit of enhancing passage of the peptide through the hydrophobic cellular membrane and into the cell. The techniques for the synthesis and the development of peptide mimetics and other non-peptide mimetics are well known in the art (see, for example, Hruby V J and Balse P M, Curr Med Chem 2000, 7:945-70; Golebiowski A et al., Curr Opin Drug Discov Devel 2001, 4: 428-34; Kim H O and Kahn M, Comb Chem High Throughput Screen 2000; 3: 167-8). For example, miniproteins and synthetic mimics able of disrupting protein-protein interactions and inhibiting protein complex formation have been described (Cochran A G, Curr Opin Chem Biol 2001, 5(6):654-659). Various methodologies, for incorporating unnatural amino acids into proteins, using both in vitro and in vivo translation systems, to probe and/or improve protein structure and function are also disclosed in the literature (see, for example, Dougherty D A, Curr Opin Chem Biol 2000, 4: 645-52).

The literature provides many models on which the selection of conservative amino acids substitutions can be performed on the basis of statistical and physico-chemical studies on the sequence and/or the structure of natural protein (for example, see Bordo and Argos, J Mol Biol 1991, 217: 721-9; Rogov and Nekrasov, Protein Eng 2001, 14: 459-463). Protein design experiments have shown that the use of specific subsets of amino acids can produce foldable and active proteins, helping in the classification of amino acid substitutions which can be more easily accommodated in protein structure, and which can be used to detect functional and structural homologs and paralogs (Murphy L R et al., Protein Eng. 2000, 13:149-52).

The peptides of the invention may form part of fusion proteins. For example, it is often advantageous to include one or more additional amino acid sequences which may contain secretory or leader sequences, pro-sequences, sequences which aid in purification, or sequences that confer higher protein stability, for example during recombinant production. Alternatively or additionally, the mature peptide may be fused with another compound, such as a compound to increase the half-life of the polypeptide (for example, polyethylene glycol). The peptides may also be fused to a biological or synthetic substance, may be conjugated to moieties such as enzymes, indicator compounds, drugs, toxins or labels (radioactive, fluorescent or other).

The peptides of the present invention can be prepared in any suitable manner. In particular, such methods of preparation include recombinant production, synthetic production or a combination of these methods. For synthetic production, t-Boc or FMOC-based chemistries may be used in solid phase peptide synthesis methods (see "Solid Phase Peptide Synthesis", eds. Stewart & Young, available from Pierce Chem. Co). Alternatively, solution phase synthesis may be applied (see "Chemical Approaches to the Synthesis of Peptides and Proteins", Lloyd-Williams, P., Albericio, F. and Giralt, E., CRC Press, 1997).

Peptides according to the invention may share significant structural homology with the peptides explicitly identified above in SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96. In particular, peptides according to the invention may share certain important hypervariable region residues with the hypervariable sequences identified in SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96. Important hypervariable region residues present in SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96 have been identified by comparison of hypervariable region sequences.

The hypervariable regions of six cross-reactive murine anti-anti-TCR Vβ IgM and IgG monoclonal antibodies were cloned and sequenced (see Examples 1 and 5 herein). Analysis of the hypervariable region sequences of those antibodies reveals important information regarding the residues required for cross-reactive anti-TCR Vβ binding (i.e. multispecific reactivity against a GPI linkage epitope as described herein).

Firstly, analysis of the sequences suggests that specific amino acids may be essential at certain positions within each CDR (see Example 5). Accordingly, the peptides of the invention may comprise or consist of one of the following sequences, wherein 'x' indicates any amino acid residue, wherein '-' indicates a peptide bond, and wherein the peptides are shown in N to C terminal orientation:

```
                                          (SEQ ID NO: 162)
Consensus 1 G-Y-x-F-T-x-x-x-x-x-W (SEQ ID NO: 163)
Consensus 2 x-I-x-x-x-x-x-x-x-Y-x-x-x-F-K-x (SEQ ID NO: 164)
Consensus 3 x-A-S-x-x-x-x-x-x-x-x (SEQ ID NO: 165)
Consensus 4 x-x-S-x-x-x-S (SEQ ID NO: 166)
Consensus 5 Q-Q-x-x-x-x-P-x-x
```

Secondly, analysis of the sequences enabled generation of a 'general formula' for each CDR based on the cloned sequences (see Example 5). Accordingly, the peptides of the invention may comprise or consist of an amino acid sequence meeting the requirements of one of the following 'general formulae', wherein one of the amino acids shown in parentheses is selected at each position where relevant, wherein '-' indicates a peptide bond, and wherein the peptides are shown in N to C terminal orientation:

```
Formula 1
                                          (SEQ ID NO: 193)
G-Y-(TA)-F-T-(RNS)-(YN)-(WGN)-(IM)-(NF)-W Formula 2
                                          (SEQ ID NO: 194)
(NWY)-I-(YND)-(PT)-(SY)-(DNT)-(SG)-(YDE)-(TP)-

(NRT)-Y-(NSA)-(QD)-(KD)-F-K-(DG)
```

```
Formula 3
(LKE)-(RG)-(GML)-(LTY)-(LTG)-(PGN)-(DY)-(YAF)

Formula 4
(KR)-A-S-(QS)-(NDS)-(VI)-(DSG)-(TNS)-(NY)-(VLY)-

(ANL)

Formula 5
(SYR)-(AT)-S-(YRI)-(RL)-(YHA)-S

Formula 6
Q-Q-(YG)-(NS)-(TS)-(YFS)-P-(LTP)-(TF)
```

The above 'general formulae' encompass all the CDR sequences of the cross-reactive antibodies that have been cloned and sequenced by the inventors.

Thirdly, analysis of the sequences enabled an amino acid formula to be generated for each CDR that takes into account not only the completely conserved amino acids, but also the most common (predominant) amino acid(s) at each position of the CDR (see Example 5). Accordingly, the peptides of the invention may comprise or consist of an amino acid sequence meeting the requirements of one of the following formulae, wherein one of the amino acids shown in parentheses is selected at each position where relevant, wherein '-' indicates a peptide bond, and wherein the peptides are shown in N to C terminal orientation:

```
Formula 7
                                          (SEQ ID NO: 177)
G-Y-T-F-T-R-(YN)-W-(IM)-NW Formula 8
                                          (SEQ ID NO: 178)
N-I-Y-P-(SY)-D-(SG)-Y-T-N-Y-N--Q-K-F-K-(DG)

Formula 9
                                          (SEQ ID NO: 179)
L-(RG)-G-L-L-F-(DY)-Y Formula 10
                                          (SEQ ID NO: 180)
K-A-S-Q-N-V-(DSG)-T-N-V-A Formula 11
                                          (SEQ ID NO: 181)
S-A-S-Y-R-Y-S Formula 12
                                          (SEQ ID NO: 182)
Q-Q-Y-N-S-Y-P-L-T
```

It is believed that peptides which comprise or consist of an amino acid sequence meeting the requirements of one or more of the above consensus sequences and formulae will have equivalent biological activity to the peptides tested in vivo in Examples 6 and 7 herein, and will be useful in accordance with the invention.

The hypervariable region sequences identified in Examples 1 and 5 were also used to identify known hypervariable region sequences with a high level of sequence identity to the sequences identified by the inventors and with relevant binding properties (see Example 8 and FIGS. 12A to 12E herein). The known hypervariable region sequences were compared to the hypervariable region sequences identified in Examples 1 and 5, to further analyse the hypervariable region residues important for cross-reactive anti-TCR Vβ binding (i.e. multispecific reactivity against a GPI linkage epitope as described herein). A further series of consensus sequences and formulae were identified using the same type of analysis as employed in Example 5 (see FIGS. 12A to 12E).

Accordingly, the peptides of the invention may comprise or consist of one of the following sequences, wherein 'x' indicates any amino acid residue, wherein '-' indicates a peptide bond, and wherein the peptides are shown in N to C terminal orientation:

```
Consensus 6
G-Y-T-F-T-x-x-x-x-x-W                     (SEQ ID NO: 167)

Consensus 7
G-Y-x-F-x-x-Y-x-M-x-W                     (SEQ ID NO: 168)

Consensus 8
x-I-x-x-x-x-x-x-x-x-Y-x-x-x-F-K-x         (SEQ ID NO: 169)

Consensus 9
x-I-x-P-x-x-x-x-T-x-Y-x-x-K-F-x-G         (SEQ ID NO: 170)

Consensus 10
x-A-S-x-x-x-x-x-x-x                       (SEQ ID NO: 171)

Consensus 11
x-A-S-x-x-x-x-x-L-x                       (SEQ ID NO: 172)

Consensus 12
x-x-S-x-x-x-S                             (SEQ ID NO: 173)

Consensus 13
x-T-S-x-L-x-x                             (SEQ ID NO: 174)

Consensus 14
Q-Q-x-x-S-x-P-x-T                         (SEQ ID NO: 175)

Consensus 15
Q-Q-x-N-x-x-P-x-x                         (SEQ ID NO: 176)
```

The peptides of the invention may also comprise or consist of an amino acid sequence meeting the requirements of one of the following 'general formulae', wherein one of the amino acids shown in parentheses is selected at each position where relevant, wherein '-' indicates a peptide bond, and wherein the peptides are shown in N to C terminal orientation:

```
Formula 13
                                          (SEQ ID NO: 195)
G-Y-T-F-T-(RNYSTDEG)-(NYF)-(WGAY)-(IMV)-(NGQH)-W Formula 14
                                          (SEQ ID NO: 196)
G-Y-(ATS)-F-(T/S)-(SDG)-Y-(NWV)-M-(FQHN)-W Formula 15
                                          (SEQ ID NO: 197)
(NWEAY)-I-(YND)-(PT)-(SYG)-(DTGY)-(SGD)-(YEGS)-

(TP)-(NTYGS)-Y-(NAI)-(QDE)-(KD)-F-K-(DGN)

Formula 16
                                          (SEQ ID NO: 198)
(YWKNLR)-I-(DN)-P-(YAEFS)-(NYS)-(GD)-(DSG)-T-

(RESKN)-Y-(SAN)-(QSEP)-K-F-(KQT)-G

Formula 17
(KR)-A-S-(QS)-(NSDT)-(VI)-(DGSR)-(TSYNK)-(NADY)-

(VYGL)-(ALD)

Formula 18
(RK)-A-S-(QR)-(DSG)-(IV)-(SN)-(NSG)-(YW)-L-(NHA)

Formula 19
(SRW)-(AT)-S-(YIT)-(RL)-(YAE)-S

Formula 20
(YLDTK)-T-S-(RNKV)-L-(HAG)-(SP)
```

```
Formula 21
                                          (SEQ ID NO: 199)
Q-Q-(YGWR)-(NSAG)-S-(YSDW)-P-(LPYI)-T Formula 22
                                          (SEQ ID NO: 200)
Q-Q-(GNSTY)-N-(TES)-(FDWY)-P-(TYRF)-P-(FT)
```

The peptides of the invention may also comprise or consist of an amino acid sequence meeting the requirements of one of the following formulae, wherein one of the amino acids shown in parentheses is selected at each position where relevant, wherein '-' indicates a peptide bond, and wherein the peptides are shown in N to C terminal orientation:

```
                                          (SEQ ID NO: 183)
Formula 23  G-Y-T-F-T-(RNS)-Y-W-(IM)-N-W (SEQ ID NO: 184)
Formula 24  G-Y-T-F-T-S-Y-W--M-H-W (SEQ ID NO: 185)
Formula 25  N-I-Y-P-S-D-S-Y-T-N-Y-N-Q-K-F-K--G (SEQ ID NO: 186)
Formula 26  (YW)-I-N-P-Y-N-G-D-T-(ES)-Y-N-Q-K-F-K-G (SEQ ID NO: 187)
Formula 27  K-A-S-Q-N-V-S-T-N-V-A (SEQ ID NO: 188)
Formula 28  R-A-S-Q-S-I-S-N-Y-L-(NA)

(SEQ ID NO: 189)
Formula 29  S-A-S-Y-R-Y-S (SEQ ID NO: 190)
Formula 30  Y-T-S-N-L-A-S (SEQ ID NO: 191)
Formula 31  Q-Q-Y-N-S-Y-P-L-T (SEQ ID NO: 192)
Formula 32  Q-Q-N-N-E-D-P-(YR)-T
```

The peptides of the invention may also comprise or consist of an amino acid sequence meeting the requirements of one of the following formulae, wherein one of the amino acids shown in parentheses is selected at each position where relevant, wherein 'x' indicates any amino acid residue, wherein '-' indicates a peptide bond, and wherein the peptides are shown in N to C terminal orientation:

```
Formula 33
(EYWSL)-I-(YSND)-(PSH)-(SGNY)-(GSNTD)-(SGD)-

(YTGS)-(TIA)-(NY)-(YN)-(NAP)-(QDSEP)-(KSL)-(FVK)-

(KQS)-(GR)

Formula 34
                                          (SEQ ID NO: 201)
E-I-(YSN)-(PS)-(SGN)-(GS)-(SG)-(TGS)-T-(NY)-Y-

(NAP)-(QDS)-(KS)-(FVK)-(KQ)-(GR)

Formula 35
                                          (SEQ ID NO: 202)
x-I-x-P-S-G-G-x-T-Y-x-k-D-(KS)-(FV)-KG
```

It is believed that peptides which comprise or consist of an amino acid sequence meeting the requirements of one or more of the above consensus sequences and formulae will also have equivalent biological activity to the peptides tested in vivo in Examples 6 and 7 above, and will be useful in accordance with the invention.

As noted elsewhere herein, the peptides of the invention may be linked together to form dimers or multimers. Thus, the invention also provides dimers or multimers of peptides which comprise or consist of an amino acid sequence meeting the requirements of one or more of the above consensus sequences and formulae. For example, the invention provides heterodimers of two peptides that comprise amino acid sequences meeting the requirements of two different consensus sequences or formulae described herein. For example, the invention provides homodimers of two peptides that comprise amino acid sequences meeting the requirements of the same consensus sequences or formulae.

The invention also provides peptides which comprise or consist of an amino acid sequence meeting the requirements of a consensus sequence or formula disclosed herein, and which amino acid sequence also has a degree of sequence identity with any one of SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96 of greater than 25%. Preferably, such peptides have a degree of identity greater than 30%, 40%, 50%, 60%, 70%, 80%, 90%, 95%, 98% or 99%, respectively with any one of SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96.

Peptides of the invention also include those which comprise or consist of an amino acid sequence meeting the requirements of one of the above consensus sequences, which include at one or more of the variable positions (i.e. the 'x' positions that are not completely conserved), any one of the amino acids disclosed in that position in a corresponding formula herein (i.e. in a formula corresponding to the same CDR).

For example, the consensus sequence and 'general formula' identified herein from the cloned CDR-H2 sequences (see Example 5) are:

```
Consensus 2
                                          (SEQ ID NO: 163)
x-I-x-x-x-x-x-x-x-Y-x-x-x-F-K-x Formula 2
                                          (SEQ ID NO: 194)
(NWY)-I-(YND)-(PT)-(SY)-(DNT)-(SG)-(YDE)-(TP)-

(NRT)-Y-(NSA)-(QD)-(KD)-F-K-(DG)
```

Thus, the peptides of the invention include combinations of those sequences, such as peptides which comprise or consist of the following sequences:

```
Combination 1
                                          (SEQ ID NO: 163)
(NWY)-I-x-x-x-x-x-x-x-Y-x-x-x-F-K-x Combination 2
                                          (SEQ ID NO: 163)
x-I-(YND)-x-x-x-x-x-x-Y-x-x-x-F-K-x Combination 3
                                          (SEQ ID NO: 163)
x-I-x-(PT)-x-x-x-x-x-Y-x-x-x-F-K-x Combination 4
                                          (SEQ ID NO: 163)
x-I-x-x-(SY)-x-x-x-x-Y-x-x-x-F-K-x Combination 5
                                          (SEQ ID NO: 163)
x-I-x-x-x-(DNT)-x-x-x-x-Y-x-x-x-F-K-x
```

-continued

Combination 6
(SEQ ID NO: 163)
x-I-x-x-x-x-(SG)-x-x-x-Y-x-x-x-F-K-x

Combination 7
(SEQ ID NO: 163)
x-I-x-x-x-x-x-(YDE)-x-x-Y-x-x-x-F-K-x

Combination 8
(SEQ ID NO: 163)
x-I-x-x-x-x-x-x-(TP)-x-Y-x-x-x-F-K-x

Combination 9
(SEQ ID NO: 163)
x-I-x-x-x-x-x-x-x-(NRT)-Y-x-x-x-F-K-x

Combination 10
(SEQ ID NO: 163)
x-I-x-x-x-x-x-x-x-x-Y-(NSA)-x-x-F-K-x

Combination 11
(SEQ ID NO: 163)
x-I-x-x-x-x-x-x-x-x-Y-x-(QD)-x-F-K-x

Combination 12
(SEQ ID NO: 163)
x-I-x-x-x-x-x-x-x-x-Y-x-x-(KD)-F-K-x

Combination 13
(SEQ ID NO: 163)
x-I-x-x-x-x-x-x-x-x-Y-x-x-xF-K-(DG)

The peptides of the invention also include more complex combinations of the consensus sequences and formulae disclosed herein. Thus, the invention also provides peptides which comprise or consist of the following sequences, for example:

Combination 14
(SEQ ID NO: 163)
(NWY)-I-(YND)-x-x-x-x-x-x-Y-x-x-x-F-K-x

Combination 15
(SEQ ID NO: 163)
(NWY)-I-x-(PT)-x-x-x-x-x-Y-x-x-x-F-K-x

Combination 16
(SEQ ID NO: 163)
(NWY)-I-x-x-(SY)-x-x-x-x-Y-x-x-x-F-K-x

Combination 17
(SEQ ID NO: 163)
(NWY)-I-x-x-x-(DNT)-x-x-x-Y-x-x-x-F-K-x

Combination 18
(SEQ ID NO: 163)
(NWY)-I-x-x-x-x-(SG)-x-x-x-Y-x-x-x-F-K-x

Combination 19
(SEQ ID NO: 163)
(NWY)-I-x-x-x-x-x-(YDE)-x-x-Y-x-x-x-F-K-x

Combination 20
(SEQ ID NO: 163)
(NWY)-I-x-x-x-x-x-x-(TP)-x-Y-x-x-x-F-K-x

Combination 21
(SEQ ID NO: 163)
(NWY)I-x-x-x-x-x-x-(NRT)-Y-x-x-x-F-K-x

Combination 22
(SEQ ID NO: 163)
(NWY)-I-x-x-x-x-x-x-x-Y-(NSA)-x-x-F-K-x

Combination 23
(SEQ ID NO: 163)
(NWY)-I-x-x-x-x-x-x-x-Y-x-(QD)-x-F-K-x

-continued

Combination 24
(SEQ ID NO: 163)
(NWY)-I-x-x-x-x-x-x-x-Y-X-x-(KD)-F-K-x

Combination 25
(SEQ ID NO: 163)
(NWY)-I-x-x-x-x-x-x-x-Y-x-x-x-F-K-(DG)

Examples 8 and 9 herein describe an analysis of known hypervariable region sequences of relevant binding specificities. That analysis was based on heavy and light chain variable region sequences available in public databases. In some embodiments, one or more of the sequences stored under the accession numbers 1921302A, 1921302B, A39276, B39276, AAA20444.1, AAA20447.1, AAB32203.1, AAB32202.1, AAB46758.1, AAB46763.1, AAB46759.1, AAB46764.1, AAB46760.1, AAB46765.1, AAB46761.1, AAB46766.1, AAB46762.1, AAB46767.1, AAB58061.1, AAB58062.1, AAC53642.1, AAC53642.1, AAD00604.1, AAD00605.1, AAD00606.1, AAD00607.1, AAE72083.1, AAE72082.1, AAG30427.1, AAG30432.1, AAG30428.1, AAG30433.1, AAG30429.1, AAG30434.1, AAG30430.1, AAG30435.1, AAG33839.1, AAG40815.1, AAK11244.1, AAL59364.1, AAL59381.1, AAL59365.1, AAL59380.1, AAL59366.1, AAL59379.1, AAL59367.1, AAL59378.1, AAL59368.1, AAL59377.1, AAL59369.1, AAL59376.1, AAL59370.1, AAL59375.1, AAL59371.1, AAL59374.1, AAL59372.1, AAL59373.1, AAL67507.1, AAL67508.1, AAL67509.1, AAL67510.1, AAL67511.1, AAP19642.1, AAP19641.1, AAR90997.1, AAS01840.1, AAR90998.1, AAS01841.1, AAR90999.1, AAR91002.1, AAS01843.1, AAR91003.1, AAS01844.1, AAR91004.1, AAR91005.1, AAR91007.1, AAS01847.1, AAT68292.1, AAT76236.1, AAT76271.1, AAT76245.1, AAT76280.1, AAT76246.1, AAT76281.1, B30502, C30502, CAA46142.1, CAA51998.1, CAA52929.1, CAA56180.1, CAA52930.1, CAA56181.1, CAA52931.1, CAA56178.1, CAA52932.1, CAA56179.1, CAA63586.1, CAA63587.1, CAA63589.1, CAA63590.1, CAA84376.1, CAA84375.1, CAB45250.1, CAB45251.1, CAB45252.1, CAB45253.1, CAB46481.1, CAB46447.1, CAB46482.1, CAB46448.1, CAC22102.1, CAC22102.1, F30502, G30502, PC4280, PC4283, PC4281, PC4282, S67941, S67940, S69897 and S69898 is/are specifically excluded from the scope of the present invention.

The first aspect of the invention also includes ligands that are functionally equivalent to the peptides that are explicitly identified herein. Functionally-equivalent ligands may be structures which are biologically derived or may be synthesised or selected from libraries (such as random or combinatorial libraries of chemical compounds) which can carry out the same functions or bind to the same target structures as the autoantibody or its representative monoclonal antibodies and derivatives thereof. For example, such compounds may share significant structural homology with the peptide sequences that are explicitly identified herein in SEQ ID NOs:2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 and 96. Such compounds may be identified by techniques such as threading (see, for example, Jones, D. T. (1997). Progress in protein structure prediction. Curr. Opin. Struct. Biol. 7(3), 377-387). Such compounds may also be identified in screening methods utilising the peptide-counteracting antibodies or functionally-equivalent ligands of the first aspect of the invention.

It is contemplated that any molecular framework capable of retaining the amino acid side-chains of these peptides in the necessary positions for binding to antigen will be suitable for use in accordance with the present invention. Of particular suitability in this respect may be cyclic peptides held in a precise framework by their linking groups and bonds. The amino acid side chains may be held in a position substantially identical to their position in wild type peptides. Preferably, the cyclic peptides comprise between 5 and 30 amino acids, preferably between 7 and 20 amino acids.

Biologically-active peptides with antigenic binding sites mimicking those according to the present invention may be generated using phage libraries. Nucleic acids encoding amino acid residues identified as participants in the antigenic site, together with nucleic acid encoding the surrounding framework residues may be fused to give a polypeptide unit of between 10 and 1000 residues, preferably between 25 and 100 residues. By fusion of this nucleic acid fragment with that encoding a phage protein, for example pIII of the bacteriophage fd, the fusion molecule may be displayed on the surface of phage. Screening of the phage library with antigen will then identify those clones of interest. These clones can then be subjected to iterative rounds of mutagenesis and screening to improve the affinity of the generated molecules for antigen.

In addition to peptide-based compounds, synthetic or organic molecules may be functionally equivalent to the peptides that are explicitly identified herein. The notion of combinatorial chemistry and the generation of combinatorial libraries has developed at great speed in recent years and has facilitated the rational design and improvement of molecules with desired properties. These techniques can be used to generate molecules possessing binding sites that are identical or similar to those of the peptides identified herein.

Such compounds may be generated by rational design, using for example standard synthesis techniques in combination with molecular modelling and computer visualisation programs. Under these techniques, the "lead" compound with a similar framework to the basic peptide is optimised by combining a diversity of scaffolds and component substituents.

Alternatively, or as one step in the structure-guided design of a molecular entity, combinatorial chemistry may be used to generate or refine the structure of compounds that mimic the antigen site of these peptides by the production of congeneric combinatorial arrays around a framework scaffold. These steps might include standard peptide or organic molecule synthesis with a solid-phase split and recombine process or parallel combinatorial unit synthesis using either solid phase or solution techniques (see, for example Hogan, 1997 and the references cited therein).

Peptide-containing Antibodies

According to a further embodiment of the first aspect of the invention, there is provided an antibody comprising a heavy chain variable region with the amino acid sequence presented in SEQ ID NOs:2, 18, 34, 50, 66 or 82. There is also provided an antibody comprising a light chain variable region with the amino acid sequence presented in SEQ ID NOs:4, 20, 36, 52, 68 or 84.

Thus, the invention provides an antibody comprising a heavy chain variable region with the amino acid sequence presented in SEQ ID NO:2 and a light chain variable region with the amino acid sequence presented in SEQ ID NO:4. The invention also provides an antibody comprising a heavy chain variable region with the amino acid sequence presented in SEQ ID NO:18 and a light chain variable region with the amino acid sequence presented in SEQ ID NO:20. The invention also provides an antibody comprising a heavy chain variable region with the amino acid sequence presented in SEQ ID NO:34 and a light chain variable region with the amino acid sequence presented in SEQ ID NO:36. The invention also provides an antibody comprising a heavy chain variable region with the amino acid sequence presented in SEQ ID NO:52 and a light chain variable region with the amino acid sequence presented in SEQ ID NO:54. The invention also provides an antibody comprising a heavy chain variable region with the amino acid sequence presented in SEQ ID NO:66 and a light chain variable region with the amino acid sequence presented in SEQ ID NO:68. The invention also provides an antibody comprising a heavy chain variable region with the amino acid sequence presented in SEQ ID NO:82 and a light chain variable region with the amino acid sequence presented in SEQ ID NO:84.

The invention also provides an antibody comprising 1, 2, 3, 4, 5 or 6 of the CDR sequences presented in SEQ ID NOs:6, 8, 10, 12, 14 and 16. The invention also provides an antibody comprising 1, 2, 3, 4, 5 or 6 of the CDR sequences presented in SEQ ID NOs:22, 24, 26, 28, 30 and 32. The invention also provides an antibody comprising 1, 2, 3, 4, 5 or 6 of the CDR sequences presented in SEQ ID NOs:38, 40, 42, 44, 46 and 48. The invention also provides an antibody comprising 1, 2, 3, 4, 5 or 6 of the CDR sequences presented in SEQ ID NOs:54, 56, 58, 60, 62 and 64. The invention also provides an antibody comprising 1, 2, 3, 4, 5 or 6 of the CDR sequences presented in SEQ ID NOs:70, 72, 74, 76, 78 and 80. The invention also provides an antibody comprising 1, 2, 3, 4, 5 or 6 of the CDR sequences presented in SEQ ID NOs:86, 88, 90, 92, 94 and 96.

The invention also provides an antibody comprising a heavy chain variable region sequence having greater than 25%, 30%, 40%, 50%, 60%, 70%, 80%, 90%, 95%, 98% or 99% identity to an amino acid sequence presented in SEQ ID NOs:2, 18, 34, 50, 66 or 82. The invention also provides an antibody comprising a light chain variable region sequence having greater than 25%, 30%, 40%, 50%, 60%, 70%, 80%, 90%, 95%, 98% or 99% identity to an amino acid sequence presented in SEQ ID NOs:4, 20, 36, 52, 68 or 84.

The invention also provides antibodies comprising 1, 2, 3, 4, 5 or 6 CDRs with greater than 25%, 30%, 40%, 50%, 60%, 70%, 80%, 90%, 95%, 98% or 99% identity to an amino acid sequence presented in SEQ ID NOs:6, 8, 10, 12, 14, 16, 22, 24, 26, 28, 30, 32, 38, 40, 42, 44, 46, 48, 54, 56, 58, 60, 62, 64, 70, 72, 74, 76, 78, 80, 86, 88, 90, 92, 94 and 96.

The invention also provides an antibody comprising 1, 2, 3, 4, 5 or 6 amino acid sequence(s) that meet the requirements of the consensus sequences and formulae disclosed herein.

The invention also provides fragments of these antibodies, such as Fab, F(ab')2, Fv and ScFv fragments as mentioned elsewhere herein.

Peptide-counteracting Antibodies

According to a further embodiment of the first aspect of the invention, there is provided an antibody, or functionally-equivalent ligand, which exhibits reactivity against a peptide of the first aspect of the invention. Such antibodies or functionally-equivalent ligands are useful in the treatment and diagnosis of disease, in particular, because they can be used therapeutically by passive transfer.

If polyclonal antibodies are desired, a selected mammal, such as a mouse, rabbit, goat or horse, may be immunised with a peptide of the first aspect of the invention. The peptide used to immunise the animal can be derived by recombinant DNA technology or can be synthesized chemically. If desired, the peptide can be conjugated to a carrier protein. Commonly used carriers to which the peptides may be chemically coupled include bovine serum albumin, thyroglobulin and keyhole limpet haemocyanin. The coupled peptide is then used to immunise the animal. Serum from the immunised animal is collected and treated according to known procedures, for example by immunoaffinity chromatography.

Monoclonal antibodies to the peptides of the first aspect of the invention can also be readily produced by one skilled in the art. The general methodology for making monoclonal antibodies using hybridoma technology is well known (see, for example, Kohler, G. and Milstein, C., Nature 256: 495-497 (1975); Kozbor et al., Immunology Today 4: 72 (1983); Cole et al., 77-96 in Monoclonal Antibodies and Cancer Therapy, Alan R Liss, Inc. (1985).

Panels of monoclonal antibodies produced against the peptides of the first aspect of the invention can be screened for various properties, i.e., for isotype, epitope, affinity, etc. Monoclonal antibodies are particularly useful in purification of the individual peptides against which they are directed. Alternatively, genes encoding the monoclonal antibodies of interest may be isolated from hybridomas, for instance by PCR techniques known in the art, and cloned and expressed in appropriate vectors.

Chimeric antibodies, in which non-human variable regions are joined or fused to human constant regions (see, for example, Liu et al., Proc. Natl. Acad. Sci. USA, 84, 3439 (1987)), may also be of use.

The antibody may be modified to make it less immunogenic in an individual, for example by humanisation (see Jones et al., Nature, 321, 522 (1986); Verhoeyen et al., Science, 239: 1534 (1988); Kabat et al., J. Immunol., 147: 1709 (1991); Queen et al., Proc. Natl Acad. Sci. USA, 86, 10029 (1989); Gorman et al., Proc. Natl. Acad. Sci. USA, 88: 34181 (1991); and Hodgson et al., Bio/Technology 9: 421 (1991)). The term "humanised antibody", as used herein, refers to antibody molecules in which the CDR amino acids and selected other amino acids in the variable domains of the heavy and/or light chains of a non-human donor antibody have been substituted in place of the equivalent amino acids in a human antibody. The humanised antibody thus closely resembles a human antibody but has the binding ability of the donor antibody.

In a further alternative, the antibody may be a "bispecific" antibody, that is an antibody having two different antigen binding domains, each domain being directed against a different epitope.

Phage display technology may be utilised to select genes which encode antibodies with binding activities towards the peptides of the invention either from repertoires of PCR amplified V-genes of lymphocytes from humans screened for possessing the relevant antibodies, or from naive libraries (McCafferty, J. et al., (1990), Nature 348, 552-554; Marks, J. et al., (1992) Biotechnology 10, 779-783). The affinity of these antibodies can also be improved by chain shuffling (Clackson, T. et al., (1991) Nature 352, 624-628).

Antibodies generated by the above techniques, whether polyclonal or monoclonal, have additional utility in that they may be employed as reagents in immunoassays, radioimmunoassays (RIA) or enzyme-linked immunosorbent assays (ELISA). In these applications, the antibodies can be labelled with an analytically-detectable reagent such as a radioisotope, a fluorescent molecule or an enzyme.

Nucleic Acid Molecules

According to a second aspect of the invention, there is provided a nucleic acid molecule encoding a peptide, antibody or functionally-equivalent ligand according to any one of the embodiments of the invention described above. A nucleic acid molecule which encodes such peptides may be identical to the coding sequence of the nucleic acid molecules recited in any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 95. These molecules also may have a different sequence which, as a result of the degeneracy of the genetic code, encodes a peptide as recited in SEQ ID NOs: 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94 or 96 respectively. Preferably, the purified nucleic acid molecule has the nucleic acid sequence as recited in any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 95, or is a redundant equivalent or fragment of any one of these sequences.

Nucleic acid molecules of the present invention may be in the form of RNA, such as mRNA, or in the form of DNA, including, for instance cDNA, synthetic DNA or genomic DNA. Such nucleic acid molecules may be obtained by cloning, by chemical synthetic techniques or by a combination thereof. The nucleic acid molecules can be prepared, for example, by chemical synthesis using techniques such as solid phase phosphoramidite chemical synthesis, from genomic or cDNA libraries or by separation from an organism. RNA molecules may generally be generated by the in vitro or in vivo transcription of DNA sequences. The nucleic acid molecules may be double-stranded or single-stranded. Single-stranded DNA may be the coding strand, also known as the sense strand, or it may be the non-coding strand, also referred to as the anti-sense strand.

The term "nucleic acid molecule" also includes analogues of DNA and RNA, such as those containing modified backbones, and peptide nucleic acids (PNA). The term "PNA", as used herein, refers to an antisense molecule or an anti-gene agent which comprises an oligonucleotide of at least five nucleotides in length linked to a peptide backbone of amino acid residues, which preferably ends in lysine. The terminal lysine confers solubility to the composition. PNAs may be pegylated to extend their lifespan in a cell, where they preferentially bind complementary single stranded DNA and RNA and stop transcript elongation (Nielsen, P. E. et al. (1993) Anticancer Drug Des. 8:53-63).

Nucleic acid molecules of the invention may include, but are not limited to, the coding sequence for the mature peptide or antibody by itself; the coding sequence for the mature peptide or antibody and additional coding sequences, such as those encoding a leader or secretory sequence, such as a pro-, pre- or prepro-polypeptide sequence; the coding sequence of the mature peptide or antibody, with or without the aforementioned additional coding sequences, together with further additional, non-coding sequences, including non-coding 5' and 3' sequences, such as the transcribed, non-translated sequences that play a role in transcription (including termination signals), ribosome binding and mRNA stability. The nucleic acid molecules may also include additional sequences which encode additional amino acids, such as those which provide additional functionalities.

Included within the scope of the invention are variant nucleic acid molecules that encode the variant peptides that are described above. Among variants in this regard are variants that differ from the nucleic acid molecules explicitly identified herein by nucleotide substitutions, deletions or insertions. The substitutions, deletions or insertions may involve one or more nucleotides. The variants may be altered in coding or non-coding regions or both. Alterations in the coding regions may produce conservative or non-conservative amino acid substitutions, deletions or insertions.

The nucleic acid molecules of the invention can also be engineered, using methods generally known in the art, for a variety of reasons, including modifying the cloning, processing, and/or expression of the gene product (the polypeptide). DNA shuffling by random fragmentation and PCR reassembly of gene fragments and synthetic oligonucleotides are mentioned as specific techniques which may be used to engineer the nucleotide sequences. Site-directed mutagenesis may be used to insert new restriction sites, alter glycosylation patterns, change codon preference, produce splice variants, introduce mutations and so forth.

Preferred embodiments of this aspect of the invention are nucleic acid molecules that are at least 25% identical over their entire length to a nucleic acid molecule as recited in any one of SEQ ID NOs:1, 3, 5, 7, 9, 11, 13, 15, 17, 19, 21, 23, 25, 27, 29, 31, 33, 35, 37, 39, 41, 43, 45, 47, 49, 51, 53, 55, 57, 59, 61, 63, 65, 67, 69, 71, 73, 75, 77, 79, 81, 83, 85, 87, 89, 91, 93 or 95. Preferably, a nucleic acid molecule according to this aspect of the invention comprises a region that is at least 30% identical over its entire length to the nucleic acid molecule having any one of these sequences, more preferably at least 40%, at least 50%, at least 60%, at least 70%, at least 80%, at least 90%, at least 95%, at least 98%, 99% or more identical.

According to a third aspect of the invention, there is provided a purified nucleic acid molecule which hybridizes under high stringency conditions with a nucleic acid molecule of the second aspect of the invention. Such molecules, which are partially or totally complementary to the nucleic acid molecules of the second aspect of the invention may be useful for antisense or probing purposes. Such antisense molecules, such as oligonucleotides, can be designed to recognise, specifically bind to and prevent transcription of a target nucleic acid encoding a polypeptide of the invention, as will be known by those of ordinary skill in the art (see, for example, Cohen, J. S., Trends in Pharm. Sci., 10, 435 (1989); Okano, J. Neurochem. 56, 560 (1991); O'Connor, J. Neurochem 56, 560 (1991); Lee et al., Nucleic Acids Res 6, 3073 (1979); Cooney et al., Science 241, 456 (1988); Dervan et al., Science 251, 1360 (1991). The term "hybridization" as used here refers to the association of two nucleic acid molecules with one another by hydrogen bonding. Typically, one molecule will be fixed to a solid support and the other will be free in solution. Then, the two molecules may be placed in contact with one another under conditions that favour hydrogen bonding. The inhibition of hybridization of a completely complementary molecule to a target molecule may be examined using a hybridization assay, as known in the art (see, for example, Sambrook et al [supra]). A substantially homologous molecule will then compete for and inhibit the binding of a completely homologous molecule to the target molecule under various conditions of stringency, as taught in Wahl, G. M. and S. L. Berger (1987; Methods Enzymol. 152:399-407) and Kimmel, A. R. (1987; Methods Enzymol. 152:507-511).

"Stringency" refers to conditions in a hybridization reaction that favour the association of very similar molecules over association of molecules that differ. High stringency hybridisation conditions are defined as overnight incubation at 42° C. in a solution comprising 50% formamide, 5×SSC 150 mM NaCl, 15 mM trisodium citrate), 50 mM sodium phosphate (pH7.6), 5×Denhardts solution, 10% dextran sulphate, and 20 microgram/ml denatured, sheared salmon sperm DNA, followed by washing the filters in 0.1×SSC at approximately 65° C. Low stringency conditions involve the hybridisation reaction being carried out at 35° C. (see Sambrook et al. [supra]). Preferably, the conditions used for hybridization are those of high stringency.

Vectors

In a fourth aspect, the invention provides a vector, such as an expression vector, that incorporates a nucleic acid molecule of the second or third aspect of the invention. The vectors of the present invention comprise nucleic acid molecules of the invention and may be cloning or expression vectors. The peptides of the invention may thus be prepared in recombinant form by expression of their encoding nucleic acid molecules in vectors contained within a host cell. Such expression methods are well known to those of skill in the art and many are described in detail by Sambrook et al (supra) and Fernandez & Hoeffler (1998, eds. "Gene expression systems. Using nature for the art of expression". Academic Press, San Diego, London, Boston, New York, Sydney, Tokyo, Toronto).

Generally, any system or vector that is suitable to maintain, propagate or express nucleic acid molecules to produce a polypeptide in the required host may be used. The appropriate nucleotide sequence may be inserted into an expression system by any of a variety of well-known and routine techniques, such as, for example, those described in Sambrook et al., (supra). Generally, the coding gene can be placed under the control of a control element such as a promoter, ribosome binding site (for bacterial expression) and, optionally, an operator, so that the DNA sequence encoding the desired polypeptide is transcribed into RNA in the transformed host cell.

Particularly suitable expression systems include microorganisms such as bacteria transformed with recombinant bacteriophage, plasmid or cosmid DNA expression vectors; yeast transformed with yeast expression vectors; insect cell systems infected with virus expression vectors (for example, baculovirus); plant cell systems transformed with virus expression vectors (for example, cauliflower mosaic virus, CaMV; tobacco mosaic virus, TMV) or with bacterial expression vectors (for example, Ti or pBR322 plasmids); or animal cell systems. Cell-free translation systems can also be employed to produce the peptides of the invention.

Introduction of nucleic acid molecules encoding a peptide of the present invention into host cells can be effected by methods described in many standard laboratory manuals, such as Davis et al., Basic Methods in Molecular Biology (1986) and Sambrook et al., [supra]. In eukaryotic cells, expression systems may either be transient (for example, episomal) or permanent (chromosomal integration) according to the needs of the system.

The encoding vector may include a sequence encoding a control sequence, such as a signal peptide or leader sequence, as desired, for example, for secretion of the translated polypeptide into the lumen of the endoplasmic reticulum, into the periplasmic space or into the extracellular environment. These signals may be endogenous to the peptide or they may be heterologous signals. Leader sequences can be removed by a bacterial host in post-translational processing.

In addition to control sequences, it may be desirable to add regulatory sequences that allow for regulation of the expression of the polypeptide relative to the growth of the host cell. Regulatory sequences are those non-translated regions of the vector, such as enhancers, promoters and 5' and 3' untranslated regions. These interact with host cellular proteins to carry out transcription and translation. Examples of regulatory sequences are those which cause the expression of a gene to be increased or decreased in response to a chemical or physical stimulus, including the presence of a regulatory compound or to various temperature or metabolic conditions. The control sequences and other regulatory sequences may be ligated to the nucleic acid coding sequence prior to insertion into a vector. Alternatively, the coding sequence can be cloned directly into an expression vector that already contains the control sequences and an appropriate restriction site.

Nucleic acid molecules according to the present invention may also be used to create transgenic animals, particularly rodent animals. Such transgenic animals form a further aspect of the present invention. This may be done locally by modification of somatic cells, or by germ line therapy to incorporate heritable modifications. Such transgenic animals may be particularly useful in the generation of animal models for drug molecules effective as modulators of the peptides of the invention.

Host Cells

In a fifth aspect, the invention provides a host cell transformed with a vector of the fourth aspect of the invention. The host cells of the invention, which may be transformed, transfected or transduced with the vectors of the invention may be prokaryotic or eukaryotic.

For long-term, high-yield production of a recombinant peptide, stable expression may be preferred. Examples of suitable mammalian cell lines available as hosts for expression are known in the art and include many immortalised cell lines available from the American Type Culture Collection (ATCC) including, but not limited to, Chinese hamster ovary (CHO), HeLa, baby hamster kidney (BHK), monkey kidney (COS), C127, 3T3, BHK, HEK 293, Bowes melanoma and human hepatocellular carcinoma (for example Hep G2) cells.

A further preferred system is the baculovirus system (commercially available in kit form from, inter alia, Invitrogen, San Diego Calif.). These techniques are generally known to those skilled in the art and are described fully in Summers and Smith, Texas Agricultural Experiment Station Bulletin No. 1555 (1987). Particularly suitable host cells for use in this system include insect cells such as *Drosophila* S2 and *Spodoptera* Sf9 cells.

There are many plant cell culture and whole plant genetic expression systems known in the art. Examples of suitable plant cellular genetic expression systems include those described in U.S. Pat. Nos. 5,693,506; 5,659,122; and 5,608,143. Additional examples of genetic expression in plant cell culture has been described by Zenk, (1991) Phytochemistry 30, 3861-3863.

Examples of particularly preferred bacterial host cells include streptococci, staphylococci, *E. coli, Streptomyces* and *Bacillus subtilis* cells. Examples of particularly suitable host cells for fungal expression include yeast cells (for example, *S. cerevisiae*) and *Aspergillus* cells.

Methods of Expressing

According to a sixth aspect of the invention, there is provided a method of expressing a peptide, antibody or equivalent ligand according to any one of the embodiments of the first aspect of the invention, the method comprising expressing a nucleic acid molecule according to the second or third aspect of the invention or a vector according to the fourth aspect of the invention in a host cell.

Treatment of Disease

In a seventh aspect, the invention provides a method of treating a disease in a patient comprising administering to the patient a peptide, antibody or equivalent ligand of the first aspect of the invention, or a nucleic acid molecule of the second or third aspect of the invention, or a vector of the fourth aspect of the invention, or a host cell of the fifth aspect of the invention. This aspect of the invention also provides a peptide, antibody or equivalent ligand of the first aspect of the invention, or a nucleic acid molecule of the second or third aspect of the invention, or a vector of the fourth aspect of the invention, or a host cell of the fifth aspect of the invention, for use in therapy or diagnosis of disease.

Diseases that are suitable for treatment or diagnosis in this manner are characterised by the presence of autoantibodies with reactivity against a GPI linkage epitope, which antibodies are preferably also reactive against epitopes in anti-TCR Vβ antibodies, molecules with signalling capacity, phospholipids including phosphatidyl inositol, phosphatidyl serine and cardiolipin (diacyl glycerol), and phospholipid glycans, second messengers of insulin action, single and double-stranded DNA and elements of the GPI-linkage. These autoantibodies have been identified by the present Applicant and the presence of such antibodies in the body is considered to accelerate ageing and age-related diseases, promote cancers, mediate the manifestation of diseases whether or not based on genetic predisposition and interfere with first line defence against infectious agents. The presence of such antibodies is thus a factor in common with all diseases that are suitable for treatment or diagnosis according to the present invention. Many of these conditions fall under the generic definitions of insulin dependent diabetes mellitus (IDDM), non-insulin dependent diabetes mellitus (NIDDM), organ or non-organ specific autoimmune disease, cardiovascular disease, cancer cachexia and cancer or any other diseases where anti-phospholipid antibodies and/or hyperinsulinemia and/or hyperglucagonaemia and/or glucose intolerance and/or insulin resistance are present. Some of these conditions are described below; it should be pointed out, however, that these diseases are listed by way of example and this list is not exhaustive.

Diseases that are suitable for treatment or diagnosis in this manner include, but are not limited to type I diabetes mellitus, type II diabetes mellitus, psoriasis, eczema, vitiligo, acanthosis, nigricans, alopecia greata, Alzheimer's disease, schizophrenia, depression, Parkinson's disease, migraine, multiple sclerosis, myasthenia gravis, amyotropic lateral sclerosis and other motor neurone disorders, progressive supranuclear palsy, Pick's disease and other neurodegenerative diseases, thyroid disease, multiple endocrine neoplasia type 2A and B, Cushing's syndrome, Addison's disease, polycystic ovary syndrome hypogonadism, premature baldness in men, obesity, syndrome X, recurrent foetal wastage, recurrent spontaneous abortion, recurrent thrombosis, systemic lupus erythematosus, Coeliac disease, autoimmune gastric disease, inflammatory bowel disease, rheumatoid arthritis, ankylosing spondylitis, asthma, cystic fibrosis, osteoporosis and osteopenia, lichen planus, leukoplakia, aplastic and other anaemias, paroxysmal nocturnal haemoglobinuria, sleep apnoea, insomnia, cancer, human immunodeficiency virus (HIV), infections, and immunoregulation diseases.

Experiments on human patients have shown that peptides according to the invention can be successfully used to improve oral glucose tolerance (see Example 6) and auto-glycaemic regulation in diabetic patients (see Example 7). Accordingly, diseases that are suitable for treatment or diagnosis according to the invention include, but are not limited to, diseases associated with glucose intolerance (i.e. associated with an abnormal response in an oral glucose tolerance test) and diseases associated with loss or deterioration of auto-glycaemic regulation.

A suitable mechanism of treatment may involve the use of the peptides described above, or functionally-equivalent ligands with the same configuration or three-dimensional structure, which could actively or passively remove the problematic autoantibodies or target autoantibody-generating cells for destruction. According to this aspect of the invention, peptides may be used either singly or in combination, alone or in conjunction with agents designed to promote their efficacy, in single, double or multiple chains with or without linker elements and carriers. One mechanism of treatment is by generating counteracting antibodies against these autoantibodies so that the antibodies generated bind to the autoantibodies and thus prevent the recognition of their target cells or molecules or complex with the autoantibodies thus aiding their removal or switch off the production of these autoantibodies.

Alternatively, counteracting antibodies or equivalent ligands may be used for passive treatment and can be derived from animal immunisations leading to the production of polyclonal or derivation of monoclonal antibodies or from immortalisation of human B cells, human monoclonal antibodies, or by screening libraries. The generation of such antibodies and equivalent ligands is described above.

Other methods of treatment may utilise principles of tolerance induction such as clonal deletion, anergy, suppressor or veto cell generation to prevent the autoantibodies from being made and/or secreted using the peptides of the invention or minimal reactive units of such peptide's or peptide-counteracting antibodies which react with the autoantibodies in a manner which will generate suppressor cells, veto cells, clonal deletion, clonal anergy or other mechanisms resulting in the prevention or formation or release of the relevant autoantibodies. These methods may include the use of peptides that are recognised by the autoantibodies or by monoclonal antibodies and their fragments that represent these autoantibodies and the sequences thereof. Autoantibodies can also be prevented from binding to their targets by competitive or non-competitive inhibitors, including peptides of the invention. Furthermore, target molecules or minimal reactive units of such molecules may be used linked to a matrix to selectively remove the relevant autoantibodies in a plasmapheresis type of procedure.

Autoantibodies can also be prevented from binding to their targets by competitive or non-competitive inhibitors designed to prevent binding of the peptides of the invention or equivalent ligands to relevant target sites on cells or molecules.

The peptides or RNA and cDNA derivatives thereof or alterations which retain efficacy or other sequences whose products utilise the same mechanism of action described herein may be used in the context taught herein, and may be packaged with suitable vectors as vaccines.

Diseases that are suitable for treatment or diagnosis according to the invention are described in more detail below.

Types I and II Diabetes Mellitus

Type I diabetes has a strongly associated genetic predisposition located in the human leukocyte antigen HLA DQ locus. Although more than 90% of the patients with type I diabetes carry the predisposing DQ8 and/or DQ2 alleles,[8,9] only a minority of susceptible individuals progress to clinical disease. Even in monozygotic twins, the concordance rate is only 50%.[10] Environmental factors play an important role in the pathogenesis of type I diabetes.[11]

Damage to β cells in the pancreatic islets during the pre-clinical period is characterised by the emergence of diabetes-associated autoantibodies. The antibodies most studied are against insulin (IAA),[12] glutamic acid decarboxylase (GADA),[13] antibodies to the protein tyrosine phosphatase-related IA-2 molecule[14] and cytoplasmic islet cell antibodies.[15]

A recently reported Finnish study of the appearance of the diabetes-associated antibodies named above in children from the age of 3 months to 2 years with genetic susceptibility revealed that seroconversion increased steadily from the age of 6 months and a significantly higher proportion of seroconversions appeared in the autumn and winter months as compared to spring and summer. This seasonal variation in the rise of autoantibodies and diagnosis of diabetes has been considered to be attributable to the preponderance of infections during these months.[9] The first autoantibody detected in the children in this study was against insulin (IAA) leading the authors to conclude that insulin may be the primary autoantigen in most cases of autoimmune type I diabetes. Observations put forward in favour of this hypothesis were that insulin is the only known true β cell specific autoantigen, secondly that IAA are very common in children with newly diagnosed type I diabetes and thirdly that type I diabetes can be transferred experimentally by insulin-reactive T cells.[16,17]

The development of anti-insulin reactivity has been postulated to be due to antigenic mimicry; however, no experimental data exist to date that link infectious agents and insulin reactivity antigenically. Key observations which precede the diagnosis of type I diabetes or are noted in newly diagnosed type I diabetics have been ignored in the formulation of concepts regarding the causation of this disease. Such observations are increased proinsulin to immunoreactive insulin ratios prior to diagnosis indicating stress on β cells and peripheral insulin resistance and dysfunction in secretion of counter-regulatory hormones such as glucagon in newly diagnosed type I diabetics.[18-20] These observations demonstrate an ongoing disease process which culminates in β cell death in type I diabetics. The same abnormalities of raised proinsulin to insulin ratios, insulin resistance and impaired profile of glucagon secretion also apply to type II diabetes.[21,22] Furthermore, both diseases have a similar profile of complications.

A unified hypothesis for the induction of both types I and II diabetes which encompasses pre-diabetic and post-diabetic phenomena has been put forward based on a newly identified autoantibody which has a broad spectrum of cross-reactive specificities. A key specificity of this autoantibody, which is indicative of its derivation, is reactivity against antibodies to TCR Vβ chains. Monoclonal antibodies produced against monoclonal anti-TCR Vβ antibodies were used as an indicator of the possible effects of autoantibodies of similar specificity. Such monoclonals raised against anti-TCR Vβ reagents had the capacity to dysregulate insulin secretion from human pancreatic islets in vitro causing cycles of hypersecretion followed by hyposecretion until the islet cells stopped secreting.

These monoclonals raised against anti-TCR Vβ antibodies were used to screen a human λgt11 cDNA library and identified clones which coded for GP-2 protein (a glycosyl phosphatidyl inositol (GPI) linked molecule), secretogranin I (an adhesive protein, serine-phosphorylated, tyrosine-sulphated, O-glycosylated doublet which binds to the membrane via an N-terminal disulphide-bonded loop peptide) laminin binding protein (metastasis-associated 67 kD, fatty acid acylated adhesive protein) ESRPI, (a newly identified N-terminal disulphide-bonded molecule) among others. These molecules have signalling properties.

The monoclonal antibodies intensely stained human islet α cells, cells in many other endocrine organs including thyroid, adrenal, stomach, gut and other tissues such as muscle and connective tissue. The monoclonal antibody-producing clones were selected by screening against an anti-TCR Vβ monoclonal reagent and cardiolipin, used as an indicator of phospholipids. Supernatents from clones with such cross-reactive specificities were also shown to react with other anionic phospholipids such as phosphatidyl inositol and phosphatidyl serine; they also reacted with single and double-stranded DNA.

It is postulated that the autoantibodies which react with anti-TCR-Vβ reagents also have the same cross-reactivities as above and are therefore the cause of dysregulated insulin secretion as demonstrated for the monoclonal antibody of similar specificity. The mechanism by which these antibodies dysregulate insulin secretion is postulated to be due to increased pressure on β cells to secrete insulin caused by dysregulation of α cells which leads to increased glucagon secretion. The potentiating effect of glucagon on insulin secretion is well known. Secretion of insulin by separated β cells is amplified by the addition of glucagon, α cells or cAMP.[6] The autoantibodies, by binding to inositol phosphoglycan moieties of GPI-linkages, can prevent their cleavage by insulin activated phospholipases and thereby affect their signalling properties. The signalling properties of such molecules have been fully described.[5,23] By the same capacity of binding to phosphoinositolglycans the autoantibodies can mop up mediators of insulin action and thereby cause insulin resistance or impaired insulin action. Inadequate generation/release of inositol phosphoglycans has been demonstrated in insulin-resistant humans.[24]

Psoriasis

Psoriasis is a disease associated with diabetes;[25,26] psoriatic patients with normal weight or overweight and without inherited diabetic predisposition are insulin resistant.[27] Psoriatic subjects with normal plasma glucose had significantly higher insulin levels compared to controls during a 2 hr. OGTT.[28] In the same study, the glucose disappearance rate during a 15 minute intravenous insulin tolerance test demonstrated a state of insulin resistance of psoriatics compared to controls. High values of cholesterol, triglycerides and depressed HDL-cholesterol were demonstrated in psoriasis consistent with dyslipidaemias associated with hyperinsulinaemia and insulin resistance.[29] Hyperactivation of the phospholipase C/protein kinase signal transduction system has also been reported in psoriasis resulting in the anticipated reduction of GPI-linked molecules in psoriatic skins and their virtual disappearance in psoriatic lesions.[30]

Eczema

Glucose tolerance is impaired in patients with eczema. Thirty nine patients were studied by the intravenous glucose tolerance test demonstrating a significant level of glucose intolerance.[31]

Vitiligo

Vitiligo is an acquired hypomelanosis which in the majority of cases corresponds to loss of melanocytes. Although melanocytes located in the basal layer of the epidermis manufacture the melanin containing organelles called melanosomes, keratinocytes are also involved by providing antioxidant molecules to melanocytes as well as cofactors in the synthesis of melanin.[32]

Vitiligo occurs in 1% of the population but in 9% of IDDM patients.[33] Vitiligo also coexists with other autoimmune disorders such as autoimmune thyroiditis, pernicious anaemia, thrombocytopenia etc.

One of the factors affecting skin pigmentation is the alphamelanocyte stimulating hormone (α-MSH). Binding of α-MSH to its receptor increases tyrosinase activity and eumelanin production.[34] The production of α-MSH is influenced by insulin levels and is directly correlated with insulin resistance, fasting insulin levels and body mass index.[35] Melanosomes under the influence of α-MSH are exocytosed from melanocytes and transferred via filopodia into keratinocytes.[36,37] However surviving melanocytes in vitiliginous skin have been shown to shed pre-melanosomes ectopically[38] indicating that regulation of melanosome maturation and exocytosis is aberrant in vitiligo. Pre-melanosome shedding parallels hyper pro-insulinaemia of pre IDDM[18] and NIDDM[21] and is analogous to β-cell stress in diabetes.

Transforming growth factor β1 (TGFβ1) also has a role in melanogenesis by down regulating tyrosinase and thereby causing hypopigmentation.[39] TGFβ also blocks the α-MSH elicited increase in number of melanosomes. TGFβ is upregulated in high glucose conditions[40] which are prevalent in diabetogenic states. TGFβ1 also has a profound effect on keratinocytes which provide cofactors to melanocytes. Keratinocytes have TGFβ binding receptors on their surface and TGFβ binding protein is a 150 kDa GPI-linked molecule. Antibody against this molecule has been shown to complex all TGFβ binding proteins demonstrating that the 150 kDa GPI-linked receptor forms heteromeric complexes with the other TGFβ receptors. Keratinocytes respond to TGF beta by downregulating their receptors and inhibiting DNA synthesis.[41] Therefore autoantibodies against the GPI-linkage of such signalling molecules can disrupt the signalling events required for normal functioning of the keratinocytes.

In the epidermis of vitiliginous skin, both lesional and perilesional, the expression of membrane cofactor protein and decay accelerating factor CD59 are lower than in non-lesional skin. CD59 is a GPI-linked molecule that protects against autologous complement lysis and its absence or downregulation (due to the autoantibodies described herein) may be associated with antimelanocyte and complement mediated destruction of melanocytes in vitiligo.[42]

Acanthosis Nigricans

Vitiligo and acanthosis nigricans are analogous to IDDM and NIDDM, acanthosis nigricans being the hyperpigmentation state (analogous to hyperinsulinaemia of NIDDM) and vitiligo the hypopigmentation state (analogous to hypoinsulinaemia of IDDM). Genetic factors account for both these presentation states which are both caused by the basic factors causing hyperinsulinaemia and insulin resistance. Melanocytes genetically susceptible to stress factors such as increased α-MSH due to increased insulin could die or reduce melanogenesis while genetic lack of susceptibility could cause hyperpigmentation. Patients with acanthosis nigricans have a high prevalence of abnormal glucose tolerance and hyperinsulinaemia.[43] Acanthosis nigricans in obese adolescents is also frequently associated with hyperinsulinaemia and insulin resistance.[44-46] Data reported on 102,733 screened children aged 8 to 15 showed 14.4% had acanthosis nigricans. Measures to reduce insulin resistance and hyperinsulinaemia are considered of importance to improve this condition.[47]

Skin

Aging skin is correlated with increased elastase activity, increased expression of matrix metalloproteinases and abnormality in cholesterase synthesis.[48-50] The GPI-linked proteoglycan glypican is present in the pericellular regions of keratinocytes, regulates growth factor availability and acts as a matrix receptor.[51] The GPI-linked urokinase-type plasminogen activator receptor, uPAR, is also present on keratinocytes and binds uPA secreted by keratinocytes. The activation of the urokinase system has been observed during wound healing and in the autoimmune blistering skin disease, pemphigus. Ultraviolet B activates this system and the results are prolonged up to 36 hours.[52] The damage that can be caused when uPAR is compromised by antibodies against elements of the GPI-linkage have been described under arthritis and related diseases. The effects of insulin on elastase and matrix metalloproteinase expression are well known[53,43]. It is conceivable that the antibodies of this invention have a role in promoting age, UV and autoimmune-related skin conditions and also in delayed wound healing.

Alopecia Areata

This is a suspected autoimmune condition which affects approximately 1% of the population by the age of 50. Peak incidence is in children and young adults.[55] Alopecia greata is associated with various atopic and autoimmune conditions. Diabetes mellitus is not increased among the patients but greatly increased among the relatives.[56-58] A study in men with early onset alopecia revealed an association with insulin resistance.[59]

It is proposed that alopecia in its various forms is another manifestation of insulin resistance in genetically susceptible individuals and is part of the spectrum of diseases covered by this invention.

Alzheimer's Disease

Alzheimer's disease is associated with features of insulin resistance and abnormal glucose tolerance. In 532 non-diabetic subjects without the apolipoprotein E4 allele, the prevalence rate of Alzheimer's disease was 7.5% among hyperinsulinaemic subjects compared to 1.4% in normoinsulinaemic subjects.[60]

Advanced glycation endproducts (AGEs) formed due to nonenzymatic covalent attachment of reducing sugars to free amino groups occur during aging and at an accelerated rate in diabetes mellitus. AGEs change physicochemical properties of affected molecules and also induce cellular signalling and gene expression that contribute to diabetic complications and Alzheimer's disease.[61]

Both Alzheimer's and type II diabetes are associated with deposition of amyloid proteins; islet amyloid polypeptide (amylin) in the pancreatic islets and amyloid beta-protein in the brain in Alzheimer's disease. Both amylin and amyloid beta-protein are degraded normally by insulin-degrading enzyme (IDE). Defective degradation of both these amyloid proteins by IDE indicates a common pathogenetic mechanism.[62,63] Proteins linked via GPI-linkages may also contribute to neurodegeneration in Alzheimer's disease. The complement defense protein CD59 is significantly decreased in the frontal cortex and hippocampus of Alzheimer's patients compared with non-demented elderly patients. Significantly less CD59 was released by PIPLC from slices of Alzheimer's brain cortex than from non-demented patients. Amyloid beta-protein was found to down-regulate CD59.[64] Autoantibodies to GPI-linkages may cause downregulation and increase susceptibility of neurons to complement lysis.

Another GPI-linked protein is the limbic-associated membrane protein (LAMP) expressed in the soma and dendrites of subpopulations of the adult neurons in the brain that are associated with limbic structures. Within the cerebral cortex, the lamp transcript is more abundant in areas associated with learning and memory and is expressed heavily in areas of the forebrain and diencephalon that have been classically considered limbic and sparsely in non-limbic, mid and hindbrain regions. It has been shown to be present in the adult brain by in situ hybridisation techniques.[65] The downregulation or dysregulation of these LAMP molecules due to anti-GPI autoantibodies could be associated with loss of cognitive functions in Alzheimer's disease or other age related mental incapacities involving learning and memory.

Cathepsin D, a GPI-inked (aspartic proteinase) lysosomal enzyme[66] may also have a role in Alzheimer's disease. Cathepsin D appears to be downregulated in the frontal cortex of Alzheimer's disease patients compared to non-Alzheimer's controls.[67] Some of the effects of Cathepsin D deficiency in mice deficient in this enzyme are profound accumulation of neuronal ceroid lipofuscin, atrophy of intestinal mucosa and lymphoid organs suggesting that Cathepsin D is essential for tissue homeostasis.[68]

Heparan sulphate proteoglycans (HSPGs) which are GPI-linked molecules are present ubiquitously on basement membranes and cell membranes and have been shown to be involved in Alzheimer's disease. One such HSPG, glypican-1, is abundantly expressed in cerebral amyloid angiopathy and Alzheimer's disease.[69] HSPGs have been localised to amyloid fibrils present in neuritic plaques and congophilic angiopathy in the brains of Alzheimer's patients. HSPGs were also demonstrated in primitive plaques suggesting that they have a role in the early stages of plaque development.[70] HSPGs interact with HDL and Apo E in the removal of excess cholesterol from the brain[71] which contributes to vascular integrity in the brain. Senile plaques are frequently seen in the vicinity of capillaries suggesting that the breakdown of the blood brain barrier may be a prerequisite to plaque formation.[72] Vascular damage is an important pathogenic factor in Alzheimer's disease and is consistent with the role of pathogenic antibodies described in this invention.

Finally, the altered glucose/energy metabolism in aging brains and the desensitisation of neuronal insulin receptors (insulin resistance) as in type II diabetes and the dysregulation of signalling and neurotropic molecules together contribute to the amyloidogenic cascade and hyperphosphorylated tau protein and the development of neurofibrillary tangles in affected neurons in Alzheimer's disease.

Schizophrenia and Depression

Schizophrenia has been described as 'cerebral diabetes' due to abnormalities in glucose metabolism in the brain in conjunction with insulin resistance.[73,74] Both glucose intolerance and type II diabetes are more common in this group than in the normal population (The British Journal of Psychiatry (2004) 184: s112-S114) (Diabetes Care 28:1063-1067, 2005). Mania and positive schizophrenia are associated with hyperglycaemia, hyperdopaminergia and hyperserotonergia while depression and negative schizophenia are associated with hypoglycaemia, hypodopaminergia and hyposerotonergia. These two states are at opposite ends of a spectrum of disease.[74] There is a positive correlation between insulin resistance and duration of illness in approximately 50% of patients with endogenous depressions. Such patients also hypersecrete cortisol.[75]

Parkinson's Disease

Parkinson's disease (PD) is characterised by progressive loss of 70-80% of dopaminergic neurons in the substantia nigra.[76] The neuronal degeneration is considered to be due to oxidative stress due to high levels of dopamine.[76] Studies of post mortem brain tissue from PD patients have provided evidence of increased oxidative stress and impaired glucose uptake in neuronal populations.[77]

It has been reported that 50% to 80% of PD patients have abnormal glucose tolerance.[78] The result of this is hyperglycaemia and consequently hyperinsulinaemia. Insulin is known to have a highly regulatory role in neuronal metabolism and signal transmission. Injection of increasing amounts of insulin into rats was shown to result in an increase of dopamine secretion.[79] Furthermore, insulin has been demonstrated to regulate the synthesis and activity of dopamine transporter,[80] and a nonapeptide from the C terminus of the insulin β chain was found to strongly inhibit dopamine uptake by the rat dopamine transporter.[81] Such transporter molecules terminate dopaminergic signalling by clearing the neurotransmitters from the synaptic spaces. Dopamine itself is known to produce hyperglycaemia by directly releasing glucose from hepatocytes.[82] This can contribute to the abnormal glucose tolerance in PD patients.

A brain derived and glial cell line derived neurotrophic factor has been shown to be a potent survival factor for dopaminergic neurons that degenerate in PD and other sympathetic, sensory and central nervous system neurons that degenerate in other neurological disorders including amyotrophic lateral sclerosis, sleep disorders, schizophrenia and Alzheimer's disease. In an in vitro system, the glial cell-derived neurotrophic factor (GDNF) reduced dopamine-induced cell death by 60-70%.[83]

A structurally related polypeptide called neurturin (NTN) has also been shown to be a potent survival factor for dopaminergic, motor, sympathetic and sensory neurons. Both receptors for GDNF (GDNFR-α) and NTN(NTNR-α) are GPI-linked proteins which share a transmembrane tyrosine kinase receptor Ret.[84] Autoantibodies to the GPI-linkage elements of these receptor proteins could inactivate their signalling activities and thereby eliminate their neurotrophic capacity.

Migraine

Antiphospholipid antibodies and abnormal glucose regulation have been noted in migraine.[85,86]

Multiple Sclerosis

In a study of 357 consecutive MS patients from an MS clinic to determine the association of MS with other autoimmune disorders, 15.4% of patients were found to have a first degree relative with MS and another autoimmune disease. Graves' disease, rheumatoid arthritis, vitiligo, type 1 insulin-dependent diabetes mellitus and uveitis were the most common autoimmune disorders associated with MS.[87]

Autoreactive T cells from diabetic and MS patients responded to both classical islet as well as CNS autoantigens. Approximately 90% of 38 MS patients responded to myelin basic protein (MPB) in T cell proliferation assays. Responses to proinsulin and IA-2 islet cell autoantigens were almost as common as in diabetes and had the same magnitude as MPB responses.[88] These responses were rare in controls. A study of T cell responses of 54 newly diagnosed diabetic children showed 53% were responding to MPB.[88] Although these overlapping T cell responses were not indicative of the clinical second disease, they are highly suggestive of a common mechanism for both diseases.

MS patients have increased susceptibility for fasting hypoglycaemia indicating a compromised glucose counter-regulatory response involving glucagon and cortisol.[89] The mechanism of hyperproinsulinaemia has already been described and the fact that MS patients have T cell responses to proinsulin indicates that subclinical β cell damage is prevalent in MS patients. The same autoantibodies that recognise anti-TCR Vβ and GPI-linked molecules can cause the β cell damage via dysregulation of pancreatic α cells and damage to the myelin sheath via the GPI-anchored proteins which are sorted to the myelin sheath during oligodendrocyte maturation.[90]

Myasthenia Gravis

Myasthenia gravis (MG) has been reported to be a component disease of the autoimmune polyglandular syndromes type 1 and type ll.[91,92] Antibodies against the acetylcholine receptor (ACHR) and acetylcholinesterase are considered to have a role in the pathogenesis of MG.[93,94] There are however patients with generalised MG who are seronegative for these antibodies indicating that other autoantibodies or factors are involved in disease induction. In generalised MG, increased levels of DNA autoantibodies have been reported[95] and high levels of lupus anticoagulant antibody have also been noted in an MG patient.[96]

MG is a disease of the neuromuscular junction involving binding of acetylcholine (ACH) to the ACHR. Acetylcholinesterase breaks down acetylcholine thus releasing receptors for renewed occupation and signal transmission. Both ACH and acetylcholinesterase are susceptible to regulation by levels of insulin and glucose. Insulin induced hypoglycaemia has been reported to cause a significant decrease in acetylcholinesterase activity in rat brain.[97] In hyperglycaemic rat brains, acetylcholine levels were reduced; insulin increased these levels.[98] In diabetic rats there is also enhanced desensitisation of the acetylcholine receptor.[99]

From the viewpoint of this invention, the autoantibodies which recognise signalling molecules, DNA and phospholipids are responsible for the neuromuscular abnormalities in MG via dysregulation of glucose metabolism and signalling molecules. Acetylcholinesterase is GPI-linked[100] and may be dysregulated due to these molecules resulting in increased levels of ACH thus damaging the ACH receptor. The expression of ciliary neurotrophic factor receptor (which is also GPI-linked) has been shown to be involved in diabetic neuropathy.[101] This receptor is decreased in muscles of seropositive MG patients[102] indicative of causative similarities between MG and diabetic neuropathies.

Amyotrophic Lateral Sclerosis, Motoneuron and Related Diseases

A significant percentage of patients with amyotrophic lateral sclerosis (ALS) are glucose intolerant. There has been controversy, however, whether this is a primary metabolic abnormality or secondary to muscle atrophy. Euglycaemic insulin clamp studies in ALS patients and two control groups for disease and body weight revealed that insulin sensitivity was diminished in ALS compared to both control groups[103]. Abnormal plasma glucagon levels have also been demonstrated in ALS patients compared to controls. Patients administered two test meals 1 week apart were shown to be hyperglucagonaemic at fasting and at ½ and 2 hours postprandial compared to controls.[104] Many ALS patients have been reported to have characteristics of type II diabetes mellitus.[105]

Advanced glycation end products (AGEs) which have been implicated in the chronic complications of diabetes have also been reported to play a role in the pathogenesis of neurodegenerative diseases such as progressive supranuclear palsy, Pick's disease, Guamanian amyotrophic lateral sclerosis/Parkinsonism-dementia complex.[106] Survival and growth of motor neurons are known to depend on neurotrophic factors. Insulin-like growth factor 1 (IGF-1) and the glial cell-derived neurotrophic factor (GDNF) are potent neurotrophic/survival factors for motor neurons.[107] A lack of trophic factors is thought to lead to degeneration of adult neurons. Although increases were found in several IGF-binding proteins in ALS patients, serum IGF-1 and insulin levels were significantly reduced.[108] Therefore improvement of glucose/insulin/glucagon metabolism would be of significant value to the survival and growth of motor neurons.

Apart from insulin and IGF-1, GDNF and neurturin also have potent effects on neuronal survival. GDNF promotes survival of motor neurons in vivo and in vitro and rescues them from cell death. The highest expression of GDNF is in human skeletal muscle, particularly at neuromuscular junctions. GDNF has also been detected within the axons and surrounding Schwann cells of peripheral nerves.[109] The GDNF receptor, GFRα-1 has been localised by immunohistology at myelinated peripheral nerves and neuromuscular junctions. Analyses by RT-PCR also showed that mRNA of GFRα-1 existed in the ventral horn of the spinal cord but not in the skeletal muscles, suggesting that this molecule plays a major role in uptake and internalisation of GDNF at the neuromuscular junction.[110] Neurturin, a neurotrophic factor related to GDNF binds to its receptor GFRα-2 and also supports neuronal survival.[111] All GFRα-1α4 receptors identified thus far which bind GDNF family ligands, are GPI-linked and signal via Ret interaction with members of the Src family kinases and this is necessary for neurite outgrowth and survival.[112]

Genetic factors are involved in neurodegeneration and non-MHC genes have been implicated.[113] It is therefore anticipated that in genetically compromised individuals, anti-GPI-linkage element antibodies can sufficiently alter the signalling of GPI-linked molecules to prevent neuronal cell survival.

Thyroid Disease

Thyroid disease covers a spectrum of conditions ranging from hypersecretion as found in Grave's disease to hyposecretion as in Hashimoto's thyroiditis. The occurrence of thyroid disease is significantly increased among diabetic patients. In a randomly selected group of 1310 diabetic adults, thyroid disease was evaluated by measuring free thyroxine and thyroid stimulating hormone (TSH) concentrations. The overall prevalence was 13.4% and the highest level was 31.4% in Type 1 diabetic females.[114]

The steps in thyroid hormone synthesis and secretion are regulated by TSH. This regulatory function involves signalling via inositolphosphoglycan (IPG) second messengers. TSH stimulates the release of the polar headgroup of IPG. This soluble IPG has been shown to modulate iodine metabolism in thyrocytes.[115] IPG isolated from porcine thyrocytes induces proliferation of fibroblasts and porcine thyrocytes.[116]

Thyrocytes are rich in GPI-linked molecules which are both apically and basolaterally distributed.[117] Some GPI-linked molecules such as HSPGs are involved in the transport of thyroglobulin (Tg) from the follicular lumen to the basolateral membrane of thyrocytes from which Tg is released into the bloodstream. Thyroglobulin interacts with surface HSPGs via a site functionally related with a megalin binding site. Megalin is a low density lipoprotein endocytic receptor which transports HSPG bound Tg through the epithelial cells.[118,119]

Immunohistochemical studies involving HSPGs and other basement membrane constituents revealed pathological basement membrane alterations in Hashimoto's thyroiditis, in hyalinising trabecular adenomas, papillary carcinomas and anaplastic carcinomas and other histopathological variants of thyroid disease.[120] A family of GPI-linked molecules (GFRα1-4) are the receptors for the glial cell line-derived neurotrophic factor (GDNF). These molecules are present in normal and thyroid tumours, in medullary thyroid carcinomas (GFRα4), pheochromocytomas, parathyroid hyperplasia, enteric ganglioneuromas, skeletal abnormalities and mucosal neuromas, collectively known as multiple endocrine neoplasia type 2A and B.[121]

Cushing's Syndrome and Addison's Disease

Cushing's disease is commonly associated with glucose intolerance, diabetes, central obesity, hirsuitism and elevated arterial blood pressure. The main diagnostic feature is hypercortisolism which may result from long standing ACTH hypersecretion in 20-40% of patients;[122] this can occur in the absence of a pituitary adenoma and increased cortisol secretion can be due to unilateral or bilateral adrenal hyperplasia with or without autonomously secreting micro or macro nodules.[123]

In a recent cross-sectional study of 90 patients with obesity and diabetes, the prevalence of Cushing's syndrome was reported to be 3.3%.[124] Preclinical and subclinical cases of Cushing's which present as poorly controlled diabetes add to this figure considerably. In analogous fashion, mild chronic hypercortisolism has been reported in type 1 diabetes reflected by elevated fasting cortisol and urinary free cortisol and an increased response to ovine corticotropin-releasing hormone.[125]

ACTH hypersecretion can occur in the absence of pituitary adenoma but in the presence of hypercortisolaemia,[126] suggesting a dysregulation of the normal negative feedback control. Several reports are indicative of the role of GPI-linked molecules and inositol phosphoglycans released by the activation of phospholipase C in the regulation of both pituitary hormone secretion and the secretion of the hormones that they stimulate from the adrenals, thyroid, gonads etc.[127-129] It is therefore anticipated that the autoantibodies described herein will have pathogenic effects ranging from disruption of pulsatile secretion of hormone to inhibited or exaggerated secretion and even the formation of tumours as antibodies to GPI-linked molecules have also been shown to induce cell proliferation by causing loss of inhibitory input to activating signals.[130,131]

Addison's disease is also a component disease of the autoimmune polyglandular syndrome type II with an increased risk of developing insulin-dependent diabetes mellitus, vitiligo, alopecia, pernicious anaemia, coeliac disease, myasthenia gravis and primary hypogonadism.[91] Together, Cushing's syndrome and Addison's disease provide another example of the consequences of endocrine overstimulation resulting from the autoantibodies. The robust endocrine gland will continue to oversecrete whereas the genetically compromised gland will fail and hyposecretion will be the consequence.

PCOS, Hypogonadism and Premature Baldness in Men

Polycystic ovary syndrome (PCOS) accounts for 95% of hyperandrogenism in women and is manifest typically by hirsutism, acne, central obesity, male pattern baldness and other physical masculinising alterations. Differential diagnosis apart from PCOS includes Cushing's syndrome and androgen producing ovarian and adrenal neoplasms. Androgenic disorders are the most common endocrinopathies affecting from 10-20% of women.[132]

Hyperandrogenism arises from a generalised dysregulation of steroidogenesis which can be of ovarian or adrenal origin. This dysregulation appears to arise from the modulation of both central and peripheral factors controlling hormone action. Increased GnRH and LH and insufficient FSH are the precipitating factors that lead to chronic anovulation in PCOS.[133] However, hyperinsulinaemia appears to have an important role in triggering latent abnormalities in the regulation of steroidogenesis in genetically compromised individuals. In male pattern baldness, both in the compromised female and male, insulin interacts with androgens to regulate hair follicle and associated sebaceous gland development.[134]

In a study of 5 families to examine disorders of insulin secretion in male and female family members of subjects with PCOS, hyperinsulinaemia was found in 69% of 24 female family members, 79% of whom had PCOS. Among the eight male members, 88% had premature baldness.[135]

Hyperinsulinaemia in PCOS is associated with glucose intolerance, increased fasting insulin levels and insulin resistance. An atherogenic lipid profile may also be present. PCOS patients show an increased incidence of type 11 diabetes and cardiovascular disease.[136]

Hyperandrogenism in insulin resistant women is thought to be due to the stimulatory effect of insulin on ovarian steroid hormone production. Insulin and insulin-like growth factor 1 (IGF-1) can amplify gonadotropin-stimulated steroidogenesis by augmenting the expression of key sterol regulatory genes in ovarian cells.[137] Insulin and IGF-1 also act synergistically with luteinising hormone to increase the activity of cytochrome P450c17 in the adrenals. Insulin induces inhibition of IGF-1 binding protein (IGFBP-1) production from cultured human granulosa cells.[138] The decrease of IGF-1 levels and IGF-1 receptors on graulosa cells reduces steroid aromatisation.[138] Inefficient aromatisation of androstenedione and testosterone to oestrone and oestradiol among other factors including increased steroidogenesis in thecal cells due to hyperinsulinaemia leads to excess free androgenic hormones in the circulation. Furthermore, in ovarian cells cultured with insulin, progesterone concentration increased dramatically compared with controls from 2.5±0.2 ng/ml to 5.4±0.3 mg/ml.[138] This hormone has a feedback relationship with the hypothalamic pulse generators for gonadotrophic releasing hormone (GnRH) which stimulates the secretion of LH and FSH from the anterior pituitary. Conversely, patients with hypogonadotrophic hypogonadism have an impaired insulin sensitivity.[140]

Apart from the multiple ways in which insulin exerts its regulatory roles, GPI-linked molecules are also involved in the ovulation process. Granulosa cells are rich in heparan sulphate proteoglycans (HSPG) which are GPI-linked. Labelling experiments demonstrated that 20-30% of heparan sulphate proteoglycans on the cell surface were GPI-linked and were removed by phosphatidyl inositol-specific phosphorylase C.[141] Follicle-stimulating hormone (FSH) and human chorionic gonadotropin induced changes in GPI concentration indicating that these molecules are hormone sensitive.[142]

The signal transducing effects of prolactin receptors on granulosa cells in the presence of prolactin were also shown to be via the generation of soluble glycosyl-phosphatidyl inositol moieties. In FSH-primed granulosa cells, both prolactin and GPI-moieties prevented the gonadotropin-stimulated 3 β-HSD activity.[143] 3 β-HSD converts cholesterol to the testosterone pathway, therefore a negative feedback mechanism is controlled by GPI moieties.

HSPGs also have anticoagulant effects and are expressed in follicles before ovulation and are transiently decreased in the postovulatory follicle. They interact with protease inhibitors suggesting their involvement in the control of fibrin deposition in the follicles.[144] Since tissue remodelling and proteolysis are required for ovulation, the disruption of HSPGs could be involved with anovulation.

HSPGs may also have a role in the development of the follicle. Studies carried out on a hepatoma cell line demonstrated that HSPGs added exogenously were internalised and free chains appeared in the nucleus. This resulted in arrest of the cells in the G1 phase.[145] Similar dysregulation of growth development may occur in follicular cells due to antibodies against such GPI-linked molecules.

Obesity

Insulin and leptin provide coordinated signals to the hypothalamus which regulate energy balance and body weight. Increasing insulin levels have been shown to stimulate leptin production.[146] Leptin receptors are on hypothalamic neurons that also express neuropeptide-Y (NPY) and proopiomelanocortin (POMC). Increasing plasma leptin has been shown to inhibit NPY production leading to reduced food intake.[147] Leptin also increases expression of the POMC precursor of α-melanocyte stimulating hormone (αMSH).[148] Alph-MSH acts in the hypothalamus to decrease food intake and mediate satiety.[149]

In obesity, hyperinsulinaemia and hyperleptinaemia coexist with insulin and leptin resistance.[150] The effect of insulin on leptin production is reduced with increasing insulin resistance.[151] It has also been demonstrated in animal studies that pretreatment with insulin for 3 days abolished leptin-induced responses.[150] It is apparent that hyperinsulinaemia and insulin resistance are critical factors in the regulation of leptin-induced control of food intake and body weight. Additionally plasma levels of free fatty acids are suppressed during physiological hyperinsulinaemia.[152] Therefore treatment of this condition in accordance with the present invention should ameliorate problems of obesity related to insulin resistant states.

Syndrome X

This is a metabolic disorder characterised by hyperinsulinaemia, hypercholesterolaemia, hypertension and coronary artery disease.[153] In atherosclerotic lesions, GPI-linked molecules such as T cadherin have been implicated.[154] The primary defect is considered to be hyperinsulinaemia consequent to insulin resistance causing the related abnormalities.[155] Since the original description of this syndrome, it has become apparent that the spectrum of diseases is broader than originally recognised. Male, non-obese patients with angina without coronary artery disease were found to be insulin resistant, hyperinsulinaemic and had higher triglycerides and lower high density lipoproteins than healthy controls; therefore myocardial ischaemia is also part of syndrome X.[156] Hyperuricaemia[157] and primary non-alcoholic steatohepatitis[158] appear to correlate with hyperinsulinaemia and insulin resistance and could therefore be considered components of the metabolic syndrome.

Insulin resistance and hyperinsulinaemia have been observed in 70% of non-obese, non-diabetic subjects with congenital hypertension. Blood pressure is correlated with insulin resistance which also correlates with salt sensitivity and angiotensin II.[159] Changes in insulin concentration in in vitro experiments and insulin sensitivity in vivo have been shown to affect $Li^+/Na^+$ and $Na^+/H^+$ counter-transport (CT). High CT is associated with cardiac and vascular remodelling in hypertension, IDDM and hypertrophic cardiomyopathy.[160] Generally benign and transient hypertrophic cardiomyopathy is recognised in infants of diabetic mothers. Foetal deaths due to this condition have been reported[161] Although, in general, events related to syndrome X are age related, there is evidence that this condition can start in childhood and adolescence.[162-164]

Diseases Related to Antiphospholipid and Lupus Anticoagulant Antibodies

Antiphospholipid and lupus anticoagulant antibodies are associated with recurrent foetal wastage, spontaneous abortions and thrombosis. In a study with 51 patients with antiphospholipid antibodies, 53 pregnancies were followed through. Aggressive therapy in 33 pregnancies resulted in 90.0% of successful outcomes; however in 48.6% of these successful cases, gestational diabetes mellitus developed.[165] This indicates that antiphospholipid antibodies may be a predisposing factor for diabetes susceptibility which was revealed by the added stress of continued pregnancy. In 1698 examinations of unselected pregnancies between gestational age 16 to 37, anticardiolipin levels above normal range were found in patients with pregnancy-induced hypertension, preeclampsia, gestational diabetes, diabetes mellitus type 1, venous thrombosis, thrombocytopenia and rheumatological diseases.[166]

In a study of 29 diabetic children and adolescents, anticardiolipin antibodies were found more frequently in IDDM patients than in controls. The antibodies were more prevalent in patients of less than 6 months diagnosis than in a group who were diabetic longer than 5 years. This was regarded as an abnormal immunological response in the early stages of diabetes mellitus.[167] In another diabetic study, the prevalence of cardiolipin antibodies was higher in complicated diabetics than in an uncomplicated group,[168] suggesting the potential role of these antibodies in diabetic complications.

Dysfunction of vascular endothelium is known to be an early step in the development of diabetic complications. In a study of 45 IDDM patients without clinically evident vascular complications, one third had higher than control levels of anticardiolipin antibodies directly correlated with levels of endothelin-1[169]

Cardiolipin is generally used as an indicative target for the presence of a variety of related phospholipids such as phosphatidyl serine, phosphatidyl ethanolamine, phosphatidyl inositol, phosphatidic acid and phosphatidyl choline. In a study of 70 samples, it was demonstrated that cardiolipin reactivity is an individual entity. Neither anticardiolipin or anticoagulant correlated with levels for the other phospholipids.[170] In a large number of sera from pathological pregnancies, 28.6% of those positive for anticardiolipin were also positive for anti-phosphatidyl serine and anti-phosphatidyl inositol, 23.8% for anti-phosphatidyl choline and 19% for anti-phosphatidyl ethanolamine. The percentages were higher for those who had IgM anti-cardiolipin antibodies.[171]

In a similar study with SLE patients, the highest % reactivity of patients was against cardiolipin followed by anti-phosphatidyl serine, phosphatidic acid and anti-phosphatidylinositol.[172] Reactivity to the last phospholipid, ie phosphatidylinositol was found to be of the highest prevalence in a group of 77 non-SLE patients under 51 years of age with cerebrovascular disease of undetermined aetiology.[173]

A study over 10 years of 39 patients with primary antiphospholipid syndrome without SLE or other connective tissue disorders revealed that 15 patients showed organ damage after 10 years follow up. Eight developed hemiparesis while 3 showed dementia; quadriplegia, dilated cardiomyopathy, myocardial infarction, pulmonary infarction and end stage renal disease were present in one patient each.[174]

Coeliac Disease

Coeliac disease with and without clinical symptoms is commonly associated with type 1 diabetes. In a recent study, the prevalence of coeliac disease among diabetic patients was found to be 5.7% and 1.9% among the relatives.[175]

The high level of subclinical or silent coeliac disease has also been noted among patients with unexplained or unresponsive disease referred to a gastroenterology clinic; 42.8% of 108 such patients were shown to have subclinical/silent coeliac disease.[176] Extraintestinal markers of subclinical coeliac disease were iron-deficiency anaemia (27%), alopecia and dermatitis herpetiformis (11.3%) and IDDM (20%). Antibodies associated with coeliac disease have been reported to increase in frequency in diabetics or their first degree relatives.[177] In the absence of coeliac disease, the prevalence of transglutaminase antibodies was 13.4% in diabetic patients and 7% in their non-diabetic relatives; 3.5% of 913 relatives had IgG transglutaminase antibodies and 44% of these had IgA endomysial antibodies.[177] Similarly, diabetes related antibodies were increased among coeliac patients. Anti-insulin antibodies were present in 27% of 15 children with coeliac disease at diagnosis and in 20% of 15 children with coeliac disease following a gluten-free diet.[178] Antibodies against glutamic acid decarboxylase were also present in 23% of coeliac disease patients.[179]

Malabsorption is a common feature of coeliac disease. A molecule which could be responsible for the iron deficiency in coeliac disease is melanotransferrin (p97) which is an iron-binding membrane glycoprotein with 40% homology to transferrin. This molecule is GPI-linked and has an apical distribution in intestinal epithelial cells.[180] Mucin binding protein, another GPI-linked molecule is an integral component of the apical epithelium of the gastrointestinal mucosa which constitutes a protective barrier.[181] Dysregulation of this molecule and similar molecules due to antibodies recognising GPI-linkage epitopes could affect the binding of mucin and breaching of the protective barrier causing damage to the gastrointestinal mucosa and intolerance to gliadin peptides in genetically susceptible individuals.

Gastritis

There is a high prevalence of gastric parietal cell antibodies (PCA) in type 1 diabetes which can be accompanied by autoimmune gastric disease.[182,183] Parietal cells have GPI-linked molecules on their surface[184] and therefore antibodies recognising GPI-linkage epitopes could be implicated in this condition.

Inflammatory Bowel Disease

Chronic inflammatory bowel disease is a paradoxical condition with growth impairment in the face of excessive growth hormone reserves rather than impaired secretion which may antecede the abdominal symptoms by some years.[185] Both fasting and postprandial lipid oxidation is significantly higher in patients with active Crohn's disease than in inactive disease.[186] Ketone body production is also significantly greater in patients.[187] Whole body glucose uptake was also shown to be higher in Crohn's patients than in normal controls assessed by an euglycaemic hyperinsulinaemic clamp study.[188] However arterial glucose concentrations were 10% lower in patients as was glucose oxidation compared to controls.[186,187]

The metabolic picture of increased fat oxidation and ketone body production appears to be glucagon driven. Dyslipidaemia involving low plasma LDL cholesterol and high triglycerides is also well documented[189] and has similarities to hyperinsulinaemia and insulin resistant states. Both in animal models of diabetes in the BB rat and dog model of coeliac disease, increased intestinal permeability is also present before the onset of disease.[190] Increased intestinal permeability is also present in Crohn's patients and their unaffected relatives.[191] Also, individuals at high risk of developing Crohn's disease have increased baseline permeability or have an exaggerated gut permeability response to damaging agents.[192]

GPI-linked molecules with functions that maintain tissue integrity and structure are abundant in gastrointestinal tissue. This is demonstrated by very high degrees of staining of gut sections with the anti-anti-TCR Vβ monoclonal antibody. A GPI-linked molecule in intestinal epithelium[193] and smooth muscle cells is T-cadherin which is an LDL binding adhesion molecule.[194] T-cadherin is also a negative regulator of smooth muscle cell growth.[195] The loss of the chromosome segment containing the T-cadherin gene correlates with cancer development and transfection of tumour cells with T-cadherin cDNA results in decreased proliferative activity and loss of cell sensitivity to growth factors.[196] Another GPI-linked molecule OCI-5 is a heparan sulphate proteoglycan related to glypican and cerebroglycan.[197] Heparan sulphate proteoglycans bind laminin. Partial proteolysis of cerebroglycan resulted in greater than 400-fold loss of laminin binding affinity.[198] The binding of autoantibodies to the GPI-elements of such molecules can foreseeably disrupt the epithelial barrier and increase intestinal permeability which is likely to be a prerequisite for disease development.

Thickening of the bowel wall particularly of the muscularis mucosae is a sign of disease activity in Crohn's disease.[199] The dysregulation of the GPI-linked molecules mentioned above among others which are expressed in the gut can explain the increased permeability, smooth muscle proliferation and bowel wall thickening and the increased collagen synthesis by the smooth muscle cells.[200]

The inflammatory bowel diseases, ulcerative colitis and Crohn's disease, have an associated increased risk of venous and arterial thrombosis. In a study of 83 patients with ulcerative colitis and 45 with Crohn's disease compared to 100 controls, a higher prevalence of anticardiolipin antibodies was observed in patients compared to the healthy controls.[201] In a similar study with 137 patients and 137 controls, anticardiolipin titres were significantly elevated in Crohn's disease and ulcerative colitis compared to controls.[202]

Arthritis and Related Diseases

Rheumatoid arthritis (RA) is a chronic progressive inflammatory disease affecting synovial joints leading to joint destruction. The synovial lining consisting of macrophages and fibroblast-like cells normally only 2 to 3 cell layers, becomes hyperplastic with concomitant angiogenesis and gains local invasive capacity at the synovial interface with the cartilage and bone. The increased mortality in RA patients is associated with accelerated atherosclerosis and cardiovascular disease. Many infectious agents have been implicated as causative agents of RA.[54]

Patients with RA and related diseases such as systemic lupus erythematosus, systemic sclerosis and gout are insulin resistant and have an abnormal glucose tolerance.[203,204] Normal weighted, previously untreated arthritic patients showed an enhanced insulin response and a reduced glucose utilisation rate in an euglycaemic clamp study compared to controls.[205] Therefore hyperinsulinaemia and insulin resistance are pathogenic features of this disease group.

In 45 untreated patients with active RA, the plasma glucagon levels were significantly lower during an intravenous glucose tolerance test than in controls, indicating abnormalities of counter-regulatory hormones.[206]

Oral glucose tolerance tests (OGTT) on 14 patients with active ankylosing spondylitis (AS) revealed that they had significantly increased insulin levels measured under the curve of the OGTT compared to controls.[207] Both in RA and spondyloarthropathies, insulin resistance correlated with dyslipidaemia.[208]

The presence of a common causative mechanism of RA and other autoimmune disorders is also demonstrated by the presence of antibodies to islet cell antigen 69 (ICA69) in 31% of RA patients compared to 6% in healthy blood donors[209] and anti-thyroglobulin antibodies in a large number of children with juvenile chronic arthritis and SLE.[210]

The proliferation of the synovial lining cells accompanied by angiogenesis are key factors in pannus formation and bone erosion in arthritis. The urokinase plasminogen activator (uPA) and its surface bound uPA receptor uPAR have a significant role in matrix degradation and tissue remodelling. uPA bound to its receptor UPAR catalyses the formation of the proteolytic enzyme plasmin from plasminogen and focuses it to the cell surface.[211] Plasminogen mediates proteolysis of extracellular matrix proteins facilitating cellular invasion. The urokinase-type plasminogen activator receptor is a GPI-linked molecule and is a ligand for integrins. uPAR-integrin interactions transduce proliferative or migratory signals to cells upon binding of uPA.[212] Urokinase has the capacity to cleave its receptor thereby inactivating its binding potential both to uPA and to vitronectin. This cleavage, however, only occurs if the GPI-linkage of uPAR is intact, even though the cleavage site is between the $1^{st}$ and $2^{nd}$ domains of the molecule and the GPI-linkage is on the $3^{rd}$ domain.[213] The intact urokinase receptor is also required for efficient binding to the integrin vitronectin.[214] The $\alpha v \beta 3$ and other receptors of vitronectin are involved in angiogenesis, cell adhesion and migration and therefore in pannus formation.[215] Under normal circumstances cleavage of uPAR by uPA would dysregulate binding of uPA to its receptor and that of UPAR to vitronectin and PAI-1 thereby reducing generation of plasmin by uPA and the proliferative and angiogenic signals via vitronectin receptors and PAI-1. These changes of uPA affinity to UPAR can be brought about by delipidation of the GPI anchor. Antibodies against uPAR peptides in the linker region of the GPI anchor only recognise GPI-linked but not soluble UPAR. This and similar changes in antigenic properties of the other GPI-linked molecules such as Thy-1, Ly-6 and carcinoembryonic antigen have been ascribed to conformational changes.[213] This invention proposes that antibodies to GPI-linked elements could sufficiently alter the conformation of such molecules to alter their reactivity with specific ligands both acting in cis and trans as has been shown for UPAR interactions with uPA and vitronectin and thereby cause autoimmune diseases, cancers and angiogenic diseases such as endometriosis.

UPAR promotes cell adhesion through interaction with vitronectin and facilitates cell migration and invasion by localising uPA to the cell surface.[213] The balance between adhesion and migration is controlled by PAI-1 which binds to the same site on vitronectin as uPAR.[216] Apart from its function as a protease inhibitor, PAI-1 has an essential role in capillary sprouting during angiogenesis.[217]

Hyperinsulinaemia and hyperglycaemia as in insulin resistant or glucose intolerant states play a role in this system and both insulin and hyperglycaemia have been shown to increase PAI-1 gene transcription; insulin also stimulates matrix metalloproteinases such as MMP-1. These are produced by the fibroblast-like synoviocytes and are involved in the remodelling and destruction of extracellular matrix.[54]

Asthma

In a recent Finnish study, a comparison was made of the cumulative incidence of asthma in children with coeliac disease, rheumatoid arthritis (RA) and IDDM during the first 7 years of life. Asthma tended to be significantly more common in children with coeliac disease, RA and IDDM than in children without these diseases.[218] Recently published studies collating findings from 23 published genome studies of autoimmune or immune mediated studies demonstrate that approximately 65% of the positive linkages of disease associated genes map non-randomly into 18 distinct clusters.[219] A number of asthma, IDDM and coeliac disease genes fall in the small cluster also including other autoimmune disease genes.[220]

Patients with asthma suffer from exaggerated bronchoconstriction to environmental stimuli and the resting airway tone is higher in asthmatic subjects than in normal controls. Resting airway tone and bronchoconstriction are controlled by acetyl choline released from pulmonary vagal nerves causing stimulation of muscarinic M3 receptors on airway smooth muscle cells and subsequent contraction. Acetyl choline also stimulates a negative feedback loop via M2 muscarinic receptors on postganglionic nerves preventing further acetyl choline release.[221]

It has been demonstrated that the increased vagally mediated bronchoconstriction in asthmatics is due to the impairment of the function of the M2 muscarinic receptor. The role of insulin in causing this impairment has been rigorously investigated by examining the bronchoconstriction responses in diabetic and insulin treated diabetic animals.[222] Untreated diabetic animals which were hyporesponsive to bronchoconstrictive stimuli became hyperresponsive upon treatment with insulin. Hyporesponsiveness was associated with a reduced level of accumulation of inflammatory cells (eosinophils) in the bronchi and in association with the nerves of diabetic animals. Treatment with insulin restored the influx of eosinophils and caused hyperresponsiveness. The loss of neuronal M2 muscarinic receptor function is due to eosinophil major basic protein which binds to M2 receptors via electrostatic interactions. Thus insulin appears to play a significant role in the development of airway inflammation. Hyperinsulinaemia could also account for the higher resting airway tone in asthmatic individuals which could be due to higher resting acetyl choline levels as insulin injected into the brain of rats caused a marked increase in acetyl choline levels.[98]

Airway smooth muscle hyperplasia is an important histopathologic finding in chronic asthma.[223] This is accompanied by hyperplasia of collagen secreted by the smooth muscle cells and is very similar to the smooth muscle cell hyperplasia and bowel wall thickening in Crohn's disease.[200] Therefore the GPI-linked adhesion and cell proliferation inhibitory molecule T-cadherin found on smooth muscle cells is implicated in the same way as discussed for Crohn's disease.

The IGF and IGFBP axis is also involved as in Crohn's disease and involves the downregulation of IGFBPs. Insulin induces inhibition of IGFBP-1 production in cultured human ovarian cells.[138] Therefore dysregulation of insulin secretion could similarly downregulate IGFBP levels in airway smooth muscle cells thereby increasing the bioavailability of free IGF which would promote smooth muscle cell proliferation.

Cystic Fibrosis

Cystic fibrosis (CF) is a disease affecting the respiratory, digestive, endocrine and reproductive systems. Many possible mutations contribute to the disease manifestations which include primarily chronic obstructive pulmonary disease, liver fibrosis, diabetes mellitus, cholelithiasis and arthritis. The primary CF defect is dysregulated ion transport via the cystic fibrosis transmembrane conductance regulator (CFTR) which is a cyclic AMP mediated chloride transepithelial transport protein at the apical membranes of secretory epithelia.[224] The CFTR malfunction in CF leads to overexpression of mucins via the tyrosine kinase-Src pathway connecting the CFTR channel with MUC 1 gene overexpression.[225] The impaired release of chloride results in dehydration of respiratory (and intestinal mucosal) linings resulting in viscous mucus which clogs the airways.

The organisation of the actin cytoskeleton is crucial to the function of CFTR molecules. Partial disruption of the actin cytoskeleton with cytochalasin D induced CFTR activation.[226] By atomic force microscopy, actin filaments were shown to be directly associated with CFTR molecules.[227]

The physiological regulation of the actin cytoskeleton both in relation to cell motility and cell adhesion appears to be strongly influenced by urokinase plasminogen activator receptor (uPAR) expression. This requires uPAR binding to vitronectin to initiate a p130Cas/Rac-dependent signalling pathway.[228] The interaction of uPAR with cytoskeleton associated structures such as integrins and small GTPases of the Rho family Rho, Rac and Cdc4z is involved in the regulation of the actin cytoskeleton for the assembly of stress fibres, lamellipodia, ruffles and filopodia.

The binding of uPAR to uPA and vitronectin requires the integrity of the full-length receptor particularly its GPI-linkage even though binding to vitronectin is via its D1 domain.[213]

UPAR and other GPI-linked molecules which have been shown to be associated with actin networks[229] may be responsible for maintaining the cytoskeleton for optimal CFTR function. The binding of antibodies of this invention to GPI-linkage epitopes may sufficiently disorganise the cytoskeleton to cause further functional deterioration of a genetically compromised CFTR molecule.

The expression of UPAR in lung epithelial cells and its upregulation by uPA and the involvement of this system in lung inflammatory tissue remodelling following injury or lung neoplasia has been reported.[230] Furthermore, UPAR appears to have a role in the recruitment of neutrophils in response to *Pseudomonas aeruginosa*. *P. aeruginosa* chronically colonises the lung in CF and causes a decrease of lung function leading to death. It has recently been demonstrated that mice deficient in UPAR (uPAR-/-) have profoundly diminished neutrophil recruitment in response to *P. aeruginosa* compared to wild type mice. The neutrophil recruitment in wild type mice is dependent on a β2 integrin-dependent mechanism.[231] It is therefore conceivable that anti-GPI antibody modified UPAR would be sufficiently compromised in this function of β2 integrin-dependent neutrophil recruitment.

The lung pathology in cystic fibrosis is aggravated by the inefficient removal of apoptotic inflammatory cells. Sputa from CF and non-CF bronchiectasis patients contain an abundance of apoptotic cells suggesting that normal apoptotic cell removal mechanisms are impaired.[232]

The GPI-linked glycoprotein CD14 on the surface of macrophages mediates the recognition and clearance of apoptotic cells.[233] Removal of apoptotic cells leading to resolution of inflammation is critical to normal tissue structure and function. Apoptotic cells undergo surface changes leading to exposure of phosphatidyl serine and this is a critical surface marker recognised by phagocytic macrophages.[234] The recognition of phosphatidyl serine on apoptotic cells and phosphatidyl inositol leads to their internalisation via the GPI-linkage of CD14. Bacterial lipopolysaccharide (LPS) also binds to the same or nearby site as the phospholipid binding site.[235] Macrophages can themselves undergo apoptosis and this is preceded by downregulation of CD14.[236] Therefore antibodies against elements of the GPI-linkage may dysregulate phagocytosis of apoptotic cells via blocking the recognition sites and internalisation of apoptotic cells and may also cause downregulation of CD14. These mechanisms could seriously disadvantage a very important component of the phagocytic system. Neutrophils are also involved in phagocytosis and move to sites of inflammation in response to chemotactic stimuli. A GPI-linked molecule, mono ADP-ribosyl transferase has been identified on the surface of neutrophils and is involved in the signalling pathway. This molecule is involved in the re-alignment of the cytoskeleton during chemotaxis.[237] The GPI-linkage is involved in the association of GPI-linked molecules to actin. Therefore anti-body-compromised GPI-linked molecules may not function efficiently as regulators of chemotaxis.

Cystic fibrosis is associated with both pancreatic exocrine and endocrine dysfunction. The exocrine acinar cell dysfunction in CFTR(-/-) mice is associated with impaired endocytosis at the apical plasma membrane of pancreatic acinar cells. This is coupled to ductal bicarbonate secretion into the lumen. Endocytosis is associated with cleavage of GP-2, a GPI-anchored protein on acinar cells tightly associated with activation of endocytosis. Cleavage of GP-2 is decreased in CFTR(-/-) mice.[238] This indicates that downregulation of GP-2 due to anti-GPI antibodies and/or obstruction of the GPI cleavage sites by antibody could impair endocytosis as seen in cystic fibrosis.

First phase C-peptide response to intravenously administered glucose is significantly impaired in CF patients with exocrine insufficiency. Alpha cell function measured as peak glucagon secretion in response to hypoglycaemia was also diminished in these patients.[239] Insulin sensitivity in CF patients with impaired and diabetic glucose tolerance is also lower than in control subjects.[240]

Although pulmonary disease is the main cause of morbidity and mortality in CF, the severity of the disease cannot always be predicted from the CFTR phenotype. In a longitudinal study of the whole Swedish CF population over the age of 7 years to correlate genetic and clinical data with the rate of decline in lung function, it was observed that concomitant diabetes mellitus of CF patients correlated most significantly with rapid deterioration of lung function as compared to *Pseudomonas* colonisation and pancreatic insufficiency.[241] It has also been observed that null or severe mutations result in absence of production of CFTR which correlates with pancreas exocrine insufficiency but less strongly with severity of lung disease. A proportion of CF patients are not diagnosed till the age of 10-15 years. Older patients with mild pulmonary disease, including bronchiectasis may not present with CF type symptoms, but on investigation are found to have CFTR mutations.[242] It is also becoming apparent that respiratory symptoms and inflammation do not necessarily correlate with lung infection.[243] Bronchopathology of CF visualised by high resolution computed tomography which correlated with lung function was shown not to correlate with sputum cytology and inflammatory markers.[244]

These findings demonstrate that lung pathology is progressive in CF and although aggravated by lung infections is not dependent on them. Pancreas pathology, particularly diabetes mellitus is the most serious predictor of severity of lung function deterioration. Arthropathy is also a concomitant disease in CF where lung function and infections do not correlate with the presence of arthritis.[245] The invention proposes that CFTR mutations render CF patients particularly susceptible to the effects of anti-GPI linkage epitope antibodies which cause the lung inflammation and other organ pathologies including diabetes mellitus common in CF.

Osteoporosis and Osteopenia

Insulin and insulin-like growth factors have an influence in bone metabolism. There is decreased bone formation in diabetes; this may explain the osteopenia but microangiopathy in the bone tissue may also be involved.[246,247] Increased osteoclast activity is responsible for the enhanced bone destruction in osteoporosis, Paget's disease, bone metastasis and the hypercalcaemia of malignancy. A GPI-linked molecule, osteoclast inhibitory peptide-1 (OIP-1) isolated from osteoclast-like multinucleated cells has been shown to inhibit osteoclast activity.[248] It is proposed that the antibodies of this invention dysregulate insulin secretion and block the action of OIP-1 or similar molecules, thus decreasing bone formation and increasing osteoclast activity.

Lichen Planus and Leukoplakia

In several studies, up to 42% of patients with active lichen planus and without family history of diabetes were shown to have abnormal glucose tolerance. The insulin response to glucose was typical of mild type 2 diabetes.[249,250]

Oral leukoplakia is also associated with abnormal glucose metabolism. There is a higher prevalence among diabetics than in controls.[251] Other less common oral manifestations in patients with previously undiagnosed diabetes included burning mouth syndrome, fungal and bacterial infections, altered taste, sialosis and sialorrhoea which generally improved with treatment to improve glycaemic control.[252]

Anaemia

Aplastic anaemia is associated with hyperinsulinaemia and insulin resistance. Of 29 patients examined 14 were previously treated cases with normal glucose tolerance, 8 were treated cases with abnormal glucose tolerance of which 6 had diabetes and seven were newly diagnosed cases with normal glucose tolerance. All were insulin resistant and hyperinsulinaemic. Patients with abnormal glucose tolerance had a delay in insulin secretion indicating deterioration of insulin reserve in the β cells.[253]

Among 26 patients with aplastic anaemia, 5 had GPI-anchored protein defects on their platelets and erythrocytes, whereas in 10 patients GPI defects were detected on monocytes and polymorphonuclear cells.[254]

Other types of anaemias are associated with overt diabetes. Fifteen type 1 diabetic patients with serious complications i.e. nephropathy, neuropathy, postural hypotension etc. were anaemic compared to diabetics without serious complications. There was no demonstrable cause for the anaemia other than erythropoietin depletion.[255] In diabetics without serious nephropathy similar reduced responsiveness of erythropoietin to anaemia was noted in 28 subjects with anaemia without identifiable causes.[256]

A GPI-linked molecule which may be of relevance to anaemias of unidentifiable origin in insulin resistant individuals or diabetics is the folate receptor. The folate receptor is internalised and recycled during folate transport.[257] However, antibodies to its GPI-linkage elements could seriously hinder folate transport. Folate, together with cobalamin participates in coupled reactions that make available the methyl groups needed for conversion of deoxyuridilate to deoxythymidilate in DNA synthesis required for erythropoiesis. These reactions may be impaired by an insufficient supply of folate within the developing red cells.

Paroxysmal Nocturnal Haemoglobinuria

Paroxysmal nocturnal haemoglobinuria (PNH) is known to result from deficiencies in the GPI-linked complement inhibitors CD55 and CD59 which predispose the red cells to lysis. The deficiencies which are present on erythrocytes and leucocytes and also on a substantial population of platelets[258] are caused by gene mutation (PIG-A) whose product, a glycosyl transferase participates in the first step of GPI-anchor biosynthesis.[259] The reason why a GPI-deficient clone gains growth advantage is still unresolved.

It has been demonstrated that Campath-1H selects for cells that are deficient in the GPI-linked CD52 molecule.[260] It is proposed herein that the presence of antibodies against GPI linkage elements can in an analogous fashion, select for GPI-deficient clones in PNH. However the PIG-A gene defect is an acquired somatic mutation.[261] In fact a number of PIG-A gene abnormalities were detected in 3 PNH patients and the abnormalities in granulocyte and erythroblasts were different in 2 of the patients.[262] It is therefore possible that the continued presence of autoantibody against the GPI-linkage elements causes the somatic mutations at the haematopoietic stem cell level.

The case of a 38 year old man was reported with a 12 year history of NIDDM with rapidly progressing haemolytic anaemia and thrombocytopenia. There were no causes for the microangiopathic anaemia except for diabetes. The patient also had lupus anticoagulant and antiphospholipid IgG antibodies. Haemodialysis resulted in spontaneous improvement of both the haemolysis and thrombocytopenia[262] Haemodialysis presumably removed the pathogenic anti-GPI antibodies as well as the ones reported in the study.

Sleep Apnoea

Disordered breathing during sleep is a common condition which may predispose individuals to impairment of daytime function and metabolic abnormalities. In a study of 150 healthy men without diabetes or cardiopulmonary disease, the prevalence of sleep apnoea ranged from 40-60% depending on the apnoea-hypopnoea index (AHI) cutoff. Severity of the condition correlated with impaired or diabetic glucose tolerance. Increasing AHI was also associated with worsening insulin resistance independent of obesity.[263] In another study of 270 subjects without known diabetes mellitus, 185 were considered to have sleep apnoea. There was a significant association of these cases with insulin resistance in both obese and non-obese subjects. Further analysis of the relationship between insulin resistance and hypertension in these subjects confirmed that the conditions were significantly related.[264]

Insomnia

Sleep irregularities are common both among the young and the old. These involve difficulty falling asleep, frequent nocturnal awakenings and early morning awakening. The pineal hormone, melatonin, which in humans is secreted only at night has been shown to induce daytime sleep when given in doses that occur at night. Melatonin is known to decrease in older people and correction to physiological levels has been shown to restore sleep.[265]

The secretion of melatonin is controlled by signals coming from the superior cervical ganglion neurones which make synaptic contact with the pineal gland and release noradrenaline from vesicles. Noradrenaline stimulates melatonin synthesis through cAMP formation.[266] cAMP acts on the penultimate enzyme in melatonin synthesis, arylalkylamine N-acetyltransferase (NAT).[267] This is a polymorphic enzyme, the mutation pattern of which has an influence in drug metabolism and confers increased susceptibility to certain cancers, food allergies and other conditions.[268-271]

Noradrenaline secretion is affected by plasma insulin concentrations. The induction of a basal hyperinsulinaemia and an exaggerated insulin response to glucose by lipid infusion in healthy volunteers resulted in significantly reduced plasma noradrenaline levels compared to controls.[272]

A state of hyperinsulinaemia therefore, due to physiological causes such as insulin resistance would be expected to correlate with reduced plasma noradrenaline levels. Diabetic patients have lower noradrenaline levels during heart failure decompensation as compared to non-diabetic patients.[273] Type I diabetic patients also have a 50% reduced noradrenaline response to hypoglycaemia within the first year of diagnosis.[274]

The above observations suggest that age related reduction in melatonin secretion could be related to hyperinsulinaemia due to increasing glucose intolerance and insulin resistance in the healthy aging population.[275] The age-related decline of pineal melatonin production is considered to be due to degenerative changes of serotonergic and noradrenergic neurones innervating the pineal gland rather than degeneration of pineal tissue.[276] This is consistent with noradrenaline insufficiency due to alterations in glucose metabolism in the aging population.

Another factor that controls sleep regulation is the prion protein (PrP). PrP is a GPI-inked glycoprotein.[277] It is present in cerebral and non-cerebral tissue, has a high level of synaptic distribution indicating an important role in neuronal function and is also found on the surface of elongating axons.[278,279] The normal prion protein binds copper and the resulting complex has anti-oxidant activity.[280] Prion protein is known to be involved in neurodegenerative diseases including fatal familial insomnia where there is profound alteration in sleep and daily rhythms of many hormones.[281] Prion protein knock-out mice showed both altered melatonin levels and sleep fragmentation and almost double the amount of short waking episodes indicating the role of this protein in sleep regulation.[282,283]

The antibodies of this invention can affect benign sleep abnormalities and pathological prion-induced conditions by the alteration of glucose metabolism and its effect on noradrenaline and melatonin secretion and also by affecting prion protein via GPI-anchor binding potential. Furthermore the antibodies recognise secretogranin 1 or chromogranin B which is a component of noradrenaline containing vesicles.[284] This may also dysregulate noradrenaline secretion.

Cancer

Many cancers including breast, colorectal, gastrointestinal, sarcoma, endometrial, prostate, head, neck and lung are known to be associated with hyperinsulinaemia, glucose intolerance, insulin resistance and an increased rate of hepatic glucose production.[285-289] A study in 1992 of 223 women with stage 1 or stage 2 breast cancer demonstrated that they had significantly higher serum levels of C-peptide than 441 control subjects. The log relative risk of breast cancer was linearly related to the log C-peptide levels independent of body mass index or waist to hip ratio.[290] A more recent study of 2569 women with histologically confirmed cases of breast cancer compared to 2588 control women noted an association of breast cancer with late onset diabetes,[291] and evidence suggests that insulin is a growth factor for tumour formation.[292]

Cancer cachexia is also characterised by glucose intolerance, increased whole-body glucose turnover rate, increased gluconeogenesis and insulin resistance leading to decreased glucose uptake and utilisation.[293] Increasing the insulin/glucagon ratio by hormone therapy selectively supported host anabolism and inhibited tumour growth kinetics in a rat model.[294] Therefore preventing the development of the diabetogenic complex of metabolic derangements will reduce the incidence of cancers and alleviate the symptoms of cancer cachexia.

The involvement of GPI-linked molecules in angiogenesis, metastasis, cancer progression and even cancer inhibition is becoming recognised. One such molecule is the urokinase-type plasminogen activator receptor uPAR. There is a strong correlation between uPAR expression and invasive cancer cell phenotype.[295] The association of the uncleaved GPI-linked uPAR occupied with its ligand uPA to heparan sulphate proteoglycans (HSPGs) and to the integrin vitronectin, focuses plasmin to the cell surface inducing proteolysis and ligation of vitronectin to its receptor $\alpha_v\beta3$ promoting angiogenesis.[211-217] uPAR also interacts with the actin cytoskeleton causing the formation of lamellipodia, ruffles and filopodia and thereby cell motility.[228]

The normal physiological functions of UPAR are regulated via the cleavage of UPAR by uPA which requires an intact GPI-linkage.[213] It has already been proposed that the disease causing properties of UPAR may be due to blockage of the GPI-linkage by antibodies of this invention.

Hyperinsulinaemia has a role in potentiating the uPAR driven mechanisms by enhancing the expression of cell associated HSPGs[296] and plasminogen activator inhibitor-1 (PAI-1).[297] In addition to binding to uPA, PAI-1 binds to vitronectin and facilitates tumour migration and invasion.[298] The uPAR-uPA-PAI-1 complex also binds to the low density lipoprotein related protein (LRP) and the whole complex is internalised in migrating cancer cells. PAI-1 has been shown to increase both filopodia formation and migration of cancer cells.[299] PAI-1 is also involved in angiogenesis. Angiogenesis was totally absent in aortic rings of PAI-1−/− mice and could be restored by addition of purified recombinant PAI-1.[300]

High levels of uPA and uPAR are associated with increased risk of relapse in breast cancer patients.[301] uPAR is also strongly expressed in thyroid cancers[302] and ovarian cancers.[303] Upregulation of HSPGs, particularly the GPI-linked glypicans have been associated with certain cancers. Glypican 1 is upregulated in pancreatic and breast cancers.[304,305] Glypican 3 is expressed in Wilm's tumours, neuroblastomas and hepatoblastomas.[306,307] Glypicans are considered to be potential regulators of heparin-binding growth factors and are stimulated by IGF-I and IGF-II.[308] Insulin suppresses IGF binding proteins making more IGFs available.[309] IGFs are involved in the progression of various cancers.[310] GPI-linked molecules are also involved in the pathophysiology of tumour formation as negative regulators of tumour growth. GPI-linked T-cadherin is downmodulated by growth factors including IGF.[311] The loss of the T-cadherin gene correlates with the development of pancreatic, lung, stomach and ovarian cancers while transfection of tumour cells with T-cadherin cDNA results in a decrease of proliferative and invasive activities of inflammatory bowel disease.[308] Downregulation or dysregulation of T-cadherin via anti-GPI antibodies of this invention could compromise the negative growth regulatory role of T-cadherin and similar molecules favouring tumour growth.

GPI-linked molecules may be involved in natural killer cell recognition of tumour cells. UL16 binding proteins (ULBPs) are GPI-linked molecules which are induced or upregulated upon cellular distress caused by heat shock, viruses, tumour transformation, carcinogens, UV etc. These molecules are ligands for the NKG2-D receptor on NK cells, NKT cells, γδ T cells as well as CD8$^+$ T cells. Masking of these GPI-linked ULBPs could cause evasion of transformed cells from NK or T cell mediated recognition.[312]

HIV

The human immunodeficiency virus type 1 (HIV-1) is preferentially monocyte/macrophage tropic and non-syncytium inducing (NSI) during the initial stages of infection.[313] The NSI viruses use the β-chemokine receptor 5 (CCR5) as a coreceptor and infect only CCR5$^+$ T cells.[313] In 50% of cases, disease progression is associated with the emergence of variants which are syncitium inducing (SI) and infect and delete all CD4$^+$ T cells including naive T cells.[313] This is based on the ability of the SI viruses to utilize CCR5 and CXCR4 receptors which are highly expressed on T-cell precursors and immature thymocytes.[314] The NSI phenotype viruses have been shown to be inhibited by the CCR5-binding β-chemokines RANTES, MIP-1α and MIP-1β; infection by NSI strains correlates with increased production of these β-chemokines.[315] The chemokines that bind the major HIV coreceptors CCR5 and CXCR4 are potent natural inhibitors of HIV. Recent data indicate that the ability of chemokines to block HIV infection can be separated from their receptor binding capacity.[316]

Chemokines establish a gradient across the extracellular matrix by ligating to and polymerising in the preserves of glycosaminoglycans such as heparan sulphate proteoglycans found on the surface of endothelial and other cells and in the tissue matrix.[317,318] Heparan sulphate proteoglycans (HSPG) also interact with the cell membrane fusion domain of the HIV glycoprotein gp41$_{FD}$. This interaction is with a specific heparan sulphate proteoglycan binding domain on the T cell surface and is spacially heterogeneous, localising to preferred sites on the membrane.[319] Removal of heparan sulphate binding sites by physical removal or blocking with IL-8 abrogated the interaction of gp41$_{FD}$ with the T cell membrane. Soluble heparan sulphate bound gp41$_{FD}$ but did not enhance membrane localisation. Therefore membrane bound HSPG is required for binding of gp41$_{FD}$ to the cell membrane. Since cell activation is required for virus replication and membrane interaction is in localised sites, GPI-linked glypican is the most likely candidate for gp41$_{FD}$-HSPG interaction.

The preferential binding of HIV and chemokines to HSPG must concentrate the inhibitory effect of the chemokines to sites of viral particle accumulation. This invention proposes that the binding of antibodies against GPI-linkage elements can sufficiently alter the conformation of GPI-linked HSPGs to render them ineffective in ligating inhibitory chemokines and focusing their effects on the virus. Furthermore, the GPI-linked urokinase-type plasminogen activator receptor (uPAR) and its ligand (uPA) are significantly involved in HIV progression. High levels of serum UPAR (suPAR) have been shown to be indicators of poor survival in AIDS patients.[320] The urokinase-type plasminogen activator uPA has been shown to bind HIV-1gp120 and to promote HIV-1 infection of macrophages.[321] The interaction of uPA and gp120 involves the functionally important V-3 loop of gp120 and the catalytic domain of uPA leaving its ligand-binding domain available for interaction with UPAR.[321] The bridging of gp120 to UPAR via UPA may ascribe an HIV coreceptor function to UPAR.

The cellular receptor for gp120 is CD4[322] and both gp120 and CD4 bind to vitronectin via interaction with heparan sulphate proteoglycans.[323] UPAR also binds to vitronectin.[214] The α$_v$β3 receptor for vitronectin is a costimulating molecule which determines the outcome of T cell receptor (TCR) engagement. Vitronectin binding to α$_v$β3 efficiently induces apoptosis of T cells.[324] This provides a mechanism by which HIV virus engagement of uPA via gp120 bound to its receptor UPAR could send an apoptotic signal to a T cell via integrin αvβ3.

As described earlier, uPA has the ability to cleave uPAR once engaged to it. Cleaved UPAR does not bind to vitronectin.[214] Unbound vitronectin would then not engage its receptor α$_v$β3. uPA however will only cleave intact UPAR molecules, and even though the cleavage site is distal to the GPI anchor, an intact anchor is required for this process. Phospholipase C-treated uPAR was shown to be resistant to cleavage by uPA.[323] This invention therefore proposes that antibodies to the GPI-linkage elements would conformationally alter UPAR and induce resistance to uPA cleavage. Binding of uPA to UPAR positively regulates UPAR expression which is correlated with increased specific uPAR mRNA.[325]

The inability of uPA to cleave conformationally altered UPAR could cause both the upregulation of UPAR able to bind virtonectin and provide binding sites for HIV virus attachment and signalling through the apoptosis-inducing α$_v$β3 receptor. Increased T cell apoptosis is a recognised and largely unexplained feature of HIV infection.[326]

Another aspect of the involvement of GPI-linked molecules in HIV infection is at the level of release of viral particles. It has been demonstrated that HIV virus produced by infected T cells preferentially acquire on their surface GPI-linked proteins known to be sequestered into lipid rafts on cell membranes.[327] These molecules such as CD55 and CD59 and others confer resistance to complement mediated destruction[328,329] in in vitro tests. GPI-coated virus on the surface of infected T cells could interact with the antibodies and link to other infected T cells thus aiding syncytium formation by SI viruses.

Finally, infection with HIV-1 is associated with dyslipidaemia, elevated glucose levels and reduced insulin sensitivity. These metabolic perturbations are exacerbated with highly-active antiretroviral therapy (HAART).[330] It may not be surprising also that there are high levels of antiphospholipid antibodies in HIV patients.[331]

Infections

Infectious organisms including bacteria, fungi and protozoa express GPI-linked molecules on their surface. These include mycobacteria, candida, *Leishmania, Schistosoma, Giardia, Toxoplasma, Trypanosoma, Plasmodium* and others.[332-339]

It has recently been demonstrated that *trypanosoma cruzi* trypomastigote GPI-mucins activated macrophages in vitro to produce cytokines, chemokines and nitric oxide.[337]

Addition of exogenous β-chemokines MIP-1α, MIP-1β, RANTES induced increased *T. cruzi* uptake leading to enhanced NO production and control of parasite replication in a dose-dependent manner.[340]

Chemokines play a significant role in host resistance to other microbial agents such as viruses, mycoplasma, fungi and helminths.[341-345] Chemokines establish a gradient across the extracellular matrix by ligating to heparan sulphate proteoglycans (HSPGs) and polymerising to enhance availability at the surface of cells and in tissue matrix.[317,318] HSPGs are either transmembrane e.g. syndecan or GPI-anchored, e.g. glypican. Surface proteins of infectious agents interact with host HSPGs which provide the first line of defence by concentrating the inflammatory chemokines and cytokines to control infection.[346,347]

There is a considerable body of evidence that infectious agents can be internalised non-opsonically via attachment to GPI-linked molecules in lipid rafts. A pathogenic strain of *E. coli* has been shown to adhere to the GPI-linked CD55 molecule on intestinal epithelial cells and induce cytoskeletal rearrangements and cell infection.[348] This would be blocked by treating the cells with phospholipase C which is known to cleave GPI anchors.[347] The stress fibre rearrangements due to binding and infection by *E. coli* could be seen to cause cell detachment from the confluent monolayers of intestinal cells.

This invention proposes that the antibodies which recognise GPI-linkage elements on HSPGs can dysregulate the focusing of chemokines onto the infectious agents thereby attenuating the host first line defense. The non-opsonic internalisation of organisms is also a component of first line defense whereby organisms can be internalised and degraded or infected cells can be detached from luminal surfaces via GPI-signalling effected actin rearrangements. Blockage of GPI would prevent such uptake and elimination of organisms.

Toxins from infectious agents also bind to GPI-linked molecules. Aerolysin, a channel forming protein from *Aeromonas* spp. known to bind to GPI-anchored proteins is structurally and functionally related to alpha toxin of *Clostridium septicum*. Mutant cell lines which cannot synthesise the GPI-anchor are insensitive to both aerolysin and alpha toxin.[349] *Helicobacter pylori* vacA toxin and tetanus neurotoxin (TeNT) produced by *Clostridium tetani* also bind to and are internalised by the GPI-anchor-inactivated endocytic pathway which is clathrin dependent.[350,351]

GPI-linked molecules are not only involved in an endocytic pathway but they form part of the endocytic vesicles, for example in bile-canalicular hepatocytes.[352] Phosphatidyl inositol 3-phosphate is reported to be part of the endosomal membrane effecting binding of early endosome autoantigen EEA1 which interacts with GTPases involved in maturation of endosomes. Phagosomes containing *M. tuberculosis* do not mature into phagolysosomes and have an immature intermediate form of cathepsin D.[353]

It is proposed herein that the uptake of toxins via GPI-linkages is a protective mechanism designed to remove toxins from blood and tissue spaces and that antibodies of this invention may interfere with this process allowing toxins to reach target organs. Furthermore internalisation of antibody-coated GPI moieties could bring the antibodies in contact with intracellular mechanisms of phagosome maturation and the endocytic pathway, thereby interfering with the intracellular control of organisms and detoxification of toxins.

The hypothesis that anti-anti-TCR Vβ and anti-GPI element antibodies arise due to polyclonal or monoclonal T cell proliferation in response to infections or directly in response to GPI-linked molecules on the surface of organisms may be borne out by the fact that particularly in GPI-bearing parasitic infections, glucose metabolism of the host is impaired. In previously untreated males with uncomplicated *P. falciparum* malaria, fasting plasma glucose and insulin levels were higher during acute illness than during convalescence. During a 2 hour glucose infusion study, plasma glucose and insulin concentrations were significantly higher during illness than in convalescence.[354] In children with schistosomiasis, there is a higher prevalence of ICA antibodies compared to siblings of diabetics and the first phase insulin response is suppressed during an i.v. glucose tolerance test.[355] Fasting plasma insulin and insulin levels 60 minutes after glucose infusion were also higher than in healthy controls. There was impaired glucose tolerance.[356]

Hyperglycaemia and diabetes are more prevalent in patients with Chagas disease than in controls.[357]

Glycaemic disorders are also prevalent in *Candida*-associated stomatitis. Thirty-five percent of all inspected patients over 50 years old had previously undiagnosed type 2 diabetes and 36% had impaired glucose tolerance.[358]

In mycobacterial tuberculosis infections, enhanced insulin secretion, persistent hyperglycaemia and the development of severe diabetes mellitus in long term disease have been noted.[359] Similarly in leprosy of more than 2 years duration, a diabetic glucose tolerance curve is commonly observed.[360]

Immunoregulation

A number of GPI-linked molecules are involved in the regulation of immune responses. These include GPI-80 on neutrophils and monocytes,[361] CD16 on neutrophils,[362] CD160 on intestinal intraepithelial lymphocytes and a subset of circulating lymphocytes including NK cells,[363] LFA-3, the lymphocyte function antigen,[364] CD48 which regulates IL-2 induced signals[365] and CDw109 on vascular endothelial cells[366] among others. Immune responses are impaired with aging[367] and antibodies to elements of the GPI-linkage could contribute to this.

Conclusion

From the above disclosures, the unifying concept that has emerged is that most diseases of infectious or non-infectious origin with or without genetic predisposition or conditions related to the ageing process become manifest or are aggravated by the emergence of the multispecific autoantibody described above. A large proportion of the population generate this autoantibody which compromises all systems and organs which are affected by blood glucose levels, insulin levels, other hormone levels controlled by or affecting insulin and/or GPI-linked molecules, other regulatory molecules recognised by the autoantibody and phospholipids. These autoantibodies potentially accelerate ageing and age-related diseases, promote cancers, mediate the manifestation of diseases whether or not based on genetic predisposition and interfere with first line defence against infectious agents. That is, there is an underlying pathogenic problem which is the production of the autoantibody which depending on individual susceptibility, leads to one or more of the conditions some of which are described above. An analogy would be that for any given drug, there may be one or more side-effects none of which would be present in the absence of the drug.

The following table summarises diseases that are suitable for treatment or diagnosis according to the invention, and further provides an indication of the link between each disease and the centralised disease mechanism disclosed herein and in WO99/05175. In the table, a score (+) in column A indicates that the disease is associated with abnormal oral glucose tolerance (in an OGTT), a score in column B indicates that the disease is one in which antiphospholipid antibodies are present, a score in column C indicates that the disease is one in which GPI-linked molecules are involved, a score in column D indicates that the disease is associated with abnormal insulin levels or insulin resistance, a score in column E indicates that the disease is more common in diabetics, and a score in column F indicates that the disease is associated with an increased risk of developing diabetes type 1 or 2.

It should be noted that the absence of a score (+) in the following table does not indicate that the relevant link has not been reported or does not exist, but merely that the inventors are not currently aware of any report of such a link in the literature.

| Disease | A | B | C | D | E | F |
|---|---|---|---|---|---|---|
| Psoriasis | + |   | + | + |   |   |
| Eczema | + |   |   |   |   |   |
| Vitiligo |   |   | + | + | + |   |
| Acanthosis nigricans | + |   |   | + |   |   |
| Alopecia areata |   |   |   | + |   |   |
| Alzheimers | + |   | + | + |   |   |
| Schizophrenia | + |   |   | + |   | + |
| Depression |   |   |   | + |   | + |
| Parkinson's disease | + |   | + | + |   |   |
| Migraine | + | + |   |   |   |   |
| Multiple sclerosis | + | + | + |   | + |   |
| Myasthenia gravis |   |   | + | + | + |   |
| Amyotropic lateral sclerosis and other motor neurone disorders | + |   | + | + |   | + |
| Progressive supranuclear palsy, Pick's disease and other neurodegenerative diseases |   |   |   | + |   |   |
| Thyroid disease |   |   | + |   | + | + |
| Multiple endocrine neoplasia type 2A and B |   |   | + |   |   |   |
| Cushing's syndrome | + |   | + |   |   | + |
| Addison's disease |   |   | + |   |   | + |
| PCOS hypogonadism | + |   | + | + |   | + |
| Premature baldness in men |   |   |   | + |   |   |
| Obesity |   |   |   | + |   |   |
| Syndrome X |   |   | + | + |   |   |
| Recurrent foetal wastage |   | + |   |   | + | + |
| Recurrent Spontaneous abortion |   | + |   |   | + | + |
| Recurrent Thrombosis |   | + |   | + |   |   |
| Systemic lupus erythematosus |   | + |   |   |   | + |
| Coeliac disease |   |   | + |   | + | + |
| Autoimmune gastric disease |   |   | + | + |   |   |
| Inflammatory bowel disease |   | + | + |   |   |   |
| Rheumatoid Arthritis | + |   | + | + |   |   |
| Ankylosing spondylitis | + |   |   | + |   |   |
| Asthma |   |   | + | + | + |   |
| Cystic Fibrosis |   |   | + |   |   | + |
| Osteoporosis and osteopenia |   |   | + |   | + |   |
| Lichen Planus | + |   |   | + |   |   |
| Leukoplakia | + |   |   |   | + |   |
| Aplastic and other anaemias | + |   | + | + | + |   |
| Paroxysmal nocturnal haemoglobinuria |   |   | + |   |   |   |
| Sleep Apnoea |   |   | + |   | + |   |
| Insomnia | + |   | + | + |   | + |
| Cancer | + |   | + | + | + | + |
| HIV | + | + | + | + |   |   |
| Infection |   |   | + |   | + |   |
| Immunoregulation diseases |   |   | + |   |   |   |

Pharmaceutical Compositions

In an eighth aspect, the invention provides a pharmaceutical composition comprising a peptide, antibody or equivalent ligand of the first aspect of the invention, or a nucleic acid molecule of the second or third aspect of the invention, or a vector of the fourth aspect of the invention, or a host cell of the fifth aspect of the invention, in conjunction with a pharmaceutically-acceptable carrier. These compositions may be suitable as therapeutic or diagnostic reagents, as vaccines, or as other immunogenic compositions, as outlined in detail below.

The pharmaceutical composition may include a combination of peptides according to the invention (for example, see Examples 6 and 7 herein). Such peptides may be incorporated into the composition as monomer entities, or may be linked so as to form double or multiple chains. Such chains may or alternatively may not include linker elements between the monomer component molecules.

The pharmaceutical compositions should preferably comprise a therapeutically effective amount of the peptide, antibody or equivalent ligand, nucleic acid molecule, vector or host cell of the invention. The term "therapeutically effective amount" as used herein refers to an amount of a therapeutic agent needed to treat, ameliorate, or prevent a targeted disease or condition, or to exhibit a detectable therapeutic or preventative effect. For any compound, the therapeutically effective dose can be estimated initially either in cell culture assays, for example, of neoplastic cells, or in animal models, usually mice, rabbits, dogs, or pigs. The animal model may also be used to determine the appropriate concentration range and route of administration. Such information can then be used to determine useful doses and routes for administration in humans.

The precise effective amount for a human subject may depend upon the severity of the disease state, general health of the subject, age, weight, and gender of the subject, diet, time and frequency of administration, drug combination(s), reaction sensitivities, and tolerance/response to therapy. This amount can be determined by routine experimentation and is within the judgement of the clinician. Generally, an effective dose will be from 0.0001 mg/kg to 50 mg/kg, preferably 0.001 mg/kg to 10 mg/kg, more preferably 0.05 mg/kg to 10 mg/kg, even more preferably 0.1 mg/kg to 10 mg/kg. Compositions may be administered individually to a patient or may be administered in combination with other agents, drugs or hormones.

Compositions comprising peptides according to the invention at doses of from 0.005 mg/kg to 0.05 mg/kg have been shown to provide useful therapeutic effects in human patients (see Examples 6 and 7 herein), without significant undesirable side-effects. Accordingly, it is envisaged by the inventors that smaller doses, equivalent doses, or larger doses, of the peptides can be used in the compositions of the invention. Thus, preferred doses may comprise at least 0.001 mg/kg, at least 0.002 mg/kg, at least 0.003 mg/kg, at least 0.004 mg/kg, at least 0.005 mg/kg, at least 0.006 mg/kg, at least 0.007 mg/kg, at least 0.008 mg/kg, at least 0.009 mg/kg, at least 0.01 mg/kg, at least 0.015 mg/kg, at least 0.02 mg/kg, at least 0.03 mg/kg, at least 0.04 mg/kg, or at least 0.05 mg/kg of the peptides according to the invention. Preferred doses may also comprise less than 1 mg/kg, less than 0.9 mg/kg, less than 0.08 mg/kg, less than 0.07 mg/kg, less than 0.06 mg/kg, or less than 0.05 mg/kg of the peptides according to the invention. Preferred doses may comprise from 0.001 mg/kg to 1.0 mg/kg, from 0.0025 mg/kg to 0.075 mg/kg, or from 0.005 mg/kg to 0.05 mg/kg of the peptides according to the invention.

A pharmaceutical composition may also contain a pharmaceutically acceptable carrier, for administration of a therapeutic agent. Such carriers include antibodies and other polypeptides, genes and other therapeutic agents such as liposomes, provided that the carrier does not itself induce the production of antibodies harmful to the individual receiving the composition, and which may be administered without undue toxicity. Suitable carriers may be large, slowly metabolised macromolecules such as proteins, polysaccharides, polylactic acids, polyglycolic acids, polymeric amino acids, amino acid copolymers and inactive virus particles.

Pharmaceutically acceptable salts can be used therein, for example, mineral acid salts such as hydrochlorides, hydrobromides, phosphates, sulphates, and the like; and the salts of organic acids such as acetates, propionates, malonates, benzoates, and the like. A thorough discussion of pharmaceutically acceptable carriers is available in Remington's Pharmaceutical Sciences (Mack Pub. Co., N.J. 1991).

Pharmaceutically acceptable carriers in therapeutic compositions may additionally contain liquids such as water, saline, glycerol and ethanol. Additionally, auxiliary substances, such as wetting or emulsifying agents, pH buffering substances, and the like, may be present in such compositions. Such carriers enable the pharmaceutical compositions to be formulated as tablets, pills, dragees, capsules, liquids, gels, syrups, slurries, suspensions, and the like, for ingestion by the patient.

Once formulated, the compositions of the invention can be administered directly to the subject. The subjects to be treated can be animals; in particular, human subjects can be treated.

The pharmaceutical compositions utilised in this invention may be administered by any number of routes including, but not limited to, oral, intravenous, intramuscular, intra-arterial, intramedullary, intrathecal, intraventricular, transdermal, transcutaneous, subcutaneous, intraperitoneal, intranasal, enteral, topical, sublingual, intravaginal or rectal means. Gene guns or hyposprays may also be used to administer the pharmaceutical compositions of the invention (see, for example, www.powderject.com). Typically, the therapeutic compositions may be prepared as injectables, either as liquid solutions or suspensions; solid forms suitable for solution in, or suspension in, liquid vehicles prior to injection may also be prepared.

Direct delivery of the compositions will generally be accomplished by injection, subcutaneously, intraperitoneally, intravenously or intramuscularly, or delivered to the interstitial space of a tissue. Dosage treatment may be a single dose schedule or a multiple dose schedule.

In one approach, expression of the genes encoding the problematic autoantibodies described above can be inhibited using expression blocking techniques, such as the use of antisense nucleic acid molecules (as described above), either internally generated or separately administered. Modifications of gene expression can be obtained by designing complementary sequences or antisense molecules (DNA, RNA, or PNA) to the control, 5' or regulatory regions (signal sequence, promoters, enhancers and introns) of the genes encoding the autoantibody. Similarly, inhibition can be achieved using "triple helix" base-pairing methodology (see Gee, J. E. et al. (1994) In: Huber, B. E. and B. I. Carr, Molecular and Immunologic Approaches, Futura Publishing Co., Mt. Kisco, N.Y.). The complementary sequence or antisense molecule may also be designed to block translation of mRNA by preventing the transcript from binding to ribosomes. Such oligonucleotides may be administered or may be generated in situ from expression in vivo.

Gene therapy may be employed to effect the endogenous production of peptides of the invention by the relevant cells in the subject. Gene therapy can occur in vivo or ex vivo. Ex vivo gene therapy requires the isolation and purification of patient cells, the introduction of a therapeutic gene and introduction of the genetically altered cells back into the patient. In contrast, in vivo gene therapy does not require isolation and purification of a patient's cells.

The therapeutic gene is typically "packaged" for administration to a patient. Gene delivery vehicles may be non-viral, such as liposomes, or replication-deficient viruses, such as adenovirus (see Berkner, K. L., in Curr. Top. Microbiol. Immunol., 158, 39-66 (1992)) or adeno-associated virus (AAV) vectors (see Muzyczka, N., in Curr. Top. Microbiol. Immunol., 158, 97-129 (1992) and U.S. Pat. No. 5,252,479). For example, a nucleic acid molecule encoding a peptide of the invention may be engineered for expression in a replication-defective retroviral vector. This expression construct may then be isolated and introduced into a packaging cell transduced with a retroviral plasmid vector containing RNA encoding the peptide, such that the packaging cell now produces infectious viral particles containing the gene of interest. These producer cells may be administered to a subject for engineering cells in vivo and expression of the polypeptide in vivo (see Chapter 20, Gene Therapy and other Molecular Genetic-based Therapeutic Approaches, (and references cited therein) in Human Molecular Genetics (1996), T Strachan and A P Read, BIOS Scientific Publishers Ltd).

Another approach is the administration of "naked DNA" in which the therapeutic gene is directly injected into the bloodstream or muscle tissue.

The invention also provides that the peptides, nucleic acid molecules, vectors and host cells of the invention can be used in vaccines to raise antibodies against the disease causing autoantibodies. Accordingly, this aspect of the invention provides a vaccine composition comprising a peptide, nucleic acid molecule, vector or host cell according to any one of the embodiments of the invention described above. Vaccines according to the invention may either be prophylactic (ie. to prevent disease) or therapeutic (ie. to treat disease after its incidence). Such vaccines comprise immunising peptide or nucleic acid, usually in combination with pharmaceutically-acceptable carriers as described above, which include any carrier that does not itself induce the production of antibodies harmful to the individual receiving the composition. Such carriers may function as immunostimulating agents ("adjuvants"). Adjuvants which may be used in the vaccine compositions of the invention include, but are not limited to, mineral-containing adjuvants (including mineral salts, such as aluminium salts and calcium salts, which may include hydroxides, phosphates, sulphates, etc.), oil emulsions, saponin formulations, virosomes and virus-like particles, bacterial and microbial derivatives, human immunomodulators, bioadhesives and mucoadhesives, microparticles, liposomes, polyoxyethylene ether and polyoxyethylene ester formulations, polyphosphazene (PCPP), muramyl peptides, imidazoquinolone compounds, thiosemicarbazone compounds and tryptanthrin compounds, or combinations thereof.

Furthermore, the peptide may be conjugated to a bacterial toxoid, such as a toxoid from diphtheria, tetanus, cholera, *H. pylori*, and other pathogens. Peptides according to the invention may be used either singly or in combination, alone or in conjunction with agents designed to promote their efficacy, in single, double or multiple chains with or without linker elements and carriers.

Since peptides may be broken down in the stomach, vaccines comprising peptides are preferably administered parenterally (for instance, subcutaneous, intramuscular, intravenous, or intradermal injection). Formulations suitable for parenteral administration include aqueous and non-aqueous sterile injection solutions which may contain anti-oxidants, buffers, bacteriostats and solutes which render the formulation isotonic with the blood of the recipient, and aqueous and non-aqueous sterile suspensions which may include suspending agents or thickening agents.

The vaccine formulations of the invention may be presented in unit-dose or multi-dose containers. For example, sealed ampoules and vials and may be stored in a freeze-dried condition requiring only the addition of the sterile liquid carrier immediately prior to use. The dosage will depend on the specific activity of the vaccine and can be readily determined by routine experimentation.

This aspect of the invention also includes a method of vaccinating an individual against a disease or disorder, comprising administering to the individual a peptide or a vaccine composition according to any one of the embodiments of the invention described above.

It may be desirable to deliver a composition of the invention to a patient over a prolonged period of time, for example for over one day, for over one week, for over one month or for over several months from a single administration. Various slow release, depot or implant dosage forms are envisaged by the inventors. For example, a dosage form can contain a pharmaceutically acceptable non-toxic salt of the peptide that has a low degree of solubility in body fluids. Additionally, the peptide can be formulated in a gel, for example, an aluminum monostearate gel with, e.g. sesame oil, suitable for injection. Another type of slow release depot formulation for injection would contain the peptide or salt dispersed for encapsulated in a slow degrading, non-toxic, non-antigenic polymer such as a polylactic acid/polyglycolic acid polymer, for example as described in U.S. Pat. No. 3,773,919. Suitable slow release, depot or implant formulations can be identified by the skilled person.

According to a still further aspect of the invention, there is provided a method of diagnosing an individual for the presence of or levels of autoimmune antibodies, the method comprising contacting a blood, plasma or serum sample or other body fluid with a peptide according to any one of the embodiments of the invention described above in the presence of a target for the autoimmune antibodies and assessing the amount of the naturally-occurring autoantibody that binds specifically to the target. Such a method involves a competitive binding assay in which target molecules that are capable of binding the autoimmune antibodies specifically compete with the peptide for binding. In this manner, the peptides can be used to detect the presence and quantity of autoimmune antibodies present in the individual. Such an assay may be based on radioimmunoassay, Western Blot analysis, Fluorescence activated cell sorting (FACS) or ELISA technology). Quantities of autoantibody expressed in subject, control and disease samples from biopsied tissues can in this way be compared with standard values. Deviation between standard and subject values establishes the parameters for diagnosing disease. Diagnostic assays may be used to distinguish between absence, presence, and excess expression of autoimmune antibody and to monitor regulation of polypeptide levels during therapeutic intervention. Such assays may also be used to evaluate the efficacy of a particular therapeutic treatment regimen in animal studies, in clinical trials or in monitoring the treatment of an individual patient.

The above method may utilise peptide that is labelled so that the labelled peptide competes with the autoantibodies for the target molecules to form complexes. In such an assay, the amount of label bound in the complexes is inversely proportional to the concentration of autoantibodies present in the sample. The peptide may be labelled with an enzyme so that the formation of the complexes inhibits or inactivates the activity of the enzyme. Alternatively, the peptide may be radioactively or fluorescently labelled. In an alternative scenario, the target molecules may be bound to an enzyme linked to a substrate such that binding of autoimmune antibody to the target molecules activates the enzyme and causes a colour change that is measurable spectrophotometrically. The target molecules may be bound to an enzyme linked to a substrate and present on a dipstick which can be contacted with the sample.

In all these methodologies, the target molecule may preferably be an anti-TCR Vβ polyclonal or monoclonal immunoglobulin molecule or any part thereof that identifies at least one epitope on T cell receptor Vβ chains in humans or any animal species.

To facilitate detection of autoantibody, the invention provides a diagnostic kit comprising a peptide according to any one of the embodiments of the invention described above; an anti-TCR Vβ polyclonal or monoclonal target immunoglobulin molecule or any part thereof that identifies at least one epitope on a T cell receptor Vβ chain; and a reagent useful for the detection of a binding reaction between autoimmune antibody and the target immunoglobulin molecule. Such kits will be of considerable use in diagnosing disease or susceptibility to disease.

According to a further aspect of the invention, there is provided an array incorporating one or more peptides according to the first aspect of the invention. Such arrays are useful for the diagnosis of disease or susceptibility to disease. Recent developments in the field of peptide, protein and antibody arrays allow the simultaneous detection of a large number of polypeptides. Low-density protein arrays on filter membranes, such as the universal protein array system (Ge H, (2000) Nucleic Acids Res. 28 (2), e3) allow imaging of arrayed antigens using standard ELISA techniques and a scanning charge-coupled device (CCD) detector on an optically flat glass plate containing 96 wells. Immuno-sensor arrays have also been developed that enable the simultaneous detection of clinical analytes. By using such protein arrays, protein expression (such as autoantibody) can be profiled in bodily fluids, such as in sera of healthy or diseased subjects, as well as in patients pre- and post-drug treatment.

In an alternative embodiment, polyclonal or monoclonal antibodies generated against the biologically expressed or synthesised peptides of the first aspect of the invention or equivalent ligands may be used in analytical techniques to qualitatively or quantitatively detect the presence of the autoantibodies or counteracting antibodies made against them. Various aspects and embodiments of the present invention will now be described in more detail by way of example, with particular reference to specific peptides. It will be appreciated that modification of detail may be made without departing from the scope of the invention.

BRIEF DESCRIPTION OF THE FIGURES

FIGS. 1A and 1B. Nucleotide and amino acid sequences of cloned antibody VH and VL regions.

FIGS. 4A to 4E. Nucleotide and amino acid sequences of cloned antibody VH and VL regions.

FIGS. 12A to 12E. Alignment of hypervariable region sequences from known VH and VL sequences against hypervariable region sequences identified herein.

EXAMPLES

Example 1

Antibody Sequencing

Figure 2:
FIG. 2. Human tumour cell line in presence of control irrelevant monoclonal antibody.

Methods
Total RNA Isolation

Poly A+ mRNA was extracted from $10^9$ frozen monoclonal cells, which secreted antibody recognizing anti-anti-TCR Vβ and an element of the GPI-linkage, using the Guanidinium isothiocyanate method. Total RNA isolation was carried out using the Ambion RNAqueous Kit (Cat No. 1912, Lot No. 019K0158). Approximately 0.3 mg of frozen hybridoma cells were resuspended in 5 ml lysis/binding solution. Following lysis 5 ml of 64% ethanol was added, mixed and the lysate/ethanol mixture was applied to RNAqueous filter units and centrifuged to bind the RNA to the filter matrix. The filters were washed once with 700 μl Wash Solution No. 1 and twice with 500 μl Wash Solution 2/3, and centrifuged after each wash step with a final centrifugation step after the final wash. RNA was eluted from the filters by applying 2×60 μl preheated (95° C.) Elution solution to the centre of the filter and centrifugation. The eluated RNA was precipitated with 0.5×Vol lithium chloride overnight at −20° C. Following washing in cold 70% ethanol, the RNA pellet was air dried and resuspended in 20 μl sterile water and stored at −70° C.

Reverse Transcription of RNA into First Strand cDNA

A complementary DNA strand was constructed using 1 μg of the RNA isolated above.

The reverse transcription reaction was set up as follows using the Ambion Retroscript kit (Cat No. 1710, Lot No. 078K0262):

| μl | |
| --- | --- |
| 1 | RNA (1 μg) |
| 4 | dNTPs mix (2.5 mM each) |
| 2 | oligo dT first strand primers |
| 9 | Sterile water |

This solution was incubated at 75° C. for 3 min and then placed on ice. The following was then added:

| μl | |
| --- | --- |
| 2 | 10 x Alternative RT-PCR buffer |
| 1 | Placental RNAase inhibitor |
| 1 | M-MLV reverse transcriptase |

The reaction was allowed to proceed at 42° C. for 90 mins and inactivated by incubation at 92° C. for 10 min. The reaction was then stored at −20° C.

Polymerase Chain Reaction of Ig Heavy and Light Chain Fragments

A Mouse Ig Primer set (Appendix 1, Novagen, Cat. No. 69831-3, Lot No. N14754) was used for the PCR of the heavy and light chain Ig fragments according to the manufacturers instructions using the first strand cDNA prepared above.

Reactions were stored at −20° C. until needed.

Cloning of PCR Products

All PCR products were cloned into a Blunt-end cloning system to facilitate sequencing. Systems used were pSTBlue-1 Perfectly Blunt™ Cloning (Novagen, Cat. No. 70191-3) and Zero Blunt™ PCR Cloning Kit (Invitrogen, 25-0162). They were then sequenced by standard procedures.

Results

The nucleotide and amino acid sequences obtained for the heavy and light chain variable regions are shown in FIGS. 1A and 1B (SEQ ID NOs:1 to 4). The hypervariable regions were deduced and are underlined in FIGS. 1A and 1B (SEQ ID NOs:6 to 16).

Example 2

Homodimer CDR Peptides

An N terminal cysteine was added to each of the hypervariable region sequences (CDR-L1-3 and CDR-H1-3, SEQ ID NOs:6 to 16) which were synthesised by Fmoc peptide synthesis and dimerised to form homodimers. Some of each of the homodimers was biotinylated; the biotinylated homodimers were then tested by fluorescence microscopy for their ability to bind to human pancreatic a cells (used as an indicator human tissue) by using fluoresceinated antibiotin as a second step reagent. It was found that homodimers from CDR-H2 (SEQ ID NO:8), CDR-H3 (SEQ ID NO:10) and CDR-L3 (SEQ ID NO:16) bound to the pancreatic α cells.

The non-biotinylated homodimer peptides were then tested by ELISAs for their ability to bind to anti-TCR Vβ antibody and to cardiolipin as an indicator of phospholipids (Table 1).

TABLE 1

Optical density readings for ELISAs showing binding of monoclonal anti-anti-TCR $V_β$ antibodies or homodimer peptides, CDR-H2, CDR-H3 and CDR-L3 to anti-TCR $V_β$ antibodies.

| Antigen | α-α-TCR $V_β$ antibody | CDR-H2 | CDR-H3 | CDR-L3 |
|---|---|---|---|---|
| α-TCRV$_β$ antibody | 0.806 ± 0.056# | 0.307 ± 0.018* | 0.182 ± 0.009* | 0.243 ± 0.008* |
| Culture medium#/PBS* | 0.372 ± 0.037# | 0.168 ± 0.010* | 0.091 ± 0.020* | 0.140 ± 0.018* |
| Ratio Test/Control | 2.17 | 1.83 | 2.00 | 1.74 |
| Cardiolipin** | 0.142 ± 0.070 | 0.151 ± 0.020 | 0.132 ± 0.009 | 0.254 ± 0.012 |
| Alcohol** | 0.038 ± 0.014 | 0.063 ± 0.012 | 0.061 ± 0.006 | 0.114 ± 0.021 |
| Ratio Test/Control | 3.74 | 2.40 | 2.16 | 2.23 |

The microtitre plate was coated with α-TCR $V_β$ and tested against α-α-TCR $V_β$ or culture medium.
*The microtitre plate was coated with CDR-H2, CDR-H3 and CDR-L3 and tested against α-TCR $V_β$ or culture medium.
**The microtitre plate was coated with either cardiolipin in ethyl alcohol or ethyl alcohol and tested against α-α-TCR $V_β$ or CDR-H2, CDR-H3 and CDR-L3. Each mean and standard deviation is for three observations.

Example 3

Identification of Autoantibodies In Vivo

Evidence for the presence in human sera of autoantibodies (represented by anti-anti-TCR VP and the peptides of this invention) that bind to anti-TCR Vβ antibodies is shown in Table 2. Since the autoantibodies are likely to become ubiquitous within the adult population, undetectable levels are most likely to be found amongst children. This is supported by the data in Table 2 which shows high levels in newly diagnosed Type I diabetic children compared to ICA positive and ICA negative controls.

TABLE 2

Reactivity of sera from newly diagnosed diabetic and non-diabetic children against monoclonal anti-TCR Vβ antibody.

| Subject Type | Total number of subjects | Number reactive against anti-TCR Vβ | Test/Control Index range* | Mean Index |
|---|---|---|---|---|
| Newly diagnosed diabetics | 8 | 7 | 1.8-3.8 | 2.7 ± 0.8 |
| Non diabetics ICA positive | 10 | 5 | 1.2-1.5 | 1.3 ± 0.1 |
| Non diabetics ICA negative | 10 | 3 | 1.2-2.1 | 1.6 ± 0.5 |

*The index range is derived by taking the ratio of the optical density measurements comparing 1 in 30 diluted test sera with the diluent (culture medium) alone.
The microtitre plate was coated with anti-TCR Vβ antibody.
The sera were diluted 1 in 30 in culture medium.
Binding was detected using anti-human Ig peroxidase and an appropriate substrate.

Example 4

Cancer Metastasis

The autoantibodies are also implicated in cancer metastases by binding to GPI-linked molecules such as UPAR which interacts with the actin cytoskeleton causing cell motility (see page 51). Other examples where UPAR or similar molecules may be responsible for maintaining the cytoskeleton are for optimal CFTR function which is compromised in cystic fibrosis (see page 54) or in arthritis where synovial cells carrying such molecules invade cartilage and bone (see page 50).

Figure 3A:
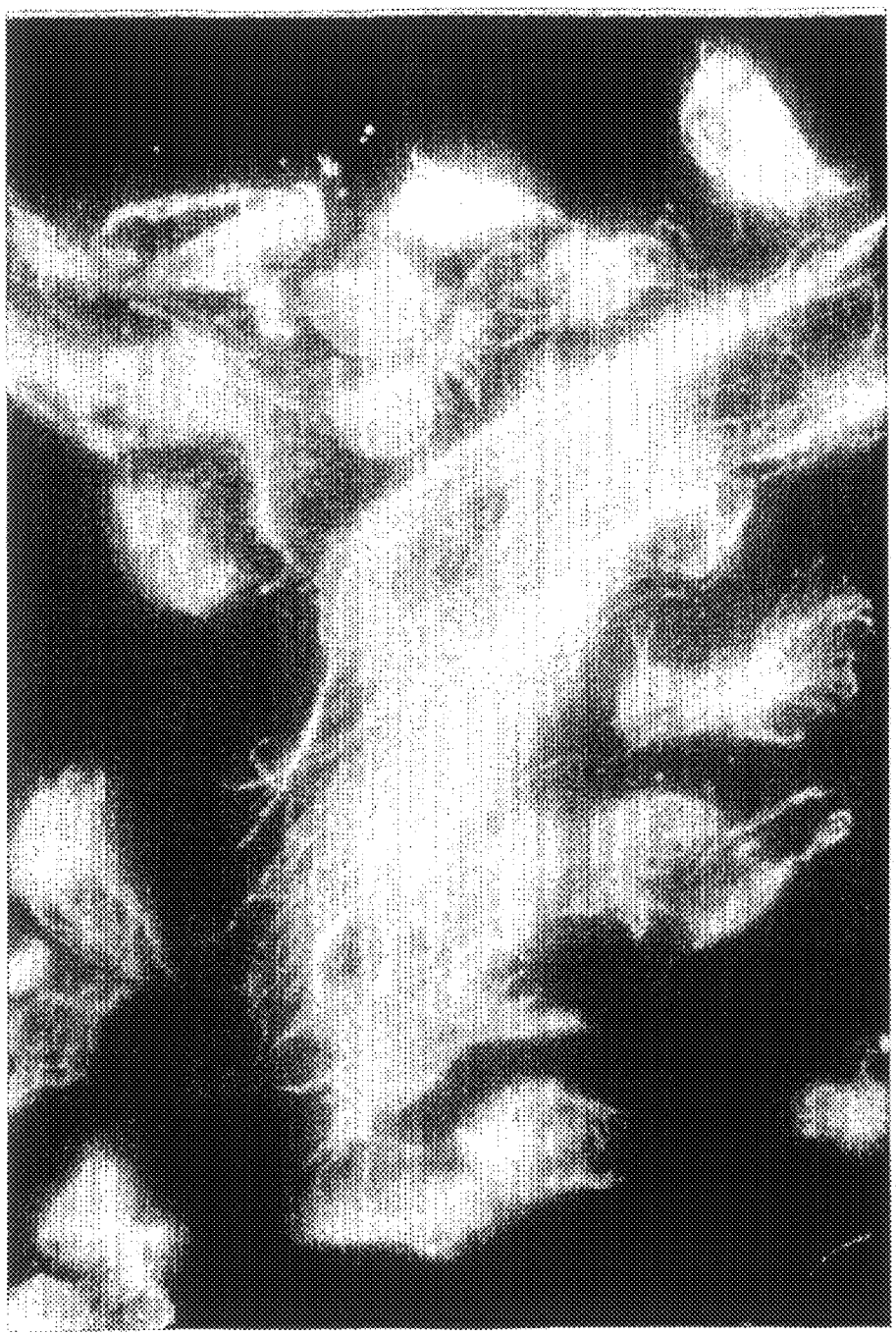
FIGS. 3A and 3B. Human tumour cell line in presence of anti-anti-TCR Vβ antibodies showing typical morphologies of the actin cytoskeleton and cell protrusions.
Figure 3B:

FIG. 2 shows a human tumour cell line in the presence of an irrelevant antibody whereas FIGS. 3a and 3b show the effect of anti-anti-TCR Vβ monoclonal antibody on the same tumour cell line demonstrating changes of the actin cytoskeleton and cell protrusions indicative of motility after 30 minutes incubation.

Example 5

Further Antibody Sequencing

Genes encoding five further cross-reactive murine anti-anti-TCR Vβ monoclonal antibodies were cloned and sequenced, using the methods described in Example 1 above. The cell lines from which the monoclonal antibody sequences were obtained are designated cell lines 13.42a, 32.15, 32.17, 32.75 and 32.2 herein. The antibodies produced by cell lines 32.15, 32.17, 32.75 and 32.2 are IgM antibodies, the same as the antibody cloned and sequenced in Example 1. The antibody produced by the cell line 13.42a is an IgG antibody.

Results

The nucleotide and amino acid sequences for the heavy and light chain variable regions are shown in FIGS. 4A to 4E. The cell line 13.42a VH and VL nucleotide and amino acid sequences are shown in FIG. 4A (SEQ ID NOs:17-20). The cell line 32.15 VH and VL nucleotide and amino acid sequences are shown in FIG. 4B (SEQ ID NOs:33-36). The cell line 32.17 VH and VL nucleotide and amino acid sequences are shown in FIG. 4C (SEQ ID NOs:49-52). The cell line 32.75 VH and VL nucleotide and amino acid sequences are shown in FIG. 4D (SEQ ID NOs:65-68). The cell line 32.2 VH and VL nucleotide and amino acid sequences are shown in FIG. 4E (SEQ ID NOs:81-84).

The hypervariable regions were deduced and are underlined in FIGS. 4A to 4E. The cell line 13.42a hypervariable region nucleotide and amino acid sequences are shown in FIG. 4A (SEQ ID NOs:21-32). The cell line 32.15 hypervariable region nucleotide and amino acid sequences are shown in FIG. 4B (SEQ ID NOs:37-48). The cell line 32.17 hypervariable region nucleotide and amino acid sequences are shown in FIG. 4C (SEQ ID NOs:53-64). The cell line 32.75 hypervariable region nucleotide and amino acid sequences are shown in FIG. 4D (SEQ ID NOs:69-80). The cell line 32.2 hypervariable region nucleotide and amino acid sequences are shown in FIG. 4E (SEQ ID NOs:85-96).

The hypervariable region sequences determined for cell lines 13.42a, 32.15, 32.17, 32.75 and 32.2 were compared to the hypervariable region sequences identified in Example 1, to establish which hypervariable region residues are important for cross-reactive anti-TCR Vβ binding (i.e. the hypervariable region residues important

Example 6

Phase I/IIa Trial

Twelve male subjects with glucose intolerance participated in a phase I/IIa double blind placebo controlled clinical trial to assess the safety and tolerability of NDX-1. NDX-1 is a mixture of three peptides according to the invention (B71, C80 and F90), mixed in a proportion of 2:1:1. B71 is a homodimer of CDR-H2 derived monomer peptides, each monomer comprising the amino acid sequence presented in SEQ ID NO:8 and additionally an N terminal cysteine residue. The amino acid sequence of the B71 monomer peptide is given in SEQ ID NO:159. C80 is a homodimer of CDR-H3 derived monomer peptides, each monomer comprising the amino acid sequence presented in SEQ ID NO:10 and additionally an N terminal cysteine residue. The amino acid sequence of the C80 monomer peptide is given in SEQ ID NO:160. F90 is a homodimer of CDR-L3 derived monomer peptides, each monomer comprising the amino acid sequence presented in SEQ ID NO:16 and additionally an N terminal cysteine residue. The amino acid sequence of the F90 monomer peptides is given in SEQ ID NO:161. Patients were randomised to receive a total of 4 intramuscular (IM) injections spaced one week apart from day 01 of either the test substance, the NDX-1 peptide mixture, or placebo injections. 3 subjects received the placebo injections composed of 0.1% alhydrogel in 1.1 ml saline. 9 subjects received 0.99 mg of the NDX-1 peptide mixture in 1.1 ml saline containing 0.1% alhydrogel. The placebo and test injections were visibly identical.

The NDX-1 peptide mixture was well tolerated. In the treated subjects, fasting concentrations of glucose, insulin and glucagon did not change significantly compared to baseline. Subjects underwent an oral glucose tolerance test (OGTT) on day 01 pre first injection and at day 43. Blood was sampled before and at 30, 60, 90, and 120 minutes after ingestion of 75 g glucose on both occasions.

Figure 5:
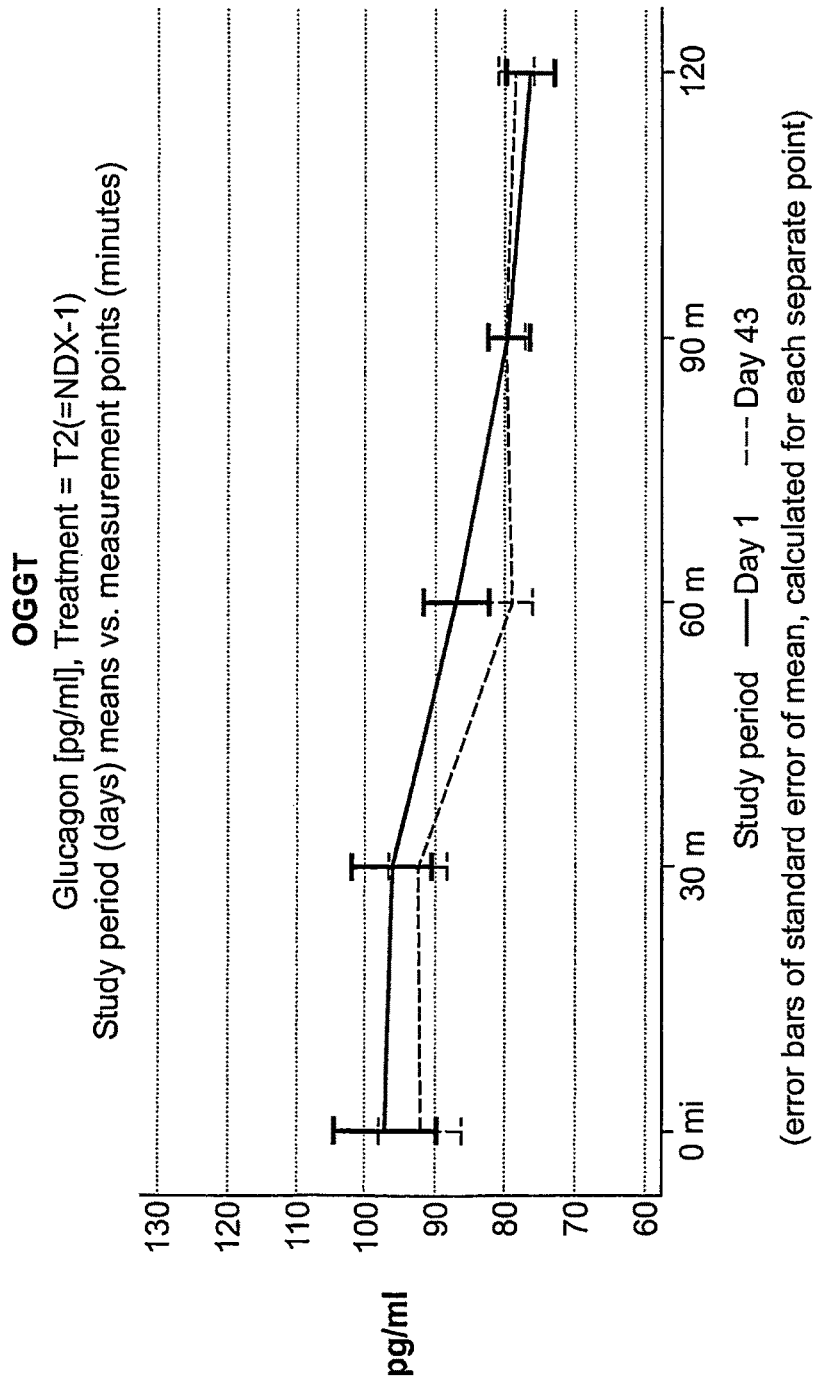
FIG. 5. Serum glucagon (mean±SD) prior to and after ingestion of 75 g glucose in NDX-1 treated group at day 01 and day 43.

The subjects who had received the NDX-1 peptide mixture showed a significant decrease in the two hour serum glucose concentration as compared with the placebo group ($p=0.03$). The time required for glucagon to reach its lowest level in the NDX-1 group was $113.3\pm13.2$ minutes at day 01 which went down to $63.3\pm41$ minutes at day 43 ($p=0.0027$; see FIG. 5). There were also significant differences in the percentage changes in plasma creatinine ($p=0.0009$), sodium ($p=0.0344$), chloride ($p=0.0041$) and plasma urea ($p=0.0156$) from baseline to the end of the trial comparing the NDX-1 and placebo groups. These changes were consistent with disease progression in the placebo group but not in the treated group. Furthermore, the 2 hour glucose and glucagon results of OGTT studies in the test group demonstrate the efficacy of NDX-1 peptide mixture in autoglycaemic regulation.

Example 7

Phase IIb Trial in Type 2 Diabetics 31 subjects (21 males and 10 females) with type 2 diabetes mellitus on one or more oral antidiabetic medication(s) were entered into a randomised double blind study of 16 weeks duration. At day 01 all antidiabetic medication was stopped. Patients were randomised to either the placebo group (group C) or one of 3 treatment groups described as Groups A, B or D. All groups received a total of 4 IM injections spaced one week apart starting from day 01. The placebo group (8 subjects) received 1.2 ml of saline containing 0.1% alhydrogel. Group A (7 subjects) received 1.51 mg of a peptide according to the invention (designated as NDX-71 herein) in 1.2 ml saline containing 0.1% alhydrogel. Group B (8 subjects) received 0.86 mg NDX-71 in 1.2 ml saline containing 0.1% alhydrogel. Group D (8 subjects) received a mixture of 3 peptides of the invention (0.92 mg NDX-71, 0.68 mg C80 and 0.71 mg F90) in 1.2 ml saline containing 0.1% alhydrogel. Placebo and study medications were visibly identical. The NDX-71 peptide used in this example was the B71 peptide used in Example 6. The C80 and F90 peptides used in this example were the C80 and F90 peptides used in Example 6.

At regular intervals throughout the study period patients underwent blood tests for clinical safety and glycaemic efficacy parameters. The test substances were well tolerated. Clinical safety parameters in all groups were unchanged from baseline. There were no adverse events reported in the study attributable to the test substances.

Figure 6:
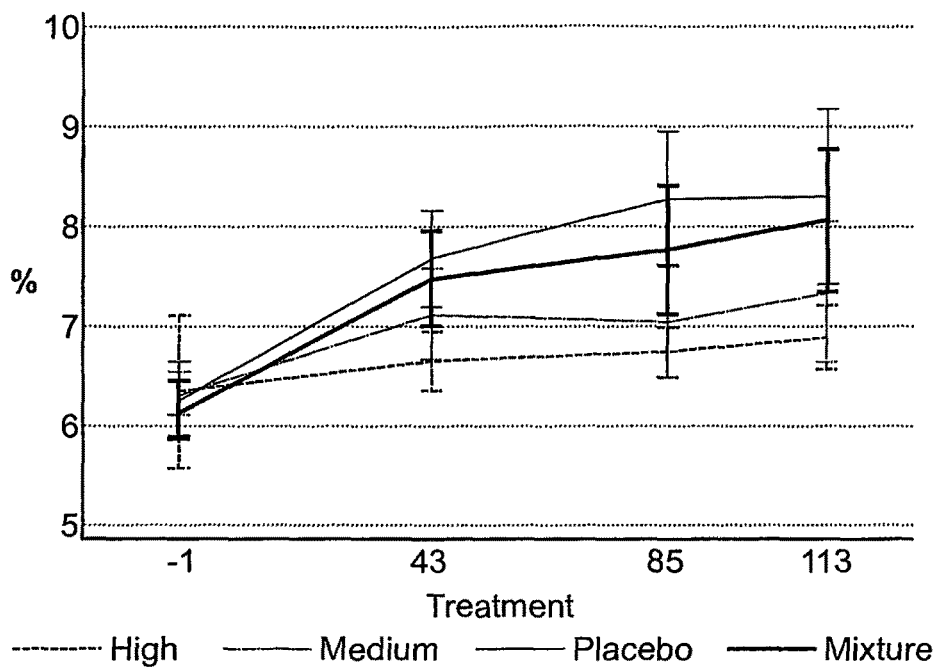
FIG. 6. HbA1 c levels in diabetes mellitus type 2 patients after withdrawal of anti-diabetic drugs. Average data from all subjects are shown; bars indicate the standard error of the mean. Data obtained from subjects, after reinstatement of anti-diabetic medication were excluded.
Figure 7:
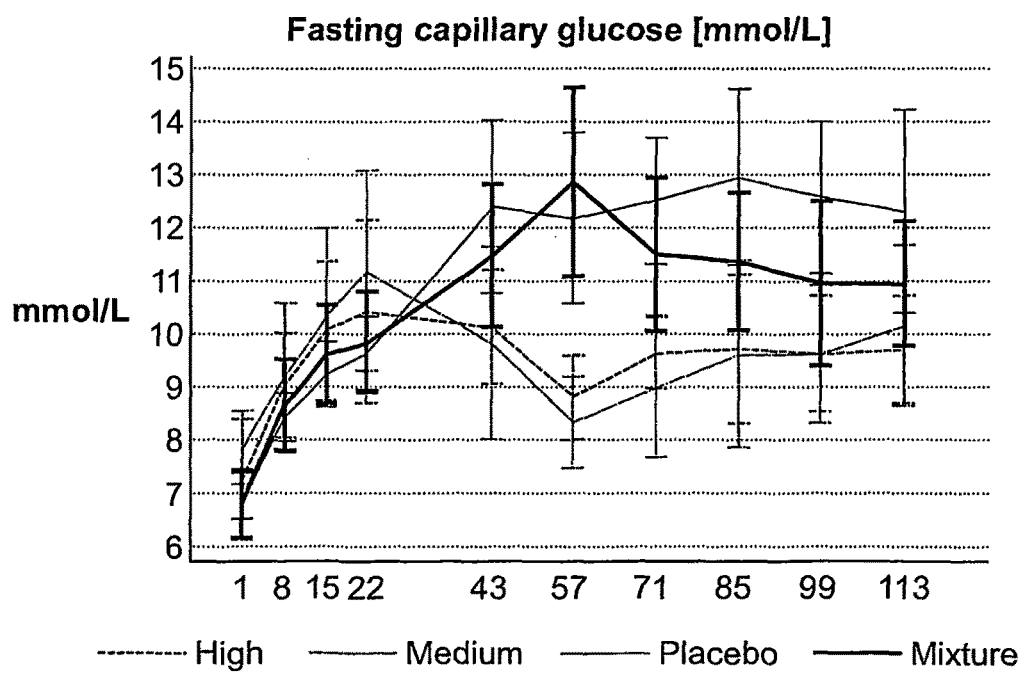
FIG. 7. Fasting capillary glucose levels in diabetes mellitus type 2 patients after cessation of anti-diabetic drugs. Average data from all subjects are shown; bars indicate the standard error of the mean. Data obtained from subjects after reinstatement of anti-diabetic medication were excluded.
Figure 8:
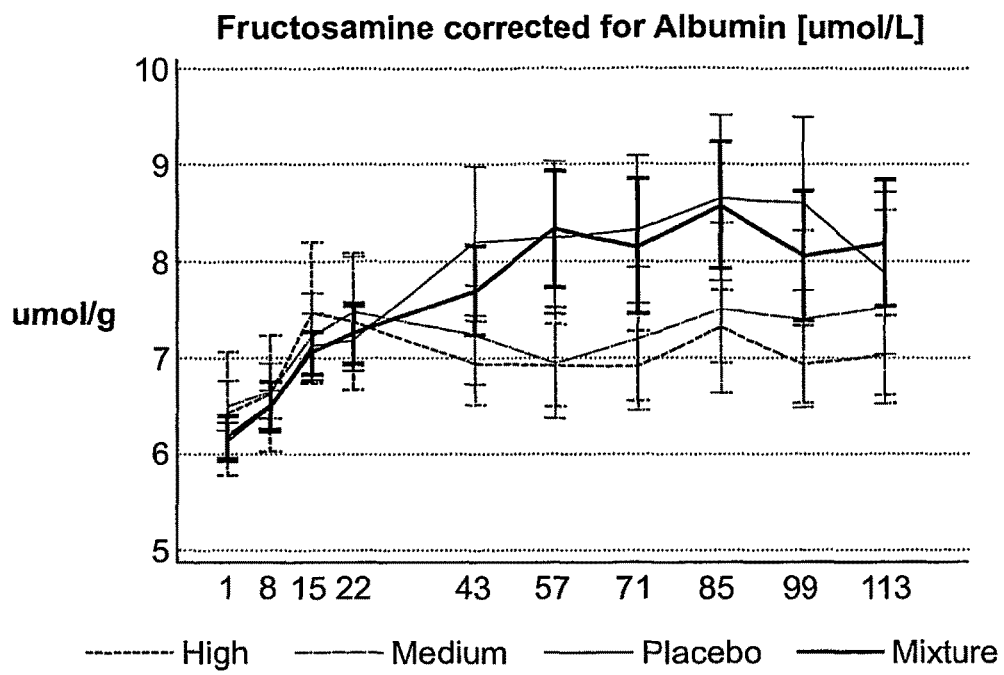
FIG. 8. Serum fructosamine levels corrected for albumin in diabetes mellitus type 2 patients after withdrawal of anti-diabetic drugs. Average data from all subjects are shown; bars indicate the standard error of the mean. Data obtained from subjects after reinstatement of anti-diabetic medication were excluded.

Over the 4 months following drug cessation there was a marked deterioration of glycaemic control in the placebo group, as measured by HbA1c, fasting blood glucose and fructosamine (see FIGS. 6-8). Mean levels of HbA1c increased from 6.3% at baseline to 8.3% at day 113. However, in the high dose treatment group HbA1c levels remained almost constant over time, from 6.3 at baseline up to 6.9 at day 113 and were significantly different from the placebo group ($p=0.02$; see FIG. 6).

Figure 9:
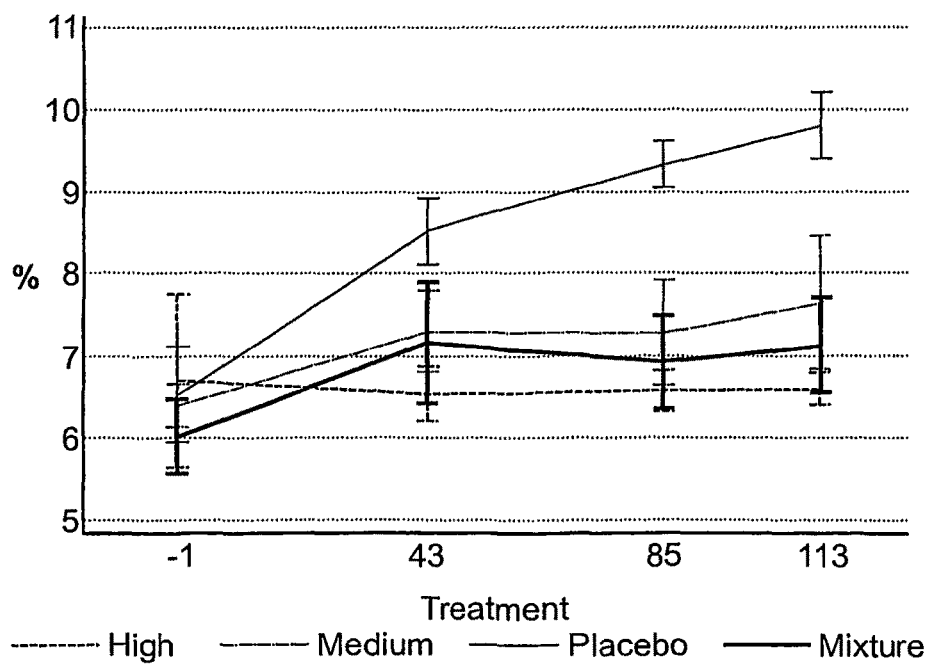
FIG. 9. HbA1c levels in male diabetes mellitus type 2 patients after withdrawal of anti-diabetic drugs. Average data subjects are shown; bars indicate the standard error of the mean. Data obtained from subjects after reinstatement of anti-diabetic medication were excluded.
Figure 10:
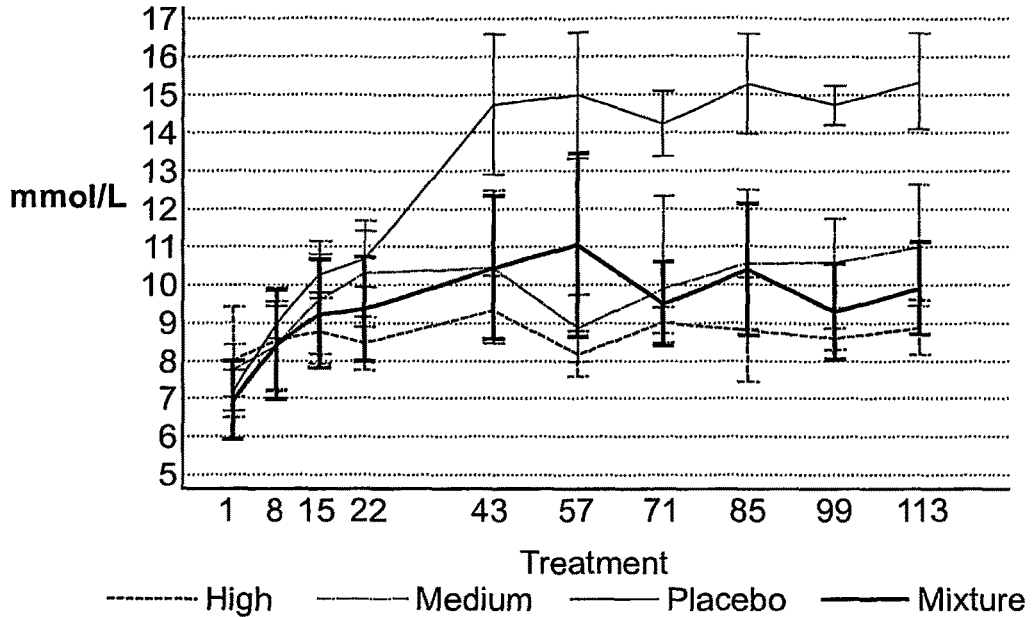
FIG. 10. Fasting capillary glucose levels in male diabetes mellitus type 2 patients after withdrawal of anti-diabetic drugs. Average data are shown; bars indicate the standard error of the mean. Data obtained from subjects after reinstatement of anti-diabetic medication were excluded.
Figure 11:
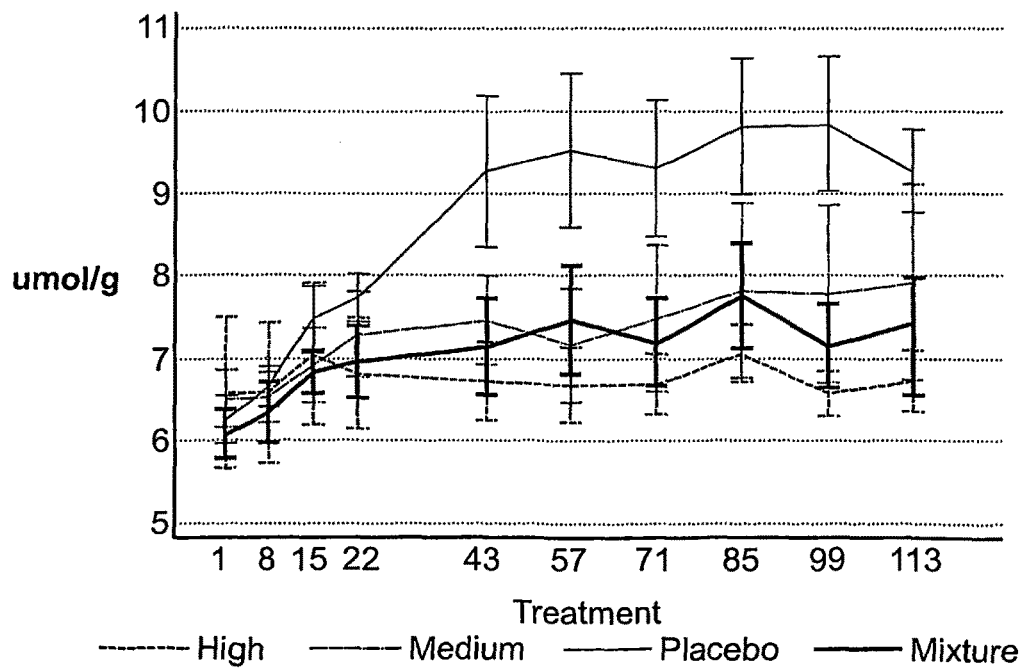
FIG. 11. Serum fructosamine levels corrected for albumin in male diabetes mellitus type 2 patients after withdrawal of anti-diabetic drugs. Average data are shown; bars indicate the standard error of the mean. Data obtained from subjects after reinstatement of anti-diabetic medication were excluded.

Subset analyses of the 21 male volunteers revealed overall significance or highly significant differences between the placebo (group C) and groups A, B and D combined for all glycaemic parameters studied i.e. HbA1c ($p=0.004$; see FIG. 9), fasting blood glucose ($p=0.024$; see FIG. 10) and corrected fructosamine, ($p=0.015$; see FIG. 11). Statistically significant treatment differences between the placebo (group C) and the high dose group (group A) for the various parameters were: HbA1c $p<0.001$, fasting glucose $p=0.005$ and corrected fructosamine $p=0.001$. Glycaemic control in treatment groups as compared with placebo demonstrates the desired effect of auto-glycaemic regulation.

This example demonstrates that after cessation of antidiabetic medication, the patients who received the 1.51 mg dose of NDX-71 were able to maintain good glycaemic control in the absence of their oral anti diabetic medication. Furthermore, the effects of NDX-71 were long lasting in that the effect was observed even 3 months after the final dose of NDX-71. The subjects who received the lower dose of 0.86 mg NDX-71 and the mixture of the three peptides also showed improvement as compared with placebo, indicating that NDX-71 has a dose response effect, and higher doses or more frequent injections may produce even more favourable results.

Example 8

Analysis of Known Sequences

Using the hypervariable region sequences identified in Examples 1 and 5, the hypervariable region sequences of known VH and VL regions with relevant binding properties were identified. The hypervariable region sequences of the known VH and VL regions were then compared to the hypervariable region sequences identified in Examples 1 and 5, to analyse the hypervariable region residues important for cross-reactive anti-TCR Vβ binding (ie. the hypervariable region residues important for multispecific reactivity against a GPI linkage epitope as described herein). By applying the same sequence analysis process as described in Example 5, a further series of consensus sequences and formulae were identified, as illustrated in FIGS. 12A to 12E.

The accession numbers for the prior art VH and VL regions that were identified are listed in FIGS. 12A to 12E. The binding specificities disclosed in the prior art for those VH and VL regions are also listed in FIGS. 12A to 12E, using the following abbreviations:

| | |
|---|---|
| Anti-RF | Anti-rheumatoid factor |
| Anti-CL | Anti-cardiolipin |
| Anti-RNA | Anti-RNA |
| Anti-sDNA | Anti-single-stranded DNA |
| Anti-NA | Anti-nuclear antibody |
| Anti-VA | Anti-variable alpha |
| Anti-CD8 | Anti-CD8 |
| Anti-TG | Anti-thyroglobulin |
| Anti-3H1 | Anti-idiotype antibody 3H1 |
| Anti-RO | Anti-Ro |
| Anti-TRKA | Anti-TrkA (high affinity NGF receptor) |

The IgG and IgM hypervariable region sequences identified in Example 1 and 5 were analysed separately in this example, because they were found to identify different consensus sequences and formulae.

For the IgM CDR-H1 sequences, the following consensus sequences and formulae were identified (see FIG. 12A):

```
IgM CDR-H1
G-Y-T-F-T-x-x-x--x--x-W

IgM CDR-H1
G-Y-T-F-T-(RNYSTDEG)-(NYF)-(WGAY)-(IMV)-(NGQH)-W

IgM CDR-H1
G-Y-T-F-T-(RNS)-Y-W-(IM)-N-W
```

For the IgG CDR-H1 sequence, the following consensus sequences and formulae were identified (see FIG. 12A):

| | |
|---|---|
| IgG CDR-H1 | G-Y-x-F-x-x-Y-x-M-x-W |
| IgG CDR-H1 | G-Y-(ATS]-F-(T/S)-(SDG)-Y-(NWV)-M-(FQHN)-W |
| IgG CDR-H1 | G-Y-T-F-T-S-Y-W-M-H-W |

For the IgM CDR-H2 sequences, the following consensus sequences and formulae were identified (see FIG. 12B):

| | |
|---|---|
| IgM CDR-H2 | x-I-x-x-x-x-x-x-x-Y-x-x-x-F-K-x |
| IgM CDR-H2 | (NWEAY)-I-(YND)-(PT)-(SYG)-(DTGY)-(SGD)-(YEGS)-(TP)-(NTYGS)-Y-(NAI)-(QDE)-(KD)-F-K-(DGN) |
| IgM CDR-H2 | N-I-Y-P-S-D-S-Y-T-N-Y-N-Q-K-F-K-G |

For the IgG CDR-H2 sequence, the following consensus sequences and formulae were identified (see FIG. 12B):

| | |
|---|---|
| IgG CDR-H2 | x-I-x-P-x-x-x-x-T-x-Y-x-x-K-F-x-G |
| IgG CDR-H2 | (YWKNLR)-I-(DN)-P-(YAEFS)-(NYS)-(GD)-(DSG)-T-(RESKN)-Y-(SAN)-(QSEP)-K-F-(KQT)-G |
| IgG CDR-H2 | (YW)-I-N-P-Y-N-G-D-T-(ES)-Y-N-Q-K-F-K-G |

No consensus sequences or formulae were identified for CDR-H3, because there was found to be a high level of sequence and length variation in that CDR.

For the IgM CDR-L1 sequences, the following consensus sequences and formulae were identified (see FIG. 12C):

| | |
|---|---|
| IgM CDR-L1 | x-A-S-x-x-x-x-x-x-x |
| IgM CDR-L1 | (KR)-A-S-(QS)-(NSDT)-(VI)-(DGSR)-(TSYNK)-(NADY)-(VYGL)-(ALD) |
| IgM CDR-L1 | K-A-S-Q-N-V-S-T-N-V-A |

For the IgG CDR-L1 sequence, the following consensus sequences and formulae were identified (see FIG. 12C):

| | |
|---|---|
| IgG CDR-L1 | x-A-S-x-x-x-x-x-x-L-x |
| IgG CDR-L1 | (RK)-A-S-(QR)-(DSG)-(IV)-(SN)-(NSG)-(YW)-L-(NHA) |
| IgG CDR-L1 | R-A-S-Q-S-I-S-N-Y-L-(NA) |

For the IgM CDR-L2 sequences, the following consensus sequences and formulae were identified (see FIG. 12D):

| | |
|---|---|
| IgM CDR-L2 | x-x-S-x-x-x-S |
| IgM CDR-L2 | (SRW)-(AT)-S-(YIT)-(RL)-(YAE)-S |
| IgM CDR-L2 | S-A-S-Y-R-Y-S |

For the IgG CDR-L2 sequence, the following consensus sequences and formulae were identified (see FIG. 12D):

| | |
|---|---|
| IgG CDR-L2 | x-T-S-x-L-x-x |
| IgG CDR-L2 | (YLDTK)-T-S-(RNKV)-L-(HAG)-(SP) |
| IgG CDR-L2 | Y-T-S-N-L-A-S |

For the IgM CDR-L3 sequences, the following consensus sequences and formulae were identified (see FIG. 12E):

| | |
|---|---|
| IgM CDR-L3 | Q-Q-x-x-S-x-P-x-T |
| IgM CDR-L3 | Q-Q-(YGWR)-(NSAG)-S-(YSDW)-P-(LPYI)-T |
| IgM CDR-L3 | Q-Q-Y-N-S-Y-P-L-T |

For the IgG CDR-L3 sequence, the following consensus sequences and formulae were identified (see FIG. 12E):

| | |
|---|---|
| IgG CDR-L3 | Q-Q-x-N-x-x-P-x-x |
| IgG CDR-L3 | Q-Q-(GNSTY)-N-(TES)-(FDWY)-P-(TYRF)-(FT) |
| IgG CDR-L3 | Q-Q-N-N-E-D-P-(YR)-T |

The VH and VL region sequences analysed in this example are all known to bind to molecules implicated in the centralised disease mechanism disclosed herein and in WO99/05175, as illustrated in FIGS. 12A to 12E. In addition, the hypervariable region sequences analysed share significant structural homology with the hypervariable region sequences identified by the inventors in Examples 1 and 5. Accordingly, it is believed that peptides which comprise or consist of an amino acid sequence meeting the requirements of one of the above consensus sequences and formulae will also have equivalent biological activity to the peptides tested in vivo in Examples 6 and 7 above, and will be useful in accordance with the invention.

Example 9

Further Analysis of CDR-H2 Sequences

Further analysis of CDR-H2 sequences in known VH and VL region sequences was performed, and revealed additional amino acid residues that are believed to be involved in cross-reactive anti-TCR Vβ binding. In particular, the CDR-H2 sequences from sixty-seven known VH region sequences with relevant binding specificities were compared to the CDR-H2 sequences identified by the inventors, to determine the residues that commonly occur at each position of CDR-H2 with the required binding specificity.

The following formula was identified, which includes at each position within CDR-H2 any residue that was found to occur at that position in six or more of the sixty-seven CDR-H2 sequences analysed:

```
cDR-H2 (EYWSL)-I-(YSND)-(PSH)-(SGNY)-(GSNTD)-(SGD)-
       (YTGS)-(TIA)-(NY)-(YN)-(NAP)-(QDSEP)-(KSL)-
       (FVK)-(KQS)-(GR)
```

The following formula was identified, which includes at each position within CDR-H2 any residue that was found to occur at that position in ten or more of the sixty-seven CDR-H2 sequences analysed:

```
CDR-H2 E-I-(YSN)-(PS)-(SGN)-(GS)-(SG)-(TGS)-T-(NY)-
       Y-(NAP)-(QDS)-(KS)-(FVK)-(KQ)-(GR)
```

The following formula was identified, which includes at each position within CDR-H2 any residue that was found to occur at that position in twenty or more of the sixty-seven CDR-H2 sequences analysed. Positions at which no amino acid was found to occur twenty or more times in the sixty-seven CDR-H2 sequences analysed are denoted by 'x', which means that any amino acid may be present at that position:

```
cDR-H2   x-I-x-P-S-G-G-x-T-Y-x-A-D-(KS)-(FV)-K-G
```

It is believed that peptides which comprise or consist of an amino acid sequence meeting the requirements of one or more of the above formulae will also have equivalent biological activity to the peptides tested in vivo in Examples 6 and 7 above, and will be useful in accordance with the invention.

REFERENCES

1. Payne J., Huber B. T., Cannon N. A., Schneider R., Schilham M. W., Acha-Orbea H., MacDonald H. R. and Hengartner H. (1988). Proc. Natl. Acad. Sci., 85:7695-7698.
2. Hooper N. M., Broomfield S. J. and Turner A. J. (1991). Biochem. J. 273:301-306.
3. Saltiel A. R. (1990). Diabetes Care 13:244-256.
4. Romero G., Luttrell L., Rogol A., Zeller K., Hewlett E. and Larner J. (1988). Science 240:509-511.
5. Perez F. R., Casabiel X., Camina J. P., Zugaza J. L. and Casanueva F. F. (1997). Endocrinology 138:264-272.
6. Pipeleers D. G., Schuit F. C., in't Veld P. A., Hooghe-Peters E. L., Van de Winkel M. and Gepts W. (1985). Endocrinology 117:824-833.
7. Marchetti P., Scharp D. W., Mclear M., Gingerich R., Finke E., Olack B., Swanson C., Giannarelli R. and Laacy P. E. (1994). Diabetes 43:827-830.
8. Todd J., Bell J. and McDevitt H. O. (1989). Nature 329: 599-604.
9. Kimpimaki T., Kupila A., Hamamainen A-M., Kukko M., Kulama P., Savola K., Simell T., Keskinen P., Ilonen J., Simell O. and Knip M. (2001). J. Clin. Endocrin. Metab. 86:4782-4788.
10. Barnett A. H., Eff C., Leslie R. D. G. and Pyke D. A. (1981). Diabetologia 20:404-409.
11. Tisch R. and McDevitt H. (1996). Review Cell 85:291-297.
12. Castano L. and Eisenbarth G. S. (1990). Ann. Rev. Immunol. 8:647-680.
13. Hagopian W. A., Karlsen A. E., Gottsater A., Landin-Olsson M., Grubin C. E., Sundkvist G., Petersen J. S., Boel E., Dysberg T. and Lernmark A. (1993). J. Clin. Invest. 91:368-374.
14. Passini N., Larigan J. D., Genovese S., Apella E., Sinigaglia F. and Rogge L. (1995). Proc. Natl. Acad. Sci. 92:9412-9416.
15. Rowe R. E., Leech N. J., Nepom G. T. and McCulloch D. K. (1994). Diabetes 43:87-94.
16. Eisenbarth G. S. (1994). Diabetes Care 17:605-607.
17. Daniel D., Gill R. G., Schloot N. and Vegmann D. (1995). Eur. J. Immunol. 25:1056-1062.
18. Roder M. E., Knip M., Hartling S. G., Karjalainen J., Akerblom H. K., Binder C. and the Childhood diabetes in Finland Study Group (1994). J. Clin. Endocrinol. Metab. 79:1570-1575.
19. Dinneen S., Alzaid A., Turk D. and Rizza R. (1995). Diabetologia 38:337-343.
20. Kleinbaum J. and Shamoon H. (1983). Diabetes 32:493-498.
21. Kahn S, and Halban P. (1997). Diabetes 46:1725-1731.
22. Bolli, G. B., Tsalikian E., Haymond M. W., Cryer P. E. and Gerich J. E. (1984). J. Clin. Invest., 73:1532-1541.
23. Low M. G. (1989). FASEB J. 3:1600-1608.
24. Shashkin P. N., Shashkina E. E., Femquist-Forbes E., Zhou Y-P., Grill V. and Katz A. (1997). Diabetologia 40:557-563.
25. Lindegard B. (1986). Dermatologica 172:298-304.
26. Christophers E. (2001). Clin. Exp. Dermatol. 26:314-320.
27. Jucci A., Vignini M., Pelfini C., Criffo A. and Fratino P. (1977). Arch. Dermatol. Res. 257:239-246.
28. Brenelli S. L., Moraes A. M., Monte-Alegre S., Carvalho O. M. and Saad M. J. (1995). Braz. J. Med. Biol. Res. 28:297-301.
29. Ena P., Madeddu P., Glorioso N., Cerimele D and Rappelli A. (1985). Acta Cardiol. 40:199-205.
30. Venneker G. T., Das P. K., Meinardi M. M., van Marle J., van Veen H. A., Bos J. D. and Asghar S. S. (1994). J. Pathol. 172: 189-197.
31. Hamza S. H., el-Mazny H. R. and Abdallah M. A. (1978). Br. J. Dermatol. 99:289-292.
32. Taieb A. (2000). Pigment Cell Res. 13 Suppl 8:41-47.
33. Romano G., Moretti G., Di Benedetto A., Giofre C., Di Cesare E., Russo G., Califano L and Cucinotta D. (1998) Diabetes Res. Clin. Pract. 39: 101-106.
34. Tsatmali M., Ancans J. and Thody A. J. (2002). J. Histochem. Cytochem. 50:125-134.
35. Katsuki A., Sumida Y., Murashima S., Furuta M., Araki-Sasaki R., Tsuchihashi K., Hori Y., Yano Y. and Adachi Y. (2000). Int. J. Obes. Relat. Metab. Disord. 24:1260-1264.
36. Scott G., Leopardi S., Printup S, and Madden B. C. (2002). J. Cell Sci. 115:1441-1451.
37. Virador V. M., Muller J., Wu X., Abdel-Malek Z. A., Yu Z. X., Ferrans V. J., Kobayashi N., Wakamatsu K., Ito S., Hammer J. A. and Hearing V. J. (2002). FASEB J. 16:105-107.

38. Tobin D. J., Swanson N. N., Pittelkow M. R., Peters E. M. and Schallreuter K. U. (2000). J. Pathol. 191:407-416.
39. Martinez-Esparza M., Ferrer C., Castells M. T., Garcia-Borron J. C. and Zuasti A. (2001). Int. J. Biochem. Cell Biol. 33:971-983.
40. Grande J. P., Warner G. M., Walker H. J., Yusufi A. N., Cheng J., Gray C. E., Kopp J. B. and Nath K. A. (2002). Exp. Biol. Med. 227:171-181.
41. Tam B. Y., Germain L. and Philip A. (1998). J. Cell. Biochem. 70:573-586.
42. van den Wijngaard R. M., Asghar S. S., Pijnenborg A. C., Tigges A. J., Westerhof W. and Das P. K. (2002). Br. J. Dermatol. 146:80-87.
43. Bener A., Lestringant G. G., Nyomba B. L., Frossard P. and Saardi H. (2000). East. Mediterr. Health J. 6:416-424.
44. Hermanns-Le T., Hermanns J. F. and Pierard G. E. (2002). Pediatr. Dermatol. 19:12-14
45. Katz A. S., Goff D.C. and Feldman S. R. (2000). Dermatol. Online J. 6:1.
46. Nguyen T. T. and Kell M. F. (2001). J. Pediatr. 138:453-454.
47. King-Tryce K., Garza L. and Ozias J. M. (2002). Texas Department of Health Disease Prevention News 62(2): 1-3.
48. Bosset S., Barre P., Chalon A., Kurfurst R., Bonte F., Andre P., Perrier P., Disant F., Le Varlet B. and Nicolas J. F. (2002). Eur. J. Dermatol. 12:247-252.
49. Chung J. H., Seo J. Y., Choi H. R., Lee M. K., Youn C. S., Rhie G., Cho K. H., Kim K. H., Park K. C. and Eun H. C. (2001). J. Invest. Dermatol. 117:1218-1224.
50. Elias P. M. and Ghadially R. (2002). Clin. Geriatr. Med. 18:103-120.
51. Lundqvist K. and Schmidtchen A. (2001). Br. J. Dermatol. 144:254-259.
52. Marschall C., Lengyel E., Nobutoh T., Braungart E., Douwes K., Simon A., Magdolen V., Reuning U. and Degitz K (1999). J. Invest. Dermatol. 113:69-76.
53. Ciaria M. V., Bocciarelli A., Di Gregorio S., Tordi A., Cotroneo P., Marra G., Ghirlanda G. and Strom R. (2001). Atherosclerosis 158:241-246.
54. Buch M. and Emery P. (2002). Hospital Pharmacist 9:5-10.
55. Sahn E. E. (1995). Semin. Dermatol. 14:9-14
56. Kumar B., Sharma V. K. and Sehgal S. (1995). Int. J. Dermatol. 34:542-545.
57. Shellow W. V., Edwards J. E. and Koo J. Y. (1992). Int. J. Dermatol. 31:186-189.
58. Wang S. J., Shohat T., Vadheim C., Shellow W., Edwards J. and Rotter J. L. (1994). Am. J. Med. Genet. 51:234-239.
59. Matilainen V., Koskela P. and Keinanen-Kiukaanniemi S. (2000). Lancet 356:1165-1166.
60. Kuusisto J., Koivisto K., Mykkanen L., Helkala E. 1., Vanhanen M., Hanninen T., Kervinen K., Kesaniemi Y. A., Riekkinen P. J. and Laakso M. (1997). BMJ. 315:1045-1049.
61. Bierhaus A., Hofmann M. A., Ziegler R. and Nawroth P. P. (1998). Cardiovasc. Res. 37:586-600.
62. Bennett R. G., Duckworth W. C. and Hamel F. G. (2000). J. Biol. Chem. 275:36621-36625.
63. Vekrellis K, Ye Z., Qiu W. Q., Walsh D., Hartley D., Chesneau V., Rosner M. R. and Selkoe D. J. (2000). J. Neurosci. 20:1657-1665.
64. Yang L. B., L. B., Meri S., Rogers J and Shen Y. (2000). J. Neurosci. 20:7505-7509.
65. Reinoso B. S., Pimenta A. F. and Levitt P. (1996). J. Comp. Neurol. 375:274-288.
66. Ogier-Denis E., Bauvy C., Couvineau A., De Stefanis D., Isidoro C. and Codogno P. (1995). Biochem. Biophys. Res. Commun. 211:935-942.
67. Haas U and Sparks D. L. (1996). Mol. Chem. Neuropathol. 29:1-14.
68. Tsukuba T., Okamoto K., Yasuda y, m Morikawa W., Nakanishi H. and Yamamoto K. (2000). Mol. Cells. 10:601-611.
69. van Horssen J., Otte-Holler I., David G., Maat-Schieman M. L., van den Heuvel L. P., Wesseling P., de Waal R. M. and Verbeek M. M. (2001). Acta Neuropathol. 102:604-614.
70. Snow A. D., Mar H., Nochlin D., Kimata K., Kato M., Suzuki S., Hassell J. and Wight T. N. (1988). Am. J. Pathol. 133:456-463.
71. Mulder M. and Terwel D. (1998). Haemostasis 28:174-194.
72. Donahue J. E., Berzin T. M., Rafii M. S., Glass D. J., Yancopoulos G. D., Fallon J. R. and Stopa E. G. (1999). Proc. Nat. Acad. Sci. 6468-6472.
73. Holden R. J. and Mooney P. A. (1994). Med. Hypotheses 43:420-435.
74. Holden R. J. (1995). Med. Hypotheses 44:379-391.
75. Nathan R. S., Sachar E. J., Asnis G. M., Halbreich U. and Halpern F. S. (1981). Psychiatry Res. 4:291-300.
76. Offen D., Shtaif B., Hadad D., Weizman A., Melamed E. and Gil-Ad I. (2001). Neurosci. Lett. 316:129-132.
77. Mattson M. P., Pedersen W. A., Duan W., Culmsee C. and Camandola S. (1999). Ann. N.Y. Acad. Sci. 893:154-175.
78. Sandyk R. (1993). Int. J. Neurosci. 69:125-130.
79. Potter G. M., Moshirfar A. and Castonguay T. W. (1999). Physiol. Behav. 65:811-816.
80. Figlewicz D. P., Patterson T. A., Zavosh A., Brot M. D., Roitman M. and Szot P. (1999). Horm. Metab. Res. 31:335-339.
81. Liu Z., Wang Y., Zhao W., Ding J., Mei Z., Guo L., Cui D. and Fei J. (2001). Neuropharmacology 41:464-471.
82. Shiroyama K., Moriwaki K. and Yuge O. (1998). In vivo 12:527-529.
83. Gong L., Wyatt R. J., Baker I. and Masserano J. M. (1999). Neurosci. Lett. 263:153-156.
84. Klein R. D., Sherman D., Ho W. H., Stone D., Bennett G. L., Moffat B., Vandlen R., Simmons L., Gu Q., Hongo J. A., Devaux R., Poulsen K., Armanini M., Nozaki C., Asai N., Goddard A., Phillips H., Henderson C. E., Takahashi M. and Rosenthal A. (1998). Nature 387:717-721.
85. Tietjen G. E., Day M., Norris L., Aurora S., Halvorsen A., Schultz L. R. and Levine S. R. (1998). Neurology 50:1433-1440.
86. Jacome D. E. (2001). Headache 41:895-898.
87. Heinzlef O., Alamowitch S., Sazdovitch V., Chillet P., Joutel A., Tournier-Lasserve E. and Roullet E. (2000). Acta Neurolog. Scand. 101:36-40.
88. Winer S., Astsaturov I., Cheung R. K., Gunaratnam L., Kubiak V., Cortez M. A., Moscarello M., O'Connor P. W., McKerlie C., Becker D. J. and Dosch H-M. (2001). J. Immunol. 166:2831-2841.
89. Procacci V., Altavilla R. A., Robert, M. G., Chicco D., Antonacci N., Vendemiale G. and Altomare E. (1990). Bollettino-Societa Italiana Biologia Sperimentale. 66:795-802.
90. Kramer E. M., Koch T., Niehaus A. and Trotter J. (1997). J. Biol. Chem. 272:8937-8945.
91. Siewert E., Silvestri A., Riehl J. and Mertens P. R. (2001). Eur. J. Med. Res. 6:21-26.
92. Green S. T., Ng J. P. and Chan-Lam D. (1988). Scott. Med. J. 33:213-214.

93. Hoch W., McConville J., Helms S., Newsom-Davis J., Melms A. and Vincent A. (2001). Nat. Med. 7:365-368.
94. Tang J., Yuan J. and Hao H. (1997). Chin. Med. J. (Engl.) 110:698-700.
95. Zhmurko V. A. (1999). Lik. Sprava Mar:67-69
96. Ishikawa S., Komiyama Y., Kobayashi H., Tsuyuzaki J., Tokunaga S., Miyazaki A., Hanyu N. and Ikeda S. (2001). Intern. Med. 40:952-955.
97. Kaur G. and Arora S. K. (1994). Mol. Chem. Neuropathol. 21:83-93.
98. Bhattacharya S. K. and Saraswati M. (1991). Indian J. Exp. Biol. 29:1095-1100.
99. Kiss G., Somogyi J., Csermely P., Szelenyi J. and Ver A. (2001). Diabetologia 44:220-223
100. Hooper N. M. (1997). Clin. Chim. Acta 266:3-12
101. Mizisin A. P., Calcutt N. A., DiStephano P. S., Acheson A. and Longo F. M. (1997). Diabetes 46:647-652.
102. Poca S., Guyon T., Levasseur P. and Berrih-Aknin S. (2001). J. Neuroimmunol. 120:180-189.
103. Reyes E. T., Perurena O. H., Feestoff B. W., Jorgensen R. and Moore W. V. (1984). J. Neurol. Sci. 63:317-324.
104. Hubbard R. W., Will A. D., Peterson G. W., Sanchez A., Gillan W. W. and Tan S. A. (1992). Neurology 42:1532-1534.
105. Festoff B. W., Yang S. X., Vaught J., Bryan C. and Ma J. Y. (1995): J. Neurol. Sci. 129 Suppl. 114-121.
106. Sasaki N., Fukatsu R., Tsuzuki K., Hayashi Y., Yoshida T., Fujii N., Koike T., Wakayama I., Yanagihara R., Garruto R., Amano N. and Malcita Z. (1998). Am. J. Path. 153: 1149-1155.
107. Bilak M. M., Corse A. M. and Kuncl R. W. (2001). Amyotroph. Lateral Scler. Other Motor Disord. 2:83-91.
108. Torres-Aleman I., Barrios V. and Berciano J. (1998). Neurology 50:772-776.
109. Suzuki H., Hase A., Miyata Y., Arahata K. and Akazawa C. (1998). J. Comp. Neurol. 402:303-312.
110. Hase A., Suzuki H., Arahata K. and Akazawa C. (1999). Neurosci. Lett. 269:55-57.
111. Hongo J. A., Tsai S. P., Moffat B., Schroeder K. A., Jung C., Chuntharapai A., Lampe P. A., Johnson E. M. Jr., de Sauvage F. J., Armanini M., Phillips H. and Devaux B. (2000). Hybridoma 19:303-315.
112. Encinas M., Tansey M. G., Tsui-Pierchala B. A., Comella J. X., Milbrandt J. and Johnson E. M. Jr. (2001). J. Neurosci. 21:1464-1472.
113. Lundberg C., Lidman O., Holmdahl R., Olsson T. and Piehl F. (2001). J. Comp. Neurol. 431:75-87.
114. Perros P., McCrimmon R. J., Shaw G. and Frier B. M. (1995). Diabet. Med. 12:622-627.
115. Jacquemin C. (1991). Biochimie 73:37-40
116. Petitfrere E., Sartelet H., Vivien D., Varela-Nieto I., Elbtaouri H., Martiny L. and Haye B. (1998). Biochimie. 80:1106-1067.
117. Zurzolo C., Lisanti M. P., Caras I. W., Nitsch L. and Rodriguez-Boulan E. (1993). J. Cell Biol. 121:1031-9.
118. Marino M., Pichera A., McCluskey R. T and Chiovato L. (2001). Thyroid 11:47-56.
119. Marino M., Andrews D. and McCluskey R. T. (2000). Thyroid 10:551-559.
120. Katoh R., Muramatsu A., Kawaoi A., Komiyama A., Suzuki K., Hemmi A. and Katayama S. (1993). 423:417-424.
121. Lindahl M., Poteryaev D., Yu L., Arumae U., Timmusk T., Bongarzone I., Aiello A., Pierotti M. A., Airaksinen M. S, and Saarma M. (2001). J. Biol. Chem. 276:9344-9351.
122. Doppman J. L., Miller D. L., Dwyer A. J., Loughlin T., Nieman L., Cutler G. B., Chrousos G. P., Oldfield E. and Loriaux D. L. (1988). Radiology 166:347-352.
123. Hermus A. R., Pieters G. F., Smals A. G., Pesman G. J., Lamberts S. W., Benraad T. J., van Haelst U. J. and Kloppenborg P. W. (1988). N. Engl. J. Med. 318:966-970.
124. Leibowitz G., Tsur A., Chayen S. D., Salameh M., Raz I., Cerasi E. and Gross D. J. (1996). Clin. Endocrinol. 44:717-722.
125. Roy M. S., Roy A., Gallucci W. T., Collier B., Young K., Kamilaris T. C. and Chrousos G. P. (1993). Metabolism 42:696-700
126. Grant W. and Liddle M. D. (1960). J. Clin. Endocrinol. Metab. 20:1539-1560.
127. Fanjul L. F., Marrero I., Estevez F., Gonzalez J., Quintana J., Santana P. and Ruiz de Galarreta C. M. (1993). J. Cell Physiol. 155:273-281.
128. Shaver J. K., Tezelman S., Siperstein A. E., Duh Q. Y. and Clark O. H. (1993). Surgery 114:1064-1069.
129. Vila M. C., Cozza E. N., Lima C., Ramirez M. I. and De Lederkremer R. M. (1995). Cell. Signal. 7:331-339.
130. Robinson P. and Hederer R. (1994). Braz. J. Med. Biol. Res. 27:263-267.
131. Benitez L., Fanjul L. F., Ruiz de Galarreta C. M., Quintana Aguiar J., Gonzalez Reyes J., Hernandez I., Santana Delgado P., Cabrera Oliva J., Alonso Solis R. and Estevez Rosas F. (1995). Neurosci. Lett. 187:37-40.
132. Redmond G. P. (1998). Int. J. Fertil. Womens Med. 43:91-97.
133. Kalro B. N., Loucks T. L and Berga S. L. (2001). Obstet. Gynecol. Clin. North Am. 28:35-62.
134. Rosenfield R. L. (2001). J. Am. Acad. Dermatol. 45 (3 Suppl.):S95-104.
135. Norman R. J., Masters S, and Hague W. (1996). Fertil. Steril. 66:942-947.
136. Pugeat M., Ducluzeau P. H. and Mallion-Donadieu. M.(2000). Horm. Res. 54:322-326.
137. Sekar N. and Veldhuis J. D. (2001). Endocrinology 142: 2921-2928.
138. Poretsky L., Seto-Young D., Shrestlia A., Dhillon S., Mirjany M., Liu H. C., Yih M. C. and Rosenwaks Z. (2001). J. Clin. Endocrinol. Metab. 86:3115-3119.
139. Kreze A. Jr., Hrnciar J., Dobakova M. and Pelcarova E. (1997). Bratisl. Lek. Listy 98:555-558.
140. Marsden P. J., Murdoch A. P. and Taylor R. (2000). Hum. Reprod. 15:1672-1678.
141. Yanagishita M. (1992). J. Biol. Chem. 267:9499-9504.
142. Fanjul L. F., Marrero I., Estevez F., Gonzalez J., Quintana J., Santana P. and Ruiz de Galarreta C. M. (1993). J. Cell. Physiol. 155:273-281.
143. Fanjul L. F., Marrero I., Gonzalez J., Quintana J., Santana P., Estevez F., Mato J. M. and Ruiz de Galarreta C. M. (1993). Eur. J. Biochem. 216:747-755.
144. Hasan S., Hosseini G., Princivalle M., Dong J. C., Birsan D., Cagide C. and de Agostini A. I. (2002). Biol. Reprod. 66:144-158.
145. Fedarko N. S., Ishihara M. and Conrad H. E. (1989). J. Cell. Physiol. 139:287-294.
146. Saad M. F., Khan A., Sharma A., Michael R., Riad-Gabriel M. G., Boyadjian R., Jingagouda S. D., Steil G. M. and Kamdar V. (1998). Diabetes 47:544-549.
147. Stephens T. W., Basinski M., Bristow P. K., Bue-Valleskey J. M., Burgett S. G., Craft L., Hale J., Hoffman J., Hsiung H: M. and Kriauciunas A. (1995). Nature 377: 530-532.

148. Baskin D. G., Figlewicz Lattemann D., Seeley R. J., Woods S. C., Porte D. Jr. and Schwartz M. W. (1999). Brain Res. 848:114-123.
149. Olszewski P. K., Wirth M. M., Shaw T. J., Grace M. K., Billington C. J., Giraudo S. Q. and Levine A. S. (2001). Am. J. Physiol. 281:R673-680.
150. Dunbar J. C. and Lu H. (2000). Brain Res. Bull. 52:123-126.
151. Maffei M., Halaas J., Ravussin E., Pratley R. E., Lee G. H., Zhang Y., Fei H., Kim S., Lallone R., Ranganatlian S., Kern P. A. and Friedman J. M. (1995). Nat. Med. 1:1155-1161.
152. Fedarko N. S., Ishihara M. and Conrad H. E. (1989). J. Cell. Physiol. 139:287-294.
153. Reaven G. M. (1988). Diabetes Metab. Rev. 37:1595-1597.
154. Ivanov D., Philippova M., Antopova J., Gubaeva F., Iljinskaya O., Tararak E., Bochov V., Erne P., Resink T. and Tkachuk V. (2001). Histochem. Cell. Biol. 115:231-242.
155. Reaven G. M. (1991). Am. Heart J. 121:1283-1288.
156. Swan J. W., Walton C., Godsland I. F., Crook D., Oliver M. F. and Stevenson J. C. (1994). Br. Heart J. 71:41-44.
157. Vuorinen-Markkola H. and Yki-Jarvinen H. (1994). J. Clin. Endocrinol. Metab. 78:25-29.
158. Pagano G., Pacini G., Musso G., Gambino R., Mecca F., Depetris N., Cassader M., David E., Cavallo-Perin P. and Rizzetto M. (2002). Hepatology 35:367-372.
159. Harano Y., Suzuki M., Koyama Y., Kanda M., Yasuda S., Suzuki K. and Takamizawa I. (2002). J. Diabetes Complications 16:19-23.
160. Semplicini A., Ceolotto G., Massimino M., Valle R., Serena L., De Toni R., Pessina A. C. and Dal Palu C. (1994). Am. J. Med. Sci. 307 Suppl. 1:S43-46.
161. Sardesai M. G., Gray A. A., McGrath M. M. and Ford S. E. (2001). Obstet. Gynecol. 98:925-927.
162. Hardin D. S., Hebert J. D., Bayden T., Dehart M. and Mazur L. (1997). Pediatrics 100(2):E5.
163. Bergstrom E., Hernell O., Persson L. A. and Vessby B. (1996). Metabolism 45:908-914.
164. Facchini F. S., Hua N., Abbasi F. and Reaven G. M. (2001). J. Clin. Endocrinol. Metab. 86:3574-3578.
165. Landy H. J., Kessler C., Kelly W. K. and Weingold A. B. (1992). Am. J. Perinatol. 9:146-151.
166. Andelova K., Sula K. and Velebil P. (1998). Ceska Gynekol. 63:446-449.
167. Lorini R., d'Annunzio G., Montecucco C., Caporali R., Vitali L., Pessino P. and Severi F. (1995). Eur J. Pediatr. 154:105-108.
168. Galtier-Dereure F., Biron C., Vies M., Bourgeois V., Schved J. F. and Bringer J. (1998). Lupus 7:469-474.
169. Ciarla M. V., Bocciarelli A., Di Gregorio S., Tordi A., Cotroneo P., Marra G., Ghirlanda G. and Strom R. (2001). Atherosclerosis 158:241-246.
170. de Maistre E., Gobert B., Bene M. C., Briquel M. E., Lecompte T. and Faure G. C. (1996). J. Clin. Lab. Anal. 10:6-12.
171. Fialova L., Mikulikova L., Matous-Malbohan I., Benesova O. and Zwinger A. (2000). Physiol. Res. 49:299-305.
172. Lopez-Soto A., Cervera R., Font J., Bove A., Reverter J. C., Munoz F. J., Miret C., Espinosa G., Ordinas A. and Ingelmo M. (1997). Clin. Exp. Rheumatol. 15:143-149.
173. Toschi V., Motta A., Castelli C., Paracchini M. L., Zerbi D. and Gibelli A. (1998). Stroke 29: 1759-1764.
174. Erkan D., Yazici Y., Sobel. R. and Lockshin M. D. (2000). J. Rheumatol. 27:2817-2821.
175. Not T., Tommasini A., Tonini G., Buratti E., Pocecco M., Tortul C., Valussi M., Crichiutti G., Berti I., Trevisiol C., Azzoni E., Neri E., Torre G., Martelossi S., Soban M., Lenhardt A., Cattin L. and Ventura A. (2001). Diabetologia. 44:151-155.
176. Tursi A., Giogetti G., Brandimarte G., Rubino E., Lombardi D. and Gasbarrini G. (2001). Hepato-Gastroenterol. 48:462-464
177. Williams A. J., Norcross A. J., Lock R. J., Unsworth D. J., Gale E. A. and Bingley P. J. (2001). Diabetes Care 24:504-509.
178. Di Mario U., Anastasi E., Mariani P., Ballati G., Perfetti R., Triglione P., Morellini M. and Bonamico M. (1992). Acta Pediatr. 81:593-597.
179. Galli-Tsinopoulo, A., Nousia-Arvanitalcis S., Dracoulacos D., Xefteri M. and Karamouzis M. (1999). Hormone Res. 52:119-124.
180. Alemany R., Vila M. R., Franci C., Egea G., Real F. X. and Thomson T. M. (1993). J. Cell Sci. 104:1155-1162.
181. Slomiany A., Grabska M. and Slomiany B. L. (2001). Mol. Med. 7: 1-10.
182. Riley W. J., Winer A. and Goldstein D. (1983). Diabetologia 24:418-421.
183. Landin-Olsson M., Karlsson F. A., Lemmark A. and Sundkvist G. (1992). Diabetes 41:1022-1027.
184. Koike S.; Takeda Y., Hozumi Y., Okazaki S., Aoyagi M. and Sendo F. (2002). Cell Tissue Res. 307:91-99.
185. Tenore A., Berman W. F., Parks J. S, and Bongiovanni A. M. (1977). J. Clin. Endocrinol. Metab. 44:622-628.
186. Al-Jaouni R., Hebuterne X., Pouget I. and Rampal P. (2000). Nutrition 16:173-178.
187. Eriksson L. S. (1983). Gut 24:1161-1168.
188. Mingrone G., DeGaetano A., Pugeat M., Capristo E., Greco A. V. and Gasbarrini G. (1999). J. Investig. Med. 47:319-325.
189. Levy E., Rizwan Y., Thibault L., Lepage G., Brunet S., Bouthillier L. and Seidman E. (2000). Am. J. Clin. Nutr. 71:807-815.
190. Meddings J. B. Jarand J., Urbanski S. J., Hardin J. and Gall D. G. (1999). Am. J. Physiol. 276:G951-957.
191. Hollander D., Vadheim C. M., Brettholz E., Petersen G. M., Delahunty T. and Rotter J. I. (1986). Ann. Intern. Med. 105:883-885.
192. Hilsden R. J., Meddings J. B. and Sutherland L. R. (1996). Gastroenterology 110:1395-1403.
193. Koller E. and Ranscht B. (1996). J. Biol. Chem. 271: 30061-30067.
194. Resink T. J., Kuzmenko Y. S., Kern F., Stambolsky D., Bochkov V. N., Tkachulc V. A., Erne P. and Niermann T. (1999). FEBS Lett. 463:29-34.
195. Kuzmeneko Y. S., Kern F., Bochlcov V. N., Tkachuk V. A. and Resink T. J. (1998). FEBS Lett. 434:183-187.
196. Ivanov D. B., Philippova M. P. and Tkachuk V. A. (2001). Biochemistry (Mosc.) 66:1174-1186.
197. Filmus J., Shi W., Wong Z. M. and Wong M. J. (1995). Biochem. J. 311:561-565.
198. Herndon M. E., Stipp C. S, and Lander A. D. (1999). Glycobiology 9:143-155.
199. Koh D. M., Miao Y., Chinn R. J., Amin Z., Zeegen R., Westaby D. and Healy J. C. (2001). Am. J. Roentgenol. 177:1325-1332.
200. Graham M. F., Diegelmann R. F., Elson C. O., Lindblad W. J., Gotschalk N., Gay S, and Gay R. (1988). Gastroenterology 94:257-265.
201. Koutroubakis I. E., Petinaki E., Anagnostopoulou E., Kritikos h., Mouzas I. A., Kouroumalis E. A. and Manousos O. N. (1998). Dig. Dis. Sci. 43:2507-2512.

202. Aichbichler B. W., Petritisch W., Reicht G. A., Wenzl H. H., Eherer A. J., Hinterleitner T. A., Auer-Grumbach P. and Krejs G. J. (1999). Dig. Dis. Sci. 44:852-856.
203. Paolisso G., Valentini G., Giugliano D., Marrazzo G., Tirri R., Gallo M., Tirri G., Varricchio M. and D'Onofrio F. (1991). Metabolism 40:902-907.
204. Takahashi S., Moriwaki Y., Tsutsumi Z., Yamakita J., Yamamoto T. and Hada T. (2001). Metabolism 50:393-398.
205. Svenson K. L., Pollare T., Lithell H. and Hallgren R. (1988). Metabolism 37:125-130.
206. Svenson K. L., Lundqvist G., Wide L. and Hallgren R. (1987). Metabolism 36:940-943.
207. Jimenez-Balderas F. J., Solis J. L. and Mintz G. (1991). Arch. Invest. Med. (Mex.) 22:121-125.
208. Dessein P. H., Joffe B. I., Stanwix A., Botha A. S. and Moomal Z. (2002). J. Rheumatol. 29:462-466.
209. Martin S., Kardorf J., Schulte B., Lampeter E. F., Gries F. A., Melchers I., Wagner R., Bertrams J., Roep B. O. and Pfutzner A. (1995). Diabetologia 38:351-355.
210. Mihailova D., Grigorova R., Vassileva B., Mladenova G., Ivanova N., Stephanov S., Lissitchky K. and Dimova E. (1999). Adv. Exp. Med. Biol. 455:55-60.
211. Slot O., Brunner N., Locht H., Oxholm P. and Stephens R. W. (1999). Ann. Rheum. Dis. 58:488-492.
212. Tarui T., Mazar A. P., Cines D. B. and Takada Y. (2001). J. Biol. Chem. 276:3983-3990.
213. Hoyer-Hansen G., Pessara U., Holm A., Pass J., Weidle U., Dano K. and Behrendt N. (2001). Biochem. J. 358:673-679.
214. Hoyer-Hansen G., Behrendt N., Ploug M., Dano K. and Preissner K. T. (1997). FEBS Lett. 420:79-85.
215. McKeown-Longo P. J. and Panetti T. S. (1996). Trends Glycosci. Glycotechnol. 8:327-340.
216. Deng G., Curriden S. A., Wang s., Rosenberg S, and Loskutoff D. J. (1996). J. Cell Biol. 134:1563-1571.
217. Bajou K., Devy L., Masson V., Albert V., Frankenne F., Noel A., and Foidart J. M. (2001). Therapie. 56:465-472.
218. Kero J., Gisler M., Hemminki E. and Isolauri E. (2001). J. Allergy Clin. Immunol. 108:781-783.
219. Becker K. G., Simon R. M., Bailey-Wilson J. E., Freidlin B., Biddison W. E., McFarland H. F. and Trent J. M. (1998). Proc. Nat. Acad. Sci. 95:9979-9984.
220. Becker K. G. (1999). Diabetes 48:1353-1358.
221. Costello R. W., Jacoby D. B. and Fryer A. D. (1998). Thorax 53:613-618.
222. Belmonte K. E., Fryer A. D. and Costello R. W. (1998). J. Appl. Physiol. 85:1708-1718.
223. Rajah R., Nachajon R. V., Collins M. H., Hakoharson H., Grunstein M. M. and Cohen P. (1999). Am. J. Respir. Cell Mol. Biol. 20:199-208.
224. Bufi P. L. (1997). Alt. Med. Rev. 2:104-115.
225. Gonzaez-Guerrico A. M., Cafferata E. G., Radrizzani m., Marcucci F., Gruenert D., Pivetta O. H., Favaloro R. R., Laguens R., Perrone S. V., Gallo G. C. and Santa-Coloma T. A. (2002). J. Biol. Chem. 277:17239-17247.
226. Cantiello H. F. (2001). Pflugers Arch. 443:S75-80.
227. Chasan B., Geisse N. A., Pedatella K., Wooster D. G., Teintze M., Carattino M. D., Goldmann W. H. and Cantiello H. F. (2002). Eur. Biophys. J. 30:617-624.
228. Koller L. and Hall. A. (2001). J. Cell Biol. 152:1145-1157.
229. Suzuki K. and Sheetz M. P. (2001). Biophys. J. 81:2181-2189.
230. Shetty. S, and Idell S. (2001). J. Biol. Chem. 276:24549-24556.
231. Gyetko M. R., Sud S., Kendall T., Fuller J. A., Newstead M. W. and Standiford T. J. (2000). J. Immunol. 165:1513-1519.
232. Letham M. I., James S. L., Marriot C. and Burke J. F. (1990). Eur. Respir. J. 3:19-23
233. Devitt A., Moffatt O. D., Raykundalia C., Capra J. D., Simmons D. L. and Gregory C. D. (1998). Nature 392:442-443.
234. Fadok V. A., deCathelineau A., Daleke D. L., Henson P. M. and Bratton D. L. (2001). J. Biol. Chem. 276:1071-1077.
235. Wang P., Kitchens R. L. and Munford R. S. (1998). J. Biol. Chem. 273:24309-24313.
236. Heidenreich S. (1999). J. Leukoc. Biol. 65:737-743.
237. Allport J. R., Donnelly L. E., Kefalas P., Lo G., Nunn A., Yadollahi-Farsani M., Rendall N. B., Murray S., Taylor G. W. and MacDermot J. (1996). Br. J. Clin. Pharmacol. 42:99-106.
238. Freedman S. D., Kern H. F. and Scheele G. A. (2001). Gastroenterology 121:950-957.
239. Moran A., Diem P., Klein D. J., Levitt M. D. and Robertson R. P. (1991). J. Pediatr. 118:715-723.
240. Lanng S., Thorsteinsson B., Roder M. E., Orskov C., Holst J. J., Nerup J. and Koch C. (1993). Acta Endocrinol. (Copenh.) 128:207-214.
241. Schaedel C., De Monestrol I., Hjelte L., Johannesson M., Kornfalt R., Lindblad A., Strandvik B., Wahlgren L. and Holmberg L. (2002). Pediatr. Pulmonol. 33:483-491.
242. Noone P. G. and Knowles M. R. (2001). Respir. Res. 2:328-332.
243. Armstrong D. S., Grimwood K., Carzino R., Carlin J. B., Olinsky A. and Phelan P. D. (1995). BMJ 310:1571-1572.
244. Dakin C. J., Pereira J. K., Henry R. L., Wang H. and Morton J. R. (2002). Pediatr. Pulmonol. 33:475-482.
245. Wulffraat N. M., de Graeff-Meeder E. R., Rijkers G. T., van der Laag H. and Kuis W. (1994). J. Pediatr. 125:374-378.
246. Leidig-Bruckner G. and Ziegler R. (2001). Exp. Clin. Endocrinol. Diabetes 109 Suppl. 2:S493-514.
247. Lopez-Ibarra P. J., Pastor M. M., Escobar-Jimenez F., Pardo M. D., Gonzalez A. G., Luna J. D., Requena M. E. and Diosdado M. A. (2001). Endocr. Pract. 7:346-351.
248. Choi S. J., Devlin R. D., Menaa C., Chung H., Roodman G. D. and Reddy S. V. (1998). J. Clin. Invest. 102:1360-1368.
249. Lowe N. J., Cudworth A. G., Clough S. A. and Bullen M. F. (1976). Br. J. Dermatol. 95:9-12.
250. Nigam P. K., Sharma L., Agrawal J. K., Singh G. and Khurana S. K. (1987). Dermatologica 175:284-289.
251. Albrecht M., Banoczy J., Dinya E. and Tamas G. Jr. (1992). J. Oral Pathol. Med. 21:364-366.
252. Gibson J., Lamey P. J., Lewis M. and Frier B. (1990). J. Oral Pathol. Med. 19:284-287.
253. Issaraagrisil S., Vannasaeng S, and Piakijagum A. (1989). Metabolism 38:204-207.
254. Vu T., Griscelli-Bennaceur A., Gluckman E., Sigaux F., Carosella E. D., Menier C., Scrobohaci M. L. and Socie G. (1996). Br. J. Haematol. 93:586-589.
255. Winkler A. S., Marsden J., Chaudhuri K. R., Hambley H. and Watkins P. J. (2000). Diabet. Med. 17:410.
256. Yun Y. S., Lee H. C., Yoo N. C., Song Y. D., Lim S. K., Kim K. R., Hahn J. S, and Huh K. B. (1999). Diabetes Res. Clin. Pract. 46:223-229.
257. Wu M., Fan J., Gunning W. and Ratnam M. (1997). J, Membr. Biol. 159:137-147.
258. Jarva H. and Meri S. (1999). Scand. J. Immunol. 49:119-125.

259. Maciejewski J. P., Young N. S., Yu M., Anderson S. M. and Sloand E. M. (1996). Thromb. Res. 83:433-447.
260. Rawstron A. C., Rollinson S. J., Richards S., Short M. A., English A., Morgan G. J., Hale G. and Hillmen P. (1999). Br. J. Haematol. 107:148-153.
261. Pakdeesuwan K., Muangsup W., Pratya Y. U., Issaragrisil S. and Wanachiwanawin W. (2001). Int. J. Haematol. 73:64-70.
262. Noji H., Shichishima T., Saitoh Y., Kai T., Yamamoto T., Ogawa K., Okamoto M., Ikeda K. and Maruyama Y. (2001). Exp. Hematol. 29:391-400.
263. Punjabi N. M., Sorkin J. D., Katzel L. I., Goldberg A. P., Schwartz A. R. and Smith P. L. (2002). Am. J. Respir. Crit. Care Med. 165:677-682.
264. Ip M. S., Lam B., Ng M. M., Lam W. K., Tsang K. W. and Lam K. S. (2002). Am. J. Respir. Crit. Care Med. 165:670-676.
265. Zhdanova I. V., Wurtman R. J., Regan M. M., Taylor J. A., Shi J. P. and Leclair O. U. (2001). J. Clin. Endocrinol. Metab. 86:4727-4730.
266. Bruls E., Crasson M. and Legros J. J. (2000). Rev. Med. Liege 55:785-792.
267. Ganguly S., Gastel J. A., Weller J. L., Schwartz C., Jaffe H., Namboodiri M. A. A., Coon S. L., Hickman A. B., Rollag M., Obsil T., Beauverger P., Ferry G., Boutin J. A. and Klein D.C. (2001). Proc. Natl. Acad. Sci. 98:8083-8088.
268. Meisel P., Arndt D., Scheuch E., Klebingat K. J. and Siegmund W. (2001). Ther. Drug Monit. 23:9-14
269. Ladero J. M., Agundez J. A., Olivera M., Lozano L., Rodriguez-Lescure A., Diaz-Rubio M. and Benitez J. (2002). Eur. J. Clin. Pharmacol. 58:115-118.
270. Varzim G., Monteiro E., Silva R., Pinheiro C. and Lopes C. (2002). J. Otorhinolaryngol. Relat. Spec. 64:206-212.
271. Gawronska-Szklaarz B., Pawlik A., Czaja-Bulsa G., Gornik W., Luszawska-Kutrzeba T. and Wrzesniewska J. (2001). Clin. Pharmacol. Ther. 69:372-378.
272. Magnan C., Cruciani C., Clement L., Adnot P., Vincent M., Kergoat M., Girard A., Elghozi J. L., Velho G., Beressi N., Bresson J. L. and Ktorza A. (2001). J. Clin. Endocrinol. Metab. 86:4901-4907.
273. Burger A. J. and Aronson D. (2001). Int. J. Cardiol. 81:243-249.
274. Damholt M. B., Christensen N.J. and Hilsted J. (2001). Scand. J. Clin. Lab. Invest. (2001).61:531-537.
275. Elahi D. and Muller D.C. (2000). Eur. J. Clin. Nutr. 54 Suppl. 3:S112-120.
276. Ruzsas C. and Mess B. (2000). Neuroendocrinol. Lett. 21:17-23.
277. Rudd P. M., Wormald M. R., Wing D. R., Prusiner S. B. and Dwek R. A. (2001). Biochemistry 40:3759-3766.
278. Moya K. L., Sales N., Hassig R., Creminon C., Grassi J. and Di Giamberardino L. (2000). Microsc. Res. Tech. 50:58-65.
279. Sales N., Hassig R., Rodolfo K., Di Giamberardino L., Traiffort E., Ruat M., Fretier P. and Moya K. L. (2002). Eur. J. Neurosci. 15:1163-1167.
280. Brown D. R. (2001). Trends Neurosci. 24:85-90.
281. Tobler I., Gaus S. E., Deboer T., Achermann P., Fischer M., Rulicke T., Moser M., Oesch B., McBride P. A. and Manson J. C. (1996). Nature 380:639-642.
282. Brown D. R., Nicholas R. S, and Canevari L. (2002). J. Neurosci. Res. 67:211-224.
283. Tobler I., Deboer T. and Fischer M. (1997). J. Neurosci. 17:1869-1879.
284. Bartlett S. F., Lagercrantz H. and Smith A. D. (1976). Neuroscience 1:339-344.
285. Tayek J. A. (1992). J. Am. Coll. Nutr. 11:445-456.
286. Copeland G. P., Leinster S. J., Davis J. C. and Hipkin L. J. (1987). Br. J. Surg. 74:1031-1035.
287. Copeland G. P., Al-Sumidaie A. M., Leinster S. J., Davis J. C. and Hipkin L. H. (1987). Eur. J. Surg. Oncol. 13:11-16.
288. Tayek J. A. (1995). J. Am. Coll. Nutr. 14:341-348.
289. Nagamani M., Hannigan E. V., Dinh T. V. and Stuart C. A. (1988). J. Clin. Endocrinol. Metab. 67:144-148.
290. Bruning P. F., Boonfrer J. M., van Noord P. A., Hart A. A., de Jong-Bakkar M. and Nooijen W. J. (1992). Int. J. Cancer 52:511-516.
291. Talamini R., Franceschi S., Favero A., Negri E., Parazzini F. and La Vecchia C. (1997). Br. J. Cancer 75:1699-1703.
292. Tran T. T., Medline a. and Bruce W. R. (1996). Cancer Epidemiol. Biomarkers Prev. 5:1013-1015.
293. Heber D., Byerley L. O. and Tchekmedyian N. S. (1992). J. Parenter. Enteral Nutr. 16:60 S-64S.
294. Bartlett D. L., Charland S. L. and Torosian M. H. (1995). Surgery 118:87-97.
295. Wang Y. (2001). Med. Res. Rev. 21:146-170.
296. Thogersen V. B., Heickendorff L. and Ledet T. (1996). Eur. J. Endocrinol. 134:326-330.
297. Anfosso F., Chomiki N., Alessi M. C., Vague P. and Juhan-Vague I. (1993). J. Clin. Invest. 91:2185-2193.
298. Arroyo De Prada N., Schroeck F., Sinner E. K., Muehlenweg B., Twellmeyer J., Sperl S., Wilhelm O. G., Schmitt M. and Magdolen V. (2002). Eur. J. Biochem. 269:184-192.
299. Chazaud B., Ricoux R., Christov C., Plonquet A., Gherardi R. K. and Barlovatz-Meimon G. (2002). Am. J. Pathol. 160:237-246.
300. Devy L., Blacher S., Grignet-Debrus C., Bajou K., Masson V., Gerard R. D., Gils A., Carmeliet P., Declerck P. J., Noel A. and Foidart J. M. (2002). FASEB J. 16:147-154.
301. Harbeck N., Kates R. E. and Schmitt M. (2002). J. Clin. Oncol. 20:1000-1007.
302. Kim S. J., Shiba E., Taguchi T., Tsukamoto F., Miyoshi Y., Tanji Y., Takai S. and Noguchi S. (2002).Anticancer Res. 22:387-393.
303. Wilhelm O. G., Wilhelm S., Escott G. M., Lutz V., Magdolen V., schmitt., M., Rifkin D. B., Wilson E. L., Graeff H. and Brunner G. (1999). J. Cell. Physiol. 180:225-235.
304. Kleeff J., Wildi S., Kumbasar A., Friess H., Lander A. D. and Korc M. (1999). Pancreas 19:281-288.
305. Matsuda K., Maruyama H., Guo F., Kleeff J., Itakura J., Matsumoto Y., Lander A. D. and Korc M. (2001). Cancer Res. 61:5562-5569.
306. Saikali Z. and Sinnett D. (2000). Int. J. Cancer 89:418-422.
307. Toretsky J. A., Zitomersky N. L., Eskenazi A. E., Voigt R. W., Strauch E. D., Sun C. C., Huber R., Meltzer S. J. and Schlessinger D. (2001). J. Pediatr. Hematol. Oncol. 23:496-499.
308. Bar R. S., Dake B. L. and Stueck S. (1987). Am. J. Physiol. 253:E21-27.
309. Kaaks R. (2001). Gynecol. Obstet. Fertil. 29:185-191.
310. Yu H., Levesque M. A., Khosravi M. J., Papanastasiou-Diamandi A., Clark G. M. and Diamandis E. P. (1996). Br. J. Cancer 74:1242-1247.
311. Kuzmenko Y. S., Stambolsky D., Kern F., Bochkov V. N., Tkachuk V. A. and Resink T. J. (1998). Biochem. Biophys. Res. Commun. 246:489-494.
312. Vivier E., Tomasello E. and Paul P. (2002). Curr. Opin. Immunol. 14:306-311.

313. Kwa D., Vingerhoed J., Boeser-Nunnink B., Broersen S, and Schuttemaker H. (2001). J. Virol. 75:10455-10459.
314. Correa R. and Munoz-Fernandez M. A. (2001). AIDS 15:1959-1963.
315. Mackewicz C. E., Barker E., Greco G., Reyes-Teran G and Levy J. A. (1997). J. Clin. Invest. 100:921-930.
316. Lusso P. (2002). Vaccine 20:1964-1967.
317. Laurence J. S., Blanpain C., De Leener A., Parmentier M. and LiWang P. J. (2001). Biochemistry 40:4990-4999.
318. Hoogewerf A. J., Kuschert G. S., Proudfoot A. E., Borlat F., Clark-Lewis I., Power C. A. and Wells T. N. (1997). Biochemisty 36:13570-13578.
319. Cladera J., Martin I. and O'Shea P. (2001). EMBO J. 20:19-26.
320. Sidenius, N., Sier C. F. C., Ullum H., Pedersen B. K., Lepri A. C., Blasi F. and Eugen-Olsen J. (2000). Blood 96:4091-4095.
321. Handley M. A., Steigbigel R. T. and Morrison S. A. (1996). J. Virol. 70:4451-4456.
322. Schreier H., Moran P. and Caras I. W. (1994). J. Biol. Chem. 269:9090-9098.
323. Su H. R. and Boackle R. J. (1994). Int. Arch. Allergy Immunol. 105:238-244.
324. Adler B., Ashkar S., Cantor H. and Weber G. F. (2001). Cell. Immunol. 210:30-40.
325. Montouri N., Salzano S., Rossi G. and Ragno P. (2000). FEBS Lett. 476:166-170.
326. Pinto L. M., Lecoeur H., Ledru E., Rapp C., Patey O. and Gougeon M. L. (2002). AIDS 16:329-339.
327. Raulin J. (2002). Prog. Lipid Res. 41:27-65.
328. Nguyen D. H. and Hildreth J. E. (2000). J. Virol. 74:3264-3272.
329. Saifuddin M., Hedayati T., Atkinson J. P., Holguin M. H., Parker C. J. and Spear G. T. (1997). J. Gen. Virol. 78:1907-1911.
330. Ware L. J., Wooton S. A., Morlese J. M., Gazzard B. G. and Jackson A. A. (2002). Proc. Nutr. Soc. 61:131-136.
331. Constans J., Guerin V., Couchouron a., Seigneur M., Ryman A., Blann A. D., Amiral J., Amara A., Peuchant E., Moreau J. F., Pellegrin I., Pellegrin J. L., Fleury H., Leng B. and Conri C. (1998). Eur. J. Clin. Invest. 28:115-122.
332. Ilangumaran S., Arni S., Poincelet M., Theler J. M., Brennan P. J., Nasir-ud-Din and Hoessli D.C. (1995). J. Immunol. 155:1334-1342.
333. Richard M., Ibata-Ombetta S., dromer F., Bordon-Pallier F., Jouault T. and Gaillardin C. (2002). Mol. Microbiol. 44:841-853.
334. Ralton J. E., Mullin K. A. and McConville M. J. (2002). Biochem. J. 363:365-375.
335. Sauma S. Y., Tanaka T. M. and Strand M. (1991). Mol. Biochem. Parasitol. 46:73-80.
336. Das S., Traynor-Kaplan A., Kachintorn U., Aley S. B. and Gillin F. D. (1994). Braz. J. Med. Biol. Res. 27:463-469.
337. Tomavo S., Dubremetz J. F. and Schwarz R. T. (1992). J. Biol. Chem. 267:21446-21458.
338. Coelho P. S., Klein A., Talvani A., Coutinho S. F., Takeuchi O., Akira S., Silva J. S., Canizzaro H., Gazzinelli R. T. and Teixeira M. M. (2002). J. Leukoc. Biol. 71:837:844.
339. Black C. G., Barnwell J. W., Huber C. S., Galinsski M. R. and Coppel R. L. (2002). Mol. Biochem. Parasitol. 120: 215-224
340. Aliberti J. C., Machado F. S., Souto J. P., Campanelli A. P., Teixeira M. M., Gazzinelli R. T. and Silva J. S. (1999). Infect. Immun. 67:4819-4826.
341. Noe K. H., Cenciarelli C., Moyer S. A., Rota P. A. and Shin M. L. (1999). J. Virol. 73:3117-3124.
342. Kazachkov M. Y., Hu P. C., Carson J. L., Murphy P. C., Henderson F. W. and Noah T. L. (2002). Exp. Biol. Med. 227:330-335.
343. Cook D. N., Beck M. A., Coffmann T. M., Kirby S. L., Sheridan J. F., Pragnell I. B. and Smithies O. (1995). Science 269:1583-1585.
344. Doyle H. A. and Murphy J. W. (1997). J. Leukoc Biol. 61:147-155.
345. Gao J.-L., Wynn T. A., Chang Y., Lee E. J., Broxrneyer H. E., Cooper S., Tiffany H. L., Westphal H., Kwon-Chung J. and Murphy P. M. (1997). J. Exp. Med. 185:1959-1968.
346. Wadstrom T and Ljungh A. (1999). J. Med. Microbiol. 48:223-233.
347. Guibinga G. H., Miyanohara A., Esko J. D. and Friedmann T. (2002). Mol. Ther. 5:538-546.
348. Peiffer I., Servin A. L. and Bernet-Camard M. F. (1998). Infect. Immun. 66:4036-4042.
349. Gordon V. M., Nelson K. L., Buckley J. T., Stevens V. L., Tweten R. K., Elwood P. C. and Leppla S. H. (1999). J. Biol. Chem. 274:27274-27280.
350. Ricci V., Galmiche A., Doye A., Necchi V., Solcia E. and Boquet P. (2000). Mol. Biol. Cell 11:3897-3909.
351. Munro P., Kojima H., Dupont J. L., Bossu J. L., Poulain B. and Boquet P. (2001). Biochem. Biophys. Res. Commun. 289:623-629.
352. Ali N. and Evans W. H. (1990). Biochem. J. 271:193-199.
353. Fratti R. A., Backer J. M., Gruenberg J., Corvera S. and Deretic V. (2001). J. Cell Biol. 154:631-644.
354. Davis T. M., Pukrittayakamee S., Supanaranond W., Looareesuwan S., Krishna S., Nagachinta B., Turner R. C. and White N.J. (1990). Clin. Endocrinol. 33:739-749.
355. Soliman A. T., El-Nawawy A. A., El-Azzouni O. F., Amer E. A., Demian S. R. and El-Sayed M. H. (1996). J. Trop. Pediatr. 42:46-49.
356. Zaki K., Kantoosh M., Hamam M. A., Shoheib S., Mikhail N., Nour H. and Zaki F. (1980). Hepatogastroenterology 27:417-422.
357. dos Santos V. M., da Cunha S. F., Teixeira V. de P., Monteiro J. P., dos Santos J. A., dos Santos T. A., dos Santos L. A. and da Cunha D. F. (1999). Rev. Soc. Bras. Med. Trop. 32:489-496.
358. Vitkov L., Weitgasser R., Lugstein A., Noack M. J., Fuchs M. and Krautgartner W. D. (1999). J. Oral Pathol. Med. 28:406-409.
359. Karachunskii M. A., Balabolkin M. I. and Beglarian N. R. (1995). Vestn. Ross. Akad. Med. Nauk. (7):18-21.
360. Garg R., Agrawal J. K., Bajpai H. S., Singh G. and Srivastava P. K. (1990). Indian J. Lepr. 62:50-54.
361. Yoshitake H., Takeda Y., Nitto T. and Sendo F. (2002). J. Leukoc. Biol. 71:205-211.
362. Middelhoven P. J., van Buul J. D., Kleijer M., Roos D. and Hordijk P. L. (1999). Biochem. Biophys. Res. Commun. 255:568-574.
363. Nikolova M., Marie-Cardine A., Boumsell L. and Bensussan A. (2002). Int. Immunol. 14:445-451.
364. Kirby A, C., Hill V., Olsen I. and Porter S. R. (1995). Biochem. Biophys. Res. Commun. 214:200-205.
365. Matko J., Bodnar A., Vereb G., Bene L., Vaamosi G., Szentesi G., Szollosi J., Gaspar R., Horejsi V., Waldmann T. A. and Damjanovich S. (2002). Eur. J. Biochem. 269: 1199-1208.
366. Haregewoin A., Solomon K., Hom R. C., Soman G., Bergelson J. M., Bhan A. K. and Finberg R. W. (1994). Cell. Immunol. 156:357-370.
367. Schinowski K., Frohlich L., Maurer K., Muller W. E. and Eckert A. (2002). Mech. Ageing Dev. 123:375-390.

The invention claimed is:

1. A dimer or multimer which comprises two or more monomer peptides linked together by a non-antibody linker, wherein each of the monomer peptides:
   (a) consists of the amino acid sequence:
      (i) NIYPSDSYTNYNQKFKD (SEQ ID NO:8); or
      (ii) YIDPYNGDTRYSQKFKG (SEQ ID NO:24); or
      (iii) WINTYTGEPTYADDFKG (SEQ ID NO:40),
      wherein the peptide is shown in N to C terminal orientation;
   (b) is a variant of a peptide according to (a) which includes 1 or 2 amino acid substitutions, and which consists of the amino acid sequence:
      x-I-x-x-x-x-x-x-x-Y-x-x-x-F-K-x (SEQ ID NO:163)
      wherein 'x' indicates any amino acid residue, '-' indicates a peptide bond and the peptide is shown in N to C terminal orientation;
   (c) is an extended variant of a peptide of (a) or (b) which includes up to 5 additional amino acid residues at the C terminal and/or N terminal; or
   (d) is a truncated variant of a peptide of (a) or (b) which includes one amino acid deletions at the C terminal and/or N terminal,
   wherein the dimer or multimer is not an antibody.

2. The dimer or multimer according to claim 1, wherein each monomer peptide comprises the amino acid sequence recited in SEQ ID NO:8, SEQ ID NO:24, or SEQ ID NO:40.

3. The dimer or multimer according to claim 1, wherein each monomer peptide consists of the amino acid sequence recited in SEQ ID NO:8, SEQ ID NO:24, or SEQ ID NO:40.

4. The dimer or multimer according to claim 1, which is a homodimer or a homomultimer.

5. The dimer or multimer according to claim 1, which is a homodimer that comprises monomer peptides linked together by a cysteine residue at the N terminal or C terminal of each monomer peptide.

6. The dimer or multimer according to claim 1, which is chemically-modified, bound to a biological or synthetic substance, or which is conjugated to an enzyme, an indicator compound, a drug, a toxin or a radioactive label.

7. The dimer or multimer according to claim 2, wherein each monomer peptide comprises the amino acid sequence recited in SEQ ID NO: 159.

8. The dimer or multimer according to claim 3, wherein each monomer peptide consists of the amino acid sequence recited in SEQ ID NO: 159.

9. The pharmaceutical composition comprising a combination of a homodimer or homomultimer of monomer peptides comprising SEQ ID NO: 8, a homodimer or homomultimer of monomer peptides comprising SEQ ID NO: 10, and/or a homodimer or homomultimer of monomer peptides comprising SEQ ID NO: 16, in conjunction with a pharmaceutically acceptable carrier, wherein the monomer peptides are linked together by a non-antibody linker, and wherein the homodimers and homomultimers are not antibodies.

10. The pharmaceutical composition comprising a combination of a homodimer or homomultimer of monomer peptides comprising SEQ ID NO:159, a homodimer or homomultimer of monomer peptides comprising SEQ ID NO:160, and/or a homodimer or homomultimer of monomer peptides comprising SEQ ID NO:161, in conjunction with a pharmaceutically acceptable carrier, wherein the monomer peptides are linked together by a non-antibody linker, and wherein the homodimers and homomultimers are not antibodies.

11. A pharmaceutical composition comprising the dimer or multimer according to claim 1, and a pharmaceutically-acceptable carrier.

12. A dimer or multimer which comprises two or more monomer peptides linked together by a non-antibody linker, wherein each of the monomer peptides:
(a) consists of the amino acid sequence:
LRGLLPDY (SEQ ID NO:10); or
KGMTTGYA (SEQ ID NO:26); or
EGLYGNYF (SEQ ID NO:42),
wherein the peptide is shown in N to C terminal orientation;
(b) is an extended variant of a peptide of (a) which includes up to 5 additional amino acid residues at the C terminal and/or N terminal; or
(c) is a truncated variant of a peptide of (a) which includes one amino acid deletion at the C terminal and/or N terminal,
and wherein the dimer or multimer is not an antibody.

13. The dimer or multimer according to claim 12, wherein each monomer peptide comprises the amino acid sequence recited in SEQ ID NO:10, SEQ ID NO:26 or SEQ ID NO:42.

14. The dimer or multimer according to claim 12, wherein each monomer peptide consists of the amino acid sequence recited in SEQ ID NO:10, SEQ ID NO:26 or SEQ ID NO:42.

15. The dimer or multimer according to claim 12, which is a homodimer or a homomultimer.

16. The dimer or multimer according to claim 12, which is a homodimer that comprises monomer peptides linked together by a cysteine residue at the N terminal or C terminal of each monomer peptide.

17. The dimer or multimer according to claim 12, which is chemically-modified, bound to a biological or synthetic substance, or which is conjugated to an enzyme, an indicator compound, a drug, a toxin or a radioactive label.

18. The dimer or multimer according to claim 13, wherein each monomer peptide comprises the amino acid sequence recited in SEQ ID NO: 160.

19. The dimer or multimer according to claim 14, wherein each monomer peptide consists of the amino acid sequence recited in SEQ ID NO: 160.

20. A pharmaceutical composition comprising the dimer or multimer according to claim 12 and a pharmaceutically-acceptable carrier.

21. A dimer or multimer which comprises two or more monomer peptides linked together by a non-antibody linker, wherein each of the monomer peptides:
(a) consists of the amino acid sequence:
QQYNSYPLT (SEQ ID NO:16); or
QQGNTFPTF (SEQ ID NO:32); or
QQGSSSPLT (SEQ ID NO:64); or
QQYNSYPPT (SEQ ID NO:80),
wherein the peptide is shown in N to C terminal orientation;
(b) is a variant of a peptide according to (a) which includes 1 or 2 amino acid substitutions, and which consists of the amino acid sequence:
Q-Q-x-x-x-x-P-x-x (SEQ ID NO:166),
wherein 'x' indicates any amino acid residue, '-' indicates a peptide bond and the peptides are shown in N to C terminal orientation;
(c) is an extended variant of a peptide of (a) or (b) which includes up to 5 additional amino acid residues at the C terminal and/or N terminal; or
(d) is a truncated variant of a peptide of (a) or (b) which includes one amino acid deletion at the C terminal and/or N terminal,
and wherein the dimer or multimer is not an antibody.

22. The dimer or multimer according to claim 21, wherein each monomer peptide comprises the amino acid sequence recited in SEQ ID NO:16, SEQ ID NO:32, SEQ ID NO:64 or SEQ ID NO:80.

23. The dimer or multimer according to claim 21, wherein each monomer peptide consists of the amino acid sequence recited in SEQ ID NO:16, SEQ ID NO:32, SEQ ID NO:64 or SEQ ID NO:80.

24. The dimer or multimer according to claim 21, which is a homodimer or a homomultimer.

25. The dimer or multimer according to claim 21, which is a homodimer that comprises monomer peptides linked together by a cysteine residue at the N terminal or C terminal of each monomer peptide.

26. The dimer or multimer according to claim 21, which is chemically-modified, bound to a biological or synthetic substance, or which is conjugated to an enzyme, an indicator compound, a drug, a toxin or a radioactive label.

27. The dimer or multimer according to claim 22, wherein each monomer peptide comprises the amino acid sequence recited in SEQ ID NO: 161.

28. The dimer or multimer according to claim 23, wherein each monomer peptide consists of the amino acid sequence recited in SEQ ID NO: 161.

29. A pharmaceutical composition comprising the dimer or multimer according to claim 21 and a pharmaceutically-acceptable carrier.

* * * * *